(12) United States Patent
Kristensen et al.

(10) Patent No.: US 12,325,871 B2
(45) Date of Patent: *Jun. 10, 2025

(54) LYSOSOMAL ENZYMES MODIFIED BY CELL BASED GLYCOENGINEERING

(71) Applicants: University of Copenhagen, Copenhagen (DK); GLYCODISPLAY APS

(72) Inventors: Claus Kristensen, Bronshoj (DK); Weihua Tian, Hvidovre (DK); Henrik Clausen, Copenhagen (DK); Zhang Yang, Gentofte (DK); Sergey Vakhrushev, Nyborg (DK)

(73) Assignees: University of Copenhagen, Copenhagen (DK); GLYCODISPLAY APS, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/199,575

(22) Filed: May 19, 2023

(65) Prior Publication Data

US 2023/0416715 A1 Dec. 28, 2023

Related U.S. Application Data

(63) Continuation of application No. 17/272,178, filed as application No. PCT/US2019/048854 on Aug. 29, 2019, now Pat. No. 11,708,569.

(60) Provisional application No. 62/724,543, filed on Aug. 29, 2018.

(51) Int. Cl.
C12N 9/40 (2006.01)
C12P 21/00 (2006.01)

(52) U.S. Cl.
CPC .......... *C12N 9/2465* (2013.01); *C12P 21/005* (2013.01); *C12Y 302/01022* (2013.01); *C12Y 302/01045* (2013.01)

(58) Field of Classification Search
None
See application file for complete search history.

(56) References Cited

U.S. PATENT DOCUMENTS

| 7,001,994 | B2 | 2/2006 | Zhu | |
| 11,708,569 | B2 * | 7/2023 | Kristensen | C12P 21/005 435/208 |
| 2011/0280856 | A1 * | 11/2011 | Selden | C12N 9/2465 435/208 |

FOREIGN PATENT DOCUMENTS

| WO | WO 2003/057138 | 7/2003 |
| WO | WO 2008/109677 | 9/2008 |
| WO | WO 2015/150490 | 10/2015 |
| WO | WO 2016/091268 | 6/2016 |
| WO | WO 2016/105889 | 6/2016 |
| WO | WO 2016/146760 | 9/2016 |
| WO | WO 2017/008982 | 1/2017 |
| WO | WO 2017/055570 | 4/2017 |
| WO | WO 2017/194699 | 11/2017 |

OTHER PUBLICATIONS

Chica, Curr Opin Biotechnol. Aug. 2005; 16(4); 378-84.
Benjamin, "Coadministration With the Pharmacological Chaperone AT 1001 Increases Recombinant Human a-Galactosidase A Tissue Uptake and Improves Substrate Reduction in Fabry Mice", *Mol Ther*, 2012, vol. 20(4), pp. 717-726.
Damme, "Chronic enzyme replacement therapy ameliorates neuropathology in alpha-mannosidosis mice",*Ann Clin Transl Neurol* 2015, vol. 2, pp. 987-1001.
Desnick, "Enzyme replacement therapy for lysosomal diseases: lessons from 20 year of experience and remaining challenges", *Annu. Rev. Genomics Hum. Genet.*, vol. 13, pp. 307-33510.
Grubb et al. (2008), "Chemically modified beta-glucuronidase crosses blood-brain barrier and clears neuronal storage in murine mucopolysaccharidosis VII", *Proc.Natl.Acad.Sci* USA 105:2616-2621.
Grubb et al. (2010), "New strategies for enzyme replacement therapy for lysosomal storage diseases", *Rejuvenation Res* 13, 229-236.
Kishnani (2015), "Challenges of Enzyme Replacement Therapy:Poor Tissue Distribution in Lysosomal Diseases Using Pompe Disease as a Model", In: Rosenberg A., Demeule B. (eds) Biobetters. AAPS Advances in the Pharmaceutical Sciences Series, vol. 19. Springer, New York, NY.
Kim et al (2009), "Carbohydrate Recognition by the Mannose 6-phosphate Receptors", *Curr Opin Struct Biol* 19(5):534-42.
Lee et al (2003), "A biochemical and pharmacological comparison of enzyme replacement therapies for the gly colipid storage disorder Fabry disease", *Glycobiology* 13(4):305-313.
Lonowski et al (2017), "Genome editing using FACS enrichment of nuclease-expressing cells and indel detection by amplicon analysis", *Nature Protocols* 12, 581-603.
Miller et al (2018), "Neuropathic pain in a Fabry disease rat model", *JCI Insight*; 3(6). pii: 99171.
Narimatsu et al (2018), "A validated gRNA library for CRISPR/Cas9 targeting of the human glycosyltransferase genome", Glycobiology 28(5):295-305.
Platt (2018), "Emptying the stores: lysosomal diseases and therapeutic strategies", *Nat Rev Drug Disc* 17: 133-150.

(Continued)

*Primary Examiner* — Christian L Fronda
(74) *Attorney, Agent, or Firm* — Mueting Raasch Group

(57) ABSTRACT

The present invention relates to lysosomal enzymes modified by use of cell based methods, a compositions comprising a modified lysosomal enzyme, as well as methods for producing a modified lysosomal enzyme and therapeutic use of such modified lysosomal enzyme. In particular, the present disclosure relates to a modified lysosomal enzyme which has low Man6P and low exposed Mannose and high sialic acid content of alpha2,3 type enabling long circulation time and improved uptake into difficult-to-reach organs like heart, kidney and brain.

13 Claims, 65 Drawing Sheets

Specification includes a Sequence Listing.

(56) References Cited

OTHER PUBLICATIONS

Rozaklis et al (2011), "Impact of high-dose, chemically modified sulfamidase on pathology in a murine model of MRS IIIA", *Experimental Neurology* 230: 123-130.

Shen et al (2016), "Mannose receptor-mediated delivery of moss-made alpha-alactosidase A efficiently corrects enzyme deficiency in Fabry mice", *J Inherit Metab Dis* 39, 293-303.

Singh, Curr Protein Pept. Sci. 2017, 18, 1-11.

Tian et al (2019), "The glycosylation design space for recombinant lysosomal replacement enzymes produced in CHO cells", *Nature Communications* 10 (1785). DOI: 10.1038/S41467-019-09809-3.

Vakhrushev et al (2009), "Software platform for high-throughput glycomics", *Anal Chem* 81, 3252-3260.

Xu et al (2015), "Coformulation of a Novel Human a-Galactosidase A With the Pharmacological Chaperone AT 1001 Leads to Improved Substrate Reduction in Fabry Mice", *Molecular Therapy* vol. 23 No. 7, 1169-1181.

Yang et al (2015), "Engineered CHO cells for production of diverse, homogeneous glycoproteins", *Nature biotechnology* 33, 842-844.

Zhu et al (2004), "Conjugation of Mannose 6-Phosphate-containing Oligosaccharides to Acid-Glucosidase Improves the Clearance of Glycogen in Pompe Mice", *The Journal of Biological Chemistry* 279: 50336-50341.

Essentials of Glycobiology. 2017, 3rd edition. Varki A, Cummings RD, Esko JD, et al., editors. Cold Spring Harbor (NY): Cold Spring Harbor Laboratory Press; Available via: https://www.ncbi.nlm.nih.gov/books/NBK310274/.

Van Meel et al (2016), "Multiple Domains of GlcNAc-1-phosphotransferase Mediate Recognition of Lysosomal Enzymes", *Journal of Biological Chemistry*, vol. 291, No. 15, p. 8295-8307.

* cited by examiner

Figure 3
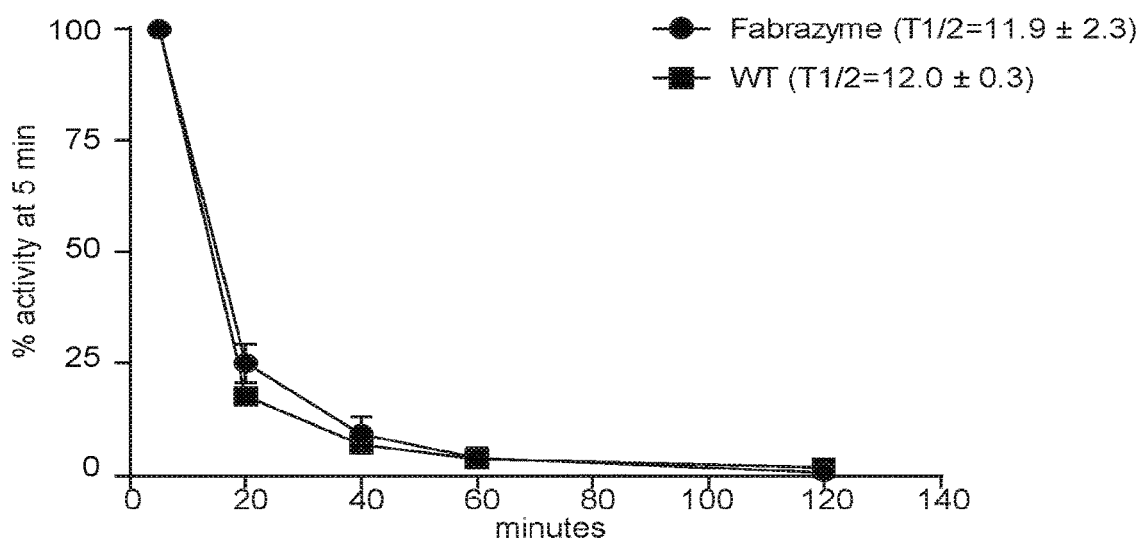
Figure 4
FIG. 4A
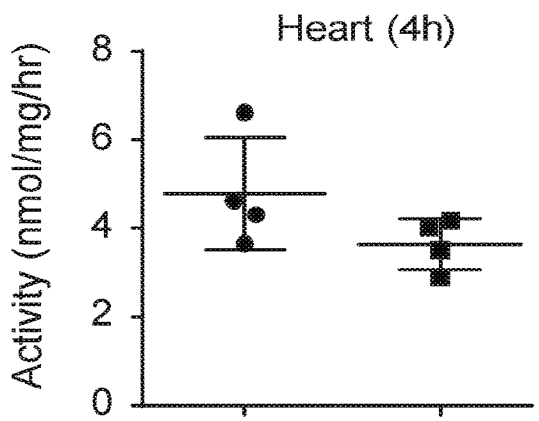
FIG. 4B
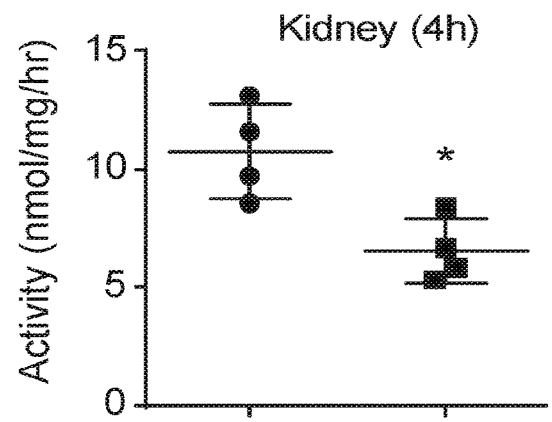

Figure 4 (continued)
FIG. 4C
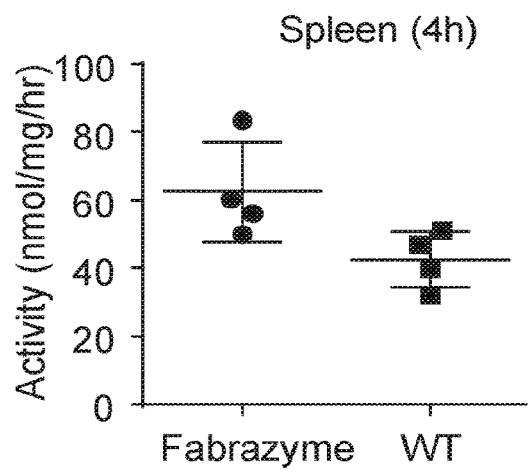
FIG. 4D
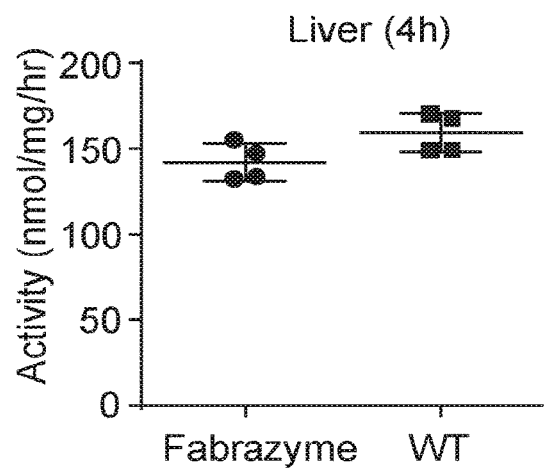
Figure 5
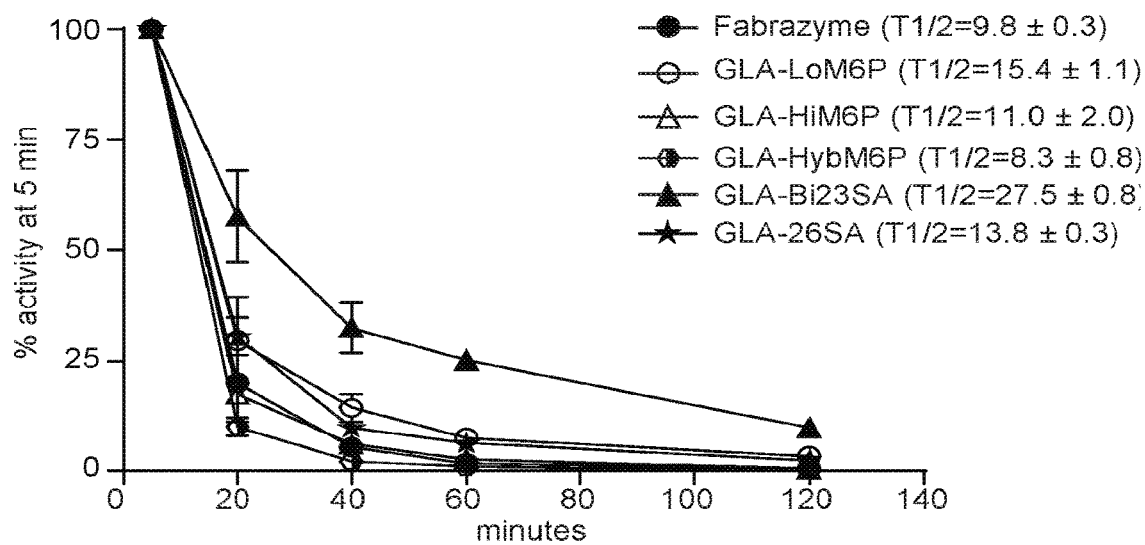

Figure 6
FIG. 6A
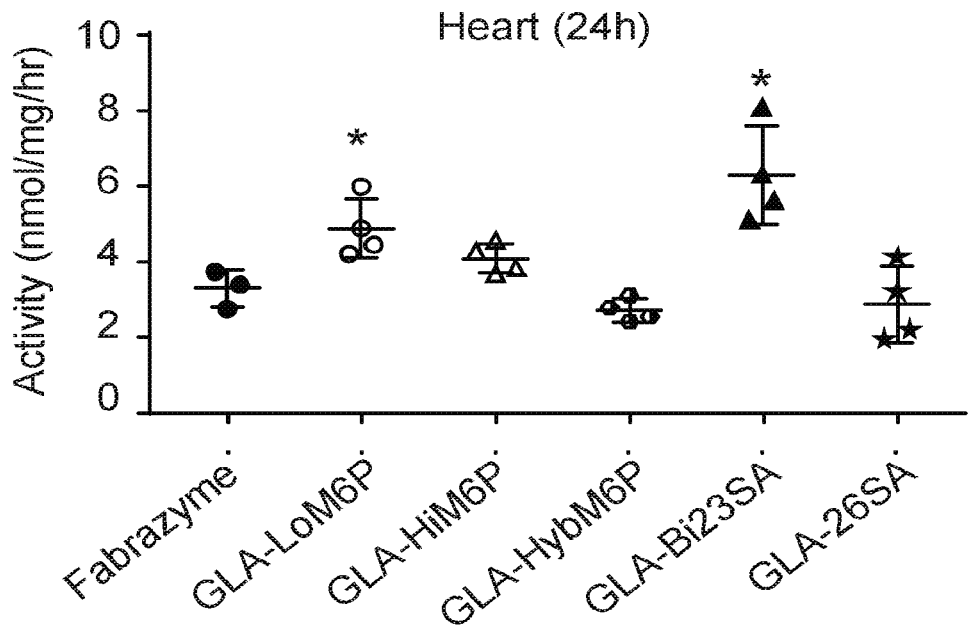
FIG. 6B
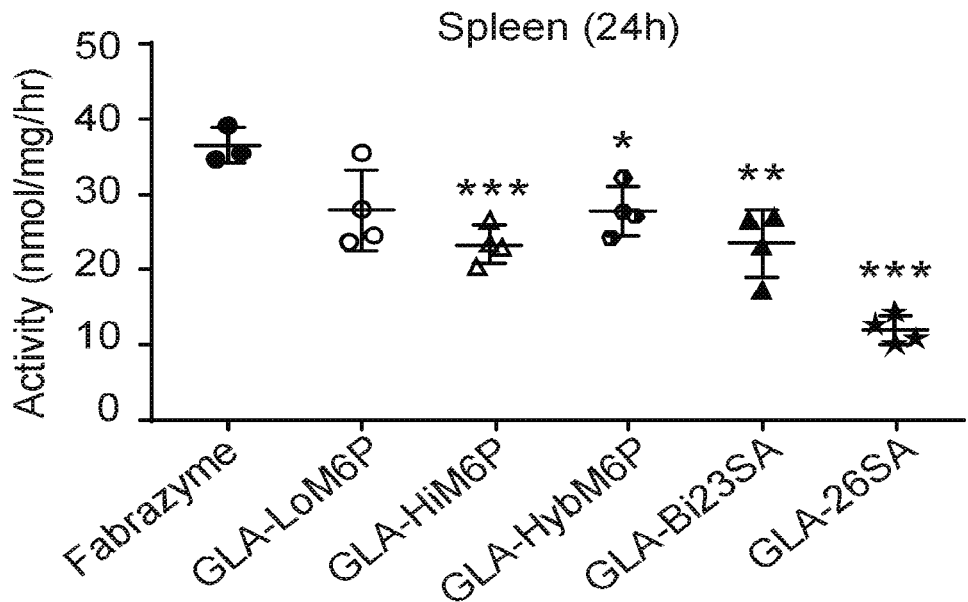

Figure 6 (continued)
FIG. 6C
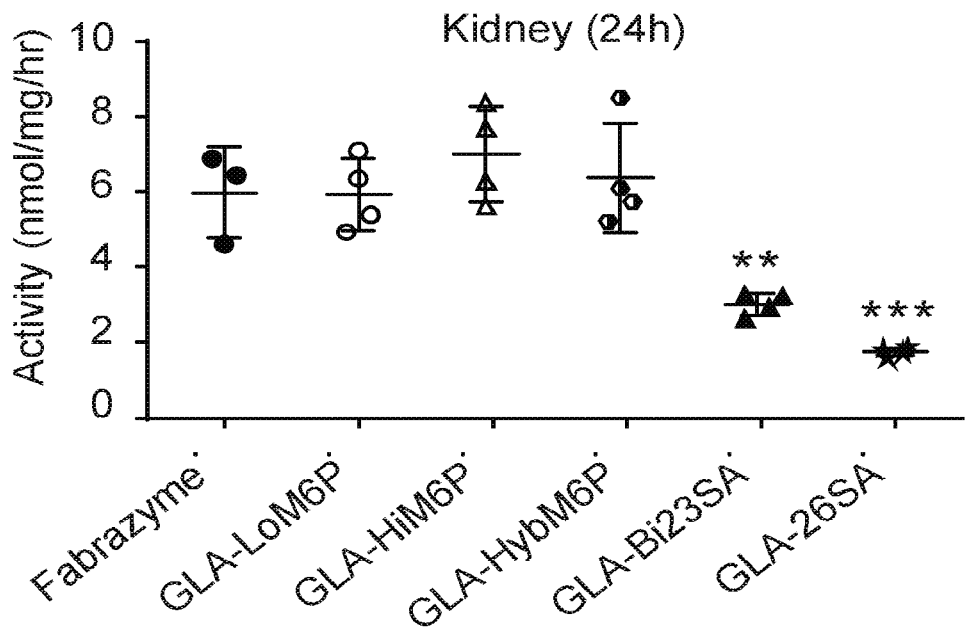
FIG. 6D
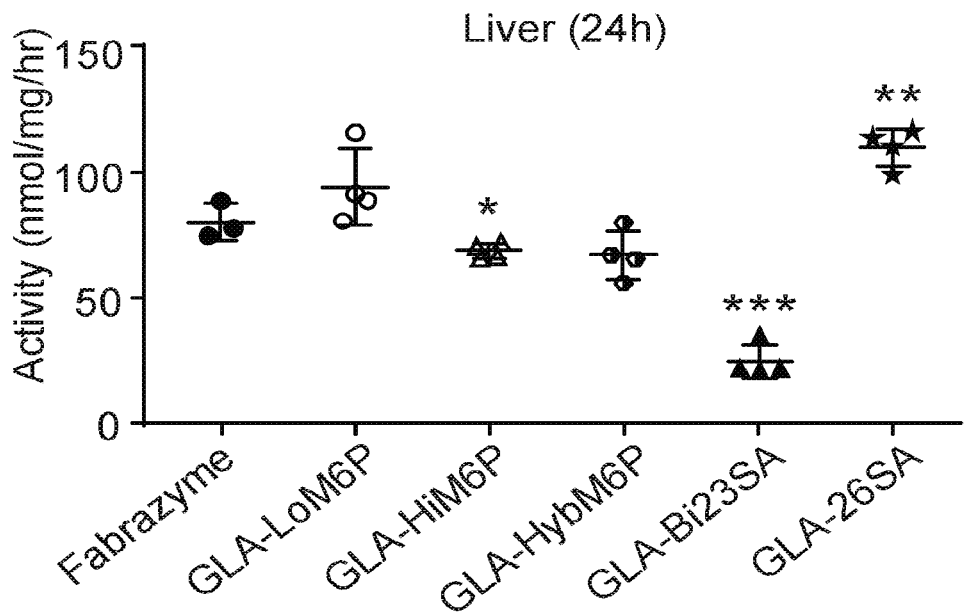

Figure 7
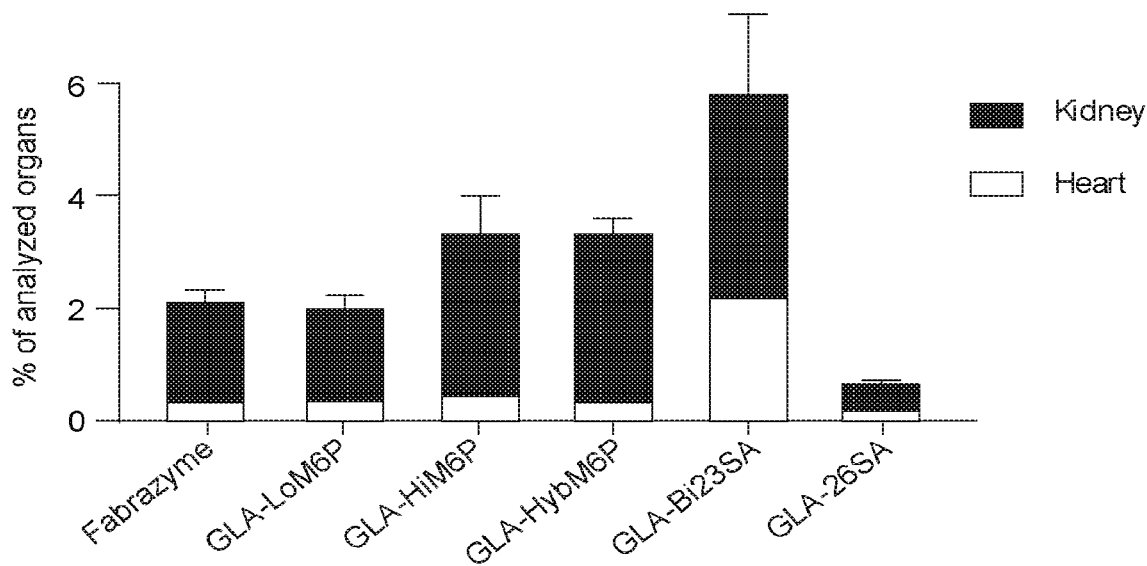
Figure 8
FIG. 8A
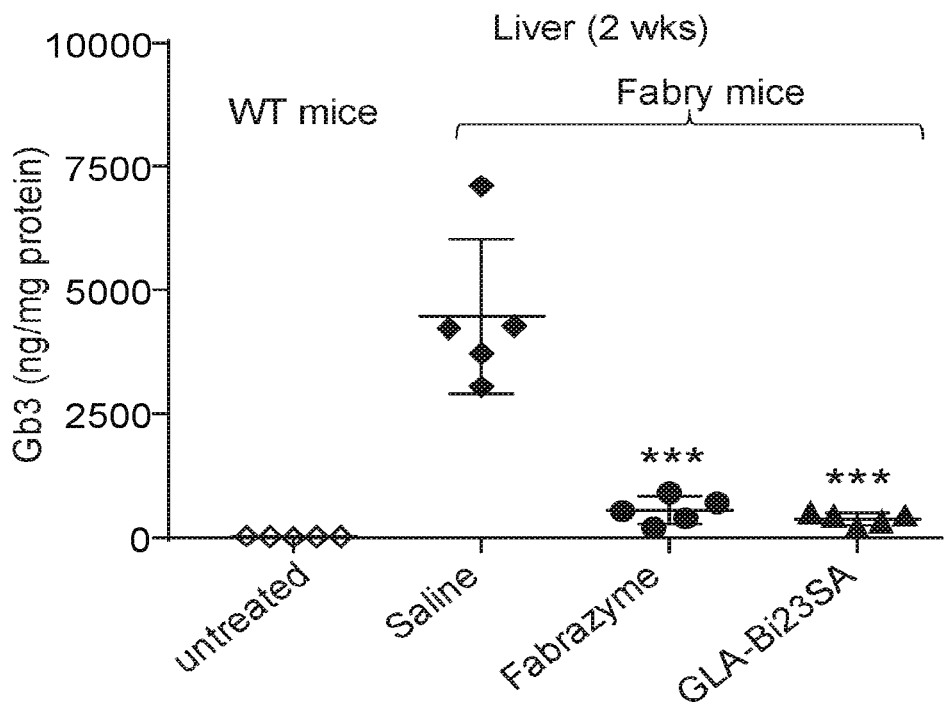

Figure 8 (continued)
FIG. 8B
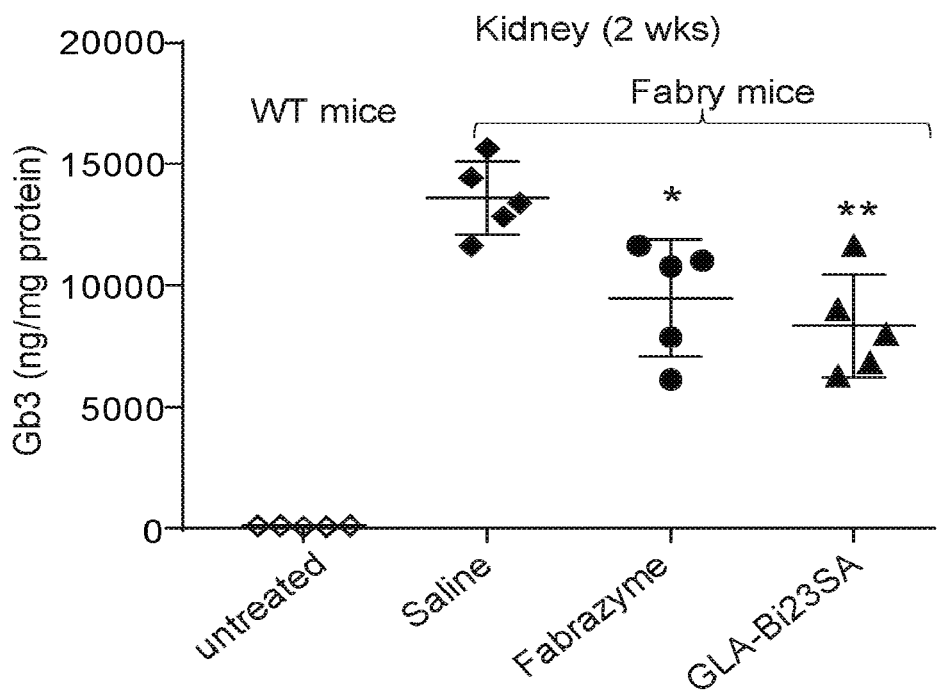
FIG. 8C
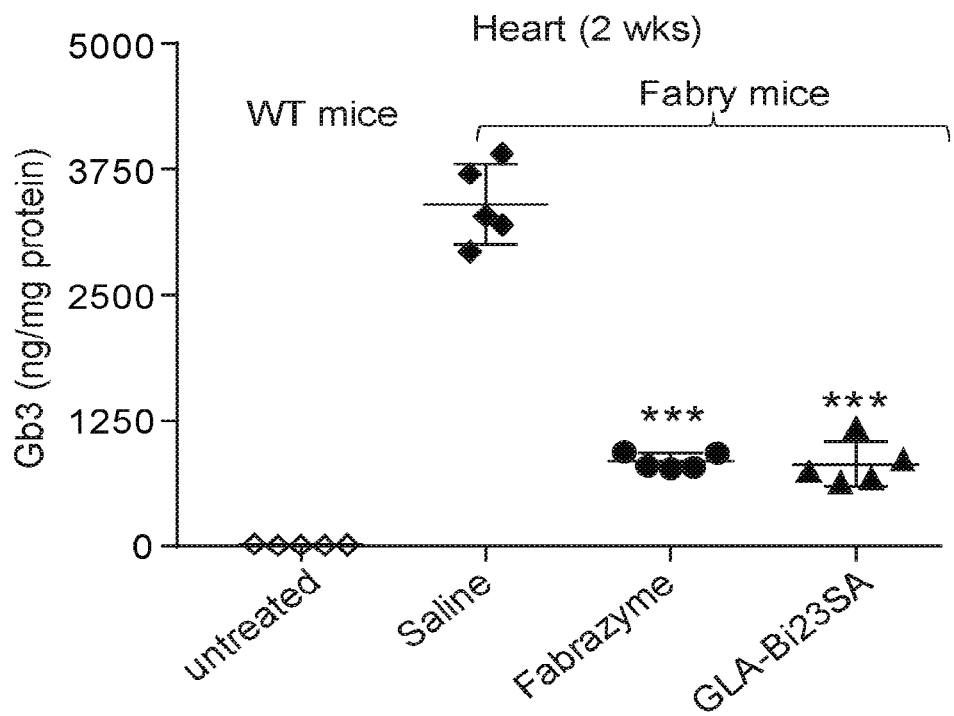

Figure 15
FIG. 15A
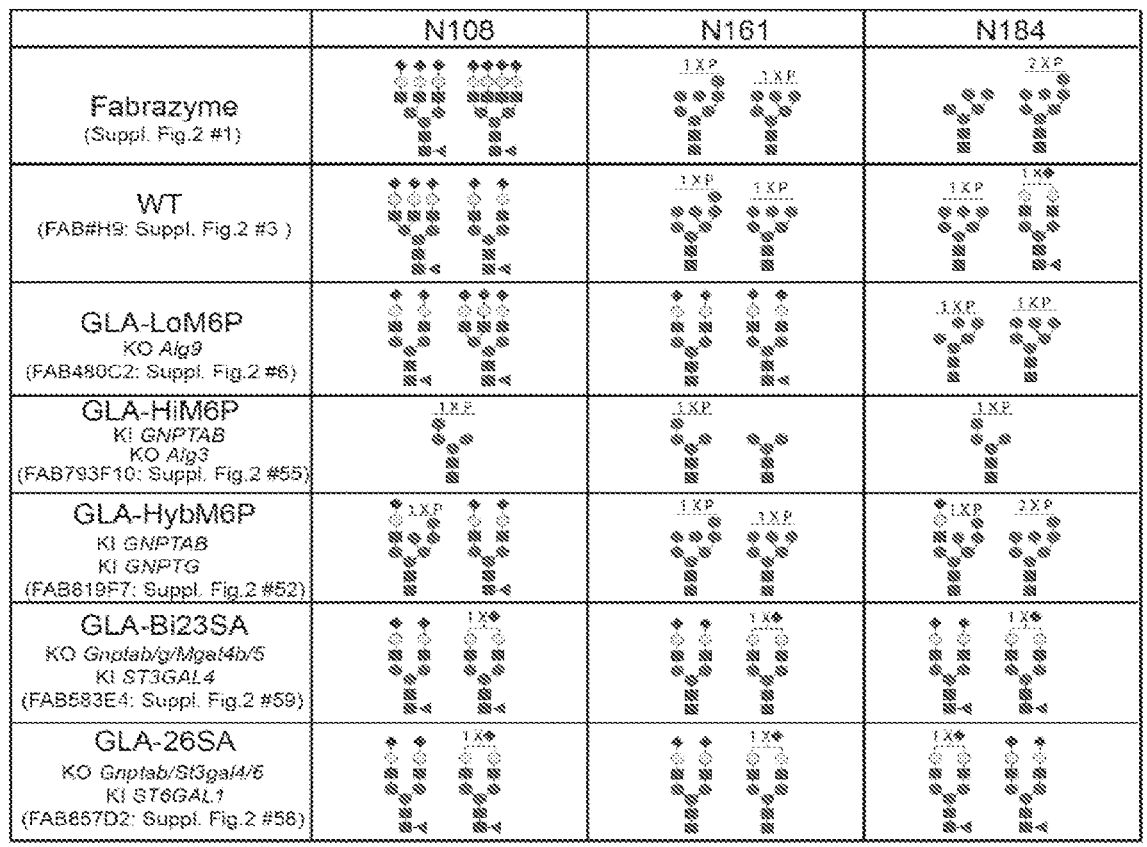
FIG. 15B
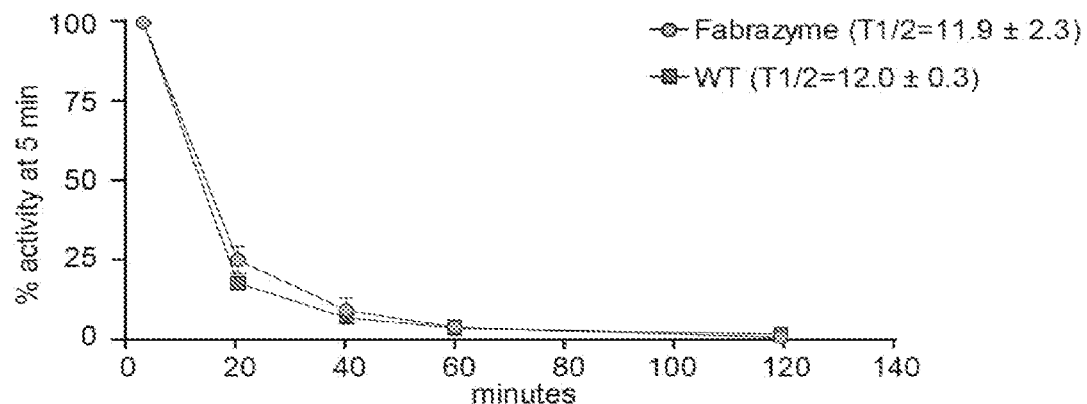

Figure 15 (continued)
FIG. 15C
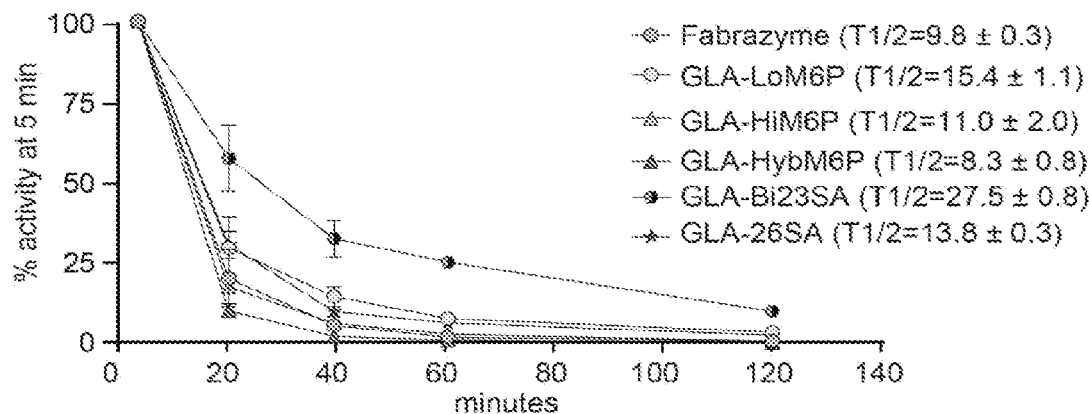
FIG. 15D
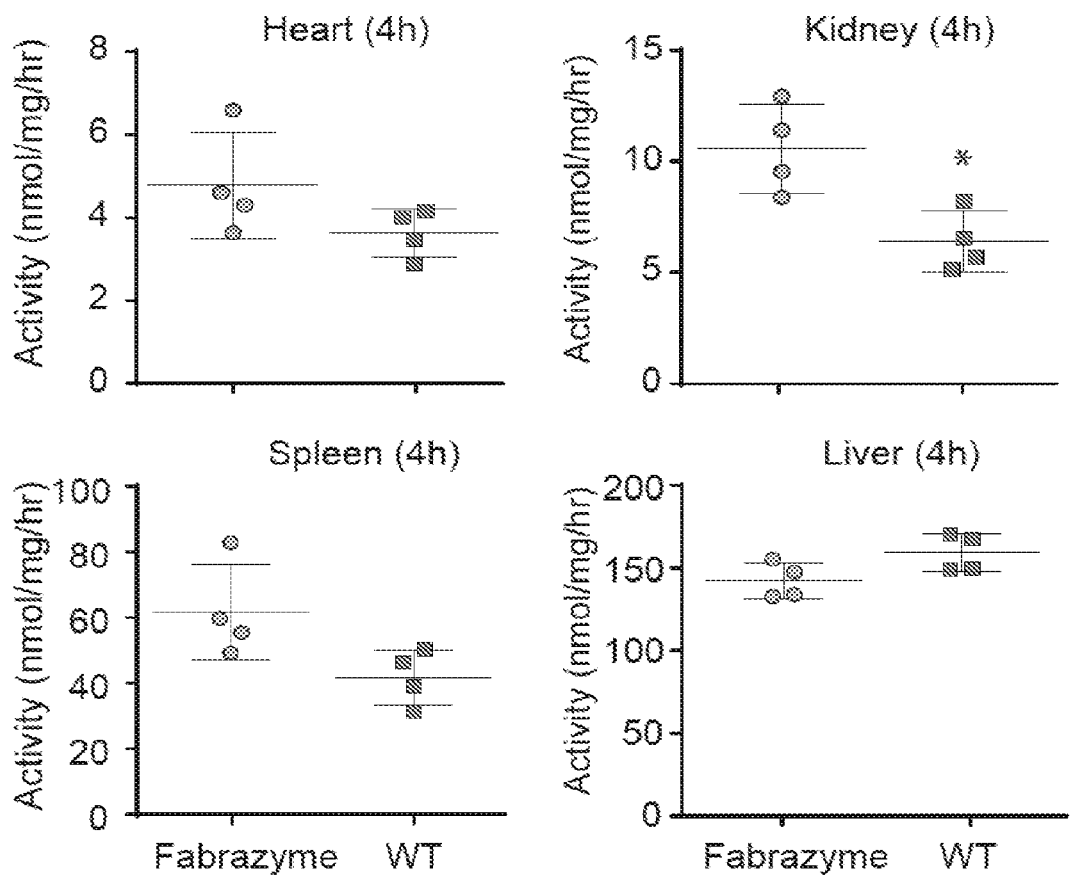

| # | | | | | | | | |
|---|---|---|---|---|---|---|---|---|
| #12 | KO Man1a1 (FAB442G8) | 100 | 51 | 43 | 20 | 14 | | |
| #13 | KO Man1a2 (FAB443C5) | 100 | 72 | 49 | 32 | 31 | | |
| | | 17 | 14 | 12 | | | | |
| #14 | KO Man1b1 (FAB444E4) | 100 | 55 | 50 | 15 | 14 | | |

| | | | | |
|---|---|---|---|---|
| 100 | 35 | 14 | 12 | |
| 100 | 73 | 37 | 37 | 24 |
| 13 | | | | |
| 100 | 87 | 44 | 42 | 17 |
| 14 | | | | |

| | | | | |
|---|---|---|---|---|
| 100 | 31 | 29 | 26 | 14 |
| 100 | 34 | 30 | 30 | 12 |
| | | | | |
| 100 | 38 | 33 | 15 | 13 |
| 12 | | | | |

| #23 | KO *Gnptab* (FAB400C7) | |
| #24 | KO *Gnptg* (FAB453C1) | |
| #25 | KO *Gnptab/g* (FAB546A2) | |

Figure 17 (Continued)

| # | | | | | | | | | |
|---|---|---|---|---|---|---|---|---|---|
| #26 | KO *Nagpa* (FAB399C3) | 100 | 53 | 44 | 39 | 27 | | | |
| | | 24 | 22 | 16 | | | | | |
| | | 100 | 46 | 17 | 15 | 12 | | | |
| | | | | | | | | | |
| #27 | KO *Acp2* (FAB451H7) | 100 | 53 | 29 | 21 | 20 | | | |
| | | 18 | | | | | | | |
| | | 100 | 78 | 52 | 39 | 32 | | | |
| | | 13 | 11 | | | | | | |
| | | 100 | 64 | 27 | 13 | 18 | | | |
| | | | | | | | | | |
| #28 | KO *Acp5* (FAB454F2) | 100 | 26 | 24 | | | | | |
| | | 100 | 79 | 73 | | | | | |
| | | 100 | 26 | 23 | 20 | 22 | | | |

| #40 | KO *Fam20c* (FAB604F9) | | | | | | | |
| #41 | KO *Golph3* (FAB605D1) | | | | | | | |
| #42 | KO *Golph3l* (FAB606E12) | | | | | | | |

Figure 17 (Continued)

| # | | | | | | | |
|---|---|---|---|---|---|---|---|
| #47 KO Gnptab/g KO Mgat4b/5 (FAB567H3) | 100 | 1X◆ 45 | | | | | |
| #48 KI GNPTG (FAB677F1) | 100 | 95 | 2X◆ 52 | 1X◆ 50 | 1XP 33 | | |
| | 3X◆ 26 | 1X◆ 11 | | | | | |
| | 1XP 100 | 1X 91 | 29 | 27 | 18 | | |
| | 1XP 100 | 1XP 54 | 1XP 27 | 1X◆ 23 | 1XP 12 | | |
| | 1XP 100 | 1X◆ 59 | 55 | 1X◆ 1X◆ 18 | 1X◆ 11 | | |
| | 1XP 100 | 2XP 24 | 2XP 21 | 16 | 15 | 1XP 10 | |
| #49 KI GNPTG (FAB677C4) | 100 | 1X◆ 68 | 2X◆ 51 | 2X◆ 33 | 3X◆ 13 | | |
| | 12 | 12 | | | | | |
| | 1XP 100 | 1XP 44 | 1XP 25 | 1X◆ 20 | | | |
| | 1XP 100 | 1XP 42 | 2XP 17 | 1XP 16 | 12 | 2X◆ 11 | |

Figure 17 (Continued)

| | | | |
|---|---|---|---|
| #50 | KI GNPTAB (FAB695A8) | [glycan structures data] | [glycan structures data] |
| #51 | KI GNPTAB (FAB695G2) | [glycan structures data] | [glycan structures data] |
| #52 | KI GNPTAB KI GNPTG (Fab819F7) | [glycan structures data] | [glycan structures data] |

Figure 17 (Continued)

| # | | | | | | | | | | |
|---|---|---|---|---|---|---|---|---|---|---|
| #53 | KI GNPTAB KI GNPTG (Fab819F6) | 100 | 35 | 74 67 | 43 35 | 2X 16 11 | | | | |
| #54 | KI GNPTAB KO Alg3 (Fab792G6) | 100 | | | | 100 | 36 | 16 | 15 | |
| #55 | KI GNPTAB KO Alg3 (Fab793F10) | 100 | | | | 100 | 20 15 | 17 11 | | |
| #56 | KO B4galt1/3 KO Gnptab/g KO Mgat4b/5 (Fab571C2) | 100 | 98 51 | 23 | | 100 26 | 94 25 | 51 19 | 48 15 | 37 |

(and additional row for #56: 100 16, 70, 51, 31, 21)

Figure 17 (Continued)

| # | | | | | | |
|---|---|---|---|---|---|---|
| #57 KO St3gal4/6 KI ST6GAL1 (Fab532D2) | 100 | 1X 26 | | | | |
| #58 KO Gnptab/St3gal4/6 KI ST6GAL1 (Fab857D2) | 100 / 1X 14 | 1X 85 | 1X 36 | 2X 26 | 23 | 100 / 1XP / 1X• / 1XP 41 / 16 / 13 / 11 |
| | | | | | | 100 / 1X / 1X / 1X 65 / 33 / 25 / 21 |
| | | | | | | 20 / 11 |
| #59 KO Gnptab/g/Mgat4b/5 KI ST3GAL4 (Fab583E4) | 100 | 1X 18 | | | | 100 / 1X 11 |
| | | | | | | 1XP / 1X• / 1XP 100 / 26 / 22 / 18 / 11 |
| | | | | | | 1X / 2X 100 / 35 / 31 / 12 |
| | | | | | | 1X 100 / 55 |

Figure 18
FIG. 18A
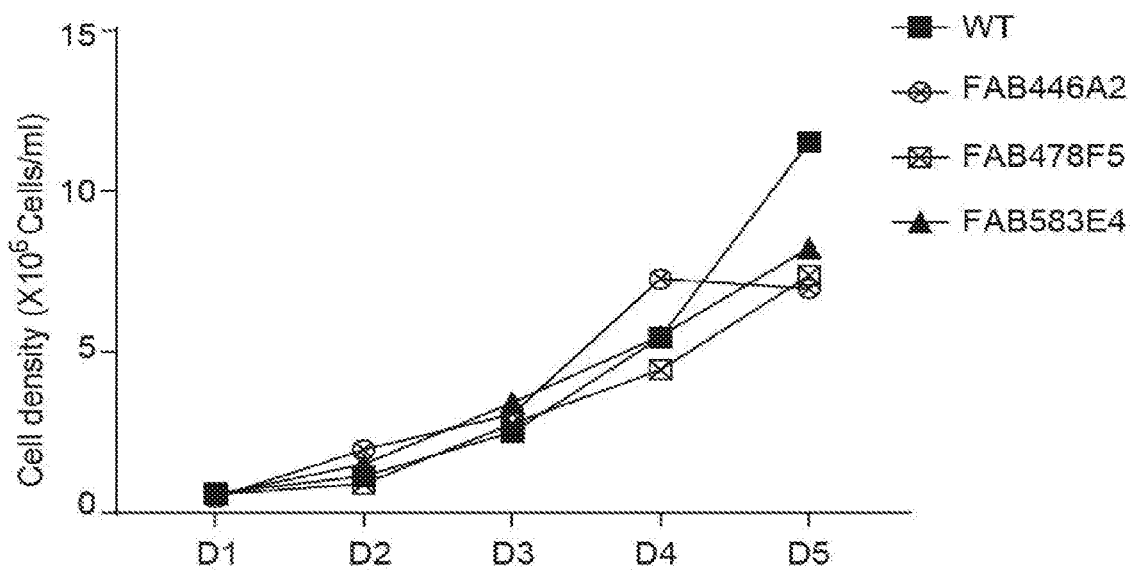
FIG. 18B
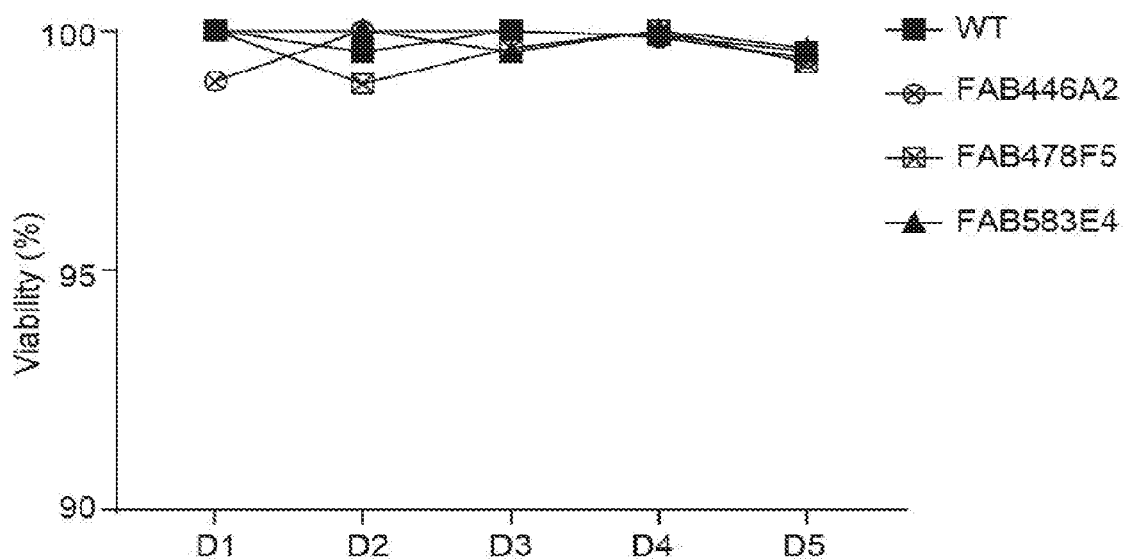

Figure 18 (continued)
FIG. 18C
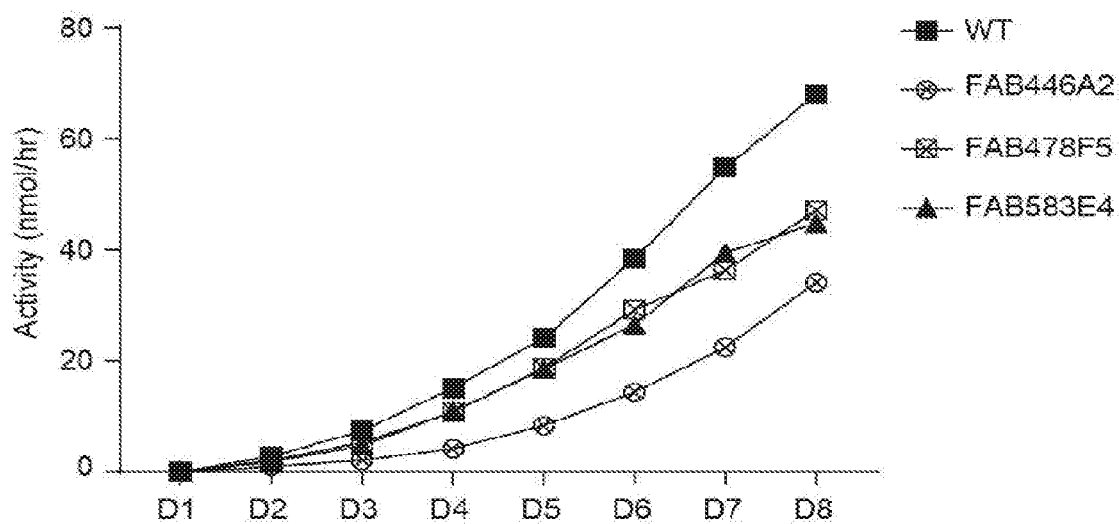
FIG. 18D
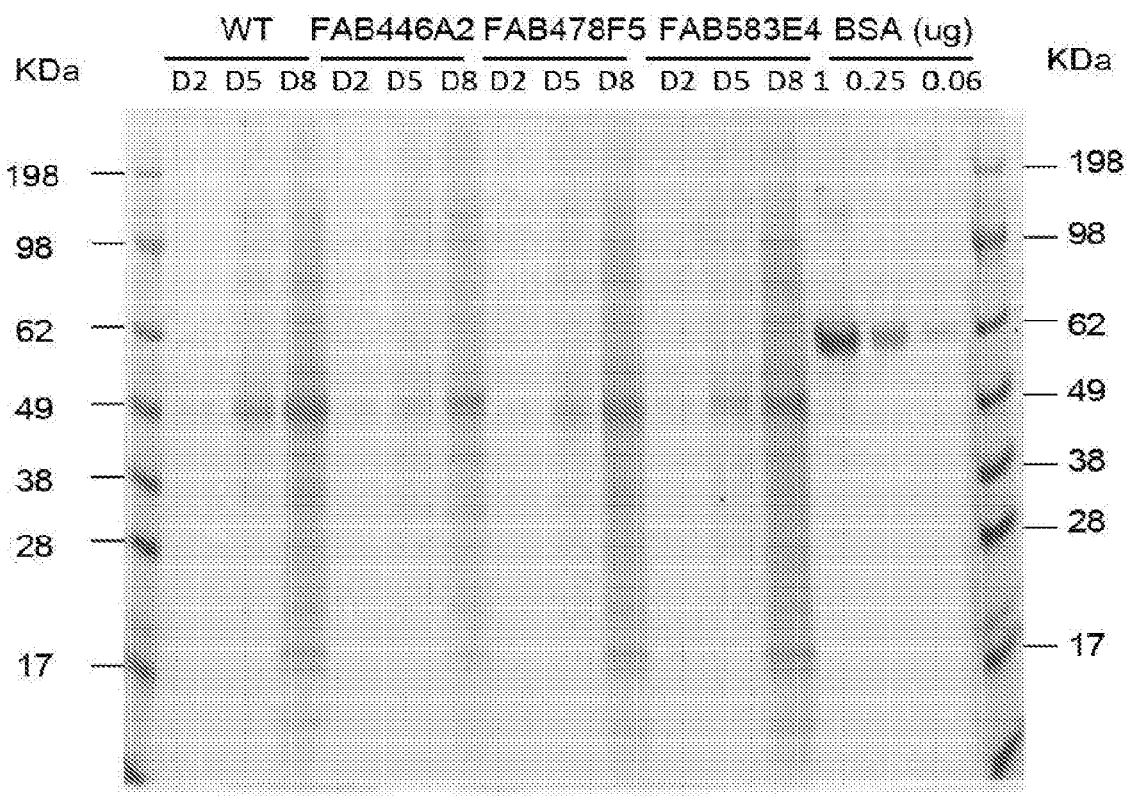

Figure 21
FIG. 21A.
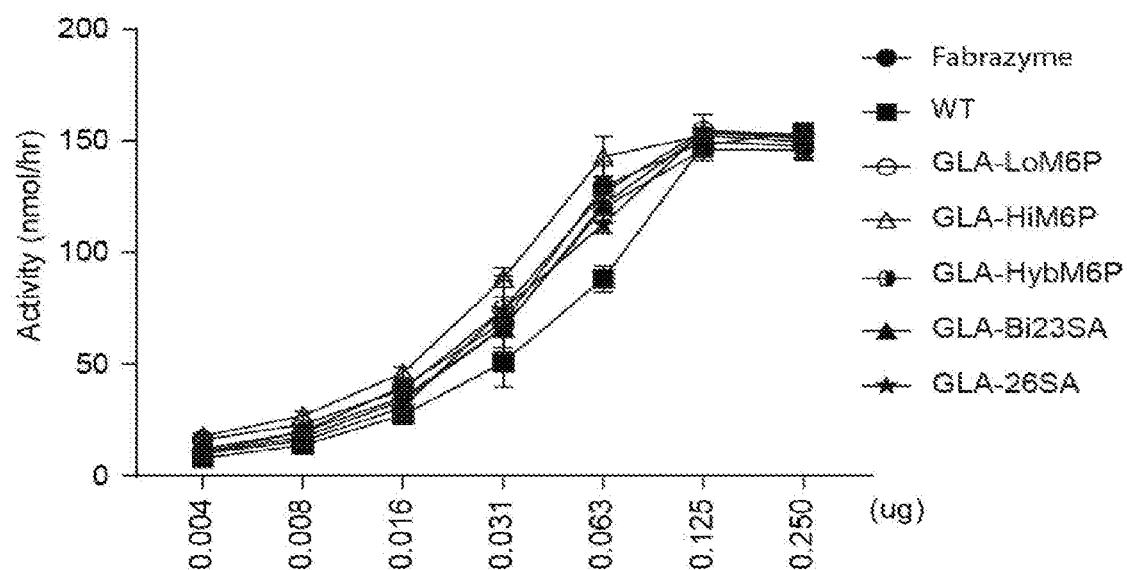
FIG. 21B.
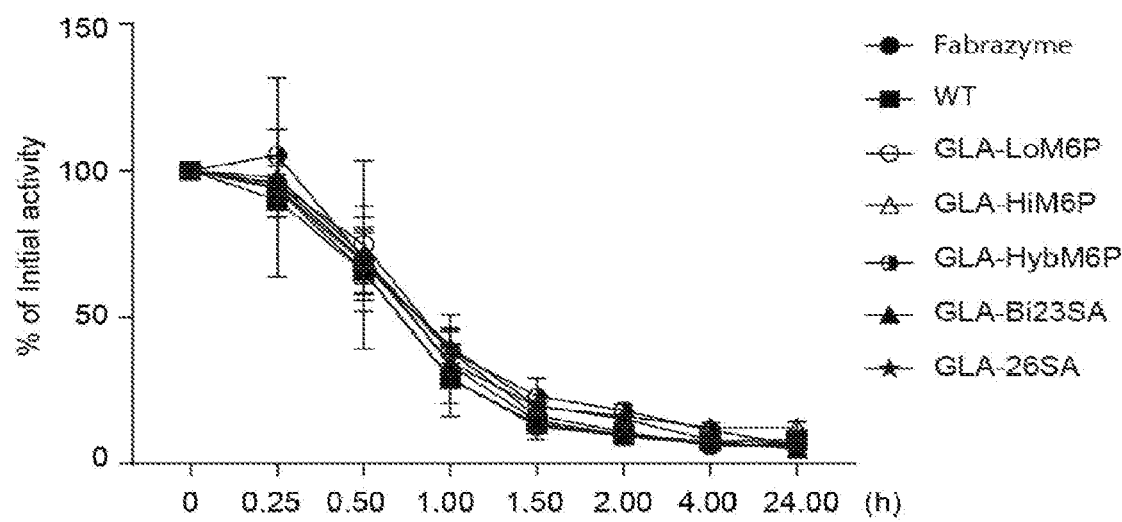

Figure 27
FIG. 27A
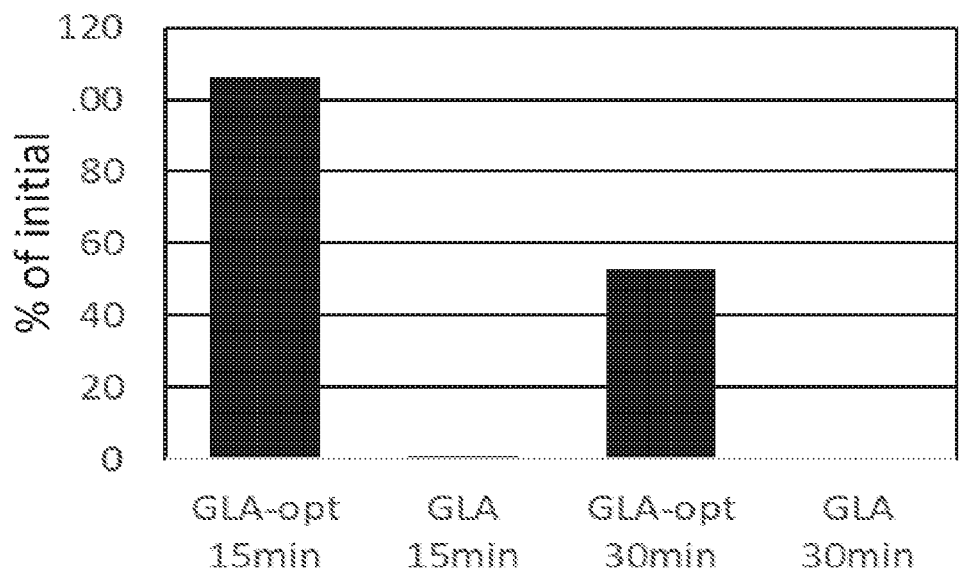
FIG. 27B
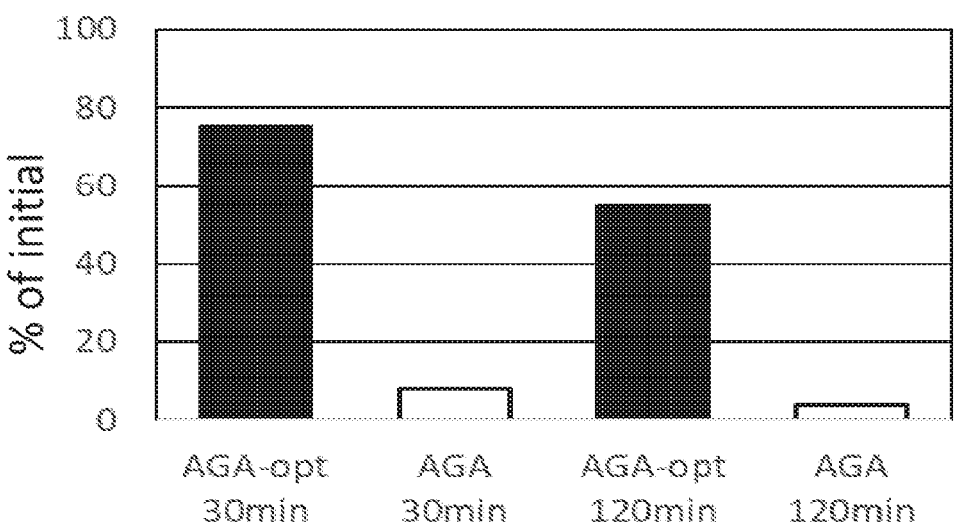

Figure 27 (continued)
FIG. 27C
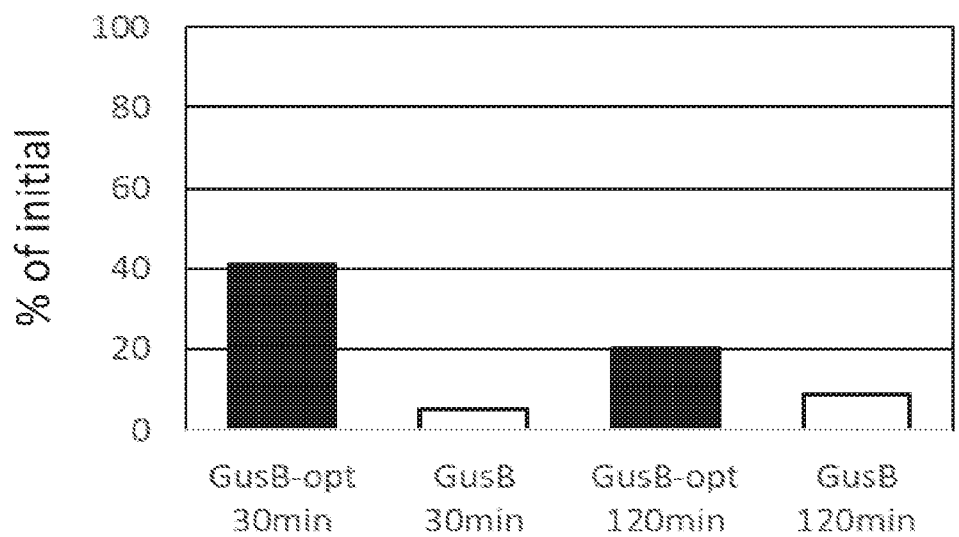
FIG. 27D
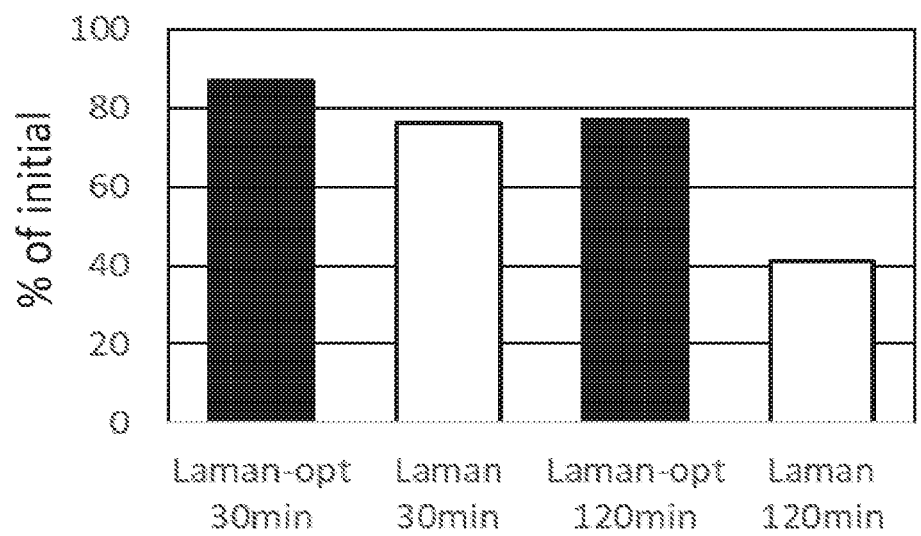

SEQUENCE LISTING

```
Sequence total quantity: 351
SEQ ID NO: 1                    moltype = DNA    length = 20
FEATURE                         Location/Qualifiers
source                          1..20
                                mol_type = other DNA
                                organism = synthetic construct
SEQUENCE: 1
gcgatggcgg tgcgggtggc                                                     20

SEQ ID NO: 2                    moltype = DNA    length = 20
FEATURE                         Location/Qualifiers
source                          1..20
                                mol_type = other DNA
                                organism = synthetic construct
SEQUENCE: 2
gtcacattca tcgcatcgag                                                     20

SEQ ID NO: 3                    moltype = DNA    length = 20
FEATURE                         Location/Qualifiers
source                          1..20
                                mol_type = other DNA
                                organism = synthetic construct
SEQUENCE: 3
ggtcgaagtg ggccgactca                                                     20

SEQ ID NO: 4                    moltype = DNA    length = 20
FEATURE                         Location/Qualifiers
source                          1..20
                                mol_type = other DNA
                                organism = synthetic construct
SEQUENCE: 4
ggagttgtga tcattgtgag                                                     20

SEQ ID NO: 5                    moltype = DNA    length = 20
FEATURE                         Location/Qualifiers
source                          1..20
                                mol_type = other DNA
                                organism = synthetic construct
SEQUENCE: 5
gagaggcagg cgctgcggga                                                     20

SEQ ID NO: 6                    moltype = DNA    length = 20
FEATURE                         Location/Qualifiers
source                          1..20
                                mol_type = other DNA
                                organism = synthetic construct
SEQUENCE: 6
gacaatctcg tcaatggcac                                                     20

SEQ ID NO: 7                    moltype = DNA    length = 20
FEATURE                         Location/Qualifiers
source                          1..20
                                mol_type = other DNA
                                organism = synthetic construct
SEQUENCE: 7
taaacaacgt caatcggcat                                                     20

SEQ ID NO: 8                    moltype = DNA    length = 20
FEATURE                         Location/Qualifiers
source                          1..20
                                mol_type = other DNA
                                organism = synthetic construct
SEQUENCE: 8
gctgctcacc caaacgcgtt                                                     20

SEQ ID NO: 9                    moltype = DNA    length = 20
FEATURE                         Location/Qualifiers
source                          1..20
                                mol_type = other DNA
                                organism = synthetic construct
SEQUENCE: 9
gctctgcggc agcgctatag                                                     20

SEQ ID NO: 10                   moltype = DNA    length = 20
FEATURE                         Location/Qualifiers
source                          1..20
                                mol_type = other DNA
                                organism = synthetic construct
```

```
SEQUENCE: 10
ggatgcacgg acggtactgc                                              20

SEQ ID NO: 11           moltype = DNA  length = 20
FEATURE                 Location/Qualifiers
source                  1..20
                        mol_type = other DNA
                        organism = synthetic construct
SEQUENCE: 11
ttctgcaaga gctcatctcg                                              20

SEQ ID NO: 12           moltype = DNA  length = 20
FEATURE                 Location/Qualifiers
source                  1..20
                        mol_type = other DNA
                        organism = synthetic construct
SEQUENCE: 12
ctgtgacgtg aagatatgga                                              20

SEQ ID NO: 13           moltype = DNA  length = 20
FEATURE                 Location/Qualifiers
source                  1..20
                        mol_type = other DNA
                        organism = synthetic construct
SEQUENCE: 13
gctgctgggc tgcggaaacg                                              20

SEQ ID NO: 14           moltype = DNA  length = 20
FEATURE                 Location/Qualifiers
source                  1..20
                        mol_type = other DNA
                        organism = synthetic construct
SEQUENCE: 14
ggactctaag ttcacttacg                                              20

SEQ ID NO: 15           moltype = DNA  length = 20
FEATURE                 Location/Qualifiers
source                  1..20
                        mol_type = other DNA
                        organism = synthetic construct
SEQUENCE: 15
tcttaatagg actcacagtg                                              20

SEQ ID NO: 16           moltype = DNA  length = 20
FEATURE                 Location/Qualifiers
source                  1..20
                        mol_type = other DNA
                        organism = synthetic construct
SEQUENCE: 16
tcggtgtact tcaaaatccg                                              20

SEQ ID NO: 17           moltype = DNA  length = 20
FEATURE                 Location/Qualifiers
source                  1..20
                        mol_type = other DNA
                        organism = synthetic construct
SEQUENCE: 17
gagcagacat ttgaaagcag                                              20

SEQ ID NO: 18           moltype = DNA  length = 20
FEATURE                 Location/Qualifiers
source                  1..20
                        mol_type = other DNA
                        organism = synthetic construct
SEQUENCE: 18
actggtgaca ttaatgtcag                                              20

SEQ ID NO: 19           moltype = DNA  length = 20
FEATURE                 Location/Qualifiers
source                  1..20
                        mol_type = other DNA
                        organism = synthetic construct
SEQUENCE: 19
aaatcaccag gcaagtcagg                                              20

SEQ ID NO: 20           moltype = DNA  length = 20
FEATURE                 Location/Qualifiers
source                  1..20
                        mol_type = other DNA
```

```
                              organism = synthetic construct
SEQUENCE: 20
gatcttgtca tcagccacgc                                                     20

SEQ ID NO: 21           moltype = DNA   length = 20
FEATURE                 Location/Qualifiers
source                  1..20
                        mol_type = other DNA
                        organism = synthetic construct
SEQUENCE: 21
ctgcggcagc tagaatcagg                                                     20

SEQ ID NO: 22           moltype = DNA   length = 20
FEATURE                 Location/Qualifiers
source                  1..20
                        mol_type = other DNA
                        organism = synthetic construct
SEQUENCE: 22
gggcggtcgt tattccccca                                                     20

SEQ ID NO: 23           moltype = DNA   length = 20
FEATURE                 Location/Qualifiers
source                  1..20
                        mol_type = other DNA
                        organism = synthetic construct
SEQUENCE: 23
gcaggacggt accggccccc                                                     20

SEQ ID NO: 24           moltype = DNA   length = 20
FEATURE                 Location/Qualifiers
source                  1..20
                        mol_type = other DNA
                        organism = synthetic construct
SEQUENCE: 24
gggaagcctg accagatcga                                                     20

SEQ ID NO: 25           moltype = DNA   length = 20
FEATURE                 Location/Qualifiers
source                  1..20
                        mol_type = other DNA
                        organism = synthetic construct
SEQUENCE: 25
gaccaagcgg gacgtgtatc                                                     20

SEQ ID NO: 26           moltype = DNA   length = 20
FEATURE                 Location/Qualifiers
source                  1..20
                        mol_type = other DNA
                        organism = synthetic construct
SEQUENCE: 26
gatccgtcca caaccttggc                                                     20

SEQ ID NO: 27           moltype = DNA   length = 20
FEATURE                 Location/Qualifiers
source                  1..20
                        mol_type = other DNA
                        organism = synthetic construct
SEQUENCE: 27
gaaggcttcg atcctctagc                                                     20

SEQ ID NO: 28           moltype = DNA   length = 20
FEATURE                 Location/Qualifiers
source                  1..20
                        mol_type = other DNA
                        organism = synthetic construct
SEQUENCE: 28
gtcacattca tcgcatcgag                                                     20

SEQ ID NO: 29           moltype = DNA   length = 20
FEATURE                 Location/Qualifiers
source                  1..20
                        mol_type = other DNA
                        organism = synthetic construct
SEQUENCE: 29
gcgatggcgg tgcgggtggc                                                     20

SEQ ID NO: 30           moltype = DNA   length = 20
FEATURE                 Location/Qualifiers
source                  1..20
```

```
                        mol_type = other DNA
                        organism = synthetic construct
SEQUENCE: 30
gaaaggctca gtgcaacact                                              20

SEQ ID NO: 31           moltype = DNA  length = 20
FEATURE                 Location/Qualifiers
source                  1..20
                        mol_type = other DNA
                        organism = synthetic construct
SEQUENCE: 31
tgacttcagt tcgacgggta                                              20

SEQ ID NO: 32           moltype = DNA  length = 20
FEATURE                 Location/Qualifiers
source                  1..20
                        mol_type = other DNA
                        organism = synthetic construct
SEQUENCE: 32
gacaaaaacc tgtcgatcag                                              20

SEQ ID NO: 33           moltype = DNA  length = 20
FEATURE                 Location/Qualifiers
source                  1..20
                        mol_type = other DNA
                        organism = synthetic construct
SEQUENCE: 33
tcacacaagg aattccagtg                                              20

SEQ ID NO: 34           moltype = DNA  length = 20
FEATURE                 Location/Qualifiers
source                  1..20
                        mol_type = other DNA
                        organism = synthetic construct
SEQUENCE: 34
gctatagatt cagagtatgc                                              20

SEQ ID NO: 35           moltype = DNA  length = 20
FEATURE                 Location/Qualifiers
source                  1..20
                        mol_type = other DNA
                        organism = synthetic construct
SEQUENCE: 35
gtaaatatac gcttcgtcgg                                              20

SEQ ID NO: 36           moltype = DNA  length = 20
FEATURE                 Location/Qualifiers
source                  1..20
                        mol_type = other DNA
                        organism = synthetic construct
SEQUENCE: 36
gtctgtgttc gtcgggtcca                                              20

SEQ ID NO: 37           moltype = DNA  length = 20
FEATURE                 Location/Qualifiers
source                  1..20
                        mol_type = other DNA
                        organism = synthetic construct
SEQUENCE: 37
gagtacatac cacctatcgg                                              20

SEQ ID NO: 38           moltype = DNA  length = 20
FEATURE                 Location/Qualifiers
source                  1..20
                        mol_type = other DNA
                        organism = synthetic construct
SEQUENCE: 38
gccccgggcg aggacgatcc                                              20

SEQ ID NO: 39           moltype = DNA  length = 20
FEATURE                 Location/Qualifiers
source                  1..20
                        mol_type = other DNA
                        organism = synthetic construct
SEQUENCE: 39
gagtgaagcc tcgatcgggt                                              20

SEQ ID NO: 40           moltype = DNA  length = 20
FEATURE                 Location/Qualifiers
```

```
source                          1..20
                                mol_type = other DNA
                                organism = synthetic construct
SEQUENCE: 40
gcccagagaa agcgtcgtcg                                                   20

SEQ ID NO: 41                   moltype = DNA  length = 20
FEATURE                         Location/Qualifiers
source                          1..20
                                mol_type = other DNA
                                organism = synthetic construct
SEQUENCE: 41
atagccaaga actatccaca                                                   20

SEQ ID NO: 42                   moltype = DNA  length = 20
FEATURE                         Location/Qualifiers
source                          1..20
                                mol_type = other DNA
                                organism = synthetic construct
SEQUENCE: 42
gaggggtcg caggcacacg                                                    20

SEQ ID NO: 43                   moltype = DNA  length = 20
FEATURE                         Location/Qualifiers
source                          1..20
                                mol_type = other DNA
                                organism = synthetic construct
SEQUENCE: 43
gcgaccggta ccgcagcgtt                                                   20

SEQ ID NO: 44                   moltype = DNA  length = 20
FEATURE                         Location/Qualifiers
source                          1..20
                                mol_type = other DNA
                                organism = synthetic construct
SEQUENCE: 44
gagaggcagg cgctgcggga                                                   20

SEQ ID NO: 45                   moltype = DNA  length = 20
FEATURE                         Location/Qualifiers
source                          1..20
                                mol_type = other DNA
                                organism = synthetic construct
SEQUENCE: 45
gacaatctcg tcaatggcac                                                   20

SEQ ID NO: 46                   moltype = DNA  length = 20
FEATURE                         Location/Qualifiers
source                          1..20
                                mol_type = other DNA
                                organism = synthetic construct
SEQUENCE: 46
ggtgtccctg ttcttctacg                                                   20

SEQ ID NO: 47                   moltype = DNA  length = 20
FEATURE                         Location/Qualifiers
source                          1..20
                                mol_type = other DNA
                                organism = synthetic construct
SEQUENCE: 47
gggctgcaga acgcgcagtt                                                   20

SEQ ID NO: 48                   moltype = DNA  length = 20
FEATURE                         Location/Qualifiers
source                          1..20
                                mol_type = other DNA
                                organism = synthetic construct
SEQUENCE: 48
ttaacagcag aggtatctgg                                                   20

SEQ ID NO: 49                   moltype = DNA  length = 20
FEATURE                         Location/Qualifiers
source                          1..20
                                mol_type = other DNA
                                organism = synthetic construct
SEQUENCE: 49
gaggcttggc aggcggacaa                                                   20

SEQ ID NO: 50                   moltype = DNA  length = 20
```

-continued

```
FEATURE                 Location/Qualifiers
source                  1..20
                        mol_type = other DNA
                        organism = synthetic construct
SEQUENCE: 50
ggtcgaagtg ggccgactca                                               20

SEQ ID NO: 51           moltype = DNA   length = 20
FEATURE                 Location/Qualifiers
source                  1..20
                        mol_type = other DNA
                        organism = synthetic construct
SEQUENCE: 51
ggagttgtga tcattgtgag                                               20

SEQ ID NO: 52           moltype = DNA   length = 20
FEATURE                 Location/Qualifiers
source                  1..20
                        mol_type = other DNA
                        organism = synthetic construct
SEQUENCE: 52
tcgtctcttc ccagacaagc                                               20

SEQ ID NO: 53           moltype = DNA   length = 20
FEATURE                 Location/Qualifiers
source                  1..20
                        mol_type = other DNA
                        organism = synthetic construct
SEQUENCE: 53
gtgcagtttt caggggcttg                                               20

SEQ ID NO: 54           moltype = DNA   length = 20
FEATURE                 Location/Qualifiers
source                  1..20
                        mol_type = other DNA
                        organism = synthetic construct
SEQUENCE: 54
ccccagtaca caactacccc                                               20

SEQ ID NO: 55           moltype = DNA   length = 20
FEATURE                 Location/Qualifiers
source                  1..20
                        mol_type = other DNA
                        organism = synthetic construct
SEQUENCE: 55
ctgctgctgg acagttccaa                                               20

SEQ ID NO: 56           moltype = DNA   length = 20
FEATURE                 Location/Qualifiers
source                  1..20
                        mol_type = other DNA
                        organism = synthetic construct
SEQUENCE: 56
tagctagaaa ccctggtgcc                                               20

SEQ ID NO: 57           moltype = DNA   length = 20
FEATURE                 Location/Qualifiers
source                  1..20
                        mol_type = other DNA
                        organism = synthetic construct
SEQUENCE: 57
tagtaggaga gagccgaccc                                               20

SEQ ID NO: 58           moltype = DNA   length = 20
FEATURE                 Location/Qualifiers
source                  1..20
                        mol_type = other DNA
                        organism = synthetic construct
SEQUENCE: 58
aagcagatgc agcccactca                                               20

SEQ ID NO: 59           moltype = DNA   length = 21
FEATURE                 Location/Qualifiers
source                  1..21
                        mol_type = other DNA
                        organism = synthetic construct
SEQUENCE: 59
gtgcagtggt ctaagaaccc a                                             21
```

-continued

| | | |
|---|---|---|
| SEQ ID NO: 60 | moltype = DNA  length = 21 | |
| FEATURE | Location/Qualifiers | |
| source | 1..21<br>mol_type = other DNA<br>organism = synthetic construct | |
| SEQUENCE: 60 | | |
| gcccaagacc atcggttaga t | | 21 |
| | | |
| SEQ ID NO: 61 | moltype = DNA  length = 22 | |
| FEATURE | Location/Qualifiers | |
| source | 1..22<br>mol_type = other DNA<br>organism = synthetic construct | |
| SEQUENCE: 61 | | |
| tgagtccctt tcttttgtg cc | | 22 |
| | | |
| SEQ ID NO: 62 | moltype = DNA  length = 21 | |
| FEATURE | Location/Qualifiers | |
| source | 1..21<br>mol_type = other DNA<br>organism = synthetic construct | |
| SEQUENCE: 62 | | |
| cagtgtgacc ttaagcaggg t | | 21 |
| | | |
| SEQ ID NO: 63 | moltype = DNA  length = 20 | |
| FEATURE | Location/Qualifiers | |
| source | 1..20<br>mol_type = other DNA<br>organism = synthetic construct | |
| SEQUENCE: 63 | | |
| agttatgaac cacggagcca | | 20 |
| | | |
| SEQ ID NO: 64 | moltype = DNA  length = 20 | |
| FEATURE | Location/Qualifiers | |
| source | 1..20<br>mol_type = other DNA<br>organism = synthetic construct | |
| SEQUENCE: 64 | | |
| tttgaccgcc caactcatca | | 20 |
| | | |
| SEQ ID NO: 65 | moltype = DNA  length = 21 | |
| FEATURE | Location/Qualifiers | |
| source | 1..21<br>mol_type = other DNA<br>organism = synthetic construct | |
| SEQUENCE: 65 | | |
| cccaaacctc acctggttga t | | 21 |
| | | |
| SEQ ID NO: 66 | moltype = DNA  length = 20 | |
| FEATURE | Location/Qualifiers | |
| source | 1..20<br>mol_type = other DNA<br>organism = synthetic construct | |
| SEQUENCE: 66 | | |
| atgccatatg caagctgctg | | 20 |
| | | |
| SEQ ID NO: 67 | moltype = DNA  length = 20 | |
| FEATURE | Location/Qualifiers | |
| source | 1..20<br>mol_type = other DNA<br>organism = synthetic construct | |
| SEQUENCE: 67 | | |
| ataggtcacc gactctccct | | 20 |
| | | |
| SEQ ID NO: 68 | moltype = DNA  length = 20 | |
| FEATURE | Location/Qualifiers | |
| source | 1..20<br>mol_type = other DNA<br>organism = synthetic construct | |
| SEQUENCE: 68 | | |
| gcccatctcg gtctcattgc | | 20 |
| | | |
| SEQ ID NO: 69 | moltype = DNA  length = 20 | |
| FEATURE | Location/Qualifiers | |
| source | 1..20<br>mol_type = other DNA<br>organism = synthetic construct | |
| SEQUENCE: 69 | | |
| agagtccatg gtgatcctgc | | 20 |

```
SEQ ID NO: 70           moltype = DNA  length = 20
FEATURE                 Location/Qualifiers
source                  1..20
                        mol_type = other DNA
                        organism = synthetic construct
SEQUENCE: 70
gtcgtcttgc caaccccaaa                                                   20

SEQ ID NO: 71           moltype = DNA  length = 20
FEATURE                 Location/Qualifiers
source                  1..20
                        mol_type = other DNA
                        organism = synthetic construct
SEQUENCE: 71
accaacgggc agattccttc                                                   20

SEQ ID NO: 72           moltype = DNA  length = 19
FEATURE                 Location/Qualifiers
source                  1..19
                        mol_type = other DNA
                        organism = synthetic construct
SEQUENCE: 72
cttccggttt tgagcgcag                                                    19

SEQ ID NO: 73           moltype = DNA  length = 20
FEATURE                 Location/Qualifiers
source                  1..20
                        mol_type = other DNA
                        organism = synthetic construct
SEQUENCE: 73
gcacaactga ctccaggatg                                                   20

SEQ ID NO: 74           moltype = DNA  length = 20
FEATURE                 Location/Qualifiers
source                  1..20
                        mol_type = other DNA
                        organism = synthetic construct
SEQUENCE: 74
ctctttccca tgttcctcca                                                   20

SEQ ID NO: 75           moltype = DNA  length = 20
FEATURE                 Location/Qualifiers
source                  1..20
                        mol_type = other DNA
                        organism = synthetic construct
SEQUENCE: 75
gctacacatg ggaggctgtt                                                   20

SEQ ID NO: 76           moltype = DNA  length = 20
FEATURE                 Location/Qualifiers
source                  1..20
                        mol_type = other DNA
                        organism = synthetic construct
SEQUENCE: 76
atcagtgccc actgcctaac                                                   20

SEQ ID NO: 77           moltype = DNA  length = 20
FEATURE                 Location/Qualifiers
source                  1..20
                        mol_type = other DNA
                        organism = synthetic construct
SEQUENCE: 77
aagggagggg tgcagttttt                                                   20

SEQ ID NO: 78           moltype = DNA  length = 20
FEATURE                 Location/Qualifiers
source                  1..20
                        mol_type = other DNA
                        organism = synthetic construct
SEQUENCE: 78
tgggcaagca cacaggttta                                                   20

SEQ ID NO: 79           moltype = DNA  length = 20
FEATURE                 Location/Qualifiers
source                  1..20
                        mol_type = other DNA
                        organism = synthetic construct
SEQUENCE: 79
```

-continued

```
ccacagggct accttgagac                                              20

SEQ ID NO: 80           moltype = DNA   length = 20
FEATURE                 Location/Qualifiers
source                  1..20
                        mol_type = other DNA
                        organism = synthetic construct
SEQUENCE: 80
agcaccagca caaagggatt                                              20

SEQ ID NO: 81           moltype = DNA   length = 20
FEATURE                 Location/Qualifiers
source                  1..20
                        mol_type = other DNA
                        organism = synthetic construct
SEQUENCE: 81
tggaggtgat ggccgaaaac                                              20

SEQ ID NO: 82           moltype = DNA   length = 20
FEATURE                 Location/Qualifiers
source                  1..20
                        mol_type = other DNA
                        organism = synthetic construct
SEQUENCE: 82
taatcacagc tgcgaggtgg                                              20

SEQ ID NO: 83           moltype = DNA   length = 20
FEATURE                 Location/Qualifiers
source                  1..20
                        mol_type = other DNA
                        organism = synthetic construct
SEQUENCE: 83
agcggcatat tcagggggaac                                             20

SEQ ID NO: 84           moltype = DNA   length = 19
FEATURE                 Location/Qualifiers
source                  1..19
                        mol_type = other DNA
                        organism = synthetic construct
SEQUENCE: 84
cgccccttg gaaaacaaa                                                19

SEQ ID NO: 85           moltype = DNA   length = 20
FEATURE                 Location/Qualifiers
source                  1..20
                        mol_type = other DNA
                        organism = synthetic construct
SEQUENCE: 85
gtgctttggg gtgctatcct                                              20

SEQ ID NO: 86           moltype = DNA   length = 20
FEATURE                 Location/Qualifiers
source                  1..20
                        mol_type = other DNA
                        organism = synthetic construct
SEQUENCE: 86
gcgacaaagg aagaacgacg                                              20

SEQ ID NO: 87           moltype = DNA   length = 20
FEATURE                 Location/Qualifiers
source                  1..20
                        mol_type = other DNA
                        organism = synthetic construct
SEQUENCE: 87
tagcctgtgt gtgtcaaccc                                              20

SEQ ID NO: 88           moltype = DNA   length = 22
FEATURE                 Location/Qualifiers
source                  1..22
                        mol_type = other DNA
                        organism = synthetic construct
SEQUENCE: 88
acctgcagag gttttcagtt ct                                           22

SEQ ID NO: 89           moltype = DNA   length = 20
FEATURE                 Location/Qualifiers
source                  1..20
                        mol_type = other DNA
                        organism = synthetic construct
```

```
SEQUENCE: 89
tttagctcag cccactccag                                                    20

SEQ ID NO: 90              moltype = DNA   length = 20
FEATURE                    Location/Qualifiers
source                     1..20
                           mol_type = other DNA
                           organism = synthetic construct
SEQUENCE: 90
agaacggtgg tttcttccgc                                                    20

SEQ ID NO: 91              moltype = DNA   length = 19
FEATURE                    Location/Qualifiers
source                     1..19
                           mol_type = other DNA
                           organism = synthetic construct
SEQUENCE: 91
aggaccatgc cctgctctc                                                     19

SEQ ID NO: 92              moltype = DNA   length = 20
FEATURE                    Location/Qualifiers
source                     1..20
                           mol_type = other DNA
                           organism = synthetic construct
SEQUENCE: 92
atgtcaccga caaacgggac                                                    20

SEQ ID NO: 93              moltype = DNA   length = 20
FEATURE                    Location/Qualifiers
source                     1..20
                           mol_type = other DNA
                           organism = synthetic construct
SEQUENCE: 93
aagagcgtgt ctgggttgtt                                                    20

SEQ ID NO: 94              moltype = DNA   length = 21
FEATURE                    Location/Qualifiers
source                     1..21
                           mol_type = other DNA
                           organism = synthetic construct
SEQUENCE: 94
tcttgggtgc ttctgagtgt g                                                  21

SEQ ID NO: 95              moltype = DNA   length = 20
FEATURE                    Location/Qualifiers
source                     1..20
                           mol_type = other DNA
                           organism = synthetic construct
SEQUENCE: 95
tagggtctgt gagccatccc                                                    20

SEQ ID NO: 96              moltype = DNA   length = 20
FEATURE                    Location/Qualifiers
source                     1..20
                           mol_type = other DNA
                           organism = synthetic construct
SEQUENCE: 96
ctccccagag taaggtccca                                                    20

SEQ ID NO: 97              moltype = DNA   length = 21
FEATURE                    Location/Qualifiers
source                     1..21
                           mol_type = other DNA
                           organism = synthetic construct
SEQUENCE: 97
agtacatgct ggccttgaac a                                                  21

SEQ ID NO: 98              moltype = DNA   length = 20
FEATURE                    Location/Qualifiers
source                     1..20
                           mol_type = other DNA
                           organism = synthetic construct
SEQUENCE: 98
attgcagaag ctcgagcgaa                                                    20

SEQ ID NO: 99              moltype = DNA   length = 21
FEATURE                    Location/Qualifiers
source                     1..21
                           mol_type = other DNA
```

```
                        organism = synthetic construct
SEQUENCE: 99
tagtgaactc acatgccacc c                                                     21

SEQ ID NO: 100          moltype = DNA   length = 20
FEATURE                 Location/Qualifiers
source                  1..20
                        mol_type = other DNA
                        organism = synthetic construct
SEQUENCE: 100
cttgggttcc tccagcaagt                                                       20

SEQ ID NO: 101          moltype = DNA   length = 21
FEATURE                 Location/Qualifiers
source                  1..21
                        mol_type = other DNA
                        organism = synthetic construct
SEQUENCE: 101
caagtgacgg acttagcagg a                                                     21

SEQ ID NO: 102          moltype = DNA   length = 19
FEATURE                 Location/Qualifiers
source                  1..19
                        mol_type = other DNA
                        organism = synthetic construct
SEQUENCE: 102
tcaaggcctg gcagcttac                                                        19

SEQ ID NO: 103          moltype = DNA   length = 21
FEATURE                 Location/Qualifiers
source                  1..21
                        mol_type = other DNA
                        organism = synthetic construct
SEQUENCE: 103
tgtccggatt tagtcttcgc t                                                     21

SEQ ID NO: 104          moltype = DNA   length = 20
FEATURE                 Location/Qualifiers
source                  1..20
                        mol_type = other DNA
                        organism = synthetic construct
SEQUENCE: 104
tcaggaacac gctgtgtcag                                                       20

SEQ ID NO: 105          moltype = DNA   length = 20
FEATURE                 Location/Qualifiers
source                  1..20
                        mol_type = other DNA
                        organism = synthetic construct
SEQUENCE: 105
caggtcatgc gtagcctgta                                                       20

SEQ ID NO: 106          moltype = DNA   length = 21
FEATURE                 Location/Qualifiers
source                  1..21
                        mol_type = other DNA
                        organism = synthetic construct
SEQUENCE: 106
ttggaagctt agccaactgg t                                                     21

SEQ ID NO: 107          moltype = DNA   length = 20
FEATURE                 Location/Qualifiers
source                  1..20
                        mol_type = other DNA
                        organism = synthetic construct
SEQUENCE: 107
agcgctcgta aaggtgctaa                                                       20

SEQ ID NO: 108          moltype = DNA   length = 21
FEATURE                 Location/Qualifiers
source                  1..21
                        mol_type = other DNA
                        organism = synthetic construct
SEQUENCE: 108
gctggctaac atcttcgttc c                                                     21

SEQ ID NO: 109          moltype = DNA   length = 20
FEATURE                 Location/Qualifiers
source                  1..20
```

```
                            mol_type = other DNA
                            organism = synthetic construct
SEQUENCE: 109
gtgggtcctg tgtcggtatc                                                       20

SEQ ID NO: 110              moltype = DNA  length = 23
FEATURE                     Location/Qualifiers
source                      1..23
                            mol_type = other DNA
                            organism = synthetic construct
SEQUENCE: 110
gccaataaca tctgcttcta cgg                                                   23

SEQ ID NO: 111              moltype = DNA  length = 21
FEATURE                     Location/Qualifiers
source                      1..21
                            mol_type = other DNA
                            organism = synthetic construct
SEQUENCE: 111
tggggaagaa gaccagaacc c                                                     21

SEQ ID NO: 112              moltype = DNA  length = 21
FEATURE                     Location/Qualifiers
source                      1..21
                            mol_type = other DNA
                            organism = synthetic construct
SEQUENCE: 112
tactgtttaa ggggaggggg a                                                     21

SEQ ID NO: 113              moltype = DNA  length = 20
FEATURE                     Location/Qualifiers
source                      1..20
                            mol_type = other DNA
                            organism = synthetic construct
SEQUENCE: 113
cacacccagt ctcttcccaa                                                       20

SEQ ID NO: 114              moltype = DNA  length = 21
FEATURE                     Location/Qualifiers
source                      1..21
                            mol_type = other DNA
                            organism = synthetic construct
SEQUENCE: 114
ctaggtgccc acccatctta g                                                     21

SEQ ID NO: 115              moltype = DNA  length = 19
FEATURE                     Location/Qualifiers
source                      1..19
                            mol_type = other DNA
                            organism = synthetic construct
SEQUENCE: 115
cagccaaggg ctttcctcg                                                        19

SEQ ID NO: 116              moltype = DNA  length = 22
FEATURE                     Location/Qualifiers
source                      1..22
                            mol_type = other DNA
                            organism = synthetic construct
SEQUENCE: 116
gagctcttca gatgccataa cc                                                    22

SEQ ID NO: 117              moltype = DNA  length = 24
FEATURE                     Location/Qualifiers
source                      1..24
                            mol_type = other DNA
                            organism = synthetic construct
SEQUENCE: 117
tgtgtgtgta taggtcttct gtgg                                                  24

SEQ ID NO: 118              moltype = DNA  length = 20
FEATURE                     Location/Qualifiers
source                      1..20
                            mol_type = other DNA
                            organism = synthetic construct
SEQUENCE: 118
caaacccaaa gctgcggaaa                                                       20

SEQ ID NO: 119              moltype = DNA  length = 20
FEATURE                     Location/Qualifiers
```

```
source                  1..20
                        mol_type = other DNA
                        organism = synthetic construct
SEQUENCE: 119
aaggaaccca ggtcaagcaa                                              20

SEQ ID NO: 120          moltype = DNA   length = 20
FEATURE                 Location/Qualifiers
source                  1..20
                        mol_type = other DNA
                        organism = synthetic construct
SEQUENCE: 120
gaccagctgt ggaactaggc                                              20

SEQ ID NO: 121          moltype = DNA   length = 20
FEATURE                 Location/Qualifiers
source                  1..20
                        mol_type = other DNA
                        organism = synthetic construct
SEQUENCE: 121
tgaccaccgg aacacgaaaa                                              20

SEQ ID NO: 122          moltype = DNA   length = 20
FEATURE                 Location/Qualifiers
source                  1..20
                        mol_type = other DNA
                        organism = synthetic construct
SEQUENCE: 122
gtccttccag gctatggctc                                              20

SEQ ID NO: 123          moltype = DNA   length = 21
FEATURE                 Location/Qualifiers
source                  1..21
                        mol_type = other DNA
                        organism = synthetic construct
SEQUENCE: 123
gctttcaccc tctcattacg c                                            21

SEQ ID NO: 124          moltype = DNA   length = 20
FEATURE                 Location/Qualifiers
source                  1..20
                        mol_type = other DNA
                        organism = synthetic construct
SEQUENCE: 124
cagtgtgcct gaagggtctc                                              20

SEQ ID NO: 125          moltype = DNA   length = 20
FEATURE                 Location/Qualifiers
source                  1..20
                        mol_type = other DNA
                        organism = synthetic construct
SEQUENCE: 125
actgctatgc acccccattc                                              20

SEQ ID NO: 126          moltype = DNA   length = 20
FEATURE                 Location/Qualifiers
source                  1..20
                        mol_type = other DNA
                        organism = synthetic construct
SEQUENCE: 126
gggactgcat acattggcct                                              20

SEQ ID NO: 127          moltype = DNA   length = 25
FEATURE                 Location/Qualifiers
source                  1..25
                        mol_type = other DNA
                        organism = synthetic construct
SEQUENCE: 127
cgaactaatt accaaccaat tgagg                                        25

SEQ ID NO: 128          moltype = DNA   length = 20
FEATURE                 Location/Qualifiers
source                  1..20
                        mol_type = other DNA
                        organism = synthetic construct
SEQUENCE: 128
tgtgactgca ctgccatagg                                              20

SEQ ID NO: 129          moltype = DNA   length = 20
```

-continued

```
FEATURE                 Location/Qualifiers
source                  1..20
                        mol_type = other DNA
                        organism = synthetic construct
SEQUENCE: 129
taggtctctg gggcagtctc                                                   20

SEQ ID NO: 130          moltype = DNA   length = 20
FEATURE                 Location/Qualifiers
source                  1..20
                        mol_type = other DNA
                        organism = synthetic construct
SEQUENCE: 130
tggggaaggg acaggttaga                                                   20

SEQ ID NO: 131          moltype = DNA   length = 21
FEATURE                 Location/Qualifiers
source                  1..21
                        mol_type = other DNA
                        organism = synthetic construct
SEQUENCE: 131
gccttcacaa caatcatgcc a                                                 21

SEQ ID NO: 132          moltype = DNA   length = 20
FEATURE                 Location/Qualifiers
source                  1..20
                        mol_type = other DNA
                        organism = synthetic construct
SEQUENCE: 132
ctccctaccc gtaccactct                                                   20

SEQ ID NO: 133          moltype = DNA   length = 20
FEATURE                 Location/Qualifiers
source                  1..20
                        mol_type = other DNA
                        organism = synthetic construct
SEQUENCE: 133
gcgttcaatg acacacgact                                                   20

SEQ ID NO: 134          moltype = DNA   length = 22
FEATURE                 Location/Qualifiers
source                  1..22
                        mol_type = other DNA
                        organism = synthetic construct
SEQUENCE: 134
atagccagat ggggacaggt ag                                                22

SEQ ID NO: 135          moltype = DNA   length = 20
FEATURE                 Location/Qualifiers
source                  1..20
                        mol_type = other DNA
                        organism = synthetic construct
SEQUENCE: 135
ccacacacca actgatcccc                                                   20

SEQ ID NO: 136          moltype = DNA   length = 20
FEATURE                 Location/Qualifiers
source                  1..20
                        mol_type = other DNA
                        organism = synthetic construct
SEQUENCE: 136
gcagggtcca cttctggatt                                                   20

SEQ ID NO: 137          moltype = DNA   length = 22
FEATURE                 Location/Qualifiers
source                  1..22
                        mol_type = other DNA
                        organism = synthetic construct
SEQUENCE: 137
ggacacagaa aatgggatgt tg                                                22

SEQ ID NO: 138          moltype = DNA   length = 23
FEATURE                 Location/Qualifiers
source                  1..23
                        mol_type = genomic DNA
                        organism = Cricetulus sp.
SEQUENCE: 138
gggctgcaga acgcgcagtt cgg                                               23
```

```
SEQ ID NO: 139         moltype = DNA  length = 24
FEATURE                Location/Qualifiers
source                 1..24
                       mol_type = other DNA
                       organism = synthetic construct
SEQUENCE: 139
gggctgcaga acgcgcaagt tcgg                                              24

SEQ ID NO: 140         moltype = DNA  length = 23
FEATURE                Location/Qualifiers
source                 1..23
                       mol_type = genomic DNA
                       organism = Cricetulus sp.
SEQUENCE: 140
gtcacattca tcgcatcgag ggg                                               23

SEQ ID NO: 141         moltype = DNA  length = 24
FEATURE                Location/Qualifiers
source                 1..24
                       mol_type = other DNA
                       organism = synthetic construct
SEQUENCE: 141
gtcacattca tcgcatccga gggg                                              24

SEQ ID NO: 142         moltype = DNA  length = 23
FEATURE                Location/Qualifiers
source                 1..23
                       mol_type = genomic DNA
                       organism = Cricetulus sp.
SEQUENCE: 142
gacaaaaacc tgtcgatcag tgg                                               23

SEQ ID NO: 143         moltype = DNA  length = 24
FEATURE                Location/Qualifiers
source                 1..24
                       mol_type = other DNA
                       organism = synthetic construct
SEQUENCE: 143
gacaaaaacc tgtcgattca gtgg                                              24

SEQ ID NO: 144         moltype = DNA  length = 23
FEATURE                Location/Qualifiers
source                 1..23
                       mol_type = genomic DNA
                       organism = Cricetulus sp.
SEQUENCE: 144
gtaaatatac gcttcgtcgg tgg                                               23

SEQ ID NO: 145         moltype = DNA  length = 21
FEATURE                Location/Qualifiers
source                 1..21
                       mol_type = other DNA
                       organism = synthetic construct
SEQUENCE: 145
gtaaatatac gctttcggtg g                                                 21

SEQ ID NO: 146         moltype = DNA  length = 23
FEATURE                Location/Qualifiers
source                 1..23
                       mol_type = genomic DNA
                       organism = Cricetulus sp.
SEQUENCE: 146
gtctgtgttc gtcgggtcca tgg                                               23

SEQ ID NO: 147         moltype = DNA  length = 24
FEATURE                Location/Qualifiers
source                 1..24
                       mol_type = other DNA
                       organism = synthetic construct
SEQUENCE: 147
gtctgtgttc gtcgggttcc atgg                                              24

SEQ ID NO: 148         moltype = DNA  length = 23
FEATURE                Location/Qualifiers
source                 1..23
                       mol_type = genomic DNA
                       organism = Cricetulus sp.
SEQUENCE: 148
gagtacatac cacctatcgg ggg                                               23
```

```
SEQ ID NO: 149          moltype = DNA   length = 24
FEATURE                 Location/Qualifiers
source                  1..24
                        mol_type = other DNA
                        organism = synthetic construct
SEQUENCE: 149
gagtacatac cacctattcg gggg                                              24

SEQ ID NO: 150          moltype = DNA   length = 23
FEATURE                 Location/Qualifiers
source                  1..23
                        mol_type = genomic DNA
                        organism = Cricetulus sp.
SEQUENCE: 150
gccccgggcg aggacgatcc cgg                                               23

SEQ ID NO: 151          moltype = DNA   length = 24
FEATURE                 Location/Qualifiers
source                  1..24
                        mol_type = other DNA
                        organism = synthetic construct
SEQUENCE: 151
gccccgggcg aggacgaatc ccgg                                              24

SEQ ID NO: 152          moltype = DNA   length = 23
FEATURE                 Location/Qualifiers
source                  1..23
                        mol_type = genomic DNA
                        organism = Cricetulus sp.
SEQUENCE: 152
ggtgtccctg ttcttctacg tgg                                               23

SEQ ID NO: 153          moltype = DNA   length = 24
FEATURE                 Location/Qualifiers
source                  1..24
                        mol_type = other DNA
                        organism = synthetic construct
SEQUENCE: 153
ggtgtccctg ttcttcttac gtgg                                              24

SEQ ID NO: 154          moltype = DNA   length = 23
FEATURE                 Location/Qualifiers
source                  1..23
                        mol_type = genomic DNA
                        organism = Cricetulus sp.
SEQUENCE: 154
gctctgcggc agcgctatag tgg                                               23

SEQ ID NO: 155          moltype = DNA   length = 24
FEATURE                 Location/Qualifiers
source                  1..24
                        mol_type = other DNA
                        organism = synthetic construct
SEQUENCE: 155
gctctgcggc agcgctaata gtgg                                              24

SEQ ID NO: 156          moltype = DNA   length = 23
FEATURE                 Location/Qualifiers
source                  1..23
                        mol_type = genomic DNA
                        organism = Cricetulus sp.
SEQUENCE: 156
gcgatggcgg tgcgggtggc cgg                                               23

SEQ ID NO: 157          moltype = DNA   length = 11
FEATURE                 Location/Qualifiers
source                  1..11
                        mol_type = other DNA
                        organism = synthetic construct
SEQUENCE: 157
cagttcttcc t                                                            11

SEQ ID NO: 158          moltype = DNA   length = 23
FEATURE                 Location/Qualifiers
source                  1..23
                        mol_type = genomic DNA
                        organism = Cricetulus sp.
SEQUENCE: 158
```

```
ggatgcacgg acggtactgc tgg                                              23

SEQ ID NO: 159          moltype = DNA   length = 24
FEATURE                 Location/Qualifiers
source                  1..24
                        mol_type = other DNA
                        organism = synthetic construct
SEQUENCE: 159
ggatgcacgg acggtacctg ctgg                                             24

SEQ ID NO: 160          moltype = DNA   length = 23
FEATURE                 Location/Qualifiers
source                  1..23
                        mol_type = genomic DNA
                        organism = Cricetulus sp.
SEQUENCE: 160
ggatgcacgg acggtactgc tgg                                              23

SEQ ID NO: 161          moltype = DNA   length = 24
FEATURE                 Location/Qualifiers
source                  1..24
                        mol_type = other DNA
                        organism = synthetic construct
SEQUENCE: 161
ggatgcacgg acggtacctg ctgg                                             24

SEQ ID NO: 162          moltype = DNA   length = 23
FEATURE                 Location/Qualifiers
source                  1..23
                        mol_type = genomic DNA
                        organism = Cricetulus sp.
SEQUENCE: 162
gctctgcggc agcgctatag tgg                                              23

SEQ ID NO: 163          moltype = DNA   length = 21
FEATURE                 Location/Qualifiers
source                  1..21
                        mol_type = other DNA
                        organism = synthetic construct
SEQUENCE: 163
gctctgcggc agcgctagtg g                                                21

SEQ ID NO: 164          moltype = DNA   length = 23
FEATURE                 Location/Qualifiers
source                  1..23
                        mol_type = genomic DNA
                        organism = Cricetulus sp.
SEQUENCE: 164
ggatgcacgg acggtactgc tgg                                              23

SEQ ID NO: 165          moltype = DNA   length = 22
FEATURE                 Location/Qualifiers
source                  1..22
                        mol_type = other DNA
                        organism = synthetic construct
SEQUENCE: 165
ggatgcacgg acggactgct gg                                               22

SEQ ID NO: 166          moltype = DNA   length = 11
FEATURE                 Location/Qualifiers
source                  1..11
                        mol_type = other DNA
                        organism = synthetic construct
SEQUENCE: 166
agatggtgtc a                                                           11

SEQ ID NO: 167          moltype = DNA   length = 23
FEATURE                 Location/Qualifiers
source                  1..23
                        mol_type = genomic DNA
                        organism = Cricetulus sp.
SEQUENCE: 167
gctctgcggc agcgctatag tgg                                              23

SEQ ID NO: 168          moltype = DNA   length = 24
FEATURE                 Location/Qualifiers
source                  1..24
                        mol_type = other DNA
                        organism = synthetic construct
```

-continued

```
SEQUENCE: 168
gctctgcggc agcgctatta gtgg                                              24

SEQ ID NO: 169          moltype = DNA   length = 23
FEATURE                 Location/Qualifiers
source                  1..23
                        mol_type = genomic DNA
                        organism = Cricetulus sp.
SEQUENCE: 169
ggatgcacgg acggtactgc tgg                                               23

SEQ ID NO: 170          moltype = DNA   length = 24
FEATURE                 Location/Qualifiers
source                  1..24
                        mol_type = other DNA
                        organism = synthetic construct
SEQUENCE: 170
ggatgcacgg acggtacgtg ctgg                                              24

SEQ ID NO: 171          moltype = DNA   length = 23
FEATURE                 Location/Qualifiers
source                  1..23
                        mol_type = genomic DNA
                        organism = Cricetulus sp.
SEQUENCE: 171
gctgctgggc tgcggaaacg cgg                                               23

SEQ ID NO: 172          moltype = DNA   length = 24
FEATURE                 Location/Qualifiers
source                  1..24
                        mol_type = other DNA
                        organism = synthetic construct
SEQUENCE: 172
gctgctgggc tgcggaaaac gcgg                                              24

SEQ ID NO: 173          moltype = DNA   length = 23
FEATURE                 Location/Qualifiers
source                  1..23
                        mol_type = genomic DNA
                        organism = Cricetulus sp.
SEQUENCE: 173
gctgctgggc tgcggaaacg cgg                                               23

SEQ ID NO: 174          moltype = DNA   length = 22
FEATURE                 Location/Qualifiers
source                  1..22
                        mol_type = other DNA
                        organism = synthetic construct
SEQUENCE: 174
gctgctgggc tgcggaacgc gg                                                22

SEQ ID NO: 175          moltype = DNA   length = 23
FEATURE                 Location/Qualifiers
source                  1..23
                        mol_type = genomic DNA
                        organism = Cricetulus sp.
SEQUENCE: 175
tcttaatagg actcacagtg cgg                                               23

SEQ ID NO: 176          moltype = DNA   length = 24
FEATURE                 Location/Qualifiers
source                  1..24
                        mol_type = other DNA
                        organism = synthetic construct
SEQUENCE: 176
tcttaatagg actcaccagt gcgg                                              24

SEQ ID NO: 177          moltype = DNA   length = 23
FEATURE                 Location/Qualifiers
source                  1..23
                        mol_type = genomic DNA
                        organism = Cricetulus sp.
SEQUENCE: 177
gagcagacat ttgaaagcag tgg                                               23

SEQ ID NO: 178          moltype = DNA   length = 24
FEATURE                 Location/Qualifiers
source                  1..24
                        mol_type = other DNA
```

```
                            organism = synthetic construct
SEQUENCE: 178
gagcagacat ttgaaaggca gtgg                                         24

SEQ ID NO: 179          moltype = DNA   length = 23
FEATURE                 Location/Qualifiers
source                  1..23
                        mol_type = genomic DNA
                        organism = Cricetulus sp.
SEQUENCE: 179
ggtcgaagtg ggccgactca ggg                                          23

SEQ ID NO: 180          moltype = DNA   length = 24
FEATURE                 Location/Qualifiers
source                  1..24
                        mol_type = other DNA
                        organism = synthetic construct
SEQUENCE: 180
ggtcgaagtg ggccgacctc aggg                                         24

SEQ ID NO: 181          moltype = DNA   length = 23
FEATURE                 Location/Qualifiers
source                  1..23
                        mol_type = genomic DNA
                        organism = Cricetulus sp.
SEQUENCE: 181
ggagttgtga tcattgtgag cgg                                          23

SEQ ID NO: 182          moltype = DNA   length = 24
FEATURE                 Location/Qualifiers
source                  1..24
                        mol_type = other DNA
                        organism = synthetic construct
SEQUENCE: 182
ggagttgtga tcattgttga gcgg                                         24

SEQ ID NO: 183          moltype = DNA   length = 23
FEATURE                 Location/Qualifiers
source                  1..23
                        mol_type = genomic DNA
                        organism = Cricetulus sp.
SEQUENCE: 183
gaggggtcg caggcacacg ggg                                           23

SEQ ID NO: 184          moltype = DNA   length = 24
FEATURE                 Location/Qualifiers
source                  1..24
                        mol_type = other DNA
                        organism = synthetic construct
SEQUENCE: 184
gaggggtcg caggcacgac gggg                                          24

SEQ ID NO: 185          moltype = DNA   length = 23
FEATURE                 Location/Qualifiers
source                  1..23
                        mol_type = genomic DNA
                        organism = Cricetulus sp.
SEQUENCE: 185
gcgaccggta ccgcagcgtt agg                                          23

SEQ ID NO: 186          moltype = DNA   length = 24
FEATURE                 Location/Qualifiers
source                  1..24
                        mol_type = other DNA
                        organism = synthetic construct
SEQUENCE: 186
gcgaccggta ccgcagccgt tagg                                         24

SEQ ID NO: 187          moltype = DNA   length = 23
FEATURE                 Location/Qualifiers
source                  1..23
                        mol_type = genomic DNA
                        organism = Cricetulus sp.
SEQUENCE: 187
gagaggcagg cgctgcggga cgg                                          23

SEQ ID NO: 188          moltype = DNA   length = 24
FEATURE                 Location/Qualifiers
source                  1..24
```

```
                              mol_type = other DNA
                              organism = synthetic construct
SEQUENCE: 188
gagaggcagg cgctgcgggg acgg                                              24

SEQ ID NO: 189           moltype = DNA   length = 23
FEATURE                  Location/Qualifiers
source                   1..23
                         mol_type = genomic DNA
                         organism = Cricetulus sp.
SEQUENCE: 189
gacaatctcg tcaatggcac agg                                               23

SEQ ID NO: 190           moltype = DNA   length = 22
FEATURE                  Location/Qualifiers
source                   1..22
                         mol_type = other DNA
                         organism = synthetic construct
SEQUENCE: 190
gacaatctcg tcaatgcaca gg                                                22

SEQ ID NO: 191           moltype = DNA   length = 23
FEATURE                  Location/Qualifiers
source                   1..23
                         mol_type = genomic DNA
                         organism = Cricetulus sp.
SEQUENCE: 191
gaggcttggc aggcggacaa agg                                               23

SEQ ID NO: 192           moltype = DNA   length = 24
FEATURE                  Location/Qualifiers
source                   1..24
                         mol_type = other DNA
                         organism = synthetic construct
SEQUENCE: 192
gaggcttggc aggcggaaca aagg                                              24

SEQ ID NO: 193           moltype = DNA   length = 23
FEATURE                  Location/Qualifiers
source                   1..23
                         mol_type = genomic DNA
                         organism = Cricetulus sp.
SEQUENCE: 193
ggtcgaagtg ggccgactca ggg                                               23

SEQ ID NO: 194           moltype = DNA   length = 24
FEATURE                  Location/Qualifiers
source                   1..24
                         mol_type = other DNA
                         organism = synthetic construct
SEQUENCE: 194
ggtcgaagtg ggccgacctc aggg                                              24

SEQ ID NO: 195           moltype = DNA   length = 23
FEATURE                  Location/Qualifiers
source                   1..23
                         mol_type = genomic DNA
                         organism = Cricetulus sp.
SEQUENCE: 195
ggagttgtga tcattgtgag cgg                                               23

SEQ ID NO: 196           moltype = DNA   length = 24
FEATURE                  Location/Qualifiers
source                   1..24
                         mol_type = other DNA
                         organism = synthetic construct
SEQUENCE: 196
ggagttgtga tcattgttga gcgg                                              24

SEQ ID NO: 197           moltype = DNA   length = 23
FEATURE                  Location/Qualifiers
source                   1..23
                         mol_type = genomic DNA
                         organism = Cricetulus sp.
SEQUENCE: 197
ttaacagcag aggtatctgg ggg                                               23

SEQ ID NO: 198           moltype = DNA   length = 24
FEATURE                  Location/Qualifiers
```

```
source                  1..24
                        mol_type = other DNA
                        organism = synthetic construct
SEQUENCE: 198
ttaacagcag aggtatcctg gggg                                              24

SEQ ID NO: 199          moltype = DNA   length = 23
FEATURE                 Location/Qualifiers
source                  1..23
                        mol_type = genomic DNA
                        organism = Cricetulus sp.
SEQUENCE: 199
tcacacaagg aattccagtg tgg                                               23

SEQ ID NO: 200          moltype = DNA   length = 24
FEATURE                 Location/Qualifiers
source                  1..24
                        mol_type = other DNA
                        organism = synthetic construct
SEQUENCE: 200
tcacacaagg aattccaagt gtgg                                              24

SEQ ID NO: 201          moltype = DNA   length = 23
FEATURE                 Location/Qualifiers
source                  1..23
                        mol_type = genomic DNA
                        organism = Cricetulus sp.
SEQUENCE: 201
gatccgtcca caaccttggc tgg                                               23

SEQ ID NO: 202          moltype = DNA   length = 25
FEATURE                 Location/Qualifiers
source                  1..25
                        mol_type = other DNA
                        organism = synthetic construct
SEQUENCE: 202
gatccgtcca caaccttggg gctgg                                             25

SEQ ID NO: 203          moltype = DNA   length = 23
FEATURE                 Location/Qualifiers
source                  1..23
                        mol_type = genomic DNA
                        organism = Cricetulus sp.
SEQUENCE: 203
gtcacattca tcgcatcgag ggg                                               23

SEQ ID NO: 204          moltype = DNA   length = 24
FEATURE                 Location/Qualifiers
source                  1..24
                        mol_type = other DNA
                        organism = synthetic construct
SEQUENCE: 204
gtcacattca tcgcatccga gggg                                              24

SEQ ID NO: 205          moltype = DNA   length = 23
FEATURE                 Location/Qualifiers
source                  1..23
                        mol_type = genomic DNA
                        organism = Cricetulus sp.
SEQUENCE: 205
gcgatggcgg tgcgggtggc cgg                                               23

SEQ ID NO: 206          moltype = DNA   length = 24
FEATURE                 Location/Qualifiers
source                  1..24
                        mol_type = other DNA
                        organism = synthetic construct
SEQUENCE: 206
gcgatggcgg tgcgggttgg ccgg                                              24

SEQ ID NO: 207          moltype = DNA   length = 23
FEATURE                 Location/Qualifiers
source                  1..23
                        mol_type = genomic DNA
                        organism = Cricetulus sp.
SEQUENCE: 207
gaccaagcgg gacgtgtatc agg                                               23

SEQ ID NO: 208          moltype = DNA   length = 24
```

```
FEATURE                 Location/Qualifiers
source                  1..24
                        mol_type = other DNA
                        organism = synthetic construct
SEQUENCE: 208
gaccaagcgg gacgtgttat cagg                                            24

SEQ ID NO: 209          moltype = DNA   length = 23
FEATURE                 Location/Qualifiers
source                  1..23
                        mol_type = genomic DNA
                        organism = Cricetulus sp.
SEQUENCE: 209
atagccaaga actatccaca agg                                             23

SEQ ID NO: 210          moltype = DNA   length = 24
FEATURE                 Location/Qualifiers
source                  1..24
                        mol_type = other DNA
                        organism = synthetic construct
SEQUENCE: 210
atagccaaga actatcccac aagg                                            24

SEQ ID NO: 211          moltype = DNA   length = 23
FEATURE                 Location/Qualifiers
source                  1..23
                        mol_type = genomic DNA
                        organism = Cricetulus sp.
SEQUENCE: 211
gagaggcagg cgctgcggga cgg                                             23

SEQ ID NO: 212          moltype = DNA   length = 24
FEATURE                 Location/Qualifiers
source                  1..24
                        mol_type = other DNA
                        organism = synthetic construct
SEQUENCE: 212
gagaggcagg cgctgcgggg acgg                                            24

SEQ ID NO: 213          moltype = DNA   length = 23
FEATURE                 Location/Qualifiers
source                  1..23
                        mol_type = genomic DNA
                        organism = Cricetulus sp.
SEQUENCE: 213
gacaatctcg tcaatggcac agg                                             23

SEQ ID NO: 214          moltype = DNA   length = 22
FEATURE                 Location/Qualifiers
source                  1..22
                        mol_type = other DNA
                        organism = synthetic construct
SEQUENCE: 214
gacaatctcg tcaatgcaca gg                                              22

SEQ ID NO: 215          moltype = DNA   length = 23
FEATURE                 Location/Qualifiers
source                  1..23
                        mol_type = genomic DNA
                        organism = Cricetulus sp.
SEQUENCE: 215
gtcacattca tcgcatcgag ggg                                             23

SEQ ID NO: 216          moltype = DNA   length = 24
FEATURE                 Location/Qualifiers
source                  1..24
                        mol_type = other DNA
                        organism = synthetic construct
SEQUENCE: 216
gtcacattca tcgcatccga gggg                                            24

SEQ ID NO: 217          moltype = DNA   length = 23
FEATURE                 Location/Qualifiers
source                  1..23
                        mol_type = genomic DNA
                        organism = Cricetulus sp.
SEQUENCE: 217
gcgatggcgg tgcgggtggc cgg                                             23
```

```
SEQ ID NO: 218          moltype = DNA   length = 24
FEATURE                 Location/Qualifiers
source                  1..24
                        mol_type = other DNA
                        organism = synthetic construct
SEQUENCE: 218
gcgatggcgg tgcgggttgg ccgg                                              24

SEQ ID NO: 219          moltype = DNA   length = 23
FEATURE                 Location/Qualifiers
source                  1..23
                        mol_type = genomic DNA
                        organism = Cricetulus sp.
SEQUENCE: 219
gagggggtcg caggcacacg ggg                                               23

SEQ ID NO: 220          moltype = DNA   length = 24
FEATURE                 Location/Qualifiers
source                  1..24
                        mol_type = other DNA
                        organism = synthetic construct
SEQUENCE: 220
gagggggtcg caggcaccac gggg                                              24

SEQ ID NO: 221          moltype = DNA   length = 23
FEATURE                 Location/Qualifiers
source                  1..23
                        mol_type = genomic DNA
                        organism = Cricetulus sp.
SEQUENCE: 221
gtcacattca tcgcatcgag ggg                                               23

SEQ ID NO: 222          moltype = DNA   length = 24
FEATURE                 Location/Qualifiers
source                  1..24
                        mol_type = other DNA
                        organism = synthetic construct
SEQUENCE: 222
gtcacattca tcgcatccga gggg                                              24

SEQ ID NO: 223          moltype = DNA   length = 23
FEATURE                 Location/Qualifiers
source                  1..23
                        mol_type = genomic DNA
                        organism = Cricetulus sp.
SEQUENCE: 223
gcgatggcgg tgcgggtggc cgg                                               23

SEQ ID NO: 224          moltype = DNA   length = 24
FEATURE                 Location/Qualifiers
source                  1..24
                        mol_type = other DNA
                        organism = synthetic construct
SEQUENCE: 224
gcgatggcgg tgcgggttgg ccgg                                              24

SEQ ID NO: 225          moltype = DNA   length = 23
FEATURE                 Location/Qualifiers
source                  1..23
                        mol_type = genomic DNA
                        organism = Cricetulus sp.
SEQUENCE: 225
gcgaccggta ccgcagcgtt agg                                               23

SEQ ID NO: 226          moltype = DNA   length = 24
FEATURE                 Location/Qualifiers
source                  1..24
                        mol_type = other DNA
                        organism = synthetic construct
SEQUENCE: 226
gcgaccggta ccgcagccgt tagg                                              24

SEQ ID NO: 227          moltype = DNA   length = 23
FEATURE                 Location/Qualifiers
source                  1..23
                        mol_type = genomic DNA
                        organism = Cricetulus sp.
SEQUENCE: 227
gtcacattca tcgcatcgag ggg                                               23
```

```
SEQ ID NO: 228          moltype = DNA   length = 24
FEATURE                 Location/Qualifiers
source                  1..24
                        mol_type = other DNA
                        organism = synthetic construct
SEQUENCE: 228
gtcacattca tcgcatccga gggg                                              24

SEQ ID NO: 229          moltype = DNA   length = 23
FEATURE                 Location/Qualifiers
source                  1..23
                        mol_type = genomic DNA
                        organism = Cricetulus sp.
SEQUENCE: 229
gcgatggcgg tgcgggtggc cgg                                               23

SEQ ID NO: 230          moltype = DNA   length = 24
FEATURE                 Location/Qualifiers
source                  1..24
                        mol_type = other DNA
                        organism = synthetic construct
SEQUENCE: 230
gcgatggcgg tgcggttgg ccgg                                               24

SEQ ID NO: 231          moltype = DNA   length = 23
FEATURE                 Location/Qualifiers
source                  1..23
                        mol_type = genomic DNA
                        organism = Cricetulus sp.
SEQUENCE: 231
gggcggtcgt tattccccca agg                                               23

SEQ ID NO: 232          moltype = DNA   length = 25
FEATURE                 Location/Qualifiers
source                  1..25
                        mol_type = other DNA
                        organism = synthetic construct
SEQUENCE: 232
gggcggtcgt tattccccgc caagg                                             25

SEQ ID NO: 233          moltype = DNA   length = 23
FEATURE                 Location/Qualifiers
source                  1..23
                        mol_type = genomic DNA
                        organism = Cricetulus sp.
SEQUENCE: 233
gcaggacggt accggccccc tgg                                               23

SEQ ID NO: 234          moltype = DNA   length = 21
FEATURE                 Location/Qualifiers
source                  1..21
                        mol_type = other DNA
                        organism = synthetic construct
SEQUENCE: 234
gcaggacggt accggccctg g                                                 21

SEQ ID NO: 235          moltype = DNA   length = 23
FEATURE                 Location/Qualifiers
source                  1..23
                        mol_type = genomic DNA
                        organism = Cricetulus sp.
SEQUENCE: 235
gagaggcagg cgctgcggga cgg                                               23

SEQ ID NO: 236          moltype = DNA   length = 24
FEATURE                 Location/Qualifiers
source                  1..24
                        mol_type = other DNA
                        organism = synthetic construct
SEQUENCE: 236
gagaggcagg cgctgcgggg acgg                                              24

SEQ ID NO: 237          moltype = DNA   length = 23
FEATURE                 Location/Qualifiers
source                  1..23
                        mol_type = genomic DNA
                        organism = Cricetulus sp.
SEQUENCE: 237
```

```
gacaatctcg tcaatggcac agg                                             23

SEQ ID NO: 238          moltype = DNA  length = 22
FEATURE                 Location/Qualifiers
source                  1..22
                        mol_type = other DNA
                        organism = synthetic construct
SEQUENCE: 238
gacaatctcg tcaatgcaca gg                                              22

SEQ ID NO: 239          moltype = DNA  length = 23
FEATURE                 Location/Qualifiers
source                  1..23
                        mol_type = genomic DNA
                        organism = Cricetulus sp.
SEQUENCE: 239
gtcacattca tcgcatcgag ggg                                             23

SEQ ID NO: 240          moltype = DNA  length = 24
FEATURE                 Location/Qualifiers
source                  1..24
                        mol_type = other DNA
                        organism = synthetic construct
SEQUENCE: 240
gtcacattca tcgcatccga gggg                                            24

SEQ ID NO: 241          moltype = DNA  length = 23
FEATURE                 Location/Qualifiers
source                  1..23
                        mol_type = genomic DNA
                        organism = Cricetulus sp.
SEQUENCE: 241
gcgatggcgg tgcgggtggc cgg                                             23

SEQ ID NO: 242          moltype = DNA  length = 24
FEATURE                 Location/Qualifiers
source                  1..24
                        mol_type = other DNA
                        organism = synthetic construct
SEQUENCE: 242
gcgatggcgg tgcgggttgg ccgg                                            24

SEQ ID NO: 243          moltype = DNA  length = 23
FEATURE                 Location/Qualifiers
source                  1..23
                        mol_type = genomic DNA
                        organism = Cricetulus sp.
SEQUENCE: 243
gaaggcttcg atcctctagc agg                                             23

SEQ ID NO: 244          moltype = DNA  length = 24
FEATURE                 Location/Qualifiers
source                  1..24
                        mol_type = other DNA
                        organism = synthetic construct
SEQUENCE: 244
gaaggcttcg atcctcttag cagg                                            24

SEQ ID NO: 245          moltype = DNA  length = 23
FEATURE                 Location/Qualifiers
source                  1..23
                        mol_type = genomic DNA
                        organism = Cricetulus sp.
SEQUENCE: 245
gagaggcagg cgctgcggga cgg                                             23

SEQ ID NO: 246          moltype = DNA  length = 24
FEATURE                 Location/Qualifiers
source                  1..24
                        mol_type = other DNA
                        organism = synthetic construct
SEQUENCE: 246
gagaggcagg cgctgcgggg acgg                                            24

SEQ ID NO: 247          moltype = DNA  length = 23
FEATURE                 Location/Qualifiers
source                  1..23
                        mol_type = genomic DNA
                        organism = Cricetulus sp.
```

```
SEQUENCE: 247
gacaatctcg tcaatggcac agg                                           23

SEQ ID NO: 248         moltype = DNA   length = 22
FEATURE                Location/Qualifiers
source                 1..22
                       mol_type = other DNA
                       organism = synthetic construct
SEQUENCE: 248
gacaatctcg tcaatgcaca gg                                            22

SEQ ID NO: 249         moltype = DNA   length = 23
FEATURE                Location/Qualifiers
source                 1..23
                       mol_type = genomic DNA
                       organism = Cricetulus sp.
SEQUENCE: 249
gtcacattca tcgcatcgag ggg                                           23

SEQ ID NO: 250         moltype = DNA   length = 24
FEATURE                Location/Qualifiers
source                 1..24
                       mol_type = other DNA
                       organism = synthetic construct
SEQUENCE: 250
gtcacattca tcgcatccga gggg                                          24

SEQ ID NO: 251         moltype = DNA   length = 23
FEATURE                Location/Qualifiers
source                 1..23
                       mol_type = genomic DNA
                       organism = Cricetulus sp.
SEQUENCE: 251
gcgatggcgg tgcgggtggc cgg                                           23

SEQ ID NO: 252         moltype = DNA   length = 24
FEATURE                Location/Qualifiers
source                 1..24
                       mol_type = other DNA
                       organism = synthetic construct
SEQUENCE: 252
gcgatggcgg tgcgggttgg ccgg                                          24

SEQ ID NO: 253         moltype = DNA   length = 23
FEATURE                Location/Qualifiers
source                 1..23
                       mol_type = genomic DNA
                       organism = Cricetulus sp.
SEQUENCE: 253
gatccgtcca caaccttggc tgg                                           23

SEQ ID NO: 254         moltype = DNA   length = 21
FEATURE                Location/Qualifiers
source                 1..21
                       mol_type = other DNA
                       organism = synthetic construct
SEQUENCE: 254
gatccgtcca caaccggctg g                                             21

SEQ ID NO: 255         moltype = DNA   length = 23
FEATURE                Location/Qualifiers
source                 1..23
                       mol_type = genomic DNA
                       organism = Cricetulus sp.
SEQUENCE: 255
gagaggcagg cgctgcggga cgg                                           23

SEQ ID NO: 256         moltype = DNA   length = 24
FEATURE                Location/Qualifiers
source                 1..24
                       mol_type = other DNA
                       organism = synthetic construct
SEQUENCE: 256
gagaggcagg cgctgcgggg acgg                                          24

SEQ ID NO: 257         moltype = DNA   length = 23
FEATURE                Location/Qualifiers
source                 1..23
                       mol_type = genomic DNA
```

```
                            -continued organism = Cricetulus sp.
SEQUENCE: 257
gacaatctcg tcaatggcac agg                                            23

SEQ ID NO: 258         moltype = DNA   length = 22
FEATURE                Location/Qualifiers
source                 1..22
                       mol_type = other DNA
                       organism = synthetic construct
SEQUENCE: 258
gacaatctcg tcaatgcaca gg                                             22

SEQ ID NO: 259         moltype = DNA   length = 23
FEATURE                Location/Qualifiers
source                 1..23
                       mol_type = genomic DNA
                       organism = Cricetulus sp.
SEQUENCE: 259
gtcacattca tcgcatcgag ggg                                            23

SEQ ID NO: 260         moltype = DNA   length = 24
FEATURE                Location/Qualifiers
source                 1..24
                       mol_type = other DNA
                       organism = synthetic construct
SEQUENCE: 260
gtcacattca tcgcatccga gggg                                           24

SEQ ID NO: 261         moltype = DNA   length = 23
FEATURE                Location/Qualifiers
source                 1..23
                       mol_type = genomic DNA
                       organism = Cricetulus sp.
SEQUENCE: 261
gcgatggcgg tgcgggtggc cgg                                            23

SEQ ID NO: 262         moltype = DNA   length = 24
FEATURE                Location/Qualifiers
source                 1..24
                       mol_type = other DNA
                       organism = synthetic construct
SEQUENCE: 262
gcgatggcgg tgcgggttgg ccgg                                           24

SEQ ID NO: 263         moltype = DNA   length = 23
FEATURE                Location/Qualifiers
source                 1..23
                       mol_type = genomic DNA
                       organism = Cricetulus sp.
SEQUENCE: 263
gggaagcctg accagatcga agg                                            23

SEQ ID NO: 264         moltype = DNA   length = 19
FEATURE                Location/Qualifiers
source                 1..19
                       mol_type = other DNA
                       organism = synthetic construct
SEQUENCE: 264
gggaagcctg accagaagg                                                 19

SEQ ID NO: 265         moltype = DNA   length = 23
FEATURE                Location/Qualifiers
source                 1..23
                       mol_type = genomic DNA
                       organism = Cricetulus sp.
SEQUENCE: 265
gaaaggctca gtgcaacact ggg                                            23

SEQ ID NO: 266         moltype = DNA   length = 24
FEATURE                Location/Qualifiers
source                 1..24
                       mol_type = other DNA
                       organism = synthetic construct
SEQUENCE: 266
gaaaggctca gtgcaaccac tggg                                           24

SEQ ID NO: 267         moltype = DNA   length = 23
FEATURE                Location/Qualifiers
source                 1..23
```

```
                        mol_type = genomic DNA
                        organism = Cricetulus sp.
SEQUENCE: 267
tgacttcagt tcgacgggta cgg                                             23

SEQ ID NO: 268          moltype = DNA  length = 23
FEATURE                 Location/Qualifiers
source                  1..23
                        mol_type = other DNA
                        organism = synthetic construct
SEQUENCE: 268
tgacttcagt tcgacgggta cgg                                             23

SEQ ID NO: 269          moltype = DNA  length = 23
FEATURE                 Location/Qualifiers
source                  1..23
                        mol_type = genomic DNA
                        organism = Cricetulus sp.
SEQUENCE: 269
tcggtgtact tcaaaatccg tgg                                             23

SEQ ID NO: 270          moltype = DNA  length = 24
FEATURE                 Location/Qualifiers
source                  1..24
                        mol_type = other DNA
                        organism = synthetic construct
SEQUENCE: 270
tcggtgtact tcaaaattcc gtgg                                            24

SEQ ID NO: 271          moltype = DNA  length = 23
FEATURE                 Location/Qualifiers
source                  1..23
                        mol_type = genomic DNA
                        organism = Cricetulus sp.
SEQUENCE: 271
aaatcaccag gcaagtcagg cgg                                             23

SEQ ID NO: 272          moltype = DNA  length = 24
FEATURE                 Location/Qualifiers
source                  1..24
                        mol_type = other DNA
                        organism = synthetic construct
SEQUENCE: 272
aaatcaccag gcaagtccag gcgg                                            24

SEQ ID NO: 273          moltype = DNA  length = 23
FEATURE                 Location/Qualifiers
source                  1..23
                        mol_type = genomic DNA
                        organism = Cricetulus sp.
SEQUENCE: 273
ggactctaag ttcacttacg agg                                             23

SEQ ID NO: 274          moltype = DNA  length = 22
FEATURE                 Location/Qualifiers
source                  1..22
                        mol_type = other DNA
                        organism = synthetic construct
SEQUENCE: 274
ggactctaag ttcactacga gg                                              22

SEQ ID NO: 275          moltype = DNA  length = 23
FEATURE                 Location/Qualifiers
source                  1..23
                        mol_type = genomic DNA
                        organism = Cricetulus sp.
SEQUENCE: 275
gggcggtcgt tattcccccca agg                                            23

SEQ ID NO: 276          moltype = DNA  length = 10
FEATURE                 Location/Qualifiers
source                  1..10
                        mol_type = other DNA
                        organism = synthetic construct
SEQUENCE: 276
ggtcgtattt                                                            10

SEQ ID NO: 277          moltype = DNA  length = 23
FEATURE                 Location/Qualifiers
```

```
source                  1..23
                        mol_type = genomic DNA
                        organism = Cricetulus sp.
SEQUENCE: 277
gcaggacggt accggccccc tgg                                              23

SEQ ID NO: 278          moltype = DNA   length = 12
FEATURE                 Location/Qualifiers
source                  1..12
                        mol_type = other DNA
                        organism = synthetic construct
SEQUENCE: 278
acatccttcc gc                                                          12

SEQ ID NO: 279          moltype = DNA   length = 15
FEATURE                 Location/Qualifiers
source                  1..15
                        mol_type = other DNA
                        organism = synthetic construct
SEQUENCE: 279
gcaggacggt acccc                                                       15

SEQ ID NO: 280          moltype = DNA   length = 23
FEATURE                 Location/Qualifiers
source                  1..23
                        mol_type = genomic DNA
                        organism = Cricetulus sp.
SEQUENCE: 280
gagtgaagcc tcgatcgggt tgg                                              23

SEQ ID NO: 281          moltype = DNA   length = 24
FEATURE                 Location/Qualifiers
source                  1..24
                        mol_type = other DNA
                        organism = synthetic construct
SEQUENCE: 281
gagtgaagcc tcgatcgggg ttgg                                             24

SEQ ID NO: 282          moltype = DNA   length = 23
FEATURE                 Location/Qualifiers
source                  1..23
                        mol_type = genomic DNA
                        organism = Cricetulus sp.
SEQUENCE: 282
gcccagagaa agcgtcgtcg agg                                              23

SEQ ID NO: 283          moltype = DNA   length = 24
FEATURE                 Location/Qualifiers
source                  1..24
                        mol_type = other DNA
                        organism = synthetic construct
SEQUENCE: 283
gcccagagaa agcgtcggtc gagg                                             24

SEQ ID NO: 284          moltype = DNA   length = 25
FEATURE                 Location/Qualifiers
source                  1..25
                        mol_type = other DNA
                        organism = synthetic construct
SEQUENCE: 284
gcccagagaa agcgtcggct cgagg                                            25

SEQ ID NO: 285          moltype = DNA   length = 23
FEATURE                 Location/Qualifiers
source                  1..23
                        mol_type = genomic DNA
                        organism = Cricetulus sp.
SEQUENCE: 285
gagtgaagcc tcgatcgggt tgg                                              23

SEQ ID NO: 286          moltype = DNA   length = 21
FEATURE                 Location/Qualifiers
source                  1..21
                        mol_type = other DNA
                        organism = synthetic construct
SEQUENCE: 286
gagtgaagcc tcgatcgttg g                                                21

SEQ ID NO: 287          moltype = DNA   length = 23
```

-continued

```
FEATURE                 Location/Qualifiers
source                  1..23
                        mol_type = genomic DNA
                        organism = Cricetulus sp.
SEQUENCE: 287
gcccagagaa agcgtcgtcg agg                                               23

SEQ ID NO: 288          moltype = DNA  length = 24
FEATURE                 Location/Qualifiers
source                  1..24
                        mol_type = other DNA
                        organism = synthetic construct
SEQUENCE: 288
gcccagagaa agcgtcggtc gagg                                              24

SEQ ID NO: 289          moltype = DNA  length = 23
FEATURE                 Location/Qualifiers
source                  1..23
                        mol_type = genomic DNA
                        organism = Cricetulus sp.
SEQUENCE: 289
gtcacattca tcgcatcgag ggg                                               23

SEQ ID NO: 290          moltype = DNA  length = 24
FEATURE                 Location/Qualifiers
source                  1..24
                        mol_type = other DNA
                        organism = synthetic construct
SEQUENCE: 290
gtcacattca tcgcatccga gggg                                              24

SEQ ID NO: 291          moltype = DNA  length = 23
FEATURE                 Location/Qualifiers
source                  1..23
                        mol_type = genomic DNA
                        organism = Cricetulus sp.
SEQUENCE: 291
gtaaatatac gcttcgtcgg tgg                                               23

SEQ ID NO: 292          moltype = DNA  length = 21
FEATURE                 Location/Qualifiers
source                  1..21
                        mol_type = other DNA
                        organism = synthetic construct
SEQUENCE: 292
gtaaatatac gctttcggtg g                                                 21

SEQ ID NO: 293          moltype = DNA  length = 23
FEATURE                 Location/Qualifiers
source                  1..23
                        mol_type = genomic DNA
                        organism = Cricetulus sp.
SEQUENCE: 293
gtctgtgttc gtcgggtcca tgg                                               23

SEQ ID NO: 294          moltype = DNA  length = 24
FEATURE                 Location/Qualifiers
source                  1..24
                        mol_type = other DNA
                        organism = synthetic construct
SEQUENCE: 294
gtctgtgttc gtcgggttcc atgg                                              24

SEQ ID NO: 295          moltype = DNA  length = 15
FEATURE                 Location/Qualifiers
source                  1..15
                        mol_type = other DNA
                        organism = synthetic construct
SEQUENCE: 295
gtctgtgttc gtcag                                                        15

SEQ ID NO: 296          moltype = DNA  length = 23
FEATURE                 Location/Qualifiers
source                  1..23
                        mol_type = genomic DNA
                        organism = Cricetulus sp.
SEQUENCE: 296
gagtacatac cacctatcgg ggg                                               23
```

```
SEQ ID NO: 297            moltype = DNA   length = 24
FEATURE                   Location/Qualifiers
source                    1..24
                          mol_type = other DNA
                          organism = synthetic construct
SEQUENCE: 297
gagtacatac cacctattcg gggg                                              24

SEQ ID NO: 298            moltype = DNA   length = 23
FEATURE                   Location/Qualifiers
source                    1..23
                          mol_type = genomic DNA
                          organism = Cricetulus sp.
SEQUENCE: 298
gccccgggcg aggacgatcc cgg                                               23

SEQ ID NO: 299            moltype = DNA   length = 24
FEATURE                   Location/Qualifiers
source                    1..24
                          mol_type = other DNA
                          organism = synthetic construct
SEQUENCE: 299
gccccgggcg aggacgaatc ccgg                                              24

SEQ ID NO: 300            moltype =       length =
SEQUENCE: 300
000

SEQ ID NO: 301            moltype = DNA   length = 23
FEATURE                   Location/Qualifiers
source                    1..23
                          mol_type = genomic DNA
                          organism = Cricetulus sp.
SEQUENCE: 301
gctatagatt cagagtatgc cgg                                               23

SEQ ID NO: 302            moltype = DNA   length = 24
FEATURE                   Location/Qualifiers
source                    1..24
                          mol_type = other DNA
                          organism = synthetic construct
SEQUENCE: 302
gctatagatt cagagtaatg ccgg                                              24

SEQ ID NO: 303            moltype = DNA   length = 23
FEATURE                   Location/Qualifiers
source                    1..23
                          mol_type = genomic DNA
                          organism = Cricetulus sp.
SEQUENCE: 303
gctgctgggc tgcggaaacg cgg                                               23

SEQ ID NO: 304            moltype = DNA   length = 24
FEATURE                   Location/Qualifiers
source                    1..24
                          mol_type = other DNA
                          organism = synthetic construct
SEQUENCE: 304
gctgctgggc tgcggaaaac gcgg                                              24

SEQ ID NO: 305            moltype = DNA   length = 22
FEATURE                   Location/Qualifiers
source                    1..22
                          mol_type = genomic DNA
                          organism = Cricetulus sp.
SEQUENCE: 305
ctgctgggct gcggaaacgc gg                                                22

SEQ ID NO: 306            moltype = DNA   length = 24
FEATURE                   Location/Qualifiers
source                    1..24
                          mol_type = other DNA
                          organism = synthetic construct
SEQUENCE: 306
gctgctgggc tgcggaaaac gcgg                                              24

SEQ ID NO: 307            moltype = DNA   length = 23
FEATURE                   Location/Qualifiers
source                    1..23
```

```
                            mol_type = genomic DNA
                            organism = Cricetulus sp.
SEQUENCE: 307
ggtcgaagtg ggccgactca ggg                                            23

SEQ ID NO: 308              moltype = DNA   length = 24
FEATURE                     Location/Qualifiers
source                      1..24
                            mol_type = other DNA
                            organism = synthetic construct
SEQUENCE: 308
ggtcgaagtg ggccgacctc aggg                                           24

SEQ ID NO: 309              moltype = DNA   length = 23
FEATURE                     Location/Qualifiers
source                      1..23
                            mol_type = genomic DNA
                            organism = Cricetulus sp.
SEQUENCE: 309
ggagttgtga tcattgtgag cgg                                            23

SEQ ID NO: 310              moltype = DNA   length = 24
FEATURE                     Location/Qualifiers
source                      1..24
                            mol_type = other DNA
                            organism = synthetic construct
SEQUENCE: 310
ggagttgtga tcattgttga gcgg                                           24

SEQ ID NO: 311              moltype = DNA   length = 23
FEATURE                     Location/Qualifiers
source                      1..23
                            mol_type = genomic DNA
                            organism = Cricetulus sp.
SEQUENCE: 311
gtcacattca tcgcatcgag ggg                                            23

SEQ ID NO: 312              moltype = DNA   length = 24
FEATURE                     Location/Qualifiers
source                      1..24
                            mol_type = other DNA
                            organism = synthetic construct
SEQUENCE: 312
gtcacattca tcgcatccga gggg                                           24

SEQ ID NO: 313              moltype = DNA   length = 23
FEATURE                     Location/Qualifiers
source                      1..23
                            mol_type = genomic DNA
                            organism = Cricetulus sp.
SEQUENCE: 313
ggtcgaagtg ggccgactca ggg                                            23

SEQ ID NO: 314              moltype = DNA   length = 24
FEATURE                     Location/Qualifiers
source                      1..24
                            mol_type = other DNA
                            organism = synthetic construct
SEQUENCE: 314
ggtcgaagtg ggccgacctc aggg                                           24

SEQ ID NO: 315              moltype = DNA   length = 23
FEATURE                     Location/Qualifiers
source                      1..23
                            mol_type = genomic DNA
                            organism = Cricetulus sp.
SEQUENCE: 315
ggagttgtga tcattgtgag cgg                                            23

SEQ ID NO: 316              moltype = DNA   length = 24
FEATURE                     Location/Qualifiers
source                      1..24
                            mol_type = other DNA
                            organism = synthetic construct
SEQUENCE: 316
ggagttgtga tcattgttga gcgg                                           24

SEQ ID NO: 317              moltype = DNA   length = 23
FEATURE                     Location/Qualifiers
```

```
source                  1..23
                        mol_type = genomic DNA
                        organism = Cricetulus sp.
SEQUENCE: 317
gtcacattca tcgcatcgag ggg                                           23

SEQ ID NO: 318          moltype = DNA  length = 24
FEATURE                 Location/Qualifiers
source                  1..24
                        mol_type = other DNA
                        organism = synthetic construct
SEQUENCE: 318
gtcacattca tcgcatccga gggg                                          24

SEQ ID NO: 319          moltype = DNA  length = 23
FEATURE                 Location/Qualifiers
source                  1..23
                        mol_type = genomic DNA
                        organism = Cricetulus sp.
SEQUENCE: 319
gatccgtcca caaccttggc tgg                                           23

SEQ ID NO: 320          moltype = DNA  length = 24
FEATURE                 Location/Qualifiers
source                  1..24
                        mol_type = other DNA
                        organism = synthetic construct
SEQUENCE: 320
gatccgtcca caacctttgg ctgg                                          24

SEQ ID NO: 321          moltype = DNA  length = 23
FEATURE                 Location/Qualifiers
source                  1..23
                        mol_type = genomic DNA
                        organism = Cricetulus sp.
SEQUENCE: 321
gtcacattca tcgcatcgag ggg                                           23

SEQ ID NO: 322          moltype = DNA  length = 24
FEATURE                 Location/Qualifiers
source                  1..24
                        mol_type = other DNA
                        organism = synthetic construct
SEQUENCE: 322
gtcacattca tcgcatccga gggg                                          24

SEQ ID NO: 323          moltype = DNA  length = 23
FEATURE                 Location/Qualifiers
source                  1..23
                        mol_type = genomic DNA
                        organism = Cricetulus sp.
SEQUENCE: 323
gctgctgggc tgcggaaacg cgg                                           23

SEQ ID NO: 324          moltype = DNA  length = 22
FEATURE                 Location/Qualifiers
source                  1..22
                        mol_type = other DNA
                        organism = synthetic construct
SEQUENCE: 324
gctgctgggc tgcggaacgc gg                                            22

SEQ ID NO: 325          moltype = DNA  length = 23
FEATURE                 Location/Qualifiers
source                  1..23
                        mol_type = genomic DNA
                        organism = Cricetulus sp.
SEQUENCE: 325
gctgctgggc tgcggaaacg cgg                                           23

SEQ ID NO: 326          moltype = DNA  length = 23
FEATURE                 Location/Qualifiers
source                  1..23
                        mol_type = other DNA
                        organism = synthetic construct
SEQUENCE: 326
ctgctgggct gcggaacacg cgg                                           23

SEQ ID NO: 327          moltype = DNA  length = 23
```

```
FEATURE                 Location/Qualifiers
source                  1..23
                        mol_type = genomic DNA
                        organism = Cricetulus sp.
SEQUENCE: 327
gaggggtcg caggcacacg ggg                                              23

SEQ ID NO: 328          moltype = DNA   length = 24
FEATURE                 Location/Qualifiers
source                  1..24
                        mol_type = other DNA
                        organism = synthetic construct
SEQUENCE: 328
gaggggtcg caggcaccac gggg                                             24

SEQ ID NO: 329          moltype = DNA   length = 23
FEATURE                 Location/Qualifiers
source                  1..23
                        mol_type = genomic DNA
                        organism = Cricetulus sp.
SEQUENCE: 329
gaggggtcg caggcacacg ggg                                              23

SEQ ID NO: 330          moltype = DNA   length = 24
FEATURE                 Location/Qualifiers
source                  1..24
                        mol_type = other DNA
                        organism = synthetic construct
SEQUENCE: 330
gaggggtcg caggcaccac gggg                                             24

SEQ ID NO: 331          moltype = DNA   length = 23
FEATURE                 Location/Qualifiers
source                  1..23
                        mol_type = genomic DNA
                        organism = Cricetulus sp.
SEQUENCE: 331
gagcagacat ttgaaagcag tgg                                             23

SEQ ID NO: 332          moltype = DNA   length = 16
FEATURE                 Location/Qualifiers
source                  1..16
                        mol_type = other DNA
                        organism = synthetic construct
SEQUENCE: 332
gagcagacat cagtgg                                                     16

SEQ ID NO: 333          moltype = DNA   length = 21
FEATURE                 Location/Qualifiers
source                  1..21
                        mol_type = other DNA
                        organism = synthetic construct
SEQUENCE: 333
gagcagacat ttgatttgtg g                                               21

SEQ ID NO: 334          moltype = DNA   length = 23
FEATURE                 Location/Qualifiers
source                  1..23
                        mol_type = genomic DNA
                        organism = Cricetulus sp.
SEQUENCE: 334
gaggggtcg caggcacacg ggg                                              23

SEQ ID NO: 335          moltype = DNA   length = 24
FEATURE                 Location/Qualifiers
source                  1..24
                        mol_type = other DNA
                        organism = synthetic construct
SEQUENCE: 335
gaggggtcg caggcaccac gggg                                             24

SEQ ID NO: 336          moltype = DNA   length = 23
FEATURE                 Location/Qualifiers
source                  1..23
                        mol_type = genomic DNA
                        organism = Cricetulus sp.
SEQUENCE: 336
gtcacattca tcgcatcgag ggg                                             23
```

```
SEQ ID NO: 337         moltype = DNA  length = 24
FEATURE                Location/Qualifiers
source                 1..24
                       mol_type = other DNA
                       organism = synthetic construct
SEQUENCE: 337
gtcacattca tcgcatccga gggg                                          24

SEQ ID NO: 338         moltype = DNA  length = 23
FEATURE                Location/Qualifiers
source                 1..23
                       mol_type = genomic DNA
                       organism = Cricetulus sp.
SEQUENCE: 338
gaggggtcg caggcacacg ggg                                            23

SEQ ID NO: 339         moltype = DNA  length = 24
FEATURE                Location/Qualifiers
source                 1..24
                       mol_type = other DNA
                       organism = synthetic construct
SEQUENCE: 339
gaggggtcg caggcaccac gggg                                           24

SEQ ID NO: 340         moltype = DNA  length = 23
FEATURE                Location/Qualifiers
source                 1..23
                       mol_type = genomic DNA
                       organism = Cricetulus sp.
SEQUENCE: 340
gtcacattca tcgcatcgag ggg                                           23

SEQ ID NO: 341         moltype = DNA  length = 24
FEATURE                Location/Qualifiers
source                 1..24
                       mol_type = other DNA
                       organism = synthetic construct
SEQUENCE: 341
gtcacattca tcgcatccga gggg                                          24

SEQ ID NO: 342         moltype = DNA  length = 23
FEATURE                Location/Qualifiers
source                 1..23
                       mol_type = genomic DNA
                       organism = Cricetulus sp.
SEQUENCE: 342
gagtgaagcc tcgatcgggt tgg                                           23

SEQ ID NO: 343         moltype = DNA  length = 19
FEATURE                Location/Qualifiers
source                 1..19
                       mol_type = other DNA
                       organism = synthetic construct
SEQUENCE: 343
gagtgaagcc tcgggttgg                                                19

SEQ ID NO: 344         moltype = DNA  length = 23
FEATURE                Location/Qualifiers
source                 1..23
                       mol_type = genomic DNA
                       organism = Cricetulus sp.
SEQUENCE: 344
gcccagagaa agcgtcgtcg agg                                           23

SEQ ID NO: 345         moltype = DNA  length = 22
FEATURE                Location/Qualifiers
source                 1..22
                       mol_type = other DNA
                       organism = synthetic construct
SEQUENCE: 345
gcccagagaa agcgtcgcga gg                                            22

SEQ ID NO: 346         moltype = DNA  length = 23
FEATURE                Location/Qualifiers
source                 1..23
                       mol_type = genomic DNA
                       organism = Cricetulus sp.
SEQUENCE: 346
gtcacattca tcgcatcgag ggg                                           23
```

```
SEQ ID NO: 347         moltype = DNA  length = 24
FEATURE                Location/Qualifiers
source                 1..24
                       mol_type = other DNA
                       organism = synthetic construct
SEQUENCE: 347
gtcacattca tcgcatccga gggg                                              24

SEQ ID NO: 348         moltype = DNA  length = 23
FEATURE                Location/Qualifiers
source                 1..23
                       mol_type = genomic DNA
                       organism = Cricetulus sp.
SEQUENCE: 348
gcgaccggta ccgcagcgtt agg                                               23

SEQ ID NO: 349         moltype = DNA  length = 24
FEATURE                Location/Qualifiers
source                 1..24
                       mol_type = other DNA
                       organism = synthetic construct
SEQUENCE: 349
gcgaccggta ccgcagccgt tagg                                              24

SEQ ID NO: 350         moltype = DNA  length = 23
FEATURE                Location/Qualifiers
source                 1..23
                       mol_type = genomic DNA
                       organism = Cricetulus sp.
SEQUENCE: 350
gtcacattca tcgcatcgag ggg                                               23

SEQ ID NO: 351         moltype = DNA  length = 24
FEATURE                Location/Qualifiers
source                 1..24
                       mol_type = other DNA
                       organism = synthetic construct
SEQUENCE: 351
gtcacattca tcgcatccga gggg                                              24
```

LYSOSOMAL ENZYMES MODIFIED BY CELL BASED GLYCOENGINEERING

CROSS-REFERENCE

This application is a Continuation Application of U.S. patent application Ser. No. 17/272,178, filed Feb. 26, 2021, which is a U.S. national phase application of International PCT Application No. PCT/US2019/048854, filed Aug. 29, 2019, which claims priority to U.S. Provisional Application No. 62/724,543, filed Aug. 29, 2018, which are incorporated by reference herein in their entireties.

STATEMENT REGARDING SEQUENCE LISTING

The Sequence Listing associated with this application is provided in XML format in lieu of a paper copy, and is hereby incorporated by reference into the specification. The name of the XML file containing the Sequence Listing is SEQ_LST-P78976con1_ST26.xml. The XML file is 303 KB, was created on Jun. 22, 2023, and is being submitted electronically via Patent Center.

FIELD OF THE INVENTION

The present disclosure relates to modified lysosomal enzymes, compositions comprising a modified lysosomal enzyme and cell based methods for producing a modified lysosomal enzyme. Furthermore, use of a modified lysosomal enzyme in therapy such as in treatment of a lysosomal storage disease is disclosed.

Also disclosed are cell based glyco-engineering method for modifying serum half-life (pharmacokinetics) and tissue distribution of a lysosomal alpha-galactosidase enzyme (GLA), wherein the enzyme has low M6P and high sialic acid capping of alpha2,3 type.

Also disclosed are methods for the treatment of lysosomal storage disease in mammals wherein the mammal is administered a therapeutically effective amount of isolated, glyco-optimized recombinant lysosomal enzyme whereby said storage disease is relieved in difficult-to-reach organs

BACKGROUND OF THE INVENTION

Lysosomal Storage Diseases (LSDs)

The lysosomal compartment functions as a catabolic machinery that degrades waste material in cells. The degradation involves a number of hydrolases and transporters specifically localized to the lysosome.

Lysosomal storage diseases are inherited metabolic diseases mainly caused by lack of a specific lysosomal hydrolase activity resulting in build-up of substrate in the cells and eventually pathological symptoms in one or more organs. There are around 50 identified lysosomal storage diseases including, e.g., Gaucher and Fabry diseases, where a link has been established between disease and mutations in genes coding for lysosomal proteins. How the accumulated storage material cause pathology is not fully understood and varies from one disease to the other.

Enzyme Replacement Therapy (ERT)

Excess storage can be reduced by administration of a lysosomal enzyme from a heterologous source. ERT's addressing all severe symptoms of Gaucher, Fabry disease or any other LSD are not available. The major limitations of ERT is lack of penetrance of the enzyme to key pathological sites or difficult-to-reach organs (for example kidney, heart, brain), leaving a large segment of LSD patients without any treatment options for their most severe symptoms.

It is well established that intravenous administration of a lysosomal enzyme results in its rapid uptake by cells via a mechanism called receptor mediated endocytosis. This endocytosis is mediated by receptors on the cell surface, and in particular the two mannose-6 phosphate receptors (M6PRs) and the mannose receptor (MR) have been shown to be pivotal for uptake of most lysosomal enzymes (Grubb 2010). The M6PR recognize phosphorylated oligomannose glycans which are characteristic for lysosomal proteins. Based on the principle of receptor mediated endocytosis, enzyme replacement therapies (ERT) are today available for a number of LSDs, including Gaucher type I, Fabry, Pompe, Wolman, Neuronal Ceroid Lipofuscinosis, and the Mucopolysaccharidosis type I, II, IVA, VI and VII diseases. These therapies are efficacious in reducing lysosomal storage in various peripheral organs and thereby ameliorate some symptoms related to the pathology. A majority of the LSDs however cause lysosomal storage in organs that are difficult to reach via the receptor mediated endocytic route, such difficult-to-reach organs include central nervous system (CNS), heart, kidney and muscle, and consequently many patients present a repertoire of serious signs and symptoms that cannot be adequately addressed with current treatments. A major drawback with intravenously administered ERT's is the poor distribution to the difficult-to-reach organs. The CNS for example is protected from exposure to blood borne compounds by the blood-brain-barrier, formed by the CNS endothelium, and since 70% of LSD's present as progressive neurodegenerative diseases (Platt 2018) many LSD patients will eventually face mental deterioration, often associated with poor/short life expectancy. For Fabry disease the current GLA enzyme treatment options does not effectively alleviate symptoms in kidney and heart and patients inevitably presents progressively severe symptoms in those organs (Desnick 2012).

Thus, the lysosomal replacement enzyme treatments available in the art have therapeutic deficiencies that differ among diseases, but in general there is insufficient or no enzyme delivery to all necessary sites of pathology; inability of the therapeutic enzyme to reach certain sanctuary sites in periphery nor pass blood-brain barrier, which causes increasingly severe CNS symptoms for most of the lysosomal diseases (Kishnani 2015, Platt 2018). Moreover, many current lysosomal replacement enzymes have very short circulation half-life. Thus there is need for ERT's with improved biodistribution and systems for screening and identifying such improved enzymes and for bringing such enzymes to benefit of patients cost-effective mammalian production systems are needed.

The present invention provides recombinant lysosomal enzymes, produced in glycoengineered mammalian cells, with modified glycostructures. The recombinant lysosomal enzymes comprise one or more glycans that have been modified compared to the glycans of the lysosomal enzyme naturally produced in humans or in standard mammalian cells and the resultant enzymes have various improved properties including, e.g., improved circulation time and/or improved targeting to hard-to-reach organs, such as kidney, heart, muscle or brain.

Glycosylation of Lysosomal Enzymes

In general, N-glycosylations can occur at a Asn-X-Ser/Thr sequence motif. To this motif the initial dolichol-linked oligosaccharide precursor is transferred by the glycosyltransferase oligosaccharyltransferase, within the lumen of the ER. This common basis for all N-linked glycans is made up of 14 residues; 3 glucose, 9 mannose, and 2 N-acetylglucosamine (FIG. 1). This ancestor is then converted into three general types of N-glycans: oligomannose, complex and hybrid, by the actions of a multitude of enzymes that both trim down the initial precursor and add new sugar moieties. Each mature N-glycan contains the common core Man(Man)2-GlcNAc-GlcNAc-Asn, where Asn is the attachment point to the protein. In addition, proteins directed to the lysosome carry one or more N-glycans which are phosphorylated. The phosphorylation occurs in the Golgi and is initiated by the addition of N-acetylglucosamine-1-phosphate to C-6 of mannose residues of oligomannose type N-glycans, a process catalyzed by the phospho-transferase complex comprising GNPTG and GNPTAB proteins (FIG. 1). The N-Acetylglucosamine is cleaved off to generate exposed Mannose-6-phospate (Man6P) residues, which are recognized by M6PRs and will facilitate the transport of the lysosomal protein to the lysosome. The resulting N-glycan is then trimmed to the point where the Man6P is the terminal group of the N-glycan chain. (Essentials of Glycobiology. $3^{rd}$ edition. Varki A, Cummings R D, Esko J D, et al, editors. Cold Spring Harbor (NY): Cold Spring Harbor Laboratory Press; 2017). The binding site of the M6PR requires a terminal Man6P group that is complete, as both the sugar moiety and the phosphate group is involved in the binding to the receptor (Kim 2009). The binding of Man6P tagged enzyme to cell based M6PRs has been considered critical for cellular uptake and subsequent pharmaceutical effect of nearly all ERT's from circulation after exogenous administration via iv route (Grubb 2010). Accordingly, typical strategies for producing ERT focus on ensuring high mannose or mannose-6 phosphate content.

The need for glycosylation on ERT's makes mammalian cells the preferred production platform, in particular the Chinese hamster ovary (CHO) cells are used extensively for production. However, use of yeast and plant cell systems have been utilized to enhance Man6P and/or exposed Man content of lysosomal enzymes in order to increase uptake by MR and M6PR. Mammalian cells such as CHO cells produce heterogeneous glycosylation of lysosomal enzymes contained variable degrees of Man6P and/or exposed Man content and complex N-glycans with sialic acids.

SUMMARY OF THE INVENTION

In some embodiments, the present disclosure relates to lysosomal enzymes produced in glycoengineered mammalian cells, wherein one or more glycans have been modified compared to glycans of the lysosomal enzyme produced in man or standard mammalian cells.

An object of the present invention is to use engineered mammalian cell lines with different glycosylation capacities to produce lysosomal enzymes with glycostructures that prolong serum half-life and/or change tissue targeting of the enzyme in mammals and thus improve efficacy of the enzyme for treating human disease.

An object of the present invention relates to use of mammalian cells with modified glycosylation capacities for producing lysosomal enzymes with improved biodistribution and efficacy for treating human disease.

An object of the present invention relates to methods to produce lysosomal enzymes without M6P and/or without high-Man content and with sialic acid capped N-glycans.

An object of the present invention relates to methods to produce lysosomal enzymes without M6P and/or without high-Man content and with alpha2-3 linked sialic acid capped N-glycans.

An object of the present invention relates to use of lysosomal enzymes without M6P and/or without high-Man content and with sialic acid capped N-glycans.

An object of the present invention relates to use of lysosomal enzymes without M6P and/or without high-Man content and with alpha2-3 linked sialic acid capped N-glycans.

In one embodiment, the present disclosure provides a modified recombinant lysosomal enzyme with increased circulation time in plasma as compared to an unmodified version of the same, said enzyme being produced in a mammalian cell line with modified glycosylation capacity due to altered expression of one or more genes involved in glycosylation. In some embodiments, the modified recombinant lysosomal enzyme comprises less than 10% mannose-6-phosphate (Man6P) and less than 0.3 mole exposed mannose (Man) per mole of enzyme. In some embodiments, the modified recombinant lysosomal enzyme comprises more than 4 mol sialic acid (SA) per mol of enzyme. In some embodiments, the modified recombinant lysosomal enzyme comprises more than 4 mol alpha2,3SA per mol of enzyme. In some embodiments, the modified recombinant lysosomal enzyme comprises more than 4.5 mol alpha2,3SA per mol of enzyme. In some embodiments, the modified recombinant lysosomal enzyme comprises more than 4 mol alpha2,3SA per mol of enzyme and less than 1 mol alpha2,6SA. In some embodiments, the modified recombinant lysosomal enzyme comprises homogeneous N glycans:
  a) with alpha2,3SA capping,
  b) without alpha2,3SA capping,
  c) with alpha2,6SA capping,
  d) without alpha2,6SA capping,
  e) with <0.3 mol Man6P per mole of enzyme, and
  h) with <0.1 mol Man6P per mole of enzyme.

In some embodiments, the mammalian cells are engineered to produce modified recombinant lysosomal enzyme with high 2,3 sialic acid capping. In some embodiments, the mammalian cells are engineered to produce modified recombinant lysosomal enzyme with biantennary N-glycan structures, tri-antennary N-glycan structures, and/or tetra-antennary, N-glycan structures. In some embodiments, the mammalian cells are engineered to produce modified recombinant lysosomal enzyme containing greater than 90% homogeneity for biantennary N-glycan structures. In some embodiments, the mammalian cells are engineered to produce modified recombinant lysosomal enzyme containing greater than 90% homogeneity for tri or tetra-antennary N-glycan structures. In some embodiments, the mammalian cells are engineered to produce modified recombinant lysosomal enzyme containing greater than 90% homogeneity for tetra-antennary N-glycan structures. In some embodiments, the modified recombinant lysosomal enzyme is selected from Aspartylglucoaminidase (AGA), Alpha-Galactosidase A (GLA), Acid ceramidase, Acid alpha-L-fucosidase, Protective protein/Cathepsin A, Acid beta-glucosidase, or glucocerebrosidase (GBA), Acid beta-galactosidase, Iduronate-2-sulfatase (IDS), Alpha-L-Iduronidase (IDUA), Galactocerebrosidase/galactosylceramidase (GALC), Acid alpha-mannosidase, Acid beta-mannosidase, Arylsulfatase B, Arylsulfatase A, Acid beta-galactosidase, N-Acetylglucosamine-1-phosphotransferase, and Lysosomal alpha-glucosidase (GAA). In some embodiments, the modified recombinant lysosomal enzyme is selected from GLA, GBA, GUS, and GAA. In some embodiments, the modified recombinant lysosomal enzyme is GLA. In some embodiments, the modified recombinant lysosomal enzyme is GBA. In some embodiments, the mammalian cells are engineered to produce modified recombinant lysosomal enzyme with no M6P, high 2,3SA, and, optionally, a biantennary, triantennary, or tetra antennary N glycan structure. In some embodiments, the modified recombinant lysosomal enzyme comprises lowered mannose-6-phosphate (M6P) tagging of N-glycans as compared to a similar unmodified recombinant lysosomal enzyme. In some embodiments, the modified recombinant lysosomal enzyme comprises increased glycosylation homogeneity as compared to a similar unmodified recombinant lysosomal enzyme. In some embodiments, the modified recombinant lysosomal enzyme comprises any glycosylation pattern that is without fucose. In some embodiments, the glycoengineered mammalian host cell comprises one or more inactivation of an endogenous glycogene and/or one or more introduction of an exogenous glycogene, wherein said glycogenes are selected from the group consisting of GNPTAB, GNPTG, NAGPA, ALG3, ALG5, ALG6, ALG8, ALG9, ALG10, ALG12, Mannosidases, MAN1A1, MAN1A2, MAN1B1, MAN1C1, MAN2A1, MAN2A2, MOGS, GANAB, MGAT1, MGAT2 and Sialyl transferases. In some embodiments, the glycoengineered mammalian host cell comprises one or more inactivation of an endogenous glycogene and/or one or more introduction of an exogenous glycogene, wherein the endogenous glycogene is one or more of St3gal4 and St3gal6. In some embodiments, the glycoengineered mammalian host cell comprises a knockout of GNPTAB and/or GNPTG. In some embodiments, the glycoengineered mammalian host cell comprises a knock-in of St3gal4 and/or St3gal6. In some embodiments, the glycoengineered mammalian host cell comprises a knockout of Mgat4b and/or Mgat5. In some embodiments, the glycoengineered mammalian host cell comprises a knockout of GNPTG and/or GNPTAB and a knock-in of St3gal4 and/or St3gal6. In some embodiments, the mammalian cells comprise a knockout of one or more of GNPTG, GNPTAB, Mgat4b, Mgat5 and a knock-in of one or more of St3gal4 and St3gal6. In some embodiments, the mammalian cells comprise a knockout of GNPTG, GNPTAB, Mgat4b, Mgat5 and a knock-in of St3gal4. In some embodiments, the cell is selected from the group consisting of CHO, HEK293, NS0, SP2/0, YB2/0, HUVEC, HKB, PER-C6, NS0, or derivatives of any of these cells. In some embodiments, the cell is a CHO cell or derivative thereof, wherein optionally the cell is a CHO cell derivative selected from CHO-K1, CHO DXB11, CHO-S, CHO-DG44 and CHO-GS.

In one embodiment, the present disclosure provides a modified recombinant lysosomal enzyme produced by a glycoengineered mammalian host cell, said enzyme comprising increased circulation time in plasma as compared to an unmodified version of the same enzyme, wherein said increased circulation time is due to the carbohydrate moieties added to the modified recombinant lysosomal enzyme by one or more glycosyltransferase enzyme expressed in the glycoengineered mammalian host, wherein the carbohydrate moieties reduce binding of the enzyme to mannose receptors and/or mannose 6-phosphate receptors, and wherein the modified recombinant lysosomal enzyme retains enzymatic activity. In some embodiments, the mammalian cells are engineered to produce modified recombinant lysosomal enzyme with high 2,3 sialic acid capping. In some embodiments, the mammalian cells are engineered to produce modified recombinant lysosomal enzyme with biantennary N-glycan structures, tri-antennary N-glycan structures, and/or tetra-antennary, N-glycan structures. In some embodiments, the mammalian cells are engineered to produce modified recombinant lysosomal enzyme containing greater than 90% homogeneity for biantennary N-glycan structures. In some embodiments, the mammalian cells are engineered to produce modified recombinant lysosomal enzyme containing greater than 90% homogeneity for tri or tetra-antennary N-glycan structures. In some embodiments, the mammalian cells are engineered to produce modified recombinant lysosomal enzyme containing greater than 90% homogeneity for tetra-antennary N-glycan structures. In some embodiments, the modified recombinant lysosomal enzyme is selected from Aspartylglucoaminidase (AGA), Alpha-Galactosidase A (GLA), Acid ceramidase, Acid alpha-L-fucosidase, Protective protein/Cathepsin A, Acid beta-glucosidase, or glucocerebrosidase (GBA), Acid beta-galactosidase, Iduronate-2-sulfatase (IDS), Alpha-L-Iduronidase (IDUA), Galactocerebrosidase/galactosylceramidase (GALC), Acid alpha-mannosidase, Acid beta-mannosidase, Arylsulfatase B, Arylsulfatase A, Acid beta-galactosidase, N-Acetylglucosamine-1-phosphotransferase, and Lysosomal alpha-glucosidase (GAA). In some embodiments, the modified recombinant lysosomal enzyme is selected from GLA, GBA, GUS, and GAA. In some embodiments, the modified recombinant lysosomal enzyme is GLA. In some embodiments, the modified recombinant lysosomal enzyme is GBA. In some embodiments, the mammalian cells are engineered to produce modified recombinant lysosomal enzyme with no M6P, high 2,3SA, and, optionally, a biantennary, triantennary, or tetra antennary N glycan structure. In some embodiments, the modified recombinant lysosomal enzyme comprises lowered mannose-6-phosphate (M6P) tagging of N-glycans as compared to a similar unmodified recombinant lysosomal enzyme. In some embodiments, the modified recombinant lysosomal enzyme comprises increased glycosylation homogeneity as compared to a similar unmodified recombinant lysosomal enzyme. In some embodiments, the modified recombinant lysosomal enzyme comprises any glycosylation pattern that is without fucose. In some embodiments, the glycoengineered mammalian host cell comprises one or more inactivation of an endogenous glycogene and/or one or more introduction of an exogenous glycogene, wherein said glycogenes are selected from the group consisting of GNPTAB, GNPTG, NAGPA, ALG3, ALG5, ALG6, ALG8, ALG9, ALG10, ALG12, Mannosidases, MAN1A1, MAN1A2, MAN1B1, MAN1C1, MAN2A1, MAN2A2, MOGS, GANAB, MGAT1, MGAT2 and Sialyl transferases. In some embodiments, the glycoengineered mammalian host cell comprises one or more inactivation of an endogenous glycogene and/or one or more introduction of an exogenous glycogene, wherein the endogenous glycogene is one or more of St3gal4 and St3gal6. In some embodiments, the glycoengineered mammalian host cell comprises a knockout of GNPTAB and/or GNPTG. In some embodiments, the glycoengineered mammalian host cell comprises a knock-in of St3gal4 and/or St3gal6. In some embodiments, the glycoengineered mammalian host cell comprises a knockout of Mgat4b and/or Mgat5. In some embodiments, the glycoengineered mammalian host cell comprises a knockout of GNPTG and/or GNPTAB and a knock-in of St3gal4 and/or St3gal6. In some embodiments, the mammalian cells comprise a knockout of one or more of GNPTG, GNPTAB, Mgat4b, Mgat5 and a knock-in of one or more of St3gal4 and St3gal6. In some embodiments, the mammalian cells comprise a knockout of GNPTG, GNPTAB, Mgat4b, Mgat5 and a knock-in of St3gal4. In some embodiments, the cell is selected from the group consisting of CHO, HEK293, NS0, SP2/0, YB2/0, HUVEC, HKB, PER-C6, NS0, or derivatives of any of these cells. In some embodiments, the cell is a CHO cell or derivative thereof, wherein optionally the cell is a CHO cell derivative selected from CHO-K1, CHO DXB11, CHO-S, CHO-DG44 and CHO-GS.

In one embodiment, the present disclosure provides an engineered mammalian cell line, comprising a knockout of one or both of Gnptg and gnptab. In some embodiments, the engineered mammalian cell line comprises a knock-in of one or both of St3gal4 and St3gal6. In some embodiments, the engineered mammalian cell line comprises a knockout of one or both of Mgat4b and Mgat5. In some embodiments, the engineered mammalian cell line comprises a knockout of one or both of Mgat4b and Mgat5 and a knock-in of one or both of St3gal4 and St3gal6. In some embodiments, the engineered mammalian cell line comprises a knock-in of one or more of St3gal4, St3gal6, Mgat4a, Mgat4b, and Mgat5. In some embodiments, the engineered mammalian cell line comprises a knockout of GNPTG, GNPTAB, Mgat4b, Mgat5 and a knock-in of St3gal4. In some embodiments, the engineered mammalian cell line is selected from the group consisting of CHO, HEK293, NS0, SP2/0, YB2/0, HUVEC, HKB, PER-C6, NS0, or derivatives of any of these cells. In some embodiments, the engineered mammalian cell line is CHO cell or derivative thereof. In some embodiments, the cell line has been engineered to produce glycans with one or more of the following:
  a) with alpha2,3SA capping,
  b) without alpha2,3SA capping,
  c) with alpha2,6SA capping,
  d) without alpha2,6SA capping,
  e) low Man6P (<0.3 mol per mol of enzyme), and
  h) no Man6P (<0.05 mol per mol of enzyme)
In some embodiments, the cell produces a modified lysosomal enzyme. In some embodiments, the cell produces any one of the modified recombinant lysosomal enzymes disclosed herein.

In one embodiment, the present disclosure provides a mammalian cell line that comprises one or more endogenous glycogene inactivated and/or exogenous glycogene introduced said glycogenes selected from the list of GNPTAB, GNPTG, NAGPA, ALG3, ALG5, ALG6, ALG8, ALG9, ALG10, ALG12, Mannosidases, MAN1A1, MAN1A2, MAN1B1, MAN1C1, MAN2A1, MAN2A2, MOGS, GANAB, MGAT1, MGAT2 and Sialyl transferases. In one embodiment, the present disclosure provides a mammalian cell line producing any one or more of the modified recombinant lysosomal enzymes disclosed herein, wherein said cell line has one or more endogenous glycogene inactivated and/or exogenous glycogene introduced said glycogenes selected from the list of GNPTAB, GNPTG, NAGPA, ALG3, ALG5, ALG6, ALG8, ALG9, ALG10, ALG12, Mannosidases, MAN1A1, MAN1A2, MAN1B1, MAN1C1, MAN2A1, MAN2A2, MOGS, GANAB, MGAT1, MGAT2 and Sialyl transferases. In some embodiments, the sialyl transferase comprises one or more of St3gal4 and St3gal6. In some embodiments, the cell comprises an inactivated GNPTAB gene. In some embodiments, the modified recombinant lysosomal enzyme contains increased sialic acids due to the inactivation of said inactivated GNPTAB gene. In some embodiments, one or more cells of the cell line contains an introduction of one or more glycosyltransferase gene selected from the group consisting of MGAT4A, MGAT4B, MGAT5 and MGAT5B. In some embodiments, one or more cells of said cell line contains an inactivation and/or introduction of one or more glycogene selected from the group consisting of ALG3, ALG6, ALG8, ALG9, ALG10, and ALG12. In some embodiments, one or more cells of said cell line contains an inactivation and/or introduction of one or more glycogene selected from the group consisting of MGAT2, MGAT4A, MGAT4B, MGAT5, and MGAT5B. In some embodiments, one or more cells of said cell line contains an inactivation and/or introduction of one or more glycogene selected from the group consisting of FUT8, ST3GAL4/6, ST6GAL1/2. In some embodiments, the mammalian cell is selected from the group consisting of CHO, HEK293, In some embodiments, the cell is a CHO cell or derivative thereof.

In some embodiments, the present disclosure provides a method for producing a lysosomal enzyme in a cell, wherein the lysosomal enzyme comprises a modified glycan profile, and wherein the cell producing the lysosomal enzyme has more than one modification of one or more glycogenes. In one embodiment, the cells have been modified by glycogene knock-out and/or knock-in of an exogenous DNA sequence coding for a glycosyltransferase.

In some embodiments, the present disclosure provides a mammalian cell capable of expressing a lysosomal enzyme, wherein the enzyme comprises one or more of the posttranslational modification patterns:
  a) with alpha2,3SA capping,
  b) without alpha2,3SA capping,
  c) with alpha2,6SA capping,
  d) without alpha2,6SA capping,
  e) with low Man6P (<0.3 mol Man6P per mole of enzyme), or
  h) with no Man6P (<0.05 mol Man6P per mole of enzyme)

In some embodiments, the present disclosure provides a method of producing a modified recombinant enzyme disclosed herein in a cell line according to the present disclosure, wherein the cell line further comprises an expression vector encoding the coding sequence of the recombinant enzyme. In some embodiments, the enzyme is selected from Aspartylglucoaminidase (AGA), Alpha-Galactosidase A (GLA), Acid ceramidase, Acid alpha-L-fucosidase, Protective protein/Cathepsin A, Acid beta-glucosidase, or glucocerebrosidase (GBA), Acid beta-galactosidase, Iduronate-2-sulfatase (IDS), Alpha-L-Iduronidase (IDUA), Galactocerebrosidase/galactosylceramidase (GALC), Acid alpha-mannosidase, Acid beta-mannosidase, Arylsulfatase B, Arylsulfatase A, Acid beta-galactosidase, N-Acetylglucosamine-1-phosphotransferase, and Lysosomal alpha-glucosidase (GAA). In some embodiments, the modified recombinant lysosomal enzyme is selected from GLA, GBA, GUS, and GAA In some embodiments, the modified recombinant lysosomal enzyme is GLA. In some embodiments, the modified recombinant lysosomal enzyme is GBA.

In some embodiments, the present disclosure provides a method of treating a lysosomal storage disorder with the modified recombinant lysosomal enzyme disclosed herein. In some embodiments, the present disclosure provides any one or more of the modified recombinant lysosomal enzyme disclosed herein for use in a therapy. In some embodiments, the enzyme is fused to a non-glycan tag designed to improve blood-brain-barrier passage. In some embodiments, the treatment is of a mammal afflicted with a lysosomal storage disease.

In some embodiments, the present disclosure provides a composition comprising a substantially pure preparation of a modified recombinant lysosomal enzyme disclosed herein. In some embodiments, the composition further comprises one or more pharmaceutically acceptable carrier, excipient, diluent, and/or surfactant. In some embodiments, the composition further comprises a compound that improves the serum stability of the enzyme. In some embodiments, the composition further comprises DGJ.

In some embodiments, the present disclosure provides a method of treating a mammal afflicted with a lysosomal storage disease, comprising administering to the mammal a therapeutically effective amount of a modified lysosomal enzyme, said modified enzyme being selected from:
a) a modified recombinant lysosomal enzyme wherein the enzyme has low mannose-6-phosphate (Man6P) and high sialic acid (SA) capping of alpha2,3 type (alpha2, 3SA);
b) a lysosomal enzyme composition that includes a substantially pure preparation of the modified recombinant lysosomal enzyme of (a), and
c) a modified lysosomal enzyme wherein the modification comprises reduction of M6P content and increase of NeuAc capping of the glycans, whereby the enzyme has reduced its activity with respect to glycan recognition receptors and increased circulatory half-life and better targeting to one or more of the difficult-to-reach organs like brain, kidney, heart and muscle. In some embodiments, the modified recombinant lysosomal enzyme is selected from Aspartylglucoaminidase (AGA), Alpha-Galactosidase A (GLA), Acid ceramidase, Acid alpha-L-fucosidase, Protective protein/Cathepsin A, Acid beta-glucosidase, or glucocerebrosidase (GBA), Acid beta-galactosidase, Iduronate-2-sulfatase (IDS), Alpha-L-Iduronidase (IDUA), Galactocerebrosidase/galactosylceramidase (GALC), Acid alpha-mannosidase, Acid beta-mannosidase, Arylsulfatase B, Arylsulfatase A, Acid beta-galactosidase, N-Acetylglucosamine-1-phosphotransferase, and Lysosomal alpha-glucosidase (GAA). In some embodiments, the modified recombinant lysosomal enzyme is selected from GLA, GBA, GUS, and GAA. In some embodiments, the modified recombinant lysosomal enzyme is GLA. In some embodiments, the modified recombinant lysosomal enzyme is GBA or GUS. In some embodiments, the lysosomal storage disease is selected from Aspartylglucoaminouria (AGU), Fabry, Farber, Fucosidosis, Galactosidosialidosis, Gaucher types 1,2, and 3, G-MI gangliosidosis, Hunter, Hurler-Scheie, Krabbe, Alpha-Mannosidosis (Laman), Beta-Mannosidosis, Maroteaux-Lamy, Metachromatic, Morquio B, Mucolipidosis II/III, and Pompe.

In some embodiments, the present disclosure provides a recombinant CHO cell line comprising a knockout of each of the Gnptab, Gnptg, Mgat4b, and Mgat5 genes and further comprising a knock-in of the ST3gal4 gene, for use in the in vitro production of a recombinant lysosomal enzyme containing homogenous N glycans containing less than 0.3 mol exposed mannose, less than 0.3 mol exposed mannose 6 phosphate, and greater than 4 mol terminal alpha2,3, sialylation per mol of enzyme. In some embodiments, the recombinant lysosomal enzyme has less than 0.5 mol alpha2,6, sialylation per mol of enzyme. In some embodiments, the recombinant lysosomal enzyme has less than 0.1 mol alpha2,6, sialylation per mol of enzyme. In some embodiments, the e recombinant lysosomal enzyme is selected from Aspartylglucoaminidase (AGA), Alpha-Galactosidase A (GLA), Acid ceramidase, Acid alpha-L-fucosidase, Protective protein/Cathepsin A, Acid beta-glucosidase, or glucocerebrosidase (GBA), Acid beta-galactosidase, Iduronate-2-sulfatase (IDS), Alpha-L-Iduronidase (IDUA), Galactocerebrosidase/galactosylceramidase (GALC), Acid alpha-mannosidase, Acid beta-mannosidase, Arylsulfatase B, Arylsulfatase A, Acid beta-galactosidase, N-Acetylglucosamine-1-phosphotransferase, and Lysosomal alpha-glucosidase (GAA). In some embodiments, the recombinant lysosomal enzyme is GLA.

In some embodiments, the present disclosure provides a method for increasing the biodistribution of a recombinant lysosomal enzyme to a difficult to reach organ, wherein the lysosomal enzyme comprises one or more N-glycan, the method comprising glycoengineering the recombinant lysosomal enzyme to homogeneously contain N-glycan structures containing low levels of exposed mannose and/or low levels of exposed mannose-6-phosphate glycans. In some embodiments, the glycoengineering is achieved by producing the recombinant lysosomal enzyme in a mammalian cell comprising one or more inactivation of an endogenous glycogene and/or one or more introduction of an exogenous glycogene. In some embodiments, the method further comprises glycoengineering the recombinant lysosomal enzyme to contain N-glycan structures with high levels of terminal sialylation. In some embodiments, the terminal sialylation is primarily alpha2,3 type. In some embodiments, the N-glycan structures contain less than 5%, less than 1%, or no detectable N-glycan structures with exposed mannose and/or exposed mannose-6-phosphate glycans. In some embodiments, the N-glycan structures contain less than 0.5 mol, less than 0.1 mol, or no detectable alpha2,6 type terminal sialylation per mol of enzyme. In some embodiments, greater than 75% or greater than 90% of the N-glycan structures are biantennary. In some embodiments, greater than 90% of the N-glycan structures are biantennary due to the inactivation of one or more branching enzyme normally expressed in the mammalian cell. In some embodiments, greater than 75% or greater than 90% of the N-glycan structures are tri- or tetra-antennary. In some embodiments, the recombinant lysosomal enzyme exhibits enzyme activity in plasma that is equal to or greater than the enzyme activity of a similar enzyme lacking said glycoengineering. In some embodiments, the recombinant lysosomal enzyme exhibits enzyme activity in a difficult to reach organ that is equal to or greater than the enzyme activity of a similar enzyme lacking said glycoengineering. In some embodiments, the recombinant lysosomal enzyme exhibits a serum half-life that is equal to or greater than the serum half-life of a similar enzyme lacking said glycoengineering. In some embodiments, the recombinant lysosomal enzyme exhibits a blood clearance that is equal to or greater than the blood clearance of a similar enzyme lacking said glycoengineering. In some embodiments, the difficult to reach organ is the heart. In some embodiments, the difficult to reach organ is the kidney. In some embodiments, the difficult to reach organ is the liver.

In some embodiments, the present disclosure provides an unpurified mammalian cell culture supernatant, the cell culture comprising a population of mammalian cells engineered to produce recombinant lysosomal enzyme with a glycosylation pattern that is more homogenous than a glycosylation pattern of the same enzyme when produced in mammalian cells that have not been similarly engineered, wherein the mammalian cells comprise at least a knockout of GNPTAB and GNPTG. In some embodiments, the mammalian cells further comprise a knockout of Mgat4b and/or Mgat5. In some embodiments, the mammalian cells comprise a knock-in of St3gal4. In some embodiments, the mammalian cells comprise a knock-in of St6gal1. In some embodiments, the mammalian cells further comprise a knockout of St3gal4 and/or St3gal6. In some embodiments, the mammalian cells comprise a knockout of one or more of GNPTG, GNPTAB, Mgat4b, Mgat5 and a knock-in of one or more of St3gal4 and St3gal6. In some embodiments, the unpurified mammalian cell culture supernatant comprises recombinant lysosomal enzyme containing substantially homogeneous glycosylation. In some embodiments, the unpurified mammalian cell culture supernatant comprises mammalian cells that are engineered to produce recombinant lysosomal enzyme:
  a) with alpha2,3SA capping,
  b) without alpha2,3SA capping,
  c) with alpha2,6SA capping,
  d) without alpha2,6SA capping,
  e) low Man6P, and
  h) no Man6P (<1%)

In some embodiments, the mammalian cells are engineered to produce recombinant lysosomal enzyme with less than <0.3 mol Man6P per mol of enzyme. In some embodiments, the mammalian cells are engineered to produce recombinant lysosomal enzyme with less than <0.05 mol Man6P per mol of enzyme. In some embodiments, the mammalian cells are engineered to produce recombinant lysosomal enzyme with high 2,3 sialic acid capping. In some embodiments, the mammalian cells are engineered to produce recombinant lysosomal enzyme containing biantennary N-glycan structures, tri-antennary N-glycan structures, and/or tetra-antennary, N-glycan structures. mammalian cells are engineered to produce recombinant lysosomal enzyme containing greater than 90% homogeneity for biantennary N-glycan structures. In some embodiments, the mammalian cells are engineered to produce recombinant lysosomal enzyme containing greater than 90% homogeneity for tri-antennary N-glycan structures. In some embodiments, the mammalian cells are engineered to produce recombinant lysosomal enzyme containing greater than 90% homogeneity for tri-antennary N-glycan structures. In some embodiments, the mammalian cells are selected from the group consisting of CHO, HEK293, NS0, SP2/0, YB2/0, HUVEC, HKB, PER-C6, NS0, or derivatives of any of these In some embodiments, the modified lysosomal enzyme is selected from Aspartylglucoaminidase (AGA), Alpha-Galactosidase A (GLA), Acid ceramidase, Acid alpha-L-fucosidase, Protective protein/Cathepsin A, Acid beta-glucosidase, or glucocerebrosidase (GBA), Acid beta-galactosidase, Iduronate-2-sulfatase (IDS), Alpha-L-Iduronidase (IDUA), Galactocerebrosidase/galactosylceramidase (GALC), Acid alpha-mannosidase, Acid beta-mannosidase, Arylsulfatase B, Arylsulfatase A, Acid beta-galactosidase, N-Acetylglucosamine-1-phosphotransferase, and Lysosomal alpha-glucosidase (GAA). In some embodiments, the modified lysosomal enzyme is selected from GLA, GBA, GUS, and GAA. In some embodiments, the modified lysosomal enzyme is GLA. In some embodiments, the modified lysosomal enzyme is GBA. In some embodiments, the cell culture comprising a population of mammalian cells engineered to produce recombinant lysosomal enzyme with a glycosylation pattern with a high mannose glycosylation content as compared to the same enzyme when produced in mammalian cells that have not been similarly engineered, wherein the mammalian cells comprise at least a knockout of Alg3 or Alg9 and at least a knock-in of GNPTAB. In some embodiments, the unpurified mammalian cell culture supernatant further comprises a knock-in of GNPTG.

In some embodiments, the present disclosure provides a composition comprising a substantially pure preparation of a lysosomal enzyme isolated from an unpurified mammalian cell culture supernatant disclosed herein or comprising a modified recombinant lysosomal enzyme disclosed herein. In some embodiments, the composition further comprises one or more pharmaceutically acceptable carrier, excipient, diluent, and/or surfactant. In some embodiments, the composition further comprises a compound which improves the serum stability of the enzyme. In some embodiments, the composition further comprises DGJ. In some embodiments, the lysosomal enzyme is fused to a non-glycan tag designed to improve blood-brain-barrier passage. In some embodiments, the non-glycan tag is selected from the group consisting of IGF2, Transferrin, Immunoglobin and a fragment or derivative thereof. In some embodiments, the composition further comprises α-Gal A and DGJ or a pharmaceutically acceptable salt thereof. In some embodiments, the composition is formulated for parenteral administration to a subject. In some embodiments, the composition is formulated for administration in an amount of 0.3, 0.5, 1, 2 or 3 mg/kg. In some embodiments, the composition is formulated for administration in an amount of 0.1, 0.3, 0.5, 1, 3, or 10 mg/kg. In some embodiments, the composition is for use in the preparation of a medicament for the treatment of Fabry disease. In some embodiments, the composition is for use in the treatment of Fabry disease. In some embodiments, the composition is for use in the preparation of a medicament for the treatment of a lysosomal storage disease. In some embodiments, the composition is for use in the treatment of a lysosomal storage disease.

BRIEF DESCRIPTION OF THE DRAWINGS

FIG. 3 shows enzyme activity in plasma at various time points after injection of GLA. Fabry mice were injected with 1 mg/kg dose of wt-CHO produced GLA or Fabrazyme via tail vein (n=4 per group, male mice, age 3.5 months). At indicated time points, small amount of blood samples were collected from tail vein and separated plasma was analyzed for GLA activity. Enzyme activities were shown as % of activity at 5 min after injection. Data are expressed as mean±S.D. (n=4). The figure show very similar plasma clearance curves for Fabrazyme and GLA produced in wt-CHO.

FIG. 4 shows tissue distribution of infused enzymes in Fabry mice. Heart (FIG. 4A), kidney (FIG. 4B), liver (FIG. 4D) and spleen (FIG. 4C) were dissected at 4 h after injection from the same mice in FIG. 3. Tissues were homogenized for enzyme assay. Data are expressed as mean±S.D. (n=4). The figure shows similar biodistribution, only significant difference was lower GLA activity level in kidney for GLA produced in wt-CHO versus Fabrazyme.

FIG. 5 shows similar pharmacokinetic experiment as described in FIG. 3. Five glycovariant GLA enzyme samples were compared with Fabrazyme.

FIG. 6 shows similar biodistribution experiment as described in FIG. 4. Tissue distribution of the five glycovariant GLA enzyme samples were compared with Fabrazyme. Heart (FIG. 6A), kidney (FIG. 6C), liver (FIG. 6D) and spleen (FIG. 6B) were dissected at 24 h after injection from the same mice in FIG. 5.

FIG. 7 shows relative distribution of GLA variants into the difficult-to-reach organs heart and kidney. GLA activities per whole organs were calculated. The sum of activities recovered from the 4 organs (FIG. 4) was taken as total activity, and ratio recovered in heart and kidney was calculated. The data shows that compared to Fabrazyme a higher proportion of the GLA-bi23SA reaches heart and kidney and a lower proportion goes to the liver.

FIG. 8 shows the clearance of Gb3 substrate in tissues of Fabry mice. Residual Gb3 contents in liver (FIG. 8A), kidney (FIG. 8B), and heart (FIG. 8C) was analyzed 2 weeks after a single injection of 1 mg/kg of GLA-bi23SA or Fabrazyme into 6 months old female Fabry mice via tail-vein. Data are presented as mean±S.D. (n=5). Statistical significance shown on top of Fabrazyme and GLA-bi23SA-injected groups indicates difference with vehicle alone (saline) treated Fabry mice. $*P<0.05$, $P<0.01$, $*P<0.001$.

FIG. 15 shows an in vivo study of the pharmacokinetics, biodistribution and Gb3 clearance of different GLA glycovariants in Fabry mice. FIG. 15A shows a summary of the glycan features of GLA glycovariants used. The two most abundant N-glycans are illustrated and detailed structures shown in FIG. 17, Panels 1, 6, 55, 52, 59 and 58). FIGS. 15B-15C show time-courses of plasma GLA activities expressed as % of activity at 5 min after injection (n=4 except for Fabrazyme in panel c where n=3). FIGS. 15D-15E show GLA enzyme activity in organs dissected after injection (same groups used as in FIGS. 15B, 15C).

FIG. 18 shows characterization of growth and yield performance of glycoengineered CHO clones expressing GLA. FIG. 18A shows viable cell density and FIG. 18B shows cell viability as determined by Trypan blue exclusion test. Data from day 1-5 are shown as accurate cell counting after day 6 was complicated by tendency for clumping of cells.

FIG. 18C shows yield of GLA enzyme activity determined in culture medium (2.5 µL) by release of p-nitrophenol per hour with a pNP-Gal enzyme assay. The substrate concentration was reduced to 1.2 mM to fit the linear regression of absorbance at 405 nm FIG. 18D shows SDS-PAGE Coomassie analysis of GLA in culture medium (10 µL loaded) after two, five and eight days of culture (D2, D5 and D8, respectively).

FIGS. 20B-20F show MS2 manual annotation of these precursors.

FIG. 21 shows in vitro assays of enzyme specific activity and plasma stability of GLA glycovariants. FIG. 21A shows specific activity of GLA variants assessed by a pNP-Gal enzyme assay. Release of p-nitrophenol per hour was used to show the enzyme activity. Each data point represents the mean of three replicates±SD. FIG. 21B shows in vitro stability of GLA variants (10 μg/ml in mice plasma) heated at 37° C. was measured by the remaining activity. Each data point represents the mean of three replicates±SD.

FIG. 27 shows enzyme activity in balb/c mice injected with 0.75 mg/kg of wild-type enzyme or optimized glycoengineered variant (-opt). For each variant blood samples were drawn at 30 and 120 min for AGA (FIG. 27B), GUSB (FIG. 27C) and Laman (FIG. 27D) enzyme and at 15 and 30 min for GLA (FIG. 27A) enzyme. Optimized enzyme variants are presented as solid boxes and wild-type enzyme is open boxes. The enzyme activity is presented as percent of the initial plasma activity.

DETAILED DISCLOSURE OF THE INVENTION

Figure 1:
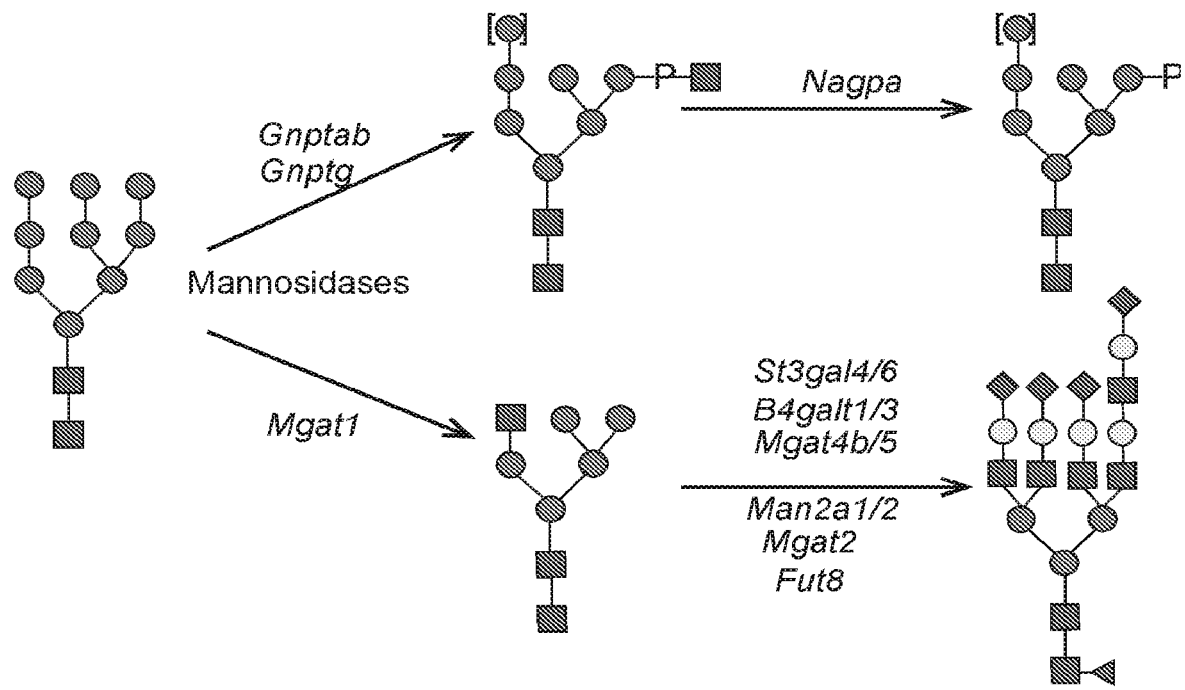
FIG. 1 shows major CHO genes involved in N-glycan processing. The core structure of 9Man and 2GlcNAc is shown on the left and the Man6P containing glycans and complex type glycans are to the top-right and lower-right respectively. Some genes addressed in the current application are in bold (Table 1).

The practice of the present invention will employ, unless indicated specifically to the contrary, conventional methods of molecular biology, recombinant DNA techniques, protein expression, and protein/peptide/carbohydrate chemistry within the skill of the art, many of which are described below for the purpose of illustration. Such techniques are explained fully in the literature. See, e.g., Sambrook, et al., Molecular Cloning: A Laboratory Manual (3rd Edition, 2000); DNA Cloning: A Practical Approach, vol. I & II (D. Glover, ed.); Oligonucleotide Synthesis (N. Gait, ed., 1984); Oligonucleotide Synthesis: Methods and Applications (P. Herdewijn, ed., 2004); Nucleic Acid Hybridization (B. Hames & S. Higgins, eds., 1985); Nucleic Acid Hybridization: Modern Applications (Buzdin and Lukyanov, eds., 2009); Transcription and Translation (B. Hames & S. Higgins, eds., 1984); Animal Cell Culture (R. Freshney, ed., 1986); Freshney, R. I. (2005) Culture of Animal Cells, a Manual of Basic Technique, 5th Ed. Hoboken NJ, John Wiley & Sons; B. Perbal, A Practical Guide to Molecular Cloning (3rd Edition 2010); Farrell, R., RNA Methodologies: A Laboratory Guide for Isolation and Characterization (3rd Edition 2005). Poly(ethylene glycol), Chemistry and Biological Applications, ACS, Washington, 1997; Veronese, F., and J. M. Harris, Eds., Peptide and protein PEGylation, Advanced Drug Delivery Reviews, 54(4) 453-609 (2002); Zalipsky, S., et al., "Use of functionalized Poly(Ethylene Glycols) for modification of polypeptides" in Polyethylene Glycol Chemistry: Biotechnical and Biomedical Applications. The publications discussed above are provided solely for their disclosure before the filing date of the present application. Nothing herein is to be construed as an admission that the invention is not entitled to antedate such disclosure by virtue of prior invention. It is an object of the present invention to provide novel glycoforms for lysosomal enzymes, resulting in modified biodistribution of enzyme replacement therapies and more efficient treatment of lysosomal storage disease.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

Reference to the term "e.g." is intended to mean "e.g., but not limited to" and thus it should be understood that whatever follows is merely an example of a particular embodiment, but should in no way be construed as being a limiting example. Unless otherwise indicated, use of "e.g." is intended to explicitly indicate that other embodiments have been contemplated and are encompassed by the present invention.

Reference throughout this specification to "embodiment" or "one embodiment" or "an embodiment" or "some embodiments" or "certain embodiments" means that a particular feature, structure or characteristic described in connection with the embodiment is included in at least one embodiment of the present invention. Thus, the appearances of the phrases "in one embodiment" or "in an embodiment" or "in certain embodiments" in various places throughout this specification are not necessarily all referring to the same embodiment. Furthermore, the particular features, structures, or characteristics may be combined in any suitable manner in one or more embodiments.

An "increased" or "enhanced" amount is typically a "statistically significant" amount, and may include an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein. Similarly, a "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

"Optional" or "optionally" means that the subsequently described event, or circumstances, may or may not occur and that the description includes instances where said event or circumstance occurs and instances in which it does not.

"Substantially" or "essentially" means nearly totally or completely, for instance, 95% or greater of some given quantity.

A "subject," as used herein, includes any animal that exhibits a symptom, or is at risk for exhibiting a symptom, which can be treated with a composition or method disclosed herein. Suitable subjects (patients) include laboratory animals (such as mouse, rat, rabbit, or guinea pig), farm animals, and domestic animals or pets (such as a cat or dog). Non-human primates and, preferably, human patients, are included.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

"Therapeutic response" refers to improvement of symptoms (whether or not sustained) based on the administration of the therapeutic response (whether or not tolerance is induced).

As used herein, the terms "therapeutically effective amount", "therapeutic dose", is the amount of the drug, e.g., a modified lysosomal enzyme described herein, needed to elicit the desired biological response following administration.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

As used herein, "carrier" includes any and all solvents, dispersion media, vehicles, coatings, diluents, antibacterial and antifungal agents, isotonic and absorption delaying agents, excipients, ionic strength modifiers, surfactants, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc. and are known in the art and discussed in greater detail below.

"Lysosomal Storage Disease" refers to inherited metabolic disorders that result from defects in lysosomal function, usually as a consequence of deficiency of a single lysosomal enzyme.

"Enzyme Replacement Therapy" refers to treatment by administration of exogenous enzyme to compensate for the enzyme activity that is deficient in a given lysosomal storage disease.

The terms "Difficult-to-reach organ" and "hard-to-reach organ" are used interchangeably to refer to organs that are poorly treated with the existing ERT's, including brain, kidney, heart and muscle and/or specific cell types in these organs.

"N-glycosylation" refers to the attachment of the sugar molecule oligosaccharide known as glycan to a nitrogen atom residue of a protein "Sialylation" is the enzymatic addition of a neuraminic acid residue.

"High" sialic acid capping is used herein to refer to more than 4 moles of sialic acid per mole of enzyme. So, for example, a lysosomal enzyme disclosed herein that is said to have "high 2,3 sialic acid capping" is to be understood to be a lysosomal enzyme with more than 4 sialic acid moieties per mole of enzyme, wherein the sialic acid moieties are attached via 2,3, sialyation.

"Neuraminic acid" (or NeuAc) is a 9-carbon monosaccharide, a derivative of a ketononose.

"Biantennary" N-linked glycan is the simplest of the complex N-linked glycans consisting of the N-glycan core (Manα1-6(Manα1-3)Manβ1-4GlcNAcβ1-4GlcNAcβ1-Asn-X-Ser/Thr) elongated with two GlcNAc residues linked to C-2 and of the mannose α1-3 and the mannose α1-6. This core structure can then be elongated or modified by various glycan structures.

"Tri-antennary" N-linked glycans are formed when an additional GlcNAc residue is added to either the C-4 of the core mannose α1-3 or the C-6 of the core mannose α1-6 of the bi-antennary core structure. This structure can then be elongated or modified by various glycan structures.

"Tetra-antennary" N-linked glycans are formed when two additional GlcNAc residues are added to either the C-4 of the core mannose α1-3 or the C-6 of the core mannose α1-6 of the bi-antennary core structure. This core structure can then be elongated or modified by various glycan structures.

"Glycoprofiling" means characterization of glycan structures resident on a biological molecule or cell.

"Glycosyltransferases" are enzymes that catalyze the formation of the glycosidic linkage to form a glycoside. These enzymes utilize 'activated' sugar phosphates as glycosyl donors, and catalyze glycosyl group transfer to a nucleophilic group, usually an alcohol. The product of glycosyl transfer may be an O-, N-, S-, or C-glycoside; the glycoside may be part of a monosaccharide, oligosaccharide, or polysaccharide.

"Glycogenes" includes glycosyltransferases and related glycogenes, wherein related glycogenes comprise any other enzyme acting on glycans to modify their structure. This included but is not limited to phosphotransferase, sulfotransferases, epimerases and deacetylases. In some embodiments the related glycogene is a phosphotransferase or subunit hereof.

"Glycosylation capacity" means the ability to produce an amount of a specific glycan structure by a given cell or a given glycosylation process.

"Modified glycan profile" refers to change in number, type or position of oligosaccharides in glycans on a given lysosomal enzyme.

In some embodiments, the term "mol" is used herein as an abbreviation for "mole" (i.e., the unit of measurement for amount of substance in the International System of Units.

More "homogeneous glycosylation" means that the proportion of identical glycan structures observed by glycoprofiling a given protein expressed in one cell is larger than the proportion of identical glycan structures observed by glycoprofiling the same protein expressed in another cell.

General Glycobiology—Basic glycobiology principles and definitions are described in Varki et al. Essentials of Glycobiology, 3rd edition, 2017.

As used herein, reference to a gene identifier, regardless of whether the gene name is in all caps, lower case, or partial caps, refers to a human form of the gene unless context dictates otherwise. Thus, one skilled in the art will understand that any reference to knocking-out a particular gene will of course refer to knocking-out the endogenously expressed gene in that organism unless explicitly stated otherwise. So, for example, although CHO cell genes are often annotated in the art with the first letter capitalized and all remaining letters in lower case (e.g., St6gal1), whereas the human version of the same is often annotated in all caps (e.g., ST6GAL1), a reference herein to knocking-out "ST6GAL1" in CHO would mean that the endogenous CHO enzyme "St6gal1" was knocked out, even though the capitalization annotation might have suggested a human enzyme was being knocked-out if stringent use of such annotation were adhered to. Similarly, unless stated otherwise herein, reference to knocking-in "St6gal1" means the human form of the gene has been knocked-in—not the CHO version. The sequences of such genes are readily available on publically available databases, e.g., the NCBI database available at the world wide web address: ncbi.nlm.nih.gov/gene/, the content of which is incorporated herein by reference in its entirety."

General DNA and molecular biology tools—Any of various techniques used for separating and recombining segments of DNA or genes, commonly by use of a restriction enzyme to cut a DNA fragment from donor DNA and inserting it into a plasmid or viral DNA. Using these techniques, DNA coding for a protein of interest is recombined/cloned (using PCR and/or restriction enzymes and DNA ligases or ligation independent methods such as USER cloning) into a plasmid (known as an expression vector), which can subsequently be introduced into a cell by transfection using a variety of transfection methods such as calcium phosphate transfection, electroporation, microinjection and liposome transfection. Overview and supplementary information and methods for constructing synthetic DNA sequences, insertion into plasmid vectors and subsequent transfection into cells can be found in Ausubel et al, 2003 and/or Sambrook & Russell, 2001.

"Gene" refers to a DNA region (including exons and introns) encoding a gene product, as well as all DNA regions which regulate the production of the gene product, whether or not such regulatory sequences are adjacent to coding and/or transcribed sequences or situated far away from the gene which function they regulate. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions. For homologous proteins the human and rodent gene names are used interchangeably (e.g. ST3GAL4, St3gal4).

"Targeted gene modifications", "gene editing" or "genome editing" refer to a process by which a specific chromosomal sequence is changed. The edited chromosomal sequence may comprise an insertion of at least one nucleotide, a deletion of at least one nucleotide, and/or a substitution of at least one nucleotide. Generally, genome editing inserts, replaces or removes nucleic acids from a genome using artificially engineered nucleases such as Zinc finger nucleases (ZFNs), Transcription Activator-Like Effector Nucleases (TALENs), the CRISPR/Cas system, and engineered meganuclease re-engineered homing endonucleases. Genome editing principles are broadly used and thus known to person skilled in the art.

"Endogenous" sequence/gene/protein refers to a chromosomal sequence or gene or protein that is native to the cell or originating from within the cell or organism analyzed.

"Exogenous" sequence or gene refers to a chromosomal sequence that is not native to the cell, or a chromosomal sequence whose native chromosomal location is in a different location in a chromosome or originating from outside the cell or organism analyzed.

"Heterologous" refers to an entity that is not native to the cell or species of interest.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide.

The terms "polypeptide" and "protein" are used interchangeably to refer to a polymer of amino acid residues. These terms may also refer to glycosylated variants of the "polypeptide" or "protein", also termed "glycoprotein." "Polypeptide", "protein" and "glycoprotein" is used interchangeably throughout this disclosure.

The term "recombination" refers to a process of exchange of genetic information between two polynucleotides. For the purposes of this disclosure, "homologous recombination" refers to the specialized form of such exchange that takes place, for example, during repair of double-strand breaks in cells. This process requires sequence similarity between the two polynucleotides, uses a "donor" or "exchange" molecule to template repair of a "target" molecule (i.e., the one that experienced the double-strand break), and is variously known as "non-crossover gene conversion" or "short tract gene conversion," because it leads to the transfer of genetic information from the donor to the target. Without being bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized homologous recombination often results in an alteration of the sequence of the target molecule such that part or all of the sequence of the donor polynucleotide is incorporated into the target polynucleotide.

Sequence identity Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Overview

The present disclosure provides novel glycoengineered lysosomal enzymes, and recombinant host cells for the homogeneous in vitro production of the same, for producing improved enzyme replacement therapy for lysosomal storage diseases including Fabry disease. In some embodiments, the novel glycoengineered lysosomal enzymes are produced in recombinant host cells engineered according to the present disclosure to be capable of producing homogeneous glycoforms of lysosomal enzyme, e.g., via the genetic knock-in and/or knock-out of one or more glycosyltransferase genes.

In some embodiments, any lysosomal enzyme may be glycoengineered according to the present disclosure. For example, in some embodiments, the lysosomal enzymes described herein that may be engineered according to the present disclosure include, human glycocerebrosidase (GC), iduronate 2-sulfatase (IDS), human arylsulfatase B (N-acetylgalactosamine-4-sulfatase) (ARSB), human lysosomal α-glucosidase (GAA), human alpha-galactosidase (GLA), human beta-glucuronidase (GUSB), human alpha-L-iduronidase (IDUA), human iduronate 2-sulfatase (IDS), human beta-hexosaminidase alpha (HEXA), human beta-hexosaminidase beta (HEXB), human lysosomal α-mannosidase (mannosidase alpha class 2B member 1) (MAN2B1), human glucosylceramidase (GBA), human lysosomal acid lipase/cholesteryl ester hydrolase (lipase A, lysosomal acid type)(LIPA), human aspartylglucosaminidase (N(4)-(beta-N-acetylglucosaminyl)-L-asparaginase) (AGA), human galactosylceramidase (GALC)., human alpha-sulfatases, human glucuronidase, human tripeptidyl peptidase 1 (TPP1), and human iduronidase.

In some aspects, the present disclosure provides novel GLA compounds allowing development of improved enzyme replacement therapy for Fabry disease.

In some aspects, the present disclosure provides lysosomal enzymes with low or no exposed mannose-6-phosphate (Man6P). In some aspects, "low" exposed Man6P means less 0.3 moles of exposed Man6P/mol enzyme. Such enzymes may display increased circulation time in plasma, e.g., due to decreased interaction with mannose-6-phosphate receptors.

In some aspects, the present disclosure provides lysosomal enzymes with and/or low or no exposed mannose (Man). Such enzymes may display increased circulation time in plasma, e.g., due to decreased interaction with mannose receptors.

In some aspects, the present disclosure provides lysosomal enzymes with high sialic acid capping and low or no exposed mannose-6-phosphate (Man6P) and/or low or no exposed mannose (Man). Such enzymes may display increased circulation time in plasma, e.g., due to decreased interaction with mannose or mannose-6-phosphate receptors. In certain particular aspects, the sialic acid capping is via 2,3 linkage, but not 2,6 linkage. In certain particular aspects, lysosomal enzymes engineered to have terminal 2,3 sialylation and low or no mannose-6-phosphate (Man6P) and/or low or no mannose (Man). In some aspects, such enzymes display (i) improved or maintained biodistribution to difficult-to-reach organs, (ii) unchanged or prolonged serum half-life, (iii) unchanged or prolonged blood clearance, and/or (iv) maintained or increased enzyme activity in plasma and/or in difficult-to-reach organs as compared to the same lysosomal enzymes lacking such engineering.

In some aspects, the present disclosure provides lysosomal enzymes with low Man6P and high sialic acid capping of alpha2,3 type.

In some aspects, the present disclosure provides mammalian cells (e.g., a CHO cell) with glycosylation capacities engineered to produce lysosomal enzymes with substantially altered content of Man6P, exposed Man, and/or content of sialic acid. Such cells may contain, e.g., one or more inactivation of an endogenous glycogene and/or one or more introduction of an exogenous glycogene. In some aspects, the glycogenes may be selected from the group consisting of GNPTAB, GNPTG, NAGPA, ALG3, ALG5, ALG6, ALG8, ALG9, ALG10, ALG12, Mannosidases, MAN1A1, MAN1A2, MAN1B1, MAN1C1, MAN2A1, MAN2A2, MOGS, GANAB, MGAT1, MGAT2 and Sialyl transferases. For example, the sialyl transferase may be St3gal4 and St3gal6.

For example, in some non-limiting aspects, the mammalian cells (e.g., CHO cells) may comprise a knockout of GNPTAB and/or a knockout of GNPTG. In some non-limiting aspects, the mammalian cells (e.g., CHO cells) may comprise a knock-in of St3gal4 and/or St3gal6. In some non-limiting aspects, the mammalian cells (e.g., CHO cells) may comprise a knockout of Mgat4b and/or a knockout of Mgat5. For example, in some non-limiting aspects, the mammalian cells (e.g., CHO cells) may comprise a knockout of GNPTG and/or GNPTAB and a knock-in of St3gal4 and/or St3gal6. In some non-limiting aspects, the mammalian cells (e.g., CHO cells) may comprise a knockout of one or more of GNPTG, GNPTAB, Mgat4b, Mgat5 and a knock-in of one or more of St3gal4 and St3gal6. For example, in one particular non-limiting aspect, the mammalian cells (e.g., CHO cells) may comprise a knockout of GNPTG, GNPTAB, Mgat4b, Mgat5 and a knock-in of St3gal4. In one particular non-limiting aspect, the mammalian cells (e.g., CHO cells) may comprise a knockout of GNPTG, GNPTAB, St3gal4, and St3gal6 and a knock-in of St6gal1. In one particular non-limiting aspect, the mammalian cells (e.g., CHO cells) may comprise a knockout of Alg3 and a knock-in of GNPTAB. In one particular non-limiting aspect, the mammalian cells (e.g., CHO cells) may comprise a knockout of ALG9. In one particular non-limiting aspect, the mammalian cells (e.g., CHO cells) may comprise a knock-in of GNPTAB and a knock-in of GNPTG.

In some embodiments of the present invention the mammalian cell is selected from the group consisting of HEK293 (e.g., HEK293-F, HEK293-H, HEK293-T, HEK293-6E), HT-1080, COS, VERO, MDCK, WI38, V79, B14AF28-G3, CHO (e.g. CHO-K1, CHO-GS, CHO-S, CHO-ZN, CHO-DUKXB11, CHO-DG44), BHK, HaK, NS0, SP2/0-Ag14, HeLa, and PERC6 or derivatives of any of these cells.

In some embodiments of the present invention is the mammalian cell a HEK293 cell.

In some embodiments of the present invention is the mammalian cell a CHO cell.

In some other embodiments of the present invention does the glycosylation of a lysosomal enzyme not comprise Man6P (for example by knock-out of Gnptg and/or Gnptab).

In some embodiments of the present invention the lysosomal enzyme contain less than 0.1 mol Man6P per mol enzyme, less than 0.2 mol Man6P per mol enzyme, less than 0.3 mol Man6P per mol enzyme; less than 0.4 mol Man6P per mol enzyme, less than 0.5 mol Man6P per mol enzyme.

In some embodiments of the present invention the lysosomal enzyme contains more than 7 mol alpha2,3SA per mol enzyme, more than 6 mol alpha2,3SA per mol enzyme, more than 5 mol alpha2,3SA per mol enzyme, more than 4.5 mol alpha2,3SA per mol enzyme, more than 4 mol alpha2,3SA per mol enzyme In some embodiments of the present invention the lysosomal enzyme contains no M6P or exposed Man, but 4-5 moles of sialic acid per mole of enzyme protein, or 5-6 moles of sialic acid per mole of enzyme, or 6-7 moles of sialic acid per mole of enzyme, or more than 7 moles of sialic acid per mole of enzyme.

In some embodiments of the present invention the lysosomal enzyme contains no M6P, but 4-5 moles of sialic acid per mole of enzyme protein, or 6-7 moles of sialic acid per mole of enzyme, or more than 7 moles of sialic acid per mole of enzyme.

In some other embodiments of the present invention does the enzyme glycosylation comprise increased sialylation (for example by knock-in of one or more of St6gal1, St3gal4 or St3gal6).

In some other embodiments of the present invention does the glycosylation comprise increased tri- and tetra-antennary structures (for example by knock-in of one or more of Mgat4A, Mgat4B or Mgat5).

In some other embodiments of the present invention does the glycosylation comprise homogeneous bi-antennary structures (for example by knock-out of one or more of Mgat4A, Mgat4B or Mgat5).

In some other embodiments of the present invention does the enzyme glycosylation comprise increased sialylation of alpha2,3 type (for example by knock-in of St3gal4 and/or St3gal6).

In some other embodiments of the present invention does the glycosylation comprise increased sialylation of homogeneous alpha2,3 type (for example by knock-out of St6gal1 combined with knock-in of St3gal4/6) and no Man6P.

The present inventors have used different nuclease-mediated (ZFN, TALEN, CRISPR/Cas9) knock-out and knock-in in mammalian cells, such as HEK293 or CHO cells, to obtain glycosylation capacities for producing glycovariants of lysosomal enzyme with improved circulation time and/or improved targeting to diseased organs, like kidney, heart, muscle or brain. As will be appreciated by the a person of average skill in the art, any location of DNA may be routinely targeted and cleaved using the ZFN, TALEN, and CRISPR/Cas9 (and other Cas) systems enabling knock-out or knock-in of genes via methods well known in the art.

A zinc finger nuclease (ZFN) is an enzyme that is able to recognize and cleave a target nucleotide sequence with specificity due to the coupling of a "zinc finger DNA binding protein" (ZFP) (or binding domain), which binds DNA in a sequence-specific manner through one or more zinc fingers, and a nuclease enzyme. ZFNs may comprise any suitable cleavage domains (e.g., a nuclease enzyme) operatively linked to a ZFP DNA-binding domain to form a engineered ZFN that can facilitate site-specific cleavage of a target DNA sequence (see, e.g., Kim et al. (1996) Proc Natl Acad Sci USA 93(3):1156-1160). For example, ZFNs may comprise a target-specific ZFP linked to a FOK1 enzyme or a portion of a FOK1 enzyme. In some embodiments, ZFN used in a ZFN-mediated targeted integration approach utilize two separate molecules, each comprising a subunit of a FOK1 enzyme each bound to a ZFP, each ZFP with specificity for a DNA sequence flanking a target cleavage site, and when the two ZFPs bind to their respective target DNA sites the FOK1 enzyme subunits are brought into proximity with one another and they bind together activating the nuclease activity which cleaves the target cleavage site. ZFNs have been used for genome modification in a variety of organisms (e.g., United States Patent Publications 20030232410; 20050208489; 20050026157; 20050064474; 20060188987; 20060063231; and International Publication WO 07/014,275, incorporated herein by reference in their entirety) Custom ZFPs and ZFNs are commercially available from, e.g., Sigma Aldrich (St. Louis, MO), and any location of DNA may be routinely targeted and cleaved using such custom ZFNs.

TALENS utilize a "TALE DNA binding domain" or "TALE," which is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. TAL-effectors may contain a nuclear localization sequence, an acidic transcriptional activation domain and a centralized domain of tandem repeats where each repeat contains approximately 34 amino acids that are key to the DNA binding specificity of these proteins. (e.g., Schornack S, et al (2006) J Plant Physiol 163(3): 256-272). TAL effectors depend on the sequences found in the tandem repeats which comprises approximately 102 bp and the repeats are typically 91-100% homologous with each other (e.g., Bonas et al (1989) Mol Gen Genet 218: 127-136). These DNA binding repeats may be engineered into proteins with new combinations and numbers of repeats, to make artificial transcription factors that are able to interact with new sequences and activate the expression of a non-endogenous reporter gene (e.g., Bonas et al (1989) Mol Gen Genet 218: 127-136). Engineered TAL proteins may be linked to a FokI cleavage half domain to yield a TAL effector domain nuclease fusion (TALEN) to cleave target specific DNA sequence (e.g., Christian et al (2010) Genetics epub 10.1534/genetics.110.120717).

Custom TALEN are commercially available from, e.g., Thermo Fisher Scientific (Waltham, MA), and any location of DNA may be routinely targeted and cleaved.

Any location of DNA may be routinely targeted and cleaved using the CRISPR/Cas9 system enabling knock-out or knock-in of genes via methods well known in the art.

A CRISPR (Clustered Regularly Interspaced Short Palindromic Repeats)/Cas (CRISPR Associated) nuclease system is an engineered nuclease system based on a bacterial system that may be used for genome engineering. It is based on part of the adaptive immune response of many bacteria and archaea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al (2012) Science 337, p. 816-821, Jinek et al, (2013), eLife 2:e00471, and David Segal, (2013) eLife 2:e00563). Thus, the CRISPR/Cas system can be engineered to create a DSB at a desired target in a genome, and repair of the DSB can be influenced by the use of repair inhibitors to cause an increase in error prone repair. As will be clear to the skill artisan, other CRISPR nucleases, in addition to Cas9, are known and are suitable for use in the present invention.

In some embodiments, the CRISPR/Cas nuclease-mediated integration utilizes a Type II CRISPR. The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to a protospacer adjacent motif (PAM), an additional requirement for target recognition. Forth, Cas9 mediates cleavage of target DNA to create a double-stranded break within the protospacer.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) Sciencexpress 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

In some embodiments, a single guide RNA containing both the crRNA and tracrRNA may be engineered to guide the Cas9 nuclease to target any desired sequence (e.g., Jinek et al (2012) Science 337, p. 816-821, Jinek et al, (2013), eLife 2:e00471, David Segal, (2013) eLife 2:e00563). Thus, the CRISPR/Cas system may be engineered to create a DSB at a desired target in a genome.

Custom CRISPR/Cas systems are commercially available from, e.g., Dharmacon (Lafayette, CO), and any location of DNA may be routinely targeted and cleaved using such custom single guide RNA sequences. Single stranded DNA templates for recombination may be synthesized (e.g., via oligonucleotide synthesis methods known in the art and commercially available) or provided in a vector, e.g., a viral vector such as an AAV.

In some aspects, the present disclosure provides mammalian cells that produce lysosomal enzyme with one or more of the following posttranslational modification patterns:
 a) Elimination of Man6P on one or more N-glycans (for example by knock-out of Gnptab and/or Gnptg),
 b) Low Man6P on one or more N-glycans (for example by knock-out of Gnptab and/or Gnptg),
 c) High sialic acid content (>4 mol SA per mol enzyme) (for example by knock-in of St3gal4/6),
 d) no exposed mannose
 e) Homogenous alpha2,3 SA capping (for example by knock-in of one or more of St3gal4, and St3gal6)
 f) Homogeneous biantennary glycans (for example by knock-out of Mgat4A, Mgat4B and/or Mgat5), or
 g) Higher number of antennae on glycans (for example by knock-in of Mgat4A, Mgat4B and/or Mgat5)

One, two, three, four, five, six or seven of these effects can be combined to generate specific posttranslational modification patterns.

In some aspects of the present invention ST6GAL1 is knocked out in a human cell leading to homogeneous alpha2,3 sialylation of N-glycans.

In some aspects of the present invention Gnptab is knocked out in the cell leading to elimination of Man6P tagging of N-glycans, decrease in exposed-Man, and increase in sialylated N-glycans of lysosomal enzyme proteins.

In some aspects of the present invention Gnptg is knocked out in the cell leading to elimination of Man6P tagging of N-glycans, decrease in exposed-Man, and increase in sialylated N-glycans of lysosomal enzyme proteins.

In some aspects of the present invention GNPTAB and ST6GAL1 are knocked out and ST3GAL4 is knocked-in in the human cell leading to N-glycans with alpha2,3-linked sialic acids and without Man6P tagging of N-glycans of lysosomal enzyme proteins.

In some aspects of the present invention Gnptab and ST3GAL4/6 are knocked out and ST6GAL1 is knocked in in the cell leading to complex type N-glycans with alpha2,6-linked sialic acids and without M6P tagging of N-glycans of lysosomal enzyme proteins.

In one aspect of the present invention is one or more of the above mentioned genes knocked out using zinc finger nucleases ZFN. ZFNs can be used for inactivation of any genes disclosed herein.

In one aspect of the present invention is one or more of the above mentioned genes knocked out using TALENs. TALENs can be used for inactivation of any genes disclosed herein.

In one aspect of the present invention is one or more of the above mentioned genes knocked out using CRISPR/Cas9. CRISPR/Cas9 can be used for inactivation of any genes disclosed herein.

In some embodiments, this disclosure provides mammalian cells with different well-defined N-glycosylation capacities that enable recombinant production of Lysosomal glycoprotein therapeutics with N-glycans with low Man6P tagging, with or without alpha2,6 SA capping, with or without alpha2,3 SA capping, and without exposed mannose.

In some aspects this disclosure provides an isolated cell comprising any of the proteins and/or polynucleotides as described herein. In certain embodiments, one or more glycosyltransferase genes are inactivated (partially or fully) in the cell. Any of the cells described herein may include additional genes that have been inactivated, for example, using zinc finger nucleases, TALENs and/or CRISPR/Cas9 designed to bind to a target sequence in the selected gene. In certain embodiments, provided herein are cells or mammalian cells in which two or more glycosyltransferase genes have been inactivated, and cells or mammalian cells in which one or more glycosyltransferase and related glycogenes have been inactivated and one or more glycosyltransferase genes introduced.

In some embodiments, this invention provides a cell with inactivation and/or modification of the Man6P tagging process of N-glycans, and that produces lysosomal enzyme proteins with no or lower levels of Man6P tagged N-glycans.

In some embodiments, introduction of one or more exogenous glycosyltransferase(s) is performed by plasmid transfection with a plasmid encoding constitutive promotor driven expression of both the glycosyltransferase gene and a selectable antibiotic marker, where the selectable marker could also represent an essential gene not present in the host cell such as GS system (Sigma/Lonza), and/or separate plasmids encoding the constitutive promotor driven glycosyltransferase gene or the selectable marker. For example, plasmids encoding ST6GAL1 and Zeocin have been transfected into cells and stable ST6GAL-I expressing lines have been selected based on zeocin resistance In some other embodiments, introduction of one or more exogenous glycosyltransferase(s) is performed by site-directed nuclease-mediated insertion.

In some aspects, the disclosure provides a method of producing a recombinant lysosomal enzyme of interest in a host cell, the method comprising the steps of: (a) providing a host cell comprising one or more endogenous glycosyltransferase genes; (b) inactivating the endogenous glycosyltransferase gene(s) of the host cell by any of the methods described herein; and (c) introducing an expression vector comprising a transgene, the transgene comprising a sequence encoding a lysosomal enzyme of interest, into the host cell, thereby producing the recombinant enzyme with low Man6P and low exposed Mannose and high sialic acid glycoforms.

In some aspects, the disclosure provides a method of producing a recombinant lysosomal enzyme of interest in a cell, the method comprising the steps of: (a) providing a cell comprising one or more endogenous glycosyltransferase gene; (b) inactivating the endogenous glycosyltransferase gene(s) of the host cell; (c) introducing one or more glycosyltransferase gene(s) in the cell by any of the methods described herein; and (d) introducing an expression vector comprising a transgene, the transgene comprising a sequence encoding a protein of interest, into the cell, thereby producing the recombinant lysosomal enzyme with low Man6P and low exposed mannose and high alpha2,3 type sialic acid glycoforms.

In some aspects, the disclosure provides a method of producing a recombinant lysosomal enzyme of interest in a cell, the method comprising the steps of: (a) introducing an expression vector comprising a transgene, the transgene comprising a sequence encoding a lysosomal enzyme of interest, into the cell (b) isolating clonal cell line producing the lysosomal enzyme; (c) inactivating one or more of the endogenous glycogene(s) of the host cell; (c) introducing one or more glycosyltransferase gene(s) in the cell by any of the methods described herein; and (d), thereby producing the recombinant lysosomal enzyme with low Man6P and low exposed mannose and high alpha2,3 type sialic acid glycoforms.

In any of the cells and methods described herein, the cell or cell line may be a HEK293 (e.g., HEK293-F, HEK293-H, HEK293-T, HEK293-6E), HT-1080, COS, VERO, MDCK, WI38, V79, B14AF28-G3, CHO (e.g. CHO-K1, CHO-GS, CHO-S, CHO-ZN, CHO-DUKXB11, CHO-DG44), BHK, HKB, HaK, NS0, SP2/0-Ag14, HeLa, and PERC6.

Knock-Out Targeting Strategy.

It is clear to the person skilled in the art that inactivation of a gene involved in glycosylation pathways can have a multitude of outcomes and effects on the transcript and/or protein product translated from this. Targeted inactivation experiments performed herein involved PCR and sequencing of the introduced alterations in the genes as well as RNAseq analysis of clones to determine whether a transcript was formed and if potential novel splice variations have possibly introduced new protein structures. Moreover, methods for determining presence of protein from such transcripts are available and include mass spectrometry and SDS-PAGE Western blot analysis with relevant antibodies detecting the most N-terminal region of the protein products.

In some embodiments the cell may express an exogenous lysosomal enzyme, which lysosomal enzyme is expressed to comprise one or more posttranslational modifications independently selected from:
  a) with alpha2,3SA capping,
  b) without alpha2,3SA capping,
  c) with alpha2,6SA capping,
  d) without alpha2,6SA capping,
  e) without Man6P,
  f) low Man6P,
  g) without exposed Mannose,
  h) low exposed Mannose,
  i) >75% biantennary structures, and
  j) >75% tri/tetra antennary structures.

In some embodiments the exogenous protein of interest is a lysosomal enzyme, and the one or more endogenous glycogene inactivated is Gnptab or Gnptg, such as in order to lower Man6P and increase sialic acids.

In some embodiments the exogenous protein of interest is a lysosomal enzyme, wherein said lysosomal enzyme has altered mannose-6-phosphate (Man6P) tagging of N-glycans and/or changed site occupancy of M6P, such as by knocking out one or both of Gnptg and Gnptab genes.

In some embodiments of the present disclosure, glycosylation on a lysosomal enzyme disclosed herein is made more homogenous.

In some other embodiments of the present disclosure, N glycans on a lysosomal enzyme disclosed herein are sialylated with at least 7 mol SA, or at least 6, at least 5, at least 4.5, or at least 4 mol SA per mol of enzyme.

In some other embodiments of the present disclosure N glycans on a lysosomal enzyme disclosed herein are alpha2,3 sialylated with at least 7 mol alpha2,3SA, or at least 6, at least 5, at least 4.5, or at least 4 mol alpha2,3SA per mol of enzyme.

In some embodiment the modified lysosomal enzyme is fused to a non-glycan tag designed to improve blood-brain-barrier passage In some embodiment the non-glycan tags fused to a modified lysosomal enzyme may include IGF2, Transferrin, Immunoglobin or any fragment or derivative of these The optimal glycoform for a lysosomal enzyme may be identified by the following process:
  (i) producing the lysosomal enzyme in a panel of isogenic cells with different glycosylation capacities, obtained by inactivating and/or introducing one or more glycogenes in said mammalian cells resulting in at least one novel glycosylation capacity,
  (ii) Optionally purify the produced glycovariants of the lysosomal enzyme,
  iii) determination of improved drug feature of each glycovariant of the enzyme in suitable assay, e.g. in-vitro assays (binding assay, enzyme assay, cell uptake assays) or animal studies (Serum half-life, targeting to diseased organs, improved biodistribution, substrate reduction). Improvement is based on comparison with a reference enzyme in same assay; and
  (iv) perform glycoanalysis for determination of the glycoform with the improved drug feature The above described process allows the identification of the optimal glycan structure for a particular lysosomal enzyme. For those skilled in the art by using the genotype fingerprint identified in (iii) may generate an efficient engineered mammalian cell line with the optimal genotype for efficient production of the lysosomal enzyme with said glycan.

One aspect of the present disclosure relates to a method for producing a lysosomal enzyme having modified glycan profile wherein the cell producing the lysosomal enzyme has more than one modification of one or more glycogenes.

In some embodiments of the present disclosure provides cells (e.g., mammalian cells) that have been modified by glycogene knock-out and/or knock-in of an exogenous DNA sequence coding for a protein involved in glycosylation (e.g. a glycosyltransferase or a phospho transferase).

In some embodiments of the present disclosure a lysosomal enzyme is produced in cells (e.g., mammalian cells) in which one or more endogenous gene selected from the group consisting of ST3GAL4/6 and ST6GAL1 have been knocked out.

In some embodiments of the present disclosure, a lysosomal enzyme is produced in cells (e.g., mammalian cells) in which one or more exogenous gene selected from the group consisting of ST3GAL4, ST3GAL6, ST6GAL1, MGAT4A, MGAT 4B, MGAT5 have been knocked in.

In some embodiments of the present disclosure, a lysosomal enzyme is produced in cells (e.g., mammalian cells) in which one or both of GNPTAB or GNPTG have been knocked out One aspect of the present disclosure relates to a method for producing a lysosomal enzyme having a plurality of glycan profiles, and from this plurality of glycovariant enzyme protein identifying glycovariants with improved (drug) properties. The selection of such glycovariants with improved (drug) properties may comprise analyzing the glycovariant enzyme for activity in comparison with a reference lysosomal enzyme in (a) suitable bioassay(s); and selection of the enzyme glycoform with the higher/highest/optimal activity.

In one aspect of the present disclosure, one or more of the above mentioned genes knocked out using transcription activator-like effector nucleases (TALENs).

In one aspect of the present disclosure, one or more of the above mentioned genes is knocked out using CRISPRs (clustered regularly interspaced short palindromic repeats).

In one aspect of the present disclosure, one or more of the above mentioned genes knocked out using ZFN (Zinc Finger Nuclease).

In some embodiments of the present disclosure, the cell producing the recombinant lysosomal enzyme is selected from the group consisting of CHO, HEK293, NS0, SP2/0, YB2/0, CAP, PERC6, HT-1080, NS0, SP2/0, and BHK cells.

In certain embodiments of the present disclosure the cell is a HEK293 cell.

In certain embodiments of the present disclosure the cell is a CHO cell.

In some embodiments, the cell may be an isolated cell, a cell in cell culture, or a cell line.

In some embodiments the "naked" cells may be glyco-engineered before expressing the lysosomal enzyme of interest in the engineered cell line.

In some embodiments a cell line producing the recombinant lysosomal enzyme of interest is glycoengineered.

In some embodiments the glyco-engineering design comprising the specific knock-outs and knock-ins giving the optimal modified lysosomal enzyme may be transferred into a novel host cell line using any gene editing technology (ZFN, TALENs or CRISPR)

In some embodiments a CHO cell line producing an optimal human lysosomal enzyme glycovariant is engineered by way of gene knock-out to inactivate the corresponding endogenous CHO lysosomal enzyme, so that only the human form of the enzyme is produced.

Due to short half-life of GLA enzyme in serum it has been co-formulated with 1-deoxygalactonojirimycin (DGJ) as disclosed in U.S. Pat. No. 9,694,056 and published in Xu 2015. The DGJ increased the physical stability, and increased the potency for GLA-mediated globotriaosylceramide reduction in cultured Fabry fibroblasts. In Fabry mice, co-formulation of 1-deoxygalactonojirimycin increased the total exposure of active enzyme, and led to greater tissue globotriaosylceramide reduction when compared with GLA alone.

In some embodiments, the present invention provides pharmaceutical compositions comprising one or more modified lysosomal enzyme disclosed herein. Such pharmaceutical compositions may comprise the one or more modified lysosomal enzyme and one or more pharmaceutically acceptable carrier, excipient, or vehicle.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, PA, USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

A pharmaceutical composition of the invention may be in unit dosage form. In such form, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition.

Pharmaceutical compositions comprising the one or more modified lysosomal enzyme may be formulated (e.g., with one or more pharmaceutically acceptable carrier, excipient, or diluent) for any suitable route and means of administration. Pharmaceutically acceptable carriers, excipients or diluents include those used in formulations suitable for e.g. oral, intravitreal, rectal, vaginal, nasal, topical, enteral or parenteral (including subcutaneous (SC), intramuscular (IM), intravenous (IV), intradermal and transdermal) administration or administration by inhalation. The formulations may conveniently be presented in unit dosage form and may be prepared by any of the methods well known in the art of pharmaceutical formulation.

Subcutaneous or transdermal modes of administration may be particularly suitable for the peptide analogues of the invention.

Further embodiments of the invention relate to devices, dosage forms and packages used to deliver the pharmaceutical formulations of the present invention. Thus, at least one peptide analogue or specified portion or variant in either the stable or preserved formulations or solutions described herein, can be administered to a patient in accordance with the present invention via a variety of delivery methods, including SC or IM injection; transdermal, pulmonary, transmucosal, implant, osmotic pump, cartridge, micro pump, or other means appreciated by the skilled artisan as well-known in the art.

Still further embodiments of the invention may relate to oral formulations and oral administration. Formulations for oral administration may rely on the co-administration of adjuvants (e.g. resorcinols and/or nonionic surfactants such as polyoxyethylene oleyl ether and n-hexadecylpolyethylene ether) to artificially increase the permeability of the intestinal walls, and/or the co-administration of enzymatic inhibitors (e.g. pancreatic trypsin inhibitors, diisopropylfluorophosphate (DFF) or trasylol) to inhibit enzymatic degradation. The active constituent compound of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents or perfuming agents.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

In some embodiments, the invention relates to a kit comprising one or more modified lysosomal enzyme of the invention. In other embodiments, the kit comprises one or more pharmaceutical compositions comprising one or more modified lysosomal enzyme. In certain embodiments, the kit further comprises packaging or instructions for use.

In some embodiments the modified lysosomal enzymes disclosed herein may be co-formulated with a compound that improves the serum stability of the enzyme. In some embodiments the modified lysosomal enzyme may co-formulated with DGJ. The present disclosure also provides for the use of a co-formulation of modified α-Gal A and DGJ or a pharmaceutically acceptable salt thereof in the preparation of a medicament for the treatment of Fabry disease, wherein the medicament is formulated for parenteral administration to a subject, and wherein the α-Gal A of the co-formulation is formulated for administration in an amount of about 0.3, 0.5, 1, 2 or 3 mg/kg, and the DGJ of the co-formulation is formulated for administration in an amount of about 0.1, 0.3, 0.5, 1, 3, or 10 mg/kg.

In some embodiments the lysosomal enzyme modifications or glycodesigns disclosed herein (e.g., any one or more of the modified GLA enzymes disclosed herein) may be combined with enzyme stabilizing technologies involving amino acid mutations in the enzyme polypeptide sequence to obtain additive or synergistic effects. In some embodiments, such mutated enzymes have improved thermal and/or physical stability and/or improved cell uptake properties.

It should be noted that embodiments and features described in the context of one of the aspects or embodiments of the present invention also apply to the other aspects and embodiments of the invention.

All patent and non-patent references cited in the present application, are hereby incorporated by reference in their entirety.

The invention will now be described in further details in the following non-limiting examples.

EXAMPLES

The following examples are given as an illustration of various embodiments of the invention and are thus not meant to limit the present invention in any way. Along with the present examples the methods described herein are exemplary, and are not intended as limitations on the scope of the invention. Changes therein and other uses which are encompassed within the spirit of the invention as defined by the scope of the claims will occur to those skilled in the art.

Example 1—Production and Characterization of Human GLA Enzyme

The alpha-galactosidase A (GLA) enzyme is 398 amino acids glycoprotein with three N-glycan sites. Lack of GLA enzyme activity is cause of the lysosomal disease called Fabry's disease. There are two replacement enzyme products available for Fabry disease and we used the Fabrazyme from Genzyme/Sanofi as control for our experiments. For producing recombinant human alpha-galactosidase A (GLA) we first generated a stable high expressing CHO cell line.

Generation of GLA Production Cell Line:

An expression construct containing the entire coding sequence of human GLA was synthesized by Genewiz (USA) and subcloned into modified pCGS3 (Merck/Sigma-Aldrich) for glutamine selection in CHOZN GS-/- cells. CHO cells were maintained as suspension cultures in EX-CELL CD CHO Fusion serum-free media (Sigma), supplemented with 4 mM L-glutamine in 50 mL TPP TubeSpin® Bioreactors with 180 rpm shaking speed at 37° C. and 5% $CO2$. Cells were seeded at 0.5 mil cells/mL in T25 flask (NUNC) one day prior to transfection. Electroporation was conducted with 2 mil cells and 8 µg endotoxin-free plasmids using Amaxa kit V and program U24 with Amaxa Nucleofector 2B (Lonza, Switzerland). Electroporated cells were plated in 6-well plates with 3 mL growth medium, and after 72 h cells were transferred to 96 w plates at 1,000 cells/well in 200 µl Minipool Plating Medium containing 80% EX CELL® CHO Cloning Medium (Cat. no C6366) and EX-CELL CHO CD Fusion serum-free medium without glutamine. High expressing clones were selected by GLA enzyme activity in the medium.

For producing GLA enzyme the CHO cell line was cultured in EX-CELL CHO CD serum-free media without L-glutamine in 50 mL TPP TubeSpin® Bioreactors or Erlenmeyer flasks and incubated with shaking (180 rpm, 37° C. and 5% $CO_2$) for 4 days Spent culture medium was collected after centrifugation at 500×g for 20 min, filtered through 0.45 m filter, diluted 3-fold with 25 mM MES (pH 6.0), and loaded onto a DEAE-Sepharose Fast Flow column (Sigma). The column was washed with 10 column volumes (CV) washing buffer (25 mM MES with 50 mM NaCl, pH 6.0) and eluted with 5 CV elution buffer (25 mM MES with 200 mM NaCl, pH 6.0). For GBA the His-tagged protein was purified by nickel affinity purification (Invitrogen, US). Culture medium was centrifuged, filtered, and mixed 3:1 (v/v) in 4× binding buffer (200 mM Tris, pH 8.0, 1.2 M NaCl) and applied to 0.3 ml packed NiNTA agarose (Invitrogen), pre-equilibrated in binding buffer (50 mM Tris, pH 8.0, 300 mM NaCl). The column was washed with binding buffer and then bound protein was eluted with binding buffer with an additional 250 mM imidazole. Purity and quantity was evaluated by SDS-PAGE Coomassie staining and enzyme activity was analyzed using GLA activity assay.

GLA Activity Assay:

GLA enzyme activity was measured with 33 mM p-nitrophenyl-α-D-galactopyranoside (pNP-Gal) substrate at 37° C. for 30 min at pH 4.6 in 20 mM citrate and 30 mM sodium phosphate, and the reaction was quenched with borate buffer (pH 9.8) and released p-nitrophenol was read at 405 nm.

Site Specific Glycoanalysis of GLA Enzyme:

To characterize the glycans of the GLA enzyme we used site-specific glycoprofiling of the secreted GLA. GLA has three N-glycosites (N108, N161, N184) and peptide digestion with chymotrypsin was used to isolate the corresponding glycopeptides. Approximately 10 µg of purified GLA in 50 mM Ammoniumbicarbonate buffer (pH 7.4) was reduced with dithiothreitol (10 mM) at 60° C. for 30 min and alkylated with iodoacetamide (20 mM) for 30 min in dark at room temperature. Chymotrypsin digestion was performed at a 1:25 enzyme: substrate ratio. The proteolytic digest was desalted by custom made modified StageTip columns containing 2 layers of C18 and 1 layer of C8 membrane (3M Empore disks, Sigma-Aldrich). Samples were eluted with 50% methanol in 0.1% formic acid, and then dried in SpeedVac and re-solubilized in 0.1% formic acid. LC MS/MS analysis was performed with an EASY-nLC 1000

LC system (ThermoFisher Scientific) interfaced via nanoSpray Flex ion source to an Orbitrap Fusion MS (ThermoFisher Scientific). Briefly, the nLC was operated in a single analytical column set up using PicoFrit Emitters (New Objectives, 75 µm inner diameter) custom packed with Reprosil-Pure-AQ C18 phase (Dr. Maisch, 1.9-µm particle size, 19-21 cm column length). Each sample was injected onto the column and eluted in a gradient from 2 to 25% B in 45 min at 200 nL/min (Solvent A, 100% $H_2O$; Solvent B, 100% acetonitrile; both containing 0.1% (v/v) formic acid). A precursor MS1 scan (m/z 350-2,000) of intact peptides was acquired in the Orbitrap Fusion at the nominal resolution setting of 120,000, followed by Orbitrap HCD-MS2 and at the nominal resolution setting of 60,000 of the five most abundant multiply charged precursors in the MS1 spectrum; a minimum MS1 signal threshold of 50,000 was used for triggering data-dependent fragmentation events. Targeted MS/MS analysis was performed by setting up a targeted $MS^n$ ($tMS^n$) Scan Properties pane.

Glycopeptide Compositional Analysis:

Analysis was performed from m/z features using in-house written SysBioWare software (Vakhrushev 2009). For m/z feature recognition from full MS scans LFQ Profiler Node of the Proteome discoverer 2.1 (ThermoFisher Scientific) was used. A list of precursor ions (m/z, charge and retention time) was imported as ASCII data into SysBioWare and compositional assignment within 4 ppm mass tolerance was performed. The main building blocks used for the compositional analysis were: NeuAc, Hex, HexNAc, dHex and phosphate. The most prominent peptides corresponding to each potential glycosites were added as an additional building block for compositional assignment. The most prominent peptide sequence related to each N-glycosite was determined experimentally by comparing the yield of deamidated peptides before and after PNGase F treatment. A list of potential glycopeptides and glycoforms for each glycosite was generated and the top 10 of the most abundant candidates for each glycosite were selected for targeted MS/MS analysis to confirm the proposed structure. Each targeted MS/MS spectrum was subjected to manual interpretation. Same N-glycan composition may represent isobaric structures, so the listed glycan structure were assisted by and in agreement with literature data, predicted enzyme functions of the targeted genes together with useful information in MS/MS fragments.

Figure 2:
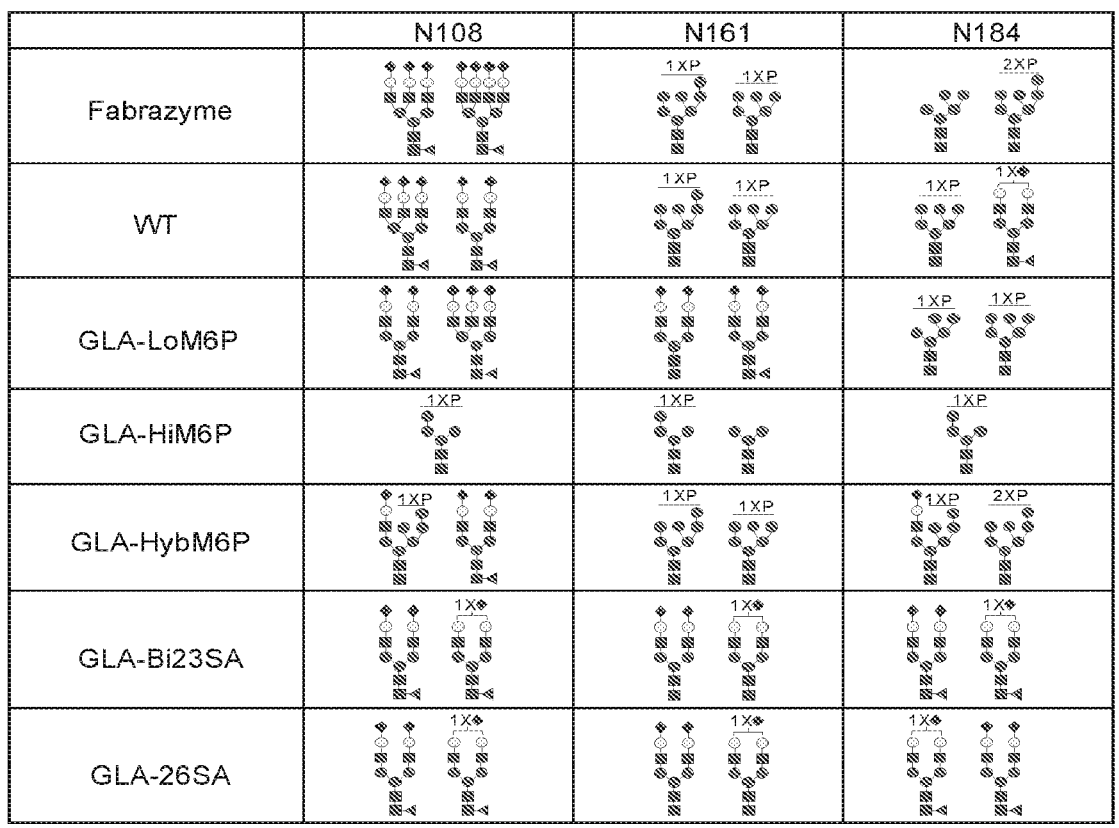
FIG. 2 shows site specific glyco-analysis of GLA expressed in wt CHO cells and five engineered cell lines. The two most abundant glycan structures at N-glycosites N108, N161 and N184 of GLA are shown, with Fabrazyme included as control.

Result of site specific glycoanalysis of GLA produced in wt CHO cells and the commercial Fabrazyme product is included in FIG. 2, showing that GLA from wt CHO cells was site-specifically glycosylated with mainly complex structures capped with SA at N-glycan site N108 and with high-mannose-type M6P glycans at sites N161 and N184

Example 2—Cell Based Glycoengineering of GLA Enzyme in CHO Cells

For producing improved enzyme the present inventors employed nuclease-mediated knock-out or knock-in in CHO cells to engineer the glycosylation capacity, enabling production of lysosomal enzymes with improved circulation time and/or improved targeting to affected organs. The genes targeted for modifying the glycans of the GLA enzyme are listed in Table 1 and their role in the glycosylation process is included in FIG. 1.

TABLE 1

List of gene modifications introduced into mammalian cells to improve GLA enzyme. For knock-outs the gRNA's used for CRISPR/Cas9 engineering of cells are included. Modifications may be introduced as single events or combined with other editing (stacked)

| Gene name | Gene origin | Cell type targeted | Knock-out or knock-in | gRNA sequence | SEQ ID NO |
|---|---|---|---|---|---|
| Gnptg | CHO | CHO | Knock-out | GCGATGGCGGTGCGGGTGGC | 1 |
| Gnptab | CHO | CHO | Knock-out | GTCACATTCATCGCATCGAG | 2 |
| St3gal4 | CHO | CHO | Knock-out | GGTCGAAGTGGGCCGACTCA | 3 |
| St3gal6 | CHO | CHO | Knock-out | GGAGTTGTGATCATTGTGAG | 4 |
| Mgat4B | CHO | CHO | Knock-out | GAGAGGCAGGCGCTGCGGGA | 5 |
| Mgat5 | CHO | CHO | Knock-out | GACAATCTCGTCAATGGCAC | 6 |
| GNPTAB | Human | Human | Knock-out | TAAACAACGTCAATCGGCAT | 7 |
| GNPTG | Human | Human | Knock-out | GCTGCTCACCCAAACGCGTT | 8 |
| ST6GAL1 | Human | CHO + human | Knock-in | na | |
| ST3GAL4 | Human | CHO + human | Knock-in | na | |

TABLE 1-continued

List of gene modifications introduced into mammalian cells to improve GLA enzyme. For knock-outs the gRNA's used for CRISPR/Cas9 engineering of cells are included. Modifications may be introduced as single events or combined with other editing (stacked)

| Gene name | Gene origin | Cell type targeted | Knock-out or knock-in | gRNA sequence | SEQ ID NO |
|---|---|---|---|---|---|
| ST3GAL6 | Human | CHO + human | Knock-in | na | |
| MGAT4A | Human | CHO + human | Knock-in | na | |
| MGAT4B | Human | CHO + human | Knock-in | na | |
| MGAT5 | Human | CHO + human | Knock-in | na | |

CRISPR/Cas9 Targeted Knock-Out in CHO Cells.

Gene targeting was performed in CHO clones stably expressing GLA (Example 1). Cells were seeded at $0.5 \times 10^6$ cells/mL in T25 flask (NUNC, Denmark) one day prior to transfection, and $2 \times 10^6$ cells and 1 μg each of endotoxin free plasmid DNA of Cas9-GFP fusion and gRNA in the plasmid U6GRNA (Addgene Plasmid #68370) were used for electroporation using Amaxa nucleofector as described in Example 1. 48 hours after transfection the 10-15% highest labeled (GFP) pool of cells was enriched by FACS, and after 1 week in culture cells were single cell sorted into 96-wells by FACS. KO clones were identified by Indel Detection by Amplicon Analysis (IDAA) as described in Lonowski 2017, as well as when possible by immunocytology with appropriate lectins or monoclonal antibodies. Selected clones were further verified by Sanger sequencing. The strategy enabled fast screening and selection of KO clones with frameshift mutations, and on average we selected 2-5 clones from each targeting event.

ZFNs/CRISPR-Mediated Knock-In in CHO Cells.

Site-specific CHO Safe-Harbor locus KI was based on ObLiGaRe strategy and performed with 2 μg of each ZFN (Merck/formerly known as Sigma-Aldrich) tagged with GFP/Crimson as previously described (Yang 2015), and 5 μg donor plasmid with full coding human genes (ST3GAL4, ST3GAL, ST6GAL1, MGAT4A, MGAT4B, MGAT5, GNPTAB, or GNPTG). In brief, the EPB69 donor plasmid contained inverted CHO Safe-Harbor locus ZFN binding sites flanking the CMV promoter-ORF-BGH polyA terminator. Mono-allelic targeted KI clones with one intact allele were selected by IDAA analysis (Lonowski 2017). To stack a second gene into a Safe-Harbor locus, we first designed gRNA for the CHO Safe-Harbor locus flanking the ZFN binding site, followed by transfection with 1 μg of a donor PCR product of gene to be inserted with 1 μg Cas9-GFP and 1 μg gRNA. In brief, the donor PCR product was generated by using EPB69 donor plasmid as template which contained the CMV promoter-ORF-BGH polyA terminator. KI clones were screened by PCR with primers specific for the junction area between the donor plasmid and the Safe-Harbor locus. A primer set flanking the targeted knock-in locus was used to characterize the allelic insertion status, and when possible, KI clones were also screened by immunocytology with lectins and monoclonal antibodies.

Overall the gene targeting experiments did not affect viability, growth, or productivity substantially in the engineered cell clones, nor was GLA enzyme activity influenced by the modification of glycans.

Site specific glycoanalysis of GLA variants and Fabrazyme control is shown in FIG. 2, demonstrating very similar glycosylation of Fabrazyme and GLA produced in wt-CHO cells, both in accordance with publication by Lee 2003. The GLA-loM6P has lost M6P on site 2 (N161) but retains some M6P on third site, whereas the GLA-hiM6P has M6P on all three sites and no sialic acids. The GLA-hybM6P show hybrid glycan structure where sites 1 and 3 have both M6P and SA, whereas site 2 only presents M6P structures. The two sialylated forms GLA-bi23SA and GLA-26SA both have lost M6P and all sites are dominated by biantennary structures with each antenna capped with 1-2 sialic acids. The types of sialic acids are homogeneous alpha2,3 or alpha2,6 respectively. FIG. 2 also depicts the various designs and glycostructures included in Table 2.

TABLE 2

The following five GLA glycovariants were selected and produced at larger scale for Fabry mouse studies:

| GLA variant | Design/Glycostructure | Cell engineering Knock-out | Cell engineering Knock-in |
|---|---|---|---|
| GLA-bi23SA | Biantennary, high SA, 2,3 linkage | Gnptab, Gnptg Mgat4b/5 | ST3GAL4 |
| GLA-26SA | Biantennary, high SA, 2,6 linkage | Gnptab/g St3gal4/6 | ST6GAL1 |
| GLA-hiM6P | High Man6P | Alg3 | GNPTAB |
| GLA-loM6P | Low Man6P | Alg9 | no |
| GLA-hybM6P | Hybrid with Man6P | no | GNPTAB GNPTG |

Example 3—Role of 2Lycans on GLA Enzyme for PK and Biodistribution in Mouse Model of Fabry Disease For characterizing pharmacodynamics and potential therapeutic effects of glycoengineered GLA a mouse model of Fabry disease was used for following experiments. Specific enzyme activity for GLA produced in wt CHO cells and all GLA glycovariants was compared to Fabrazyme and no differences were found.

Experiment 1—Test PK and Biodistribution of GLA in Fabry Mouse Model

Fabrazyme or CHO-GLA (GLA produced in CHO cells, Example 1) was injected into 3,5 month old male Fabry mice via tail vein at a dose of 1 mg/kg body weight (n=4 mice per enzyme). Blood samples were collected by tail bleed at 5, 20, 40, 60 and 120 min after injection. Enzyme activity in plasma was measured, and the plasma clearance rate was determined. Four hours after injection mice were sacrificed and liver, spleen, heart and kidney were harvested. Biodistribution was determined by measuring GLA activity in the tissue lysates.

For pharmacokinetics the blood clearance of GLA produced in wt cells and Fabrazyme was very similar (FIG. 3) and half-lives were 12.0±0.3 and 11.9±2.3 minutes respectively. Overall the biodistribution among the 4 major organs was similar albeit the GLA produced in our CHO cell line had slightly lower activity in kidney (FIG. 4).

Experiment 2—Test PK and Biodistribution of Five Glycovariant Forms of GLA in Fabry Mice The following enzyme variants were tested; GLA-bi23SA, GLA-26SA, GLA-HiM6P, GLA-LoM6P, GLA-HybM6P (see Table 2) and Fabrazyme was included as control. Enzyme preparations (1 mg/kg) were iv injected into 2 months old male Fabry mice via tail-vein (n=4 per group). At time points (5 min, 20 min, 40 min, 1 h, 2 h, 4 h and 24 h post-injection), small amount of blood samples were collected from tail vein. Plasma was separated by centrifugation, and was used for enzyme assay (see Experiment1).

After 24 hours mice were sacrificed and heart, kidney, liver and spleen were dissected. GLA activity was measured using standard 4MU method; the data were expressed as nmol/hr/mg total protein.

The pharmacokinetics of four of the variants tested were similar to Fabrazyme, however, the GLA-bi23SA variant showed a clearly prolonged blood clearance profile (FIG. 5) and an increased half-life by three fold (27.5±0.8 min versus 9.8±0.3 min for Fabrazyme) was observed. This suggests different uptake or clearance mechanisms for the GLA-bi23SA glycovariant with high SA of alpha2,3 type. The GLA-26SA variant, which also has high SA, but homogeneous alpha2,6 type, had same kinetics as Fabrazyme and the other glycovariants and accordingly the alpha2,3 linkage of the sialic acids is causal for increasing the plasma half-life.

FIG. 6 shows the distribution of GLA variants into heart, kidney, liver and spleen and based on this the relative distribution of GLA variants into the difficult-to-reach organs heart and kidney was calculated and is shown in FIG. 7. The figures show that altering content of Man6P of GLA (GLA-Lo/Hi/HybM6P) produce differences in organ distributions. Surprisingly, GLA with alpha2,3 SA and no Man6P (GLA-Bi23SA) showed clear uptake in organs with improved biodistribution characterized by lower levels in liver and spleen (FIGS. 6B and 6D) and significantly higher levels in heart compared to Fabrazyme (FIGS. 6A and 7). This demonstrates for the first time that a lysosomal enzyme without M6P and/or exposed Man are taken up by cells and distributed better to hard-to-reach organs compared to current lysosomal enzymes with Man6P content. Moreover, surprisingly, GLA with alpha2,6 SA and no Man6P (GLA-26SA) showed clear uptake in organs with improved biodistribution characterized by higher levels in liver and significantly lower levels in spleen and kidney compared to Fabrazyme. This demonstrates for the first time that a therapeutic glycoprotein with alpha2,6 SA on N-glycans selectively is distributed to the liver. FIG. 7 illustrates the significant changes in relative distribution of GLA variants to hard-to-reach organs showing highly improved biodistribution of GLA-Bi23SA.

Example 4—Substrate Reduction in Fabry Mice

Gb3 is substrate for the GLA enzyme and accumulation of Gb3 in various tissues is a characteristic feature of the Fabry disease. To test the efficacy of the GLA-Bi23SA for reducing Gb3 levels in selected organs in the Fabry mouse the following experiment was performed.

GLA-Bi23SA or Fabrazyme enzyme preparations (1 mg/kg) or vehicle alone (saline) were injected into 6 months old female Fabry mice via tail-vein (n=5 per group). Age- and sex-matched untreated WT mice were used as WT controls (n=5). At 2 weeks after injection, heart, kidney and liver were dissected, and Gb3 levels were measured using mass-spectrometry. The data are expressed as ng/mg total protein (FIG. 8). In agreement with the surprising biodistribution results the GLA-Bi23SA variant showed equivalent or better reduction in Gb3 content not only in heart, but also in liver and kidney compared to Fabrazyme two weeks after the single dose of 1 mg/kg enzymes. Importantly, the lower levels of GLA-Bi23SA activity distributed to liver and kidney did not adversely affect the decrease in Gb3 substrate in these organs compared to Fabrazyme. The higher levels of GLA-Bi23SA activity distributed to the heart did not produce a significant lowering of Gb3 substrate compared to Fabrazyme, although clearly a tendency towards lower detectable levels were found (FIG. 8). These results clearly suggest that lower doses of GLA-Bi23SA and repeat infusions of GLA-Bi23SA will be superior to Fabrazyme.

Example 5—Cellular Localization of Modified GLA (IHC)

For immunohistochemical analysis (IHC) enzyme preparations were injected into ~3.5 month old male Fabry mice via tail-vein at a dose of 2 mg/kg body weight. Heart, kidney and liver were harvested 24 h after enzyme infusion. Untreated Fabry mouse tissues were used as negative controls. Tissues were fixed in formalin, embedded in paraffin, and 5-micron sections were made. IHC was performed by Histopathology and Tissue Shared Resource in Georgetown University (Washington, D.C.). In brief, after heat-induced epitope retrieval in citrate buffer, sections were treated with 3% hydrogen peroxide and 10% normal goat serum, and were incubated with rabbit polyclonal antibody to human α-gal A (Shire). After incubation with HRP-labeled secondary antibody, signals were detected by DAB chromogen, and the sections were counterstained with hematoxylin. Signal specificity was verified with control staining, in which the primary antibody incubation was omitted.

Figure 9A:
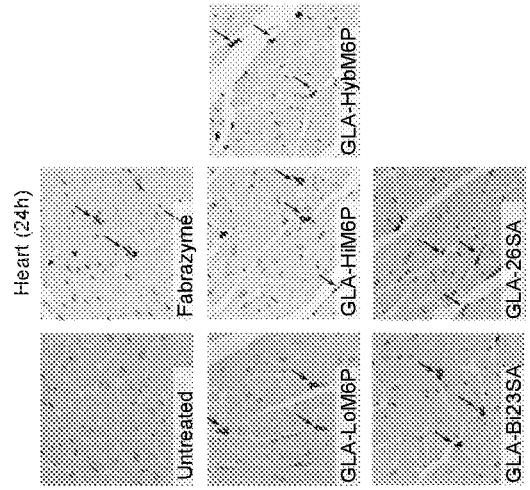
FIG. 9 shows immunohistochemistry showing the cellular distribution of infused enzymes in liver (FIG. 9A), kidney (FIG. 9B), and heart (FIG. 9C) of Fabry mice. Annotation in liver IHC: hepatocytes (small arrows), putative Kupffer cells (arrowheads), endothelial cells of sinusoidal capillaries (large arrows) and punctate lysosome-like distribution of positive signals (small arrows); Annotation in kidney IHC: cortical tubules (indicated as 'T'), glomeruli (indicated as 'G'), and tubular epithelial cells (arrows); Annotation in heart IHC: vascular and perivascular cells (arrows).
Figure 9B:
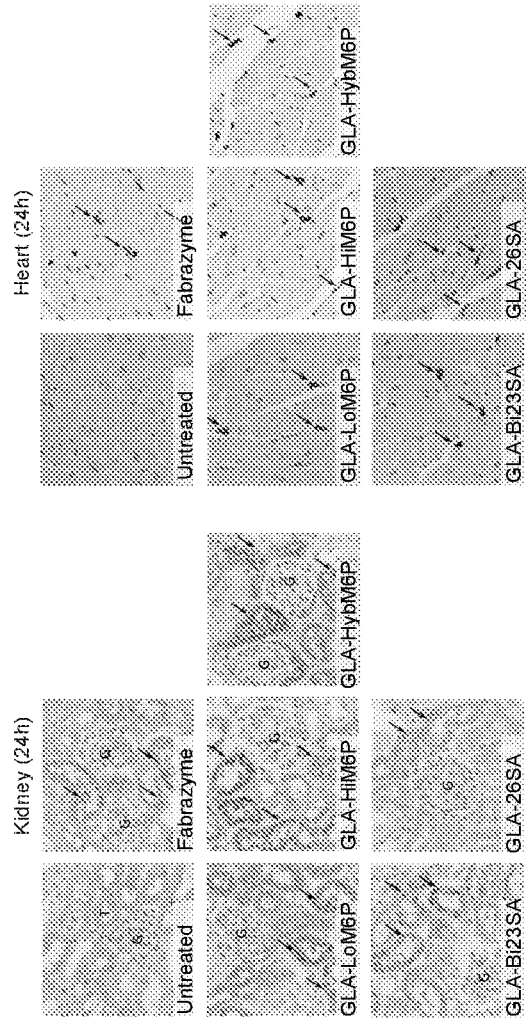
Figure 9C:
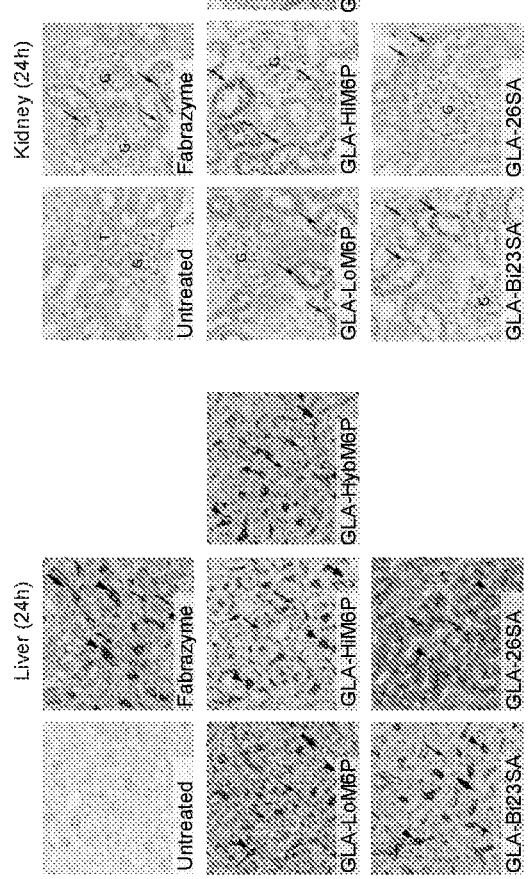

Cellular localization of Fabrazyme and the glycovariants in the heart, kidney and liver was assessed by immunohistochemistry (IHC) (FIG. 9). The localization pattern of Fabrazyme in these organs was consistent with that of agalsidase alfa reported in previous studies by Shen (2016) and Damme (2015). In the heart, Fabrazyme and all five glycovariants were detected in vascular and/or perivascular cells, but not in cardiomyocytes (FIG. 9C). There were no clear differences between the tested variants. In the kidney, Fabrazyme and GLA-LoM6P, GLA-HiM6P, GLA-HybM6P, and GLA-Bi23SA were predominantly detected in tubular epithelial cells (FIG. 9B). However, GLA-26SA had decreased number and intensity of positive signals in tubules compared to the other variants tested. In the liver, Fabrazyme, GLA-LoM6P, GLA-HiM6P, and GLA-HybM6P were detected in hepatocytes, putative Kupffer cells and endothelial cells of sinusoidal capillaries (FIG. 9A). GLA-Bi23SA was also detected in these cell types; however, the number of positive signals in hepatocytes was decreased compared to Fabrazyme. Distribution of GLA-26SA in the liver was remarkably different from the other variants and Fabrazyme; GLA-26SA was detected almost exclusively in hepatocytes, and the number of positive signals in hepatocytes was clearly increased compared to Fabrazyme. This shows that the alpha2-6 SA glycoform can be used for selective targeting to hepatocytes.

In the heart all GLA variants produced distinct positive signals in vascular and/or perivascular cells, but not in cardiomyocytes (FIG. 9C). All staining signals were with a granular cytoplasmic pattern indicating correct localization to the lysosome.

Example 6—Production and Analysis of Wycoengineered GBA

Glucocerebrosidase (GBA) is a lysosomal β-glucosidase that degrades glucosylceramide. Its deficiency results in Gaucher disease (GD). The mature GBA enzyme is a 495 amino acids glycoprotein with four N-glycan sites. Enzyme replacement therapy of macrophage-targeted recombinant human GBA markedly improves visceral symptomatology in GD patients, but the inability of the infused enzyme to pass the blood-brain barrier prohibits the prevention and correction of neurological manifestations (Desnick 2012).

For producing recombinant human glucocerebrosidase A (GBA) we first generated a stable high expressing CHO cell line. Full length cDNA of human GBA1 with His tag was purchased from Sino Biological Inc. and subcloned into modified pCGS3 (Merck/Sigma-Aldrich) for glutamine selection in CHOZN GS−/− cells. Subsequent selection and isolation of a clonal cell line producing GBA was performed as described in Example 1.

For optimization the GBA glycodesigns shown in Table 3 were planned and cell engineering was done according to protocol described in example 2. Cell clones were analyzed using GBA ELISA assay.

TABLE 3

The following GBA glycovariants were pursued:

| GBA variant | Design/Glycostructure | Cell engineering Knock-out | Cell engineering Knock-in |
|---|---|---|---|
| GBA-23SA | No M6P, 2,3 SA linkage | Gnptab | no |
| GBA-hi23SA | No M6P, high SA, 2.3 linkage | Gnptab | ST3GAL4 |

TABLE 3-continued

The following GBA glycovariants were pursued:

| GBA variant | Design/Glycostructure | Cell engineering Knock-out | Cell engineering Knock-in |
|---|---|---|---|
| GBA-HiMan | No M6P, high man | Gnptab, Mgat1 | no |
| GBA-Hybrid (3 mannoses) | No M6P, hybrid with 3 man on alpha 1,6 branch | Gnptab, Man2a1/2 | no |
| GBA-Hybrid (1 mannose) | No M6P, hybrid with 1 man on alpha 1,6 branch | Gnptab, Mgat2 | no |

Example 7—Glycoengineering of GLA in Human Cells

For glycoengineering in human cells (like HEK293) the knock-outs were generated using gRNA addressing human genes. For all human glycosyltransferase genes optimized gRNA's were described in Narimatsu 2018 and for human GNPTAB and GNPTG optimized gRNA sequences are included in Table 1. Human cells predominantly produce alpha2,6 sialic acid capping on the N-glycans and therefore for obtaining homogeneous alpha2,3 SA capping knock-out of the alpha2,6 capping enzyme ST6GAL1 is needed.

The following engineering is performed:
1) HEK293 with knock-out of GNPTAB
2) HEK293 cell with knock-out of GNPTAB/ST6GAL1
3) HEK293 cell with knock-out of GNPTAB/ST6GAL1 and knock-in of ST3GAL4
4) HEK293 with knock-out of GNPTG/GNPTAB/ST6GAL1 and knock-in of ST3GAL4
5) HEK293 with knock-out of GNPTG/GNPTAB/ST6GAL1/MGAT4B/MGAT5 and knock-in of ST3GAL4

For transient expression in HEK293 cells an expression constructs containing the entire coding sequence of human GLA was cloned into BamH1 site of the pTT5 expression vector (Durocher 2002). Engineered HEK293-6E cells were cultured in DMEM/high glucose medium supplemented with 10% FBS and 1% Glutamax. 60% confluent cells were seeded in T75 flasks the day prior to transfection. Plasmid was transfected into cells using PEI, by mixing 30 ul PEI (0.1% linear 25 k Polyethylenimin in 150 mM NaCl, pH 7.0) with 10 ug-GLA.pTT5 expression plasmid in 2 ml Opti-MEM Medium. One day after transfection, culture medium was changed to F17 Medium supplemented with 2% Glutamax and 1% TN1 (Tryptone N1). Culture supernatant was collected after incubating the cells at 37 C for another 2 to 3 days in F17 medium. Secreted GLA was purified from culture supernatant by ion exchange on a DEAE column. The culture supernatant was centrifuged at 3,000 g for 20 min and then further filtered for clarification through a 0.45 m filter. After dilution with 3 volumes of 25 mM MES (pH 6.0) the resulting solution was loaded onto a DEAE sepharose fast-flow column pre-equilibrated with the same buffer. Elution was carried out by applying 0.2 M sodium chloride in 25 mM MES (pH 6.0) and the fractions containing the recombinant GLA were determined by enzyme activity assay and collected. Purity and rough titer of GLA was evaluated by Coomassie staining of SDS-PAGE gels. Site specific N-glycan profiling was done according to procedure described in Example 1.

Figure 10:
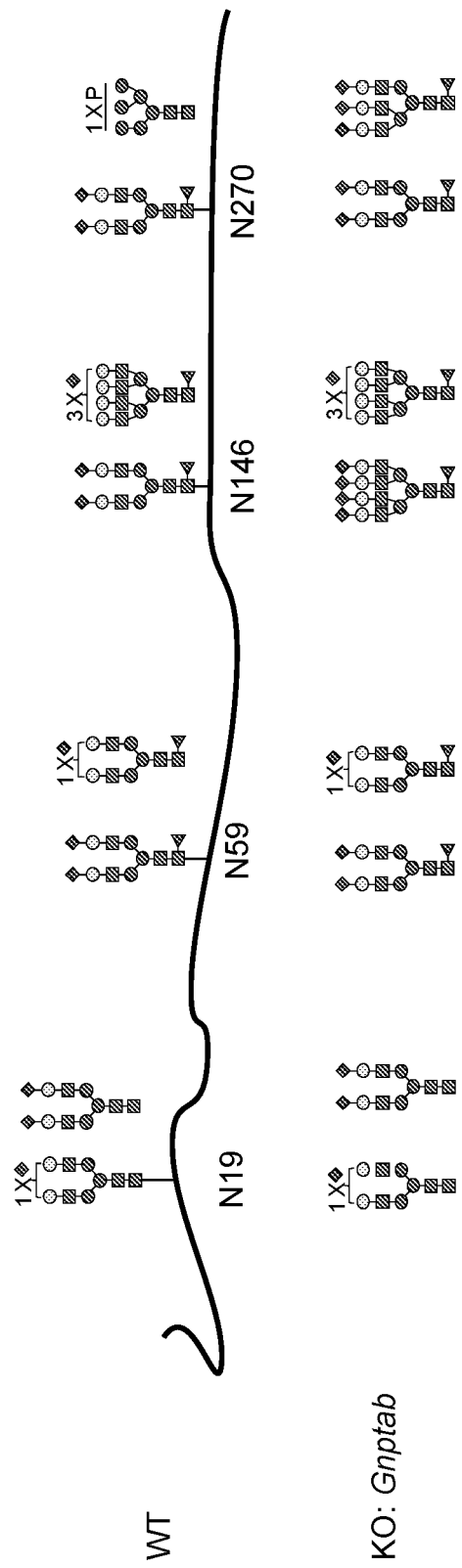
FIG. 10 shows site specific glycoanalysis of GBA expressed in wt CHO cells or an engineered cell line with knock-out of Gnptab. The two most abundant glycan structures at each of the four N-glycosites N19, N59, N146 and N270 of GBA are shown.

Site specific glycoprofiling of GBA produced in wt HEK293 cells or HEK293 cells with GNPTAB knock-out is shown in FIG. 10. The capping of wt glycans produced in HEK293 are similar to CHO (FIG. 2) albeit the CHO cells produced more tri-tetra antennae where HEK293 mostly produce biantennary forms. The knock-out of GNPTAB abolishes the Man6P capping on sites 2 and 3 which were major forms in wt GBA.

Example 8—GLA with Increased Sialylation (Tri/Tetra Antennary)

To increase sialic acid content of a lysosomal enzyme the total number of antennae on the glycans may be increased. For increasing number of antennae and obtain higher alpha2, 3SA content, the inventors generate CHO cell lines with various combinations of MGAT4A/MGAT4B/MGAT5/ST3GAL4 knock-in combined with knock-out of Gnptab and/or gnptg. These engineered cell lines are used to produce novel GLA glycovariants, and variants with most promising glycoforms are analyzed in PK/PD mouse studies. For example, as is discussed further in Example 16 and shown in FIG. 27A, GLA sialic acid content may be optimized by producing the enzyme in CHO cells containing knock-outs of Gnptab and MGAT4B/5 and further containing knock-in of ST3GAL4 and MGAT4A/5. Such a glycostructure-optimized GLA enzyme comprises no Man6P and has high-antennary glycans with high 2,3 sialic acid content, and these changes result in higher enzyme activity in plasma compared to GLA produced in unmodified wild-type CHO cells (FIG. 27A). Other GLA glycostructures are similarly produced as disclosed herein, to modulate PK/PD properties.

Example 9—Cell Based Glycoengineering of Other Lysosomal Enzymes

Optimized glycans may be displayed on any lysosomal enzyme including, e.g., human iduronate 2-sulfatase (IDS), human arylsulfatase B (N-acetylgalactosamine-4-sulfatase) (ARSB), human lysosomal α-glucosidase (GAA), human alpha-galactosidase (GLA), human beta-glucuronidase (GUSB), human alpha-L-iduronidase (IDUA), human iduronate 2-sulfatase (IDS), human beta-hexosaminidase alpha (HEXA), human beta-hexosaminidase beta (HEXB), human lysosomal α-mannosidase (mannosidase alpha class 2B member 1) (MAN2B1), human glucosylceramidase (GBA), human lysosomal acid lipase/cholesteryl ester hydrolase (lipase A, lysosomal acid type)(LIPA), human aspartylglucosaminidase (N(4)-(beta-N-acetylglucosaminyl)-L-asparaginase) (AGA), and human galactosylceramidase (GALC), by producing such enzymes in the modified cells disclosed herein, e.g., CHO cells or HEK cells containing knock-in and/or knock-out of glycosyltransferase genes.

For example, as is discussed further in Example 16 and shown in FIGS. 27B-D, the lysosomal enzymes GUSB, AGA and Laman were optimized by producing these enzyme in CHO cells containing various glycosyltransferase gene knock-outs and, optionally knock-in to produce optimized enzymes with no Man6P and, optionally, High 2,3 SA, resulting in higher enzyme activity in plasma compared to enzyme produced in unmodified wild-type CHO cells. Thus, these data demonstrate that the optimized glycodesign methods disclosed herein are broadly applicable to any lysosomal enzymes. Such modified enzymes may be useful in treating lysosomal storage diseases such as, e.g., any one or more of those shown in Table 4.

TABLE 4

Lysomal Storage Diseases and Contributing Defective Enzymes

| LYSOSOMAL STORAGE DISEASE | DEFECTIVE ENZYME |
|---|---|
| Aspartylglucoaminouria (AGU) | Aspartylglucoaminidase (AGA) |
| Fabry | Alpha-Galactosidase A (GLA) |
| Farber | Acid ceramidase |
| Fucosidosis | Acid alpha-L-fucosidase |
| Galactosidosialidosis | Protective protein/Cathepsin A |
| Gaucher types 1,2, and 3 | Acid beta-glucosidase, or glucocerebrosidase (GBA) |
| G-M1 gangliosidosis | Acid beta-galactosidase |
| Hunter | Iduronate-2-sulfatase (IDS) |
| Hurler-Scheie | Alpha-L-Iduronidase (IDUA) |
| Krabbe | Galactocerebrosidase/galactosylceramidase (GALC) |
| Alpha-Mannosidosis (Laman) | Acid alpha-mannosidase |
| Beta-Mannosidosis | Acid beta-mannosidase |
| Maroteaux-Lamy | Arylsulfatase B |
| Metachromatic | Arylsulfatase A |
| Morquio B | Acid beta-galactosidase |
| Mucolipidosis II/III | N-Acetylglucosamine-1-phosphotransferase |
| Pompe | Lysosomal alpha-glucosidase (GAA) |

Example 10—Identifying Optimal Glycovariant for a Lysosomal Enzyme

A systematic approach for determining which glycomodification that influence and improve activity of an lysosomal enzyme, may comprise the following:

1) Generating a multiplicity of mammalian cells with modification of genes resulting in modified N-glycans (high/low) with respect to the following parameters: M6P content, Sialic Acid content, Ratio between α2,3/α2,6 Sialic acids, and exposed Mannose content.
2) Express the enzyme in the glycoengineered cell lines and produce a multiplicity of glycovariants of the enzyme
3) Screen the multiplicity of enzyme glycovariants for optimized drug effect in relevant in-vitro assay and/or animal model
4) Identify which glycovariants (and glycodesigns) that have improved drug function Additional round(s) of glycoengineering and screening (steps 1-4) may be applied to secure optimal glycovariant candidate.

The optimization aims at identifying a glycovariant of the enzyme which ultimately give improved clinical performance with respect to one or more parameters including efficacy, dosing, potency, purity, less side-effects and better safety. The assays used for screening will monitor biomarkers/reporters for one or more of these parameters.

For an enzyme glycovariant with improved drug function a production cell line may be developed by transferring the glycodesign to any mammalian cell based production platform.

The examples demonstrate application of a novel cell based glycoengineering platform to generate lysosomal enzymes with improved biodistribution. The cell based production of the final modified enzyme enable easy transfer into industrial manufacturing facilities and rapid and cost-effective development of novel improved ERT's for lysosomal storage diseases

Example 11—Stabilizing the Optimized GLA Variant with 1-Deoxygalactonoiirimycin (DGJ)

For stabilizing the glycooptimized GLA-bi23SA it was mixed and/or coformulated with 1-deoxygalactonojirimycin (DGJ).

Physical stability of modified GLA is established by thermal stability assay e.g. using method described in Benjamin 2012. Briefly GLA was combined with fluorescent SYPRO Orange and various concentrations of DGJ and fluorescence was monitored over time.

In vitro plasma stability of the modified GLA was determined by mixing GLA (1 mg/ml) and DGJ (1/3/10 mg/ml) and mixing with plasma (mouse or human). GLA activity was measured at various time points and in-vitro plasma half-life was established.

In-vivo stability and pharmacokinetics of modified GLA with varying concentrations of DGJ was established by coformulating and administrating modified GLA (0.1/0.2/0.5 or 1.0 mg/kg) with DGJ (0.1/0.3/0.5/1/3/10 mg/kg) to Fabry mice. Pharmacokinetics was established as described in Example 3.

Example 12—the Glycosylation Design Space for Recombinant Lysosomal Replacement Enzymes in CHO Cells Lysosomal replacement enzymes are essential therapeutic options for rare congenital lysosomal enzyme deficiencies, but enzymes in clinical use are only partially effective due to short circulatory half-life and inefficient biodistribution. Replacement enzymes are primarily taken up by cell surface receptors recognizing glycans, and the structures of glycans influence uptake, biodistribution, and circulation time. It has not been possible to design and systematically study effects of different glycan features in the past, but here we present a comprehensive gene engineering screen in Chinese hamster ovary (CHO) cells that for the first time enables production of lysosomal enzymes with N-glycans custom designed to affect key glycan features guiding cellular uptake and circulation. We demonstrate distinct predicted organ distribution and circulation time of different glycoforms of α-galactosidase A in a Fabry disease mouse model, and find that an α2-3 sialylated glycoform designed to eliminate uptake by the mannose 6-phosphate and mannose receptors exhibits improved targeting to hard-to-reach organs such as heart, and longer circulation time. This may suggest a paradigm shift in design of some replacement enzymes, and the developed design matrix and engineered CHO cell lines now enables systematic studies towards improving enzyme replacement therapeutics.

Lysosomal storage diseases (LSDs) are characterized by the progressive accumulation of undegraded metabolites that lead to lysosomal and cellular dysfunction. At present ~70 LSDs are known and most are caused by inherited gene mutations that impair targeting or function of lysosomal enzymes. During the past three decades, a variety of therapeutic approaches have been developed for LSDs with intravenous enzyme replacement therapies (ERTs) being the most prevalent, and currently replacement enzymes for Fabry disease, Gaucher disease type I, mucopolysaccharidoses (MPS I, II, IVA, VI and VII5), Neuronal Ceroid Lipofuscinosis (CLN2)6, Wolman disease, and Pompe disease are in use, and more and more are in clinical trials. Despite more than 25 years of clinical experience, ERTs for LSDs still face major challenges, and the most important may be the delivery of the infused recombinant enzymes to hard-to-reach organs such as bone, cartilage, kidney, heart, and brain.

Lysosomal enzymes are glycoproteins with N-glycans and the cellular uptake of replacement enzymes is thought to primarily rely on cell-surface receptors recognizing N-glycan features. A number of glycan-binding receptors are found on different cell types including the mannose 6-phosphate (M6P) receptors (MPRs), Ashwell-Morell receptor (AMR) or asialoglycoprotein receptor (ASGPR), and mannose receptor (MR), and these participate in cellular uptake and lysosomal delivery of therapeutic glycoproteins. The MPRs specifically recognize terminal M6P attached to high-mannose and hybrid-type N-glycans, and they direct both intracellular delivery of endogenously produced lysosomal enzymes as well as the uptake and delivery of exogenous M6P-containing glycoproteins from circulation and extracellular space. The AMR expressed primarily on liver hepatocytes recognizes glycoproteins with uncapped terminal galactose (Gal) or N-Acetyl-galactosamine (GalNAc) residues, usually as a result of insufficient addition of sialic acids or loss due to sialidase activities, and mediates rapid clearance from the circulation. The MR expressed primarily on mononuclear macrophages binds mainly exposed mannose (Man), N-Acetyl-glucosamine (GlcNAc) and fucose (Fuc) residues on N-glycans, and directs uptake of glycoproteins and targeting to endosomes and lysosomes. Tissue distribution and circulation time of infused replacement enzymes are at least partly dependent on the expression of these receptors. A number of other glycan-binding proteins and receptors including Siglecs and Galectins could potentially bind therapeutic N-glycoproteins, and glycan-independent uptake of lysosomal enzymes by e.g. the low-density lipoprotein receptor proteins (LRPs). The glycosylation states of most replacement enzymes are critical for the pharmacokinetic properties and therapeutic effect, with the key determining factors believed to be a balance between N-glycan features that include the degree of M6P-tagging and exposure of terminal Man, Gal, and/or GlcNAc residues in a complex interplay yet unexplored. Most currently approved ERTs have highly heterogeneous N-glycan structures, often with low M6P stoichiometry, as dictated by the inherent glycosylation capacity of CHO cells. However, there have been limited options for custom design of the glycosylation capacity of CHO cells and thus for testing specific ERTs with different N-glycan features to explore potential improved therapeutic performance.

Different strategies have been undertaken to explore glycoengineering as a means to improve delivery of ERTs, including use of exoglycosidases for postproduction enzyme modification, as well as the use of engineered yeast and plant production platforms. Pioneering work originally demonstrated how glycosidase trimming of N-glycans on the lysosomal enzyme β-glucoscerebrosidase (GBA) resulted in efficient targeting of macrophages through the MR and provided a successful therapy for non-neuropathic Gaucher disease. The first recombinant GBA replacement enzyme was produced in CHO cells with Man terminated (high-Man)N-glycans by postproduction exoglycosidase treatment, and other two produced either in human cells by use of an inhibitor of mannosidase I (kifunensine) or in carrot cells. Most strategies for glycoengineering of lysosomal enzymes have sought to improve targeting by MPRs and MRs by increasing the content of M6P or exposed Man residues. However, these glycoforms will cause rapid and efficient uptake by especially the liver and spleen, while targeting to other organs may be limited. Early studies have demonstrated that increased content of sialic acid (SA) on lysosomal enzymes isolated from plasma improves their circulation time similar to other types of therapeutic glycoproteins. Further studies of such glycoforms have been hampered by lack of suitable methods to produce these recombinantly. A different strategy to eliminate lectin-mediated interactions by MPRs, MR and other lectins including the AMR employing oxidative degradation and reduction of recombinant enzymes has demonstrated therapeutic efficacy with extended circulation time and wider biodistribution in some cases. However, the procedure partly inactivates the enzyme and may not be easy to control for clinical production.

Most enzymes used for ERTs are produced in CHO cells, and with the advent of efficient precise gene editing tools it is now possible to introduce extensive engineering designs to optimize the glycosylation capacity of CHO cells. Here, we present a first comprehensive screen of engineering options for lysosomal enzymes in CHO cells, and we provide a panel of glycoengineered CHO cell lines with different capacities for producing lysosomal enzymes furnished with all the key glycan features known to affect cellular uptake and circulation time. The extensive engineering performed provides a genetic design matrix that makes it possible to produce and investigate optimal glycoform(s) with high/low/no M6P-tagging, varying exposure of Man, Gal, and GlcNAc residues, and different capping by SA for any lysosomal replacement enzyme without the need for using postproduction enzyme modifications or alternative yeast and plant expression systems. Using the α-galactosidase A (GLA) as a representative of lysosomal enzyme replacement enzyme therapeutics in a mouse model of Fabry disease, we demonstrate how distinct glycoforms of GLA are differentially targeted to liver, spleen, kidney and the heart. We tested the performance of glycoforms without M6P and exposed Man residues to explore glycoforms without ligands for the major MPRs and MR receptors, and present the first evidence that glycoforms capped with α2-3 linked sialic acids (α2-3SA), but surprisingly not α2-6SA, exhibit improved circulation and biodistribution, and importantly with higher uptake in heart compared to the current leading agalsidase beta (Fabrazyme) ERT. Thus, in contrast to the current dogma α2-3SA capped glycoforms of at least lysosomal enzymes may represent a new strategy to overcome the most critical problems of rapid clearance in liver and poor biodistribution found with current ERTs.

Results

Figure 11:
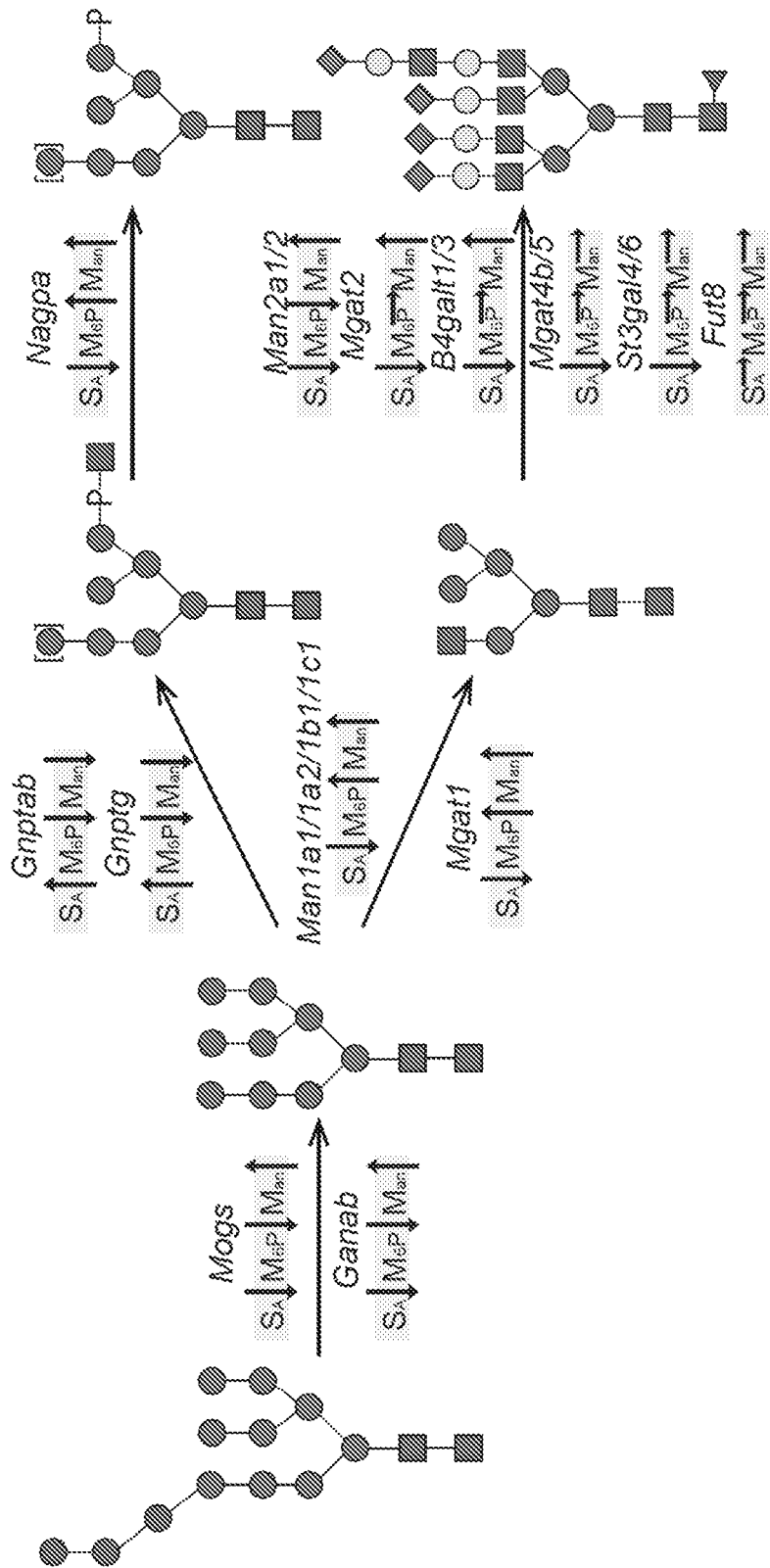
FIG. 11 shows a graphic depiction of gene targeting screen performed in CHO cells with general trend effects on N-glycosylation of GLA. CRISPR/Cas9 targeted genes are indicated with their predicted functions. The general trend effects of KO targeting are indicated for changes in total sialic acid capping (SA), M6P-tagging (M6P), and exposed terminal mannose (Man) with arrows indicating increase/decrease. Glycan symbols according to SNFG format (Varki, A. et al. Symbol Nomenclature for Graphical Representations of Glycans. Glycobiology 25, 1323-1324 (2015), incorporated herein by reference in its entirety).
Figure 11:
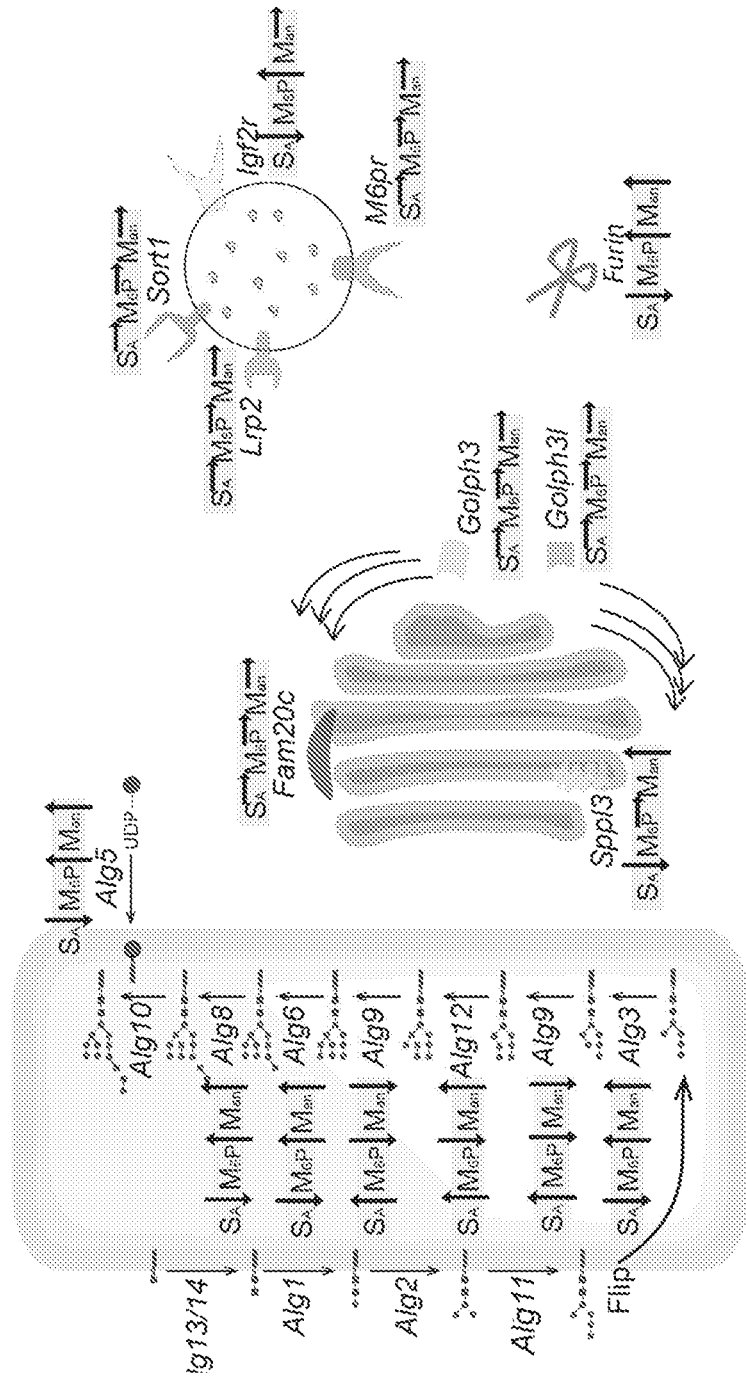
Figure 16:
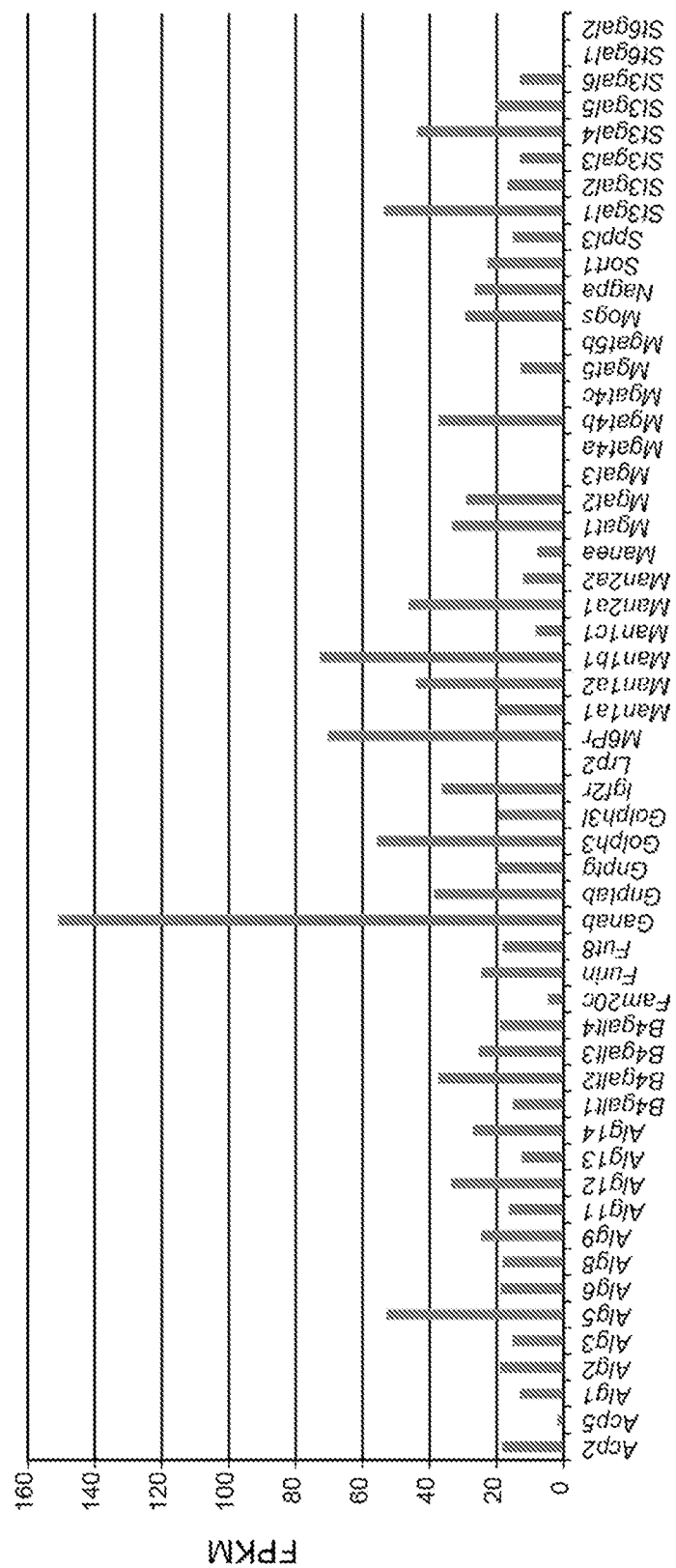
FIG. 16 shows RNAseq transcriptome profiling of CHO cells showing predicted expression of selected genes. RNAseq analysis was performed with CHO GS−/− cells as previously reported.[34] Genes known to function in N-glycosylation and M6P-tagging, including glycosyltransferases, glycosylhydrolases, enzymes involved in dolichol-linked precursor oligosaccharide synthesis, and other related genes, are shown.

Exploring the Glycoengineering Design Space for Lysosomal Enzymes Produced in CHO Cells We first established a stable wildtype (WT) CHO clone expressing high levels of human GLA, which is one of the most widely used ERTs today. Next, we performed a clustered regularly interspaced short palindromic repeat and CRISPR-associated protein 9 (CRISPR/Cas9) mediated gene knockout (KO) targeting screen in the GLA expressing CHO cell line considering all glycosyltransferases and glycosylhydrolases with known or putative functions in N-glycosylation and M6P processing pathways, including enzymes involved in assembly of the lipid-linked oligosaccharide precursor (FIG. 11). We also targeted the MPRs and other receptors known to direct transport of lysosomal enzymes, as well as a heterogeneous group of enzymes known to affect stability and processing of glycosyltransferases (FIG. 11). RNAseq expression profiling was used to identify relevant genes expressed in CHO cells (FIG. 16). We designed and tested 3-4 gRNAs per gene for all such genes with a high throughput work-flow as reported previously (Narimatsu, Y. et al. A validated gRNA library for CRISPR/Cas9 targeting of the human glycosyltransferase genome. Glycobiology 28, 295-305 (2018), incorporated herein by reference in its entirety). GFP-tagged Cas9 nuclease was used to enrich for high Cas9 expression by FACS, and the cutting efficiency and indel profile of each gRNA characterized by Indel Detection by Amplicon Analysis (IDAA)(Yang, Z. et al. Fast and sensitive detection of indels induced by precise gene targeting. Nucleic Acids Res 43, e59 (2015), incorporated herein by reference in its entirety). We developed 43 validated gRNAs constructs (Table 5) and more than 200 CHO cell clones with different gene engineering (Tables 6 and 7). In general, the gene targeting did not affect viability, growth, or productivity substantially in the mutant cell clones.

TABLE 5

CRISPR gRNA design and list of PCR primers used for gRNA target sites.

| Gene | gRNA | #* | Forward primer (5'-3') | #* | Reverse primer (5'-3') | #* |
|------|------|-----|------------------------|-----|------------------------|-----|
| Acp2 | GCTCTGCGGCAGCGCTATAG | 9 | TCGTCTCTTCCCAGACAAGC | 52 | TAGGGTCTGTGAGCCATCCC | 95 |
| Acp5 | GGATGCACGGACGGTACTGC | 10 | GTGCAGTTTTCAGGGGCTTG | 53 | CTCCCCAGAGTAAGGTCCCA | 96 |
| Alg1 | TTCTGCAAGAGCTCATCTCG | 11 | CCCCAGTACACAACTACCCC | 54 | AGTACATGCTGGCCTTGAACA | 97 |
| Alg2 | CTGTGACGTGAAGATATGGA | 12 | CTGCTGCTGGACAGTTCCAA | 55 | ATTGCAGAAGCTCGAGCGAA | 98 |
| Alg3 | GCTGCTGGGCTGCGGAAACG | 13 | TAGCTAGAAACCCTGGTGCC | 56 | TAGTGAACTCACATGCCACCC | 99 |
| Alg5 | GGACTCTAAGTTCACTTACG | 14 | TAGTAGGAGAGAGCCGACCC | 57 | CTTGGGTTCCTCCAGCAAGT | 100 |
| Alg6 | TCTTAATAGGACTCACAGTG | 15 | AAGCAGATGCAGCCCACTCA | 58 | CAAGTGACGGACTTAGCAGGA | 101 |
| Alg8 | TCGGTGTACTTCAAAATCCG | 16 | GTGCAGTGGTCTAAGAACCCA | 59 | TCAAGGCCTGGCAGCTTAC | 102 |
| Alg9 | GAGCAGACATTTGAAAGCAG | 17 | GCCCAAGACCATCGGTTAGAT | 60 | TGTCCGGATTTAGTCTTCGCT | 103 |
| Alg11 | ACTGGTGACATTAATGTCAG | 18 | TGAGTCCCTTTCTTTTTGTGCC | 61 | TCAGGAACACGCTGTGTCAG | 104 |
| Alg12 | AAATCACCAGGCAAGTCAGG | 19 | CAGTGTGACCTTAAGCAGGGT | 62 | CAGGTCATGCGTAGCCTGTA | 105 |
| Alg13 | GATCTTGTCATCAGCCACGC | 20 | AGTTATGAACCACGGAGCCA | 63 | TTGGAAGCTTAGCCAACTGGT | 106 |

TABLE 5-continued

CRISPR gRNA design and list of PCR primers used for gRNA target sites.

| Gene | gRNA | #* | Forward primer (5'-3') | #* | Reverse primer (5'-3') | #* |
|---|---|---|---|---|---|---|
| Alg14 | CTGCGGCAGCTAGAATCAGG | 21 | TTTGACCGCCCAACTCATCA | 64 | AGCGCTCGTAAAGGTGCTAA | 107 |
| 84galt1 | GGGCGGTCGTTATTCCCCCA | 22 | CCCAAACCTCACCTGGTTGAT | 65 | GCTGGCTAACATCTTCGTTCC | 108 |
| 84galt3 | GCAGGACGGTACCGGCCCCC | 23 | ATGCCATATGCAAGCTGCTG | 66 | GTGGGTCCTGTGTCGGTATC | 109 |
| Fam20c | GGGAAGCCTGACCAGATCGA | 24 | ATAGGTCACCGACTCTCCCT | 67 | GCCAATAACATCTGCTTCTACGG | 110 |
| Furin | GACCAAGCGGGACGTGTATC | 25 | GCCCATCTCGGTCTCATTGC | 68 | TGGGGAAGAAGACCAGAACCC | 111 |
| Fut8 | GATCCGTCCACAACCTTGGC | 26 | AGAGTCCATGGTGATCCTGC | 69 | TACTGTTTAAGGGGAGGGGAA | 112 |
| Ganab | GAAGGCTTCGATCCTCTAGC | 27 | GTCGTCTTGCCAACCCCAAA | 70 | CACACCCAGTCTCTTCCCAA | 113 |
| Gnptab | GTCACATTCATCGCATCGAG | 28 | ACCAACGGGCAGATTCCTTC | 71 | CTAGGTGCCCACCCATCTTAG | 114 |
| Gnptg | GCGATGGCGGTGCGGGTGGC | 29 | CTTCCGGTTTTGAGCGCAG | 72 | CAGCCAAGGGCTTTCCTCG | 115 |
| Golph3 | GAAAGGCTCAGTGCAACACT | 30 | GCACAACTGACTCCAGGATG | 73 | GAGCTCTTCAGATGCCATAACC | 116 |
| Golph3l | TGACTTCAGTTCGACGGGTA | 31 | CTCTTTCCCATGTTCCTCCA | 74 | TGTGTGTGTATAGGTCTTCTGTGG | 117 |
| Igf2r | GACAAAAACCTGTCGATCAG | 32 | GCTACACATGGGAGGCTGTT | 75 | CAAACCCAAAGCTGCGGAAA | 118 |
| Lrp2 | TCACACAAGGAATTCCAGTG | 33 | ATCAGTGCCCACTGCCTAAC | 76 | AAGGAACCCAGGTCAAGCAA | 119 |
| M6Pr | GCTATAGATTCAGAGTATGC | 34 | AAGGGAGGGGTGCAGTTTTT | 77 | GACCAGCTGTGGAACTAGGC | 120 |
| Man1a1 | GTAAATATACGCTTCGTCGG | 35 | TGGGCAAGCACACAGGTTTA | 78 | TGACCACCGGAACACGAAAA | 121 |
| Man1a2 | GTCTGTGTTCGTCGGGTCCA | 36 | CCACAGGGCTACCTTGAGAC | 79 | GTCCTTCCAGGCTATGGCTC | 122 |
| Mon1b1 | GAGTACATACCACCTATCGG | 37 | AGCACCAGCACAAAGGGATT | 80 | GCTTTCACCCTCTCATTACGC | 123 |
| Man1c1 | GCCCCGGGCGAGGACGATCC | 38 | TGGAGGTGATGGCCGAAAAC | 81 | CAGTGTGCCTGAAGGGTCTC | 124 |
| Man2a1 | GAGTGAAGCCTCGATCGGGT | 39 | TAATCACAGCTGCGAGGTGG | 82 | ACTGCTATGCACCCCCATTC | 125 |
| Man2a2 | GCCCAGAGAAAGCGTCGTCG | 40 | AGCGGCATATTCAGGGGAAC | 83 | GGGACTGCATACATTGGCCT | 126 |
| Monea | ATAGCCAAGAACTATCCACA | 41 | CGCCCCCTTGGAAAACAAA | 84 | CGAACTAATTACCAACCAATTGAGG | 127 |
| Mgat1 | GAGGGGGTCGCAGGCACACG | 42 | GTGCTTTGGGGTGCTATCCT | 85 | TGTGACTGCACTGCCATAGG | 128 |
| Mgat2 | GCGACCGGTACCGCAGCGTT | 43 | GCGACAAAGGAAGAACGACG | 86 | TAGGTCTCTGGGGCAGTCTC | 129 |
| Mgat4b | GAGAGGCAGGCGCTGCGGGA | 44 | TAGCCTGTGTGTGTCAACCC | 87 | TGGGGAAGGGACAGGTTAGA | 130 |
| Mgat5 | GACAATCTCGTCAATGGCAC | 45 | ACCTGCAGAGGTTTTCAGTTCT | 88 | GCCTTCACAACAATCATGCCA | 131 |
| Mogs | GGTGTCCCTGTTCTTCTACG | 46 | TTTAGCTCAGCCCACTCCAG | 89 | CTCCCTACCCGTACCACTCT | 132 |
| Nagpa | GGGCTGCAGAACGCGCAGTT | 47 | AGAACGGTGGTTTCTTCCGC | 90 | GCGTTCAATGACACACGACT | 133 |
| Sort1 | TTAACAGCAGAGGTATCTGG | 48 | AGGACCATGCCCTGCTCTC | 91 | ATAGCCAGATGGGGACAGGTAG | 134 |
| Sppl3 | GAGGCTTGGCAGGCGGACAA | 49 | ATGTCACCGACAAACGGGAC | 92 | CCACACACCAACTGATCCCC | 135 |
| St3gal4 | GGTCGAAGTGGGCCGACTCA | 50 | AAGAGCGTGTCTGGGTTGTT | 93 | GCAGGGTCCACTTCTGGATT | 136 |
| St3gal6 | GGAGTTGTGATCATTGTGAG | 51 | TCTTGGGTGCTTCTGAGTGTG | 94 | GGACACAGAAAATGGGATGTTG | 137 |

*In Table 5, # denotes the SEQ ID NO of the given gRNA or primer sequence.

TABLE 6

Summary of CHO mutant clones stably expressing GLA and cell line ancestry.

| Project number | Targeted genes | Parental CHO line |
|---|---|---|
| FAB399 | KO Nagpa | WT#H9* |
| FAB400 | KO Gnptab | WT#H9 |
| FAB441 | KO Igf2r | WT#H9 |
| FAB442 | KO Man1a1 | WT#H9 |

TABLE 6-continued

Summary of CHO mutant clones stably expressing GLA and cell line ancestry.

| Project number | Targeted genes | Parental CHO line |
|---|---|---|
| FAB443 | KO Man1a2 | WT#H9 |
| FAB444 | KO Man1b1 | WT#H9 |
| FAB445 | KO Man1c1 | WT#H9 |
| FAB446 | KO Mogs | WT#H9 |
| FAB451 | KO Acp2 | WT#H9 |
| FAB453 | KO Gnptg | WT#H9 |
| FAB454 | KO Acp5 | WT#H9 |
| FAB462 | KO Acp2/5 | WT#H9 |
| FAB478 | KO Alg3 | WT#H9 |
| FAB479 | KO Alg6 | WT#H9 |
| FAB480 | KO Alg9 | WT#H9 |
| FAB494 | KO St3gal4/6 | WT#H9 |
| FAB495 | KO Mgat1 | WT#H9 |
| FAB496 | KO Mgat2 | WT#H9 |
| FAB497 | KO Mgat4b/5 | WT#H9 |
| FAB499 | KO Sppl3 | WT#H9 |
| FAB532 | KI ST6GAL1/KO St3gal4/6 | FAB494 B4 |
| FAB534 | KO Sort1 | WT#H9 |
| FAB535 | KO Lrp2 | WT#H9 |
| FAB540 | KO Fut8 | WT#H9 |
| FAB546 | KO Gnptab/g | WT#H9 |
| FAB555 | KO Furin | WT#H9 |
| FAB560 | KO Manea | WT#H9 |
| FAB567 | KO Mgat4b/5/Gnptab/g | FAB546A2 |
| FAB568 | KO Mgat1/Gnptab/g | FAB546A2 |
| FAB570 | KO Mgat2/Gnptab/g | FAB546A2 |
| FAB571 | KO B4galt1/3/Mgat4b/5/Gnptab/g | FAB567H3 |
| FAB572 | KO Ganab | WT#H9 |
| FAB583 | KI ST3GAL4/ KOMgat4b/5/Gnptab/g | FAB567H3 |
| FAB584 | KO Fut8/Mgat4b/5/Gnptab/g | FAB567H3 |
| FAB604 | KO Fam20c | WT#H9 |
| FAB605 | KO Golph3 | WT#H9 |
| FAB606 | KO Golph3l | WT#H9 |
| FAB611 | KO Alg3/Mgat1 | FAB495B10 |
| FAB662 | KO Alg8 | WT#H9 |
| FAB664 | KO Alg12 | WT#H9 |
| FAB667 | KO Alg5 | WT#H9 |
| FAB677 | KI GNPTG | WT#H9 |
| FAB688 | KO B4galt1/3 | WT#H9 |
| FAB695 | KI GNPTAB | WT#H9 |
| FAB712 | KO Man2a1/2 | WT#H9 |
| FAB713 | KO Man2a1/2/Gnptab | FAB400C7 |
| FAB725 | KO Man1a1/1a2/1b1/1c1 | FAB442G8 |
| FAB791 | KO M6pr | WT#H9 |
| FAB792 | KI GNPTAB/KO Alg3 | FAB695G2 |
| FAB793 | KI GNPTAB/KO Alg3 | FAB695A8 |
| FAB819 | KI GNPTAB/G | FAB695G2 |
| FAB857 | KI ST6GAL1/KO St3gal4/6/Gnptab | FAB532D2 |
| FAB870 | KI ST6GAL1/KO St3gal4/6/Gnptab/Fut8 | FAB857D2 |

*Clone WT#H9 was used as parental clone for all gene engineering.

TABLE 7

Sequence analysis of CHO mutant clones stably expressing GLA.

| Clone | Targeted genes | InDel | Alignment | SEQ ID NO: |
|---|---|---|---|---|
| FAB399C3 | KO Nagpa | | | |
| | WT | | GGGCTGCAGAACGCGCAGTTCGG | 138 |
| | KO | +1 bp | GGGCTGCAGAACGCGCAaGTTCGG | 139 |
| FAB400C7 | KO Gnptab | | | |
| | WT | | GTCACATTCATCGCATCGAGGGG | 140 |
| | KO | +1 bp | GTCACATTCATCGCATCcGAGGGG | 141 |
| FAB441C2 | KO Igf2r | | | |
| | WT | | GACAAAAACCTGTCGATCAGTGG | 142 |
| | KO | +1 bp | GACAAAAACCTGTCGATcCAGTGG | 143 |
| FAB442G8 | KO Man1a1 | | | |
| | WT | | GTAAATATACGCTTCGTCGGTGG | 144 |
| | KO | -2 bp | GTAAATATACGCTT*CG*TCGGTGG | 145 |
| FAB443C5 | KO Man1a2 | | | |
| | WT | | GTCTGTGTTCGTCGGGTCCATGG | 146 |
| | KO | +1 bp | GTCTGTGTTCGTCGGGTtCCATGG | 147 |
| FAB444E7 | KO Man1b1 | | | |
| | WT | | GAGTACATACCACCTATCGGGGG | 148 |
| | KO | +1 bp | GAGTACATACCACCTATtCGGGGG | 149 |
| FAB445H5 | KO Man1c1 | | | |
| | WT | | GCCCCGGGCGAGGACGATCCCGG | 150 |
| | KO | +1 bp | GCCCCGGGCGAGGACGAaTCCCGG | 151 |
| FAB446A2 | KO Mogs | | | |
| | WT | | GGTGTCCCTGTTCTTCTACGTGG | 152 |
| | KO | +1 bp | GGTGTCCCTGTTCTTCTtACGTGG | 153 |
| FAB451H7 | KO Acp2 | | | |
| | WT | | GCTCTGCGGCAGCGCTATAGTGG | 154 |
| | KO | +1 bp | GCTCTGCGGCAGCGCTAaTAGTGG | 155 |

TABLE 7-continued

Sequence analysis of CHO mutant clones stably expressing GLA.

| Clone | Targeted genes | InDel | Alignment | SEQ ID NO: |
|---|---|---|---|---|
| FAB453C1 | KO Gnptg | | | |
| | WT | | GCGATGGCGGTGCGGGTGGCCGG | 156 |
| | KO | -57 bp | CAGTTC--*57 bp deleted*--TTCCT | 157 |
| FAB454F2 | KO Acp5 | | | |
| | WT | | GGATGCACGGACGGTACTGCTGG | 158 |
| | KO | +1 bp | GGATGCACGGACGGTACcTGCTGG | 159 |
| FAB454F2 | KO Acp5 | | | |
| | WT | | GGATGCACGGACGGTACTGCTGG | 160 |
| | KO | +1 bp | GGATGCACGGACGGTACcTGCTGG | 161 |
| FAB462C1 | KO Acp2 | | | |
| | WT | | GCTCTGCGGCAGCGCTATAGTGG | 162 |
| | KO | -2 bp | GCTCTGCGGCAGCGCTATAGTGG | 163 |
| | KO Acp5 | | | |
| | WT | | GGATGCACGGACGGTACTGCTGG | 164 |
| | KO-alle1 | -1 bp | GGATGCACGGACGGTACTGCTGG | 165 |
| | KO-alle2 | -20 bp | AGATGG--*20 bp deleted*--TGTCA | 166 |
| FAB462B2 | KO Acp2 | | | |
| | WT | | GCTCTGCGGCAGCGCTATAGTGG | 167 |
| | KO | +1 bp | GCTCTGCGGCAGCGCTAtTAGTGG | 168 |
| | KO Acp5 | | | |
| | WT | | GGATGCACGGACGGTACTGCTGG | 169 |
| | KO | +1 bp | GGATGCACGGACGGTACgTGCTGG | 170 |
| FAB478H2 | KO Alg3 | | | |
| | WT | | GCTGCTGGGCTGCGGAAACGCGG | 171 |
| | KO | +1 bp | GCTGCTGGGCTGCGGAAaACGCGG | 172 |
| FAB478F5 | KO Alg3 | | | |
| | WT | | GCTGCTGGGCTGCGGAAACGCGG | 173 |
| | KO | -1 bp | GCTGCTGGGCTGCGGAAACGCGG | 174 |
| FAB479A8 | KO Alg6 | | | |
| | WT | | TCTTAATAGGAC TCACAGTGCGG | 175 |
| | KO | +1 bp | TCTTAATAGGACTCACcAGTGCGG | 176 |
| FAB480C2 | KO Alg9 | | | |
| | WT | | GAGCAGACATTTGASAAGCAGTGG | 177 |
| | KO | +1 bp | GAGCAGACATTTGAAAGgCAGTGG | 178 |
| FAB494B4 | KO St3gal4 | | | |
| | WT | | GGTCGAAGTGGGCCGACTCAGGG | 179 |
| | KO | +1 bp | GGTCGAAGTGGGCCGACcTCAGGG | 180 |
| | KO St3gal6 | | | |
| | WT | | GGAGTTGTGATCATTGTGAGCGG | 181 |
| | KO | +1 bp | GGAGTTGTGATCATTGTtGAGCGG | 182 |
| FAB495B10 | KO Mgat1 | | | |
| | WT | | GAGGGGGTCGCAGGCACACGGGG | 183 |
| | KO | +1 bp | GAGGGGGTCGCAGGCACgACGGGG | 184 |
| FAB496E4 | KO Mgat2 | | | |
| | WT | | GCGACCGGTACCGCAGCGTTAGG | 185 |
| | KO | +1 bp | GCGACCGGTACCGCAGCcGTTAGG | 186 |
| FAB497G4 | KO Mgat4b | | | |
| | WT | | GAGAGGCAGGCGCTGCGGGACGG | 187 |
| | KO | +1 bp | GAGAGGCAGGCGCTGCGgGACGG | 188 |
| | KO Mgat5 | | | |
| | WT | | GACAATCTCGTCAATGGCACAGG | 189 |
| | KO | -1 bp | GACAATCTCGTCAATGGCACAGG | 190 |
| FAB499B1 | KO Sppl3 | | | |
| | WT | | GAGGCTTGGCAGGCGGACAAAGG | 191 |
| | KO | +1 bp | GAGGCTTGGCAGGCGGAaCAAAGG | 192 |

TABLE 7-continued

Sequence analysis of CHO mutant clones stably expressing GLA.

| Clone | Targeted genes | InDel | Alignment | SEQ ID NO: |
|---|---|---|---|---|
| FAB532D2 | KO St3gal4 WT | | GGTCGAAGTGGGCCGACTCAGGG | 193 |
| | KO | +1 bp | GGTCGAAGTGGGCCGACcTCAGGG | 194 |
| | KO St3gal6 WT | | GGAGTTGTGATCATTGTGAGCGG | 195 |
| | KO | +1 bp | GGAGTTGTGATCATTGTtGAGCGG | 196 |
| | KI ST6AL1 | | | |
| FAB534F1 | KO Sort1 WT | | TTAACAGCAGAGGTATCTGGGGG | 197 |
| | KO | +1 bp | TTAACAGCAGAGGTATCcTGGGGG | 198 |
| FAB535C2 | KO Lrp2 WT | | TCACACAAGGAATTCCAGTGTGG | 199 |
| | KO | +1 bp | TCACACAAGGAATTCCAaGTGTGG | 200 |
| FAB540E9 | KO Fut8 WT | | GATCCGTCCACAACCTTGGCTGG | 201 |
| | KO | +2 bp | GATCCGTCCACAACCTTggGGCTGG | 202 |
| FAB546A2 | KO Gnptab WT | | GTCACATTCATCGCATCGAGGGG | 203 |
| | KO | +1 bp | GTCACATTCATCGCATCcGAGGGG | 204 |
| | KO Gnptg WT | | GCGATGGCGGTGCGGGTGGCCGG | 205 |
| | KO | +1 bp | GCGATGGCGGTGCGGGTtGGCCGG | 206 |
| FAB555E6 | KO Furin WT | | GACCAAGCGGGACGTGTATCAGG | 207 |
| | KO | +1 bp | GACCAAGCGGGACGTGTtATCAGG | 208 |
| FAB560A4 | KO Manea WT | | ATAGCCAAGAACTATCCACAAGG | 209 |
| | KO | +1 bp | ATAGCCAAGAACTATCCcACAAGG | 210 |
| FAB567H3 | KO Mgat4b WT | | GAGAGGCAGGCGCTGCGGGACGG | 211 |
| | KO | +1 bp | GAGAGGCAGGCGCTGCGgGGACGG | 212 |
| | KO Mgat5 WT | | GACAATCTCGTCAATGGCACAGG | 213 |
| | KO | -1 bp | GACAATCTCGTCAATGgCACAGG | 214 |
| | KO Gnptab WT | | GTCACATTCATCGCATCGAGGGG | 215 |
| | KO | +1 bp | GTCACATTCATCGCATCcGAGGGG | 216 |
| | KO Gnptg WT | | GCGATGGCGGTGCGGGTGGCCGG | 217 |
| | KO | +1 bp | GCGATGGCGGTGCGGGTtGGCCGG | 218 |
| FAB568A8 | KO Mgat1 WT | | GAGGGGGTCGCAGGCACACGGGG | 219 |
| | KO | +1 bp | GAGGGGGTCGCAGGCACcACGGGG | 220 |
| | KO Gnptab WT | | GTCACATTCATCGCATCGAGGGG | 221 |
| | KO | +1 bp | GTCACATTCATCGCATCcGAGGGG | 222 |
| | KO Gnptg WT | | GCGATGGCGGTGCGGGTGGCCGG | 223 |
| | KO | +1 bp | GCGATGGCGGTGCGGGTtGGCGGG | 224 |
| FAB570B7 | KO Mgat2 WT | | GCGACCGGTACCGCAGCGTTAGG | 225 |
| | KO | +1 bp | GCGACCGGTACCGCAGCcGTTAGG | 226 |
| | KO Gnptab WT | | GTCACATTCATCGCATCGAGGGG | 227 |
| | KO | +1 bp | GTCACATTCATCGCATCcGAGGGG | 228 |

TABLE 7-continued

Sequence analysis of CHO mutant clones stably expressing GLA.

| Clone | Targeted genes | InDel | Alignment | SEQ ID NO: |
|---|---|---|---|---|
| | KO Gnptg WT | | GCGATGGCGGTGCGGGTGGCCGG | 229 |
| | KO | +1 bp | GCGATGGCGGTGCGGGTtGGCCGG | 230 |
| FAB571C2 | KO B4galt1 WT | | GGGCGGTCGTTATTCCCCAAGG | 231 |
| | KO | +2 bp | GGGCGGTCGTTATTCCCcgCCAAGG | 232 |
| | KO B4galt3 WT | | GCAGGACGGTACCGGCCCCCTGG | 233 |
| | KO | -2 bp | GCAGGACGGTACCGGCCCCTGG | 234 |
| | KO Mgat4b WT | | GAGAGGCAGGCGCTGCGGGACGG | 235 |
| | KO | +1 bp | GAGAGGCAGGCGCTGCGgGGACGG | 236 |
| | KO Mgat5 WT | | GACAATCTCGTCAATGGCACAGG | 237 |
| | KO | -1 bp | GACAATCTCGTCAATGgCACAGG | 238 |
| | KO Gnptab WT | | GTCACATTCATCGCATCGAGGGG | 239 |
| | KO | +1 bp | GTCACATTCATCGCATCcGAGGGG | 240 |
| | KO Gnptg WT | | GCGATGGCGGTGCGGGTGGCCGG | 241 |
| | KO | +1 bp | GCGATGGCGGTGCGGGTtGGCCGG | 242 |
| FAB572E8 | KO Ganab WT | | GAAGGCTTCGATCCTCTAGCAGG | 243 |
| | KO | +1 bp | GAAGGCTTCGATCCTCTtAGCAGG | 244 |
| FAB583E4 | KO Mgat4b WT | | GAGAGGCAGGCGCTGCGGGACGG | 245 |
| | KO | +1 bp | GAGAGGCAGGCGCTGCGgGGACGG | 246 |
| | KO Mgat5 WT | | GACAATCTCGTCAATGGCACAGG | 247 |
| | KO | -1 bp | GACAATCTCGTCAATGgCACAGG | 248 |
| | KO Gnptab WT | | GTCACATTCATCGCATCGAGGGG | 249 |
| | KO | +1 bp | GTCACATTCATCGCATCcGAGGGG | 250 |
| | KO Gnptg WT | | GCGATGGCGGTGCGGGTGGCCGG | 251 |
| | KO KI ST3GAL4 | +1 bp | GCGATGGCGGTGCGGGTtGGCCGG | 252 |
| FAB584G10 | KO Fut8 WT | | GATCCGTCCACAACCTTGGCTGG | 253 |
| | KO | -2 bp | GATCCGTCCACACCTTGGCTGG | 254 |
| | KO Mgat4b WT | | GAGAGGCAGGCGCTGCGGGACGG | 255 |
| | KO | +1 bp | GAGAGGCAGGCGCTGCGgGGACGG | 256 |
| | KO Mgat5 WT | | GACAATCTCGTCAATGGCACAGG | 257 |
| | KO | -1 bp | GACAATCTCGTCAATGgCACAGG | 258 |
| | KO Gnptab WT | | GTCACATTCATCGCATCGAGGGG | 259 |
| | KO | +1 bp | GTCACATTCATCGCATCcGAGGGG | 260 |
| | KO Gnptg WT | | GCGATGGCGGTGCGGGTGGCCGG | 261 |
| | KO | +1 bp | GCGATGGCGGTGCGGGTtGGCCGG | 262 |
| FAB604F9 | KO Fam20c WT | | GGGAAGCCTGACCAGATCGAAGG | 263 |
| | KO | -4 bp | GGGAAGCCTGACCAGATCGAAGG | 264 |

TABLE 7-continued

Sequence analysis of CHO mutant clones stably expressing GLA.

| Clone | Targeted genes | InDel | Alignment | SEQ ID NO: |
|---|---|---|---|---|
| FAB605D1 | KO Golph3 | | | |
| | WT | | GAAAGGCTCAGTGCAACACTGGG | 265 |
| | KO | +1 bp | GAAAGGCTCAGTGCAACcACTGGG | 266 |
| FAB606E12 | KO Golph3l | | | |
| | WT | | TGACTTCAGTTCGACGGGTACGG | 267 |
| | KO | +1 bp | TGACTTCAGTTCGACGGGgTACGG | 268 |
| FAB662F5 | KO Alg8 | | | |
| | WT | | TCGGTGTACTTCAAAATCCGTGG | 269 |
| | KO | +1 bp | TCGGTGTACTTCAAAATtCCGTGG | 270 |
| FAB664B2 | KO Alg12 | | | |
| | WT | | AAATCACCAGGCAAGTCAGGCGG | 271 |
| | KO | +1 bp | AAATCACCAGGCAAGTCcAGGCGG | 272 |
| FAB667E12 | KO Alg5 | | | |
| | WT | | GGACTCTAAGTTCACTTACGAGG | 273 |
| | KO | -1 bp | GGACTCTAAGTTCACT*TACG*AGG | 274 |
| FAB677F4/C4 | KI GNPTG | | | |
| FAB688F7 | KO B4galt1 | | | |
| | WT | | GGGCGGTCGTTATTCCCCAAGG | 275 |
| | KO | -22 bp | GG*GCGG*TC--*18 bp deleted*--GTATTT | 276 |
| | KO B4galt3 | | | |
| | WT | | GCAGGACGGTACCGGCCCCCTGG | 277 |
| | KO-alle1 | — | ACATCC--*37 bp deleted*--TTCCGC | 278 |
| | KO-alle2 | -16 bp | GCAGGACGGTACC-*16 bp deleted*-CC | 279 |
| FAB695G2/A8 | KI GNPTAB | | | |
| FAB712D1 | KO Man2a1 | | | |
| | WT | | GAGTGAAGCCTCGATCGGGTTGG | 280 |
| | KO | +1 bp | GAGTGAAGCCTCGATCGgGGTTGG | 281 |
| | KO Man2a2 | | | |
| | WT | | GCCCAGAGAAAGCGTCGTCGAGG | 282 |
| | KO-alle1 | +1 bp | GCCCAGAGAAAGCGTCGgTCGAGG | 283 |
| | KO-alle2 | +2 bp | GCCCAGAGAAAGCGTCGGcTCGAGG | 284 |
| FAB713A7 | KO Man2a1 | | | |
| | WT | | GAGTGAAGCCTCGATCGGGTTGG | 285 |
| | KO | -2 bp | GAGTGAAGCCTCGATC*GG*GTTGG | 286 |
| | KO Man2a2 | | | |
| | WT | | GCCCAGAGAAAGCGTCGTCGAGG | 287 |
| | KO | +1 bp | GCCCAGAGAAAGCGTCGgTCGAGG | 288 |
| | KO Gnptab | | | |
| | WT | | GTCACATTCATCGCATCGAGGGG | 289 |
| | KO | +1 bp | GTCACATTCATCGCATCcGAGGGG | 290 |
| FAB725G5 | KO Man1a1 | | | |
| | WT | | GTAAATATACGCTTCGTCGGTTGG | 291 |
| | KO | -2 bp | GTAAATATACGCTT*CG*TCGGTTGG | 292 |
| | KO Man1a2 | | | |
| | WT | | GTCTGTGTTCGTCGGGTCCATGG | 293 |
| | KO-alle1 | +1 bp | GTCTGTGTTCGTCGGGTTCCATGG | 294 |
| | KO-alle2 | -13 bp | GTCTGTGTTCGT-*13 bp deleted*-CAG | 295 |
| | KO Man1b1 | | | |
| | WT | | GAGTACATACCACCTATCGGGGG | 296 |
| | KO | +1 bp | GAGTACATACCACCTATtCGGGGG | 297 |
| | KO Man1c1 | | | |
| | WT | | GCCCCGGGCGAGGACGATCCCGG | 298 |
| | KO-alle1 | +1 bp | GCCCCGGGCGAGGACGAaTCCCGG | 299 |
| | KO-alle2 | -17 bp | *GCCCCGGGCGAGGACGAT*CCCGG | 300 |

TABLE 7-continued

Sequence analysis of CHO mutant clones stably expressing GLA.

| Clone | Targeted genes | InDel | Alignment | SEQ ID NO: |
|---|---|---|---|---|
| FAB791F5 | KO M6pr | | | |
| | WT | | GCTATAGATTCAGAGTATGCCGG | 301 |
| | KO | +1 bp | GCTATAGATTCAGAGTAaTGCCGG | 302 |
| FAB792G6 | KO Alg3 | | | |
| | WT | | GCTGCTGGGCTGCGGAAACGCGG | 303 |
| | KO | +1 bp | GCTGCTGGGCTGCGGAAaACGCGG | 304 |
| | KI GNPTAB | | | |
| FAB793F10 | KO Alg3 | | | |
| | WT | | GCTGCTGGGCTGCGGAAACGCGG | 305 |
| | KO | +1 bp | GCTGCTGGGCTGCGGAAaACGCGG | 306 |
| | KI GNPTAB | | | |
| FAB819F7/F6 | KI GNPTAB/G | | | |
| FAB857D2 | KO St3gal4 | | | |
| | WT | | GGTCGAAGTGGGCCGACTCAGGG | 307 |
| | KO | +1 bp | GGTCGAAGTGGGCCGACcTCAGGG | 308 |
| | KO St3gal6 | | | |
| | WT | | GGAGTTGTGATCATTGTGAGCGG | 309 |
| | KO | +1 bp | GGAGTTGTGATCATTGTtGAGCGG | 310 |
| | KI ST6GAL1 | | | |
| | KO Gnptab | | | |
| | WT | | GTCACATTCATCGCATCGAGGGG | 311 |
| | KO | +1 bp | GTCACATTCATCGCATCcGAGGGG | 312 |
| FAB870B1 | KO St3gal4 | | | |
| | WT | | GGTCGAAGTGGGCCGACTCAGGG | 313 |
| | KO | +1 bp | GGTCGAAGTGGGCCGACcTCAGGG | 314 |
| | KO St3gal6 | | | |
| | WT | | GGAGTTGTGATCATTGTGAGCGG | 315 |
| | KO | +1 bp | GGAGTTGTGATCATTGTtGAGCGG | 316 |
| | KI ST6GAL1 | | | |
| | KO Gnptab | | | |
| | WT | | GTCACATTCATCGCATCGAGGGG | 317 |
| | KO | +1 bp | GTCACATTCATCGCATCcGAGGGG | 318 |
| | KO Fut8 | | | |
| | WT | | GATCCGTCCACAACCTTGGCTGG | 319 |
| | KO | +1 bp | GATCCGTCCACAACCTTtGGCTGG | 320 |

NOTE:
Nucleic acids UNDERLINED are the gRNA targeting sequence,
Nucleic acids in BOLD and UNDERLINED are the PAM sequence,
Nucleic acids in lower case letters are insertions,
Nucleic acids in BOLD and *ITALICS* are deletions.

We used site-specific glycoprofiling of the secreted purified GLA to monitor effects on glycosylation. GLA has three N-glycosites (N108, N161, N184), and when expressed in WT CHO cells GLA was site-specifically glycosylated with mainly complex structures capped with SA at N108 and with high-mannose-type M6P glycans at N161 and N184 (FIG. 12a and FIG. 17, Panels 1-3), in agreement with previous reports. We targeted 43 genes individually or in rational combinations guided by the sequential biosynthetic pathway of N-glycans and known groups of isoenzymes with overlapping functions (Supplementary Table 2 and 3). FIG. 11 presents a summary of the observed general trend effects of the screen for SA, M6P and Man, which are the most important parameters known to affect biodistribution of ERTs. The specific effects of each gene targeting on the glycosylation at individual N-glycosites in GLA are shown in FIG. 17.

Targeting the lipid-linked oligosaccharide precursor assembly on the cytosolic side (Alg1/2/11/13/14) was not successful since viable cells with bi-allelic KO could not be established in agreement with similar observations in yeast, however, targeting the precursor assembly on the ER luminal side (Alg3/5/6/8/9/12) produced surprising options for site-specific engineering of M6P-tagging of GLA. KO of Alg3 substantially enhanced M6P-tagging at N108, while reducing M6P at N161 (FIG. 12b and FIG. 17, Panels 4, 5). KO of Alg9 reduced M6P at N161 and increased tagging at N184 (FIG. 12c and FIG. 17, Panel 6). KO of Alg12 reduced M6P at N161 and increased M6P at N184 (FIG. 12d and FIG. 17, Panel 7). KO of Alg6 and Alg8 enhanced hybrid structures with one branch capped by SA and one with M6P at N161 (FIG. 12e, FIG. 12f and FIG. 17, Panels 9, 10). KO of cis-Golgi mannosidases (Man1a1/1a2/1b1/1c1) enriched oligomannose structures and enhanced M6P at all three glycosites (FIG. 12g and FIG. 17, Panels 12-16), which is supported by previous studies. KO of medial Golgi mannosidase (Man2a1/2) created hybrid N-glycans with one branch capped by SA and one with oligomannose at the expense of reduced M6P (FIG. 12h and FIG. 17, Panel 17). KO of Mgat1 as expected completely eliminated complex N-glycans, and interestingly enhanced M6P-tagging at the normal sites, N161 and N184, without inducing M6P-tagging at N108 (FIG. 12i and FIG. 17, Panel 18). KO of Mgat2 produced the mono-antennary hybrid-type N-glycan at N108 without affecting M6P at N161 and N184 (FIG. 12j and FIG. 17, Panel 19), while KO of Mgat4b/5 completely eliminated tri and tetra antennary N-glycans and increased homogeneity (FIG. 12k and FIG. 17, Panel 20). The results demonstrate how the content and position of M6P and exposed Man on lysosomal enzymes can be fine-tuned in great detail by gene engineering of CHO cells. Targeting the N-glycan ER glucosidases (Mogs/Ganab) to probe the role of the Glc residues and chaperone interactions, did not affect secretion of GLA substantially (FIG. 18), and demonstrated that GLA glycoforms with retained Glc residues and M6P-tagging can be produced (FIG. 12l, FIG. 12m and FIG. 17, Panels 21, 22).

We also targeted the M6P-tagging process. KO of Gnptab or Gnptg of the GlcNAc-1-phosphotransferase complex enabled production of GLA with rather homogeneous complex N-glycans capped by SA at all N-glycosites but lacking M6P residues (FIG. 12n, FIG. 12o and FIG. 17, Panels 23, 24). In addition, KO of the GlcNAc-I-phosphate hydrolase (Nagpa) uncovering enzyme resulted in GLA with GlcNAc residues retained on M6P (M6P-GlcNAc) and interestingly increased M6P-tagging including substantial increase in two M6P tags (bis-M6P) (FIG. 12p and FIG. 17, Panel 26). In addition to two high affinity M6P binding sites, the large cation-independent mannose 6-phosphate receptor (CI-MPR) contains another preferential binding site for M6P-GlcNAc, but how such glycoforms would circulate and interact with other receptors is unknown. Targeting the M6P-tagging process may also affect lysosomal targeting of some endogenous CHO cell lysosomal enzymes, and resulting changes in secreted lysosomal glycosylhydrolases like e.g. neuraminidase 1 (Neu1) may affect glycan structures of recombinant expressed enzymes.

Figure 17:
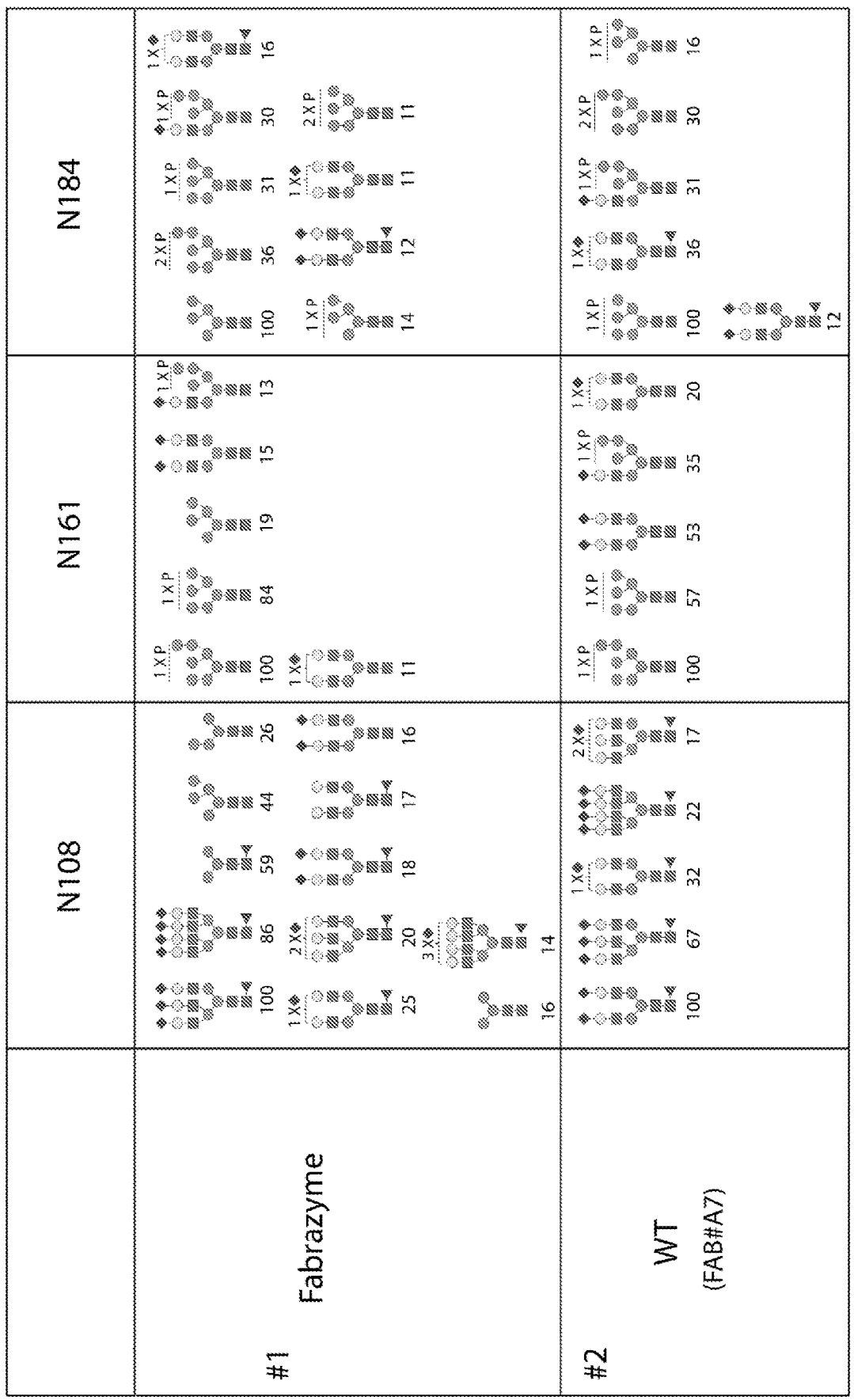
FIG. 17 shows detailed presentation of N-glycans identified by site-specific N-glycan profiling of GLA produced in CHO WT and engineered KO/KI clones as indicated. N-glycan structures and their relative abundances at each of the three N-glycosites (N108, N161, and N184) of GLA are illustrated with their relative abundance adjusted to the most abundant structure. Minor glycoforms identified with relative abundance less than 10% are not shown. Same N-glycan composition may represent isobaric structures.
Figure 17:
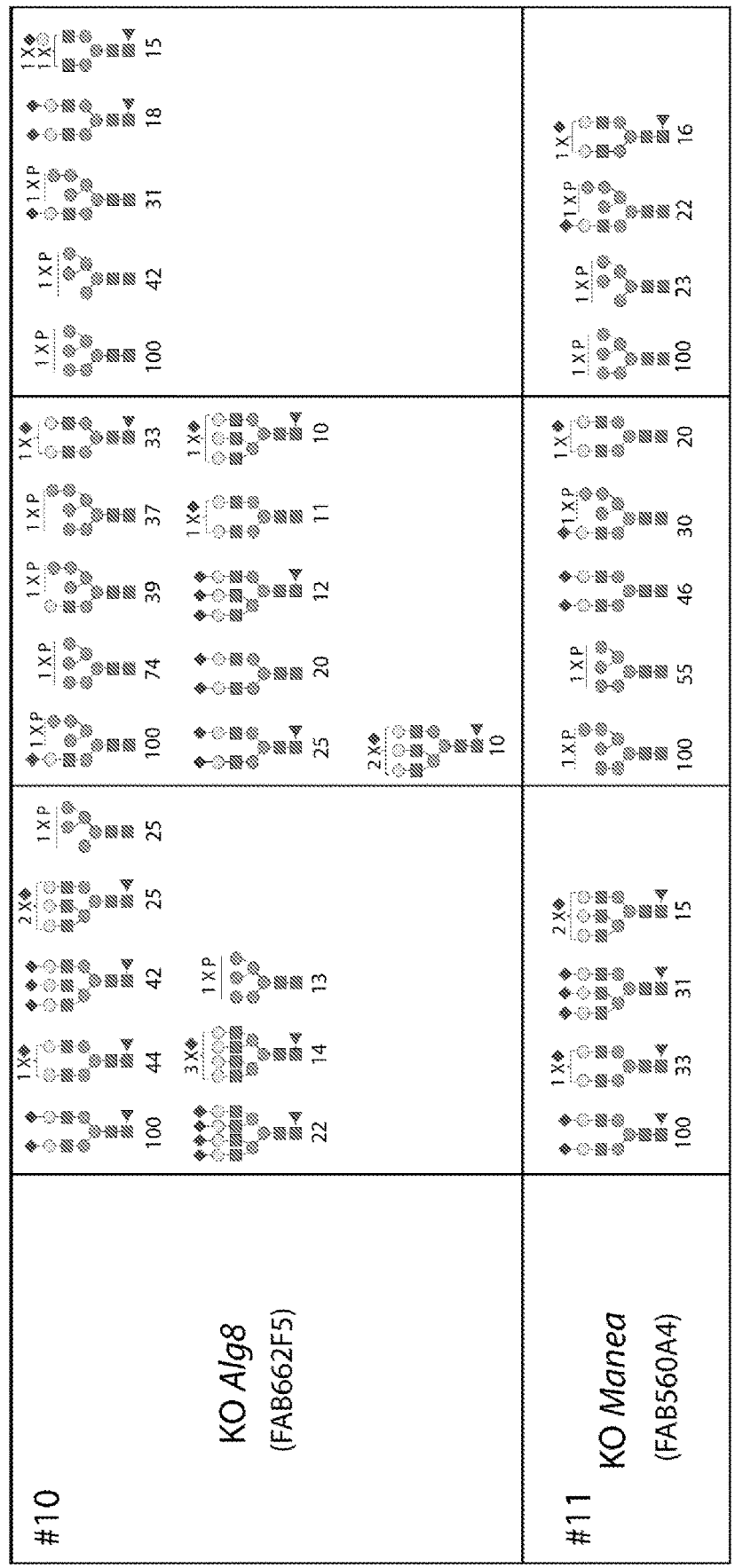
Figure 17:
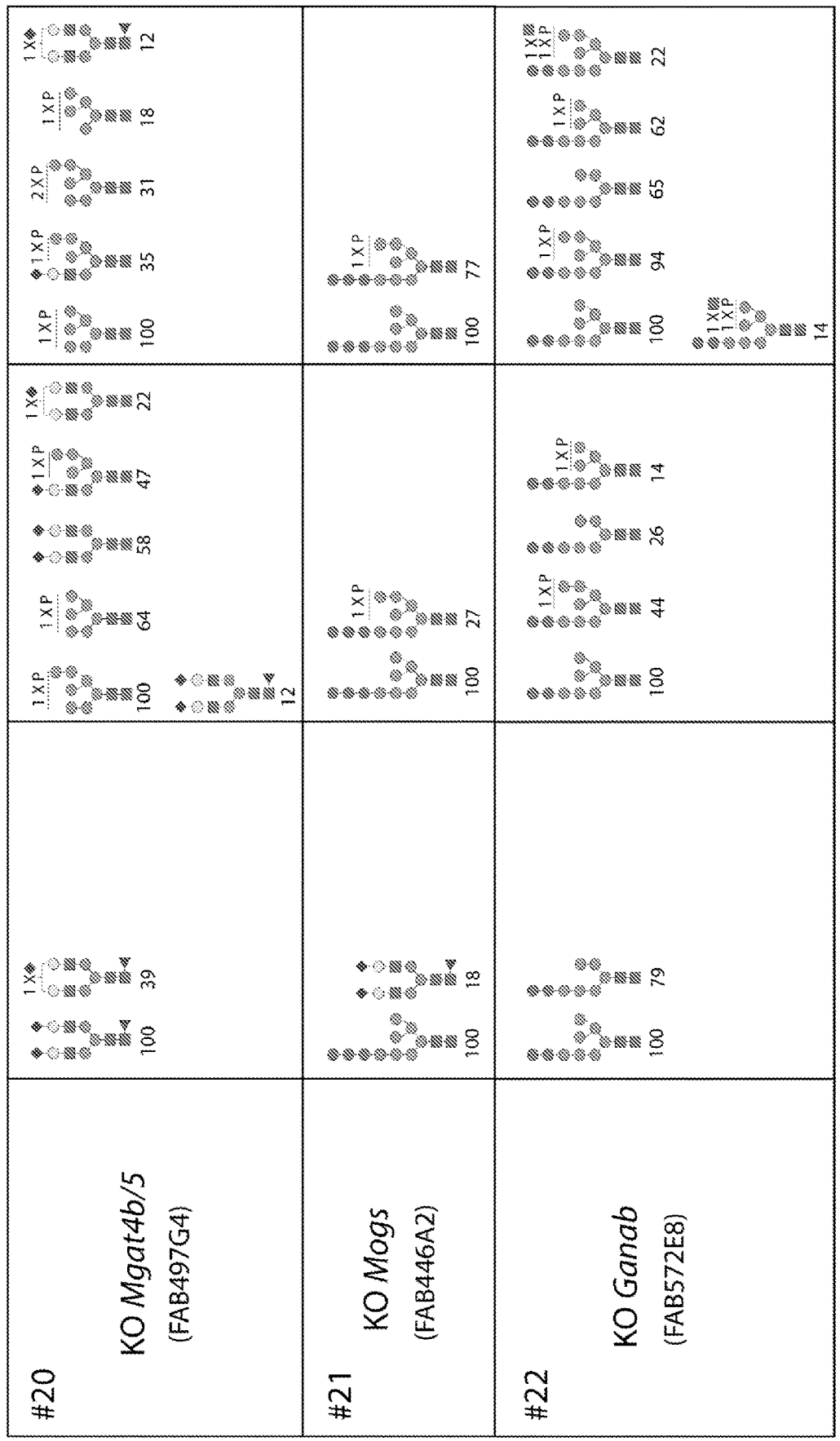
Figure 17:
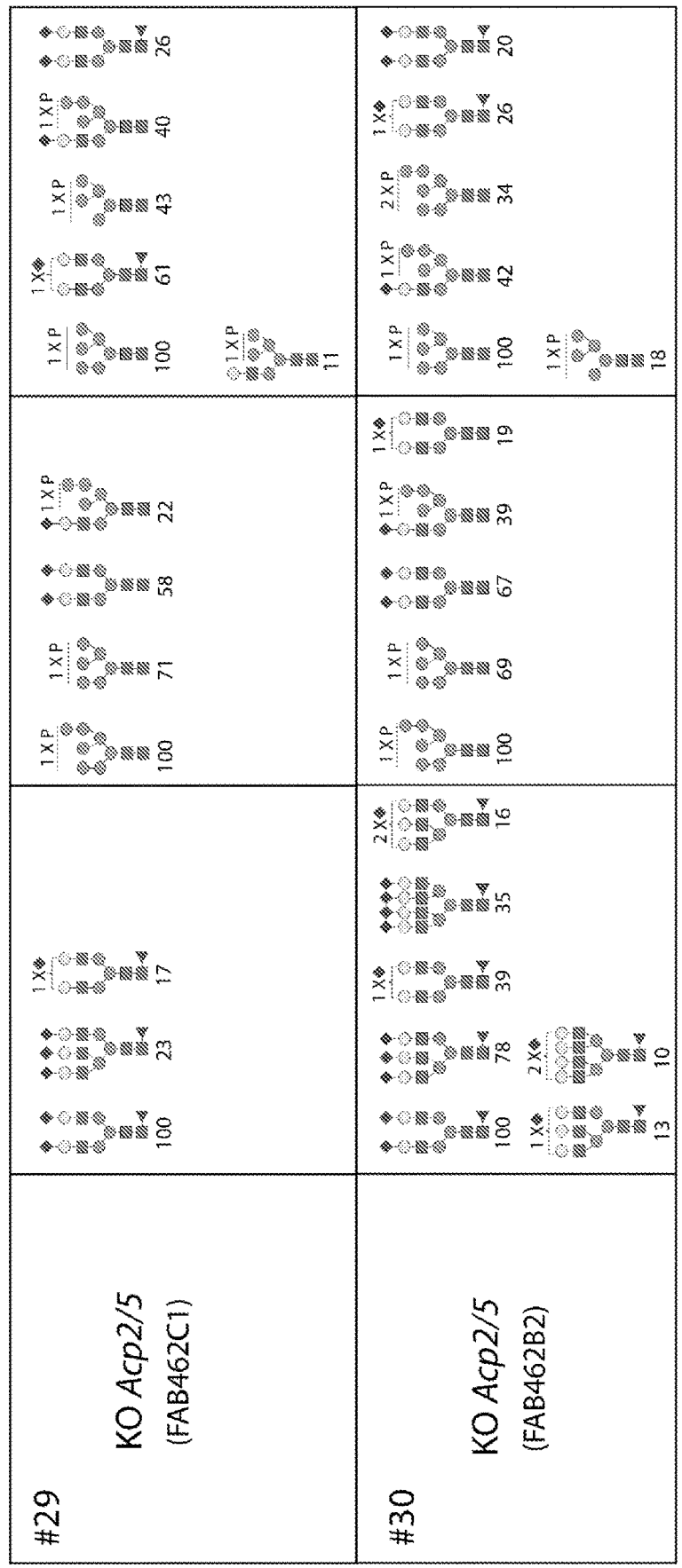
Figure 17:
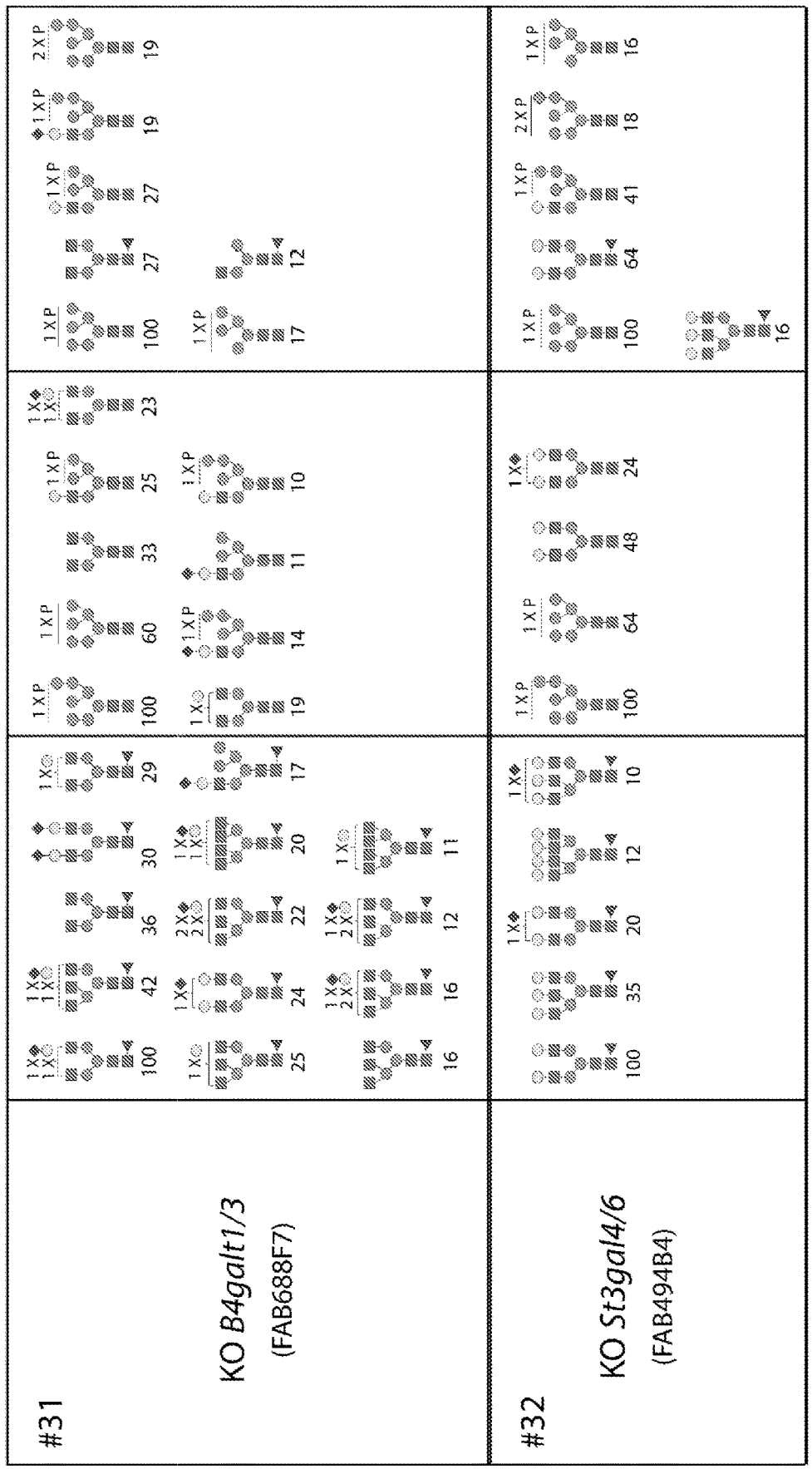
Figure 17:
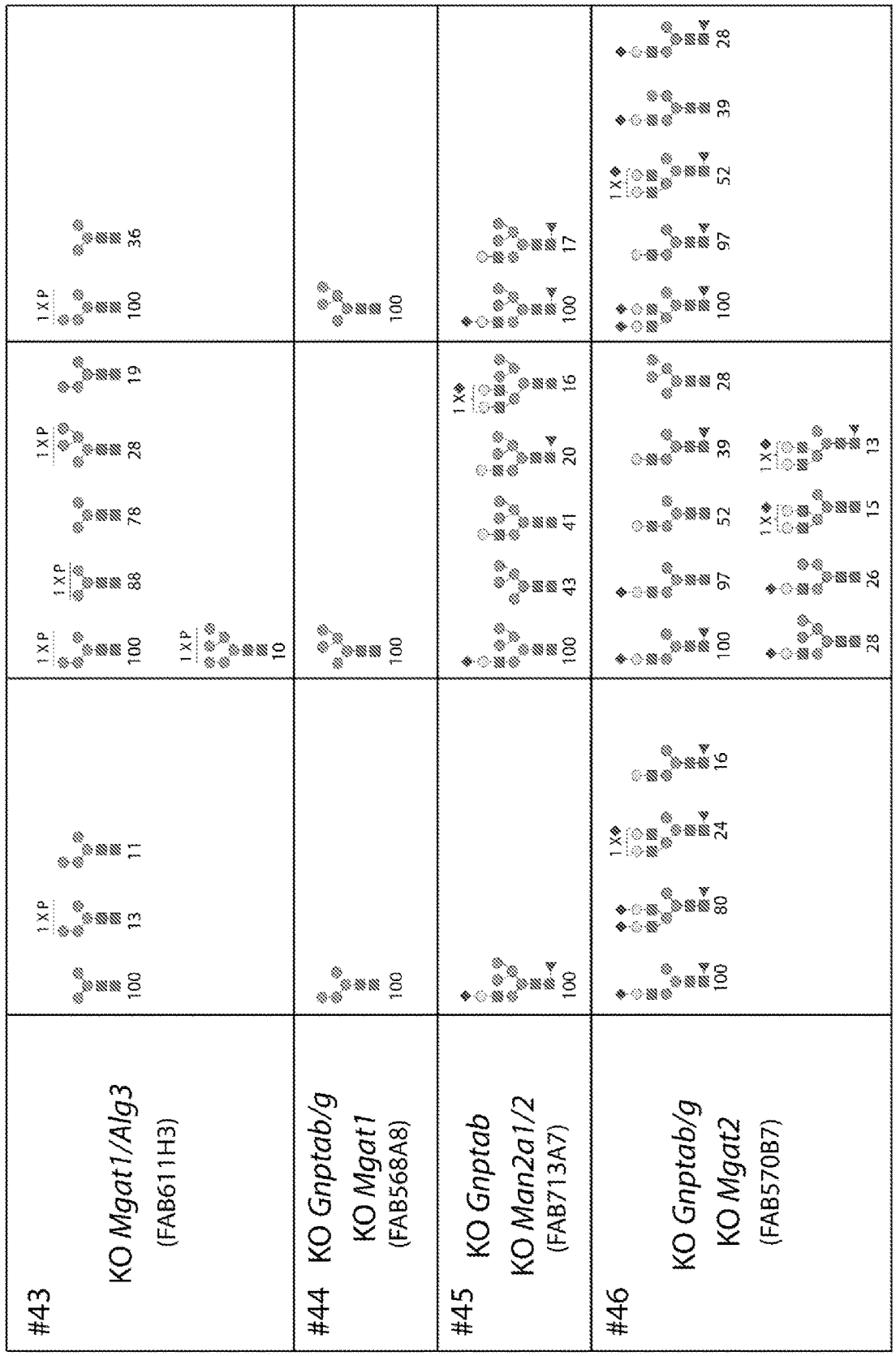
Figure 17:
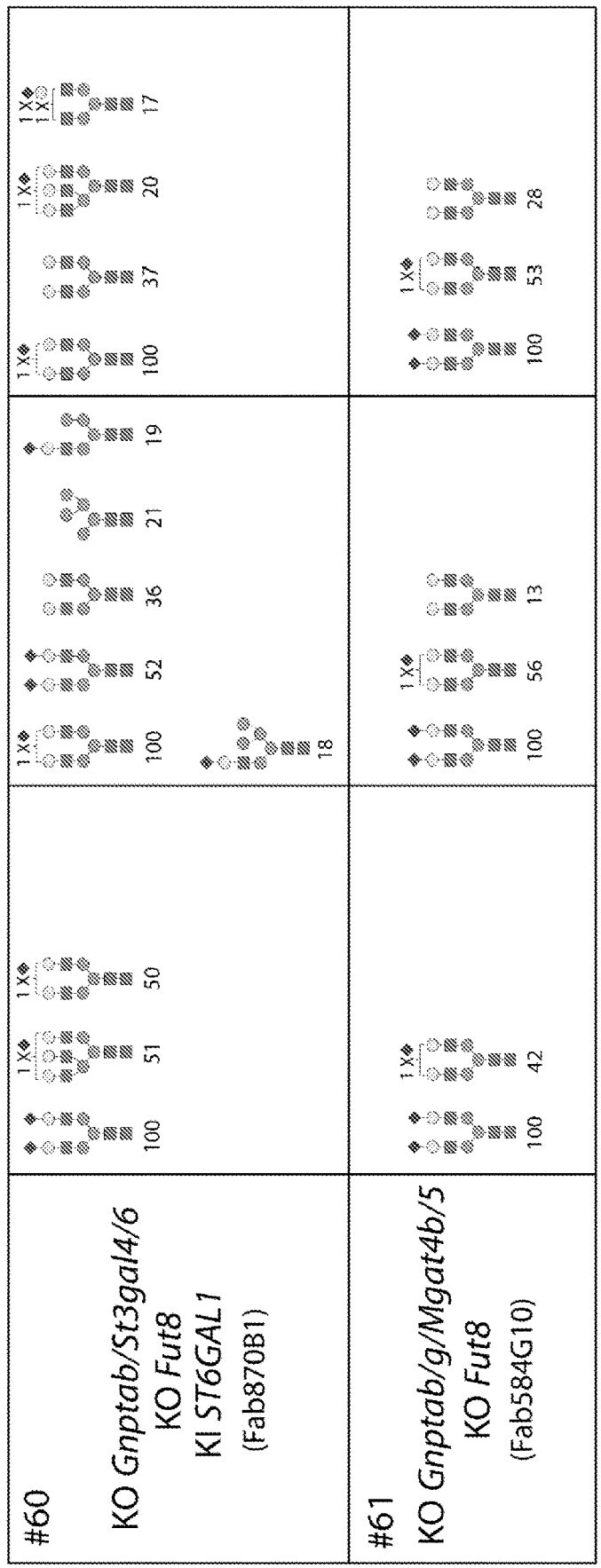

To explore exposure of GlcNAc we targeted the galactosylation process by double KO of B4galt1/3, which substantially reduced galactosylation and resulted in exposed terminal GlcNAc residues on complex N-glycans primarily at N108 (FIG. 12q and FIG. 17, Panel 31). Targeting the sialylation by double KO of St3gal4/6 substantially reduced sialic acid capping and resulted in exposure of terminal Gal residues (FIG. 12r and FIG. 17, Panel 32). Furthermore, targeting the core fucosylation by KO of Fut8 eliminated core fucose without affecting other features (FIG. 12s and FIG. 17, Panel 33).

We also targeted the genes encoding the M6P receptors CI-MPR (Igf2r) and CD-MPR (M6pr), which may bias the pool of secreted GLA by directing high-affinity glycoforms to the lysosome, and while this did not substantially affect glycosylation of the secreted GLA, KO of Igf2r slightly increased bis-M6P-tagging at the N184 glycosite (FIG. 17, Panels 34, 35). Targeting the late-acting signal peptidase, Sppl3, shown to play a role in shedding of glycosyltransferases45, induced a slight increase of exposed Man (FIG. 17, Panel 38). KO of Furin that is important for activation of Nagpa46, resulted in similar N-glycan profile with accumulation of GlcNAc-1-P residues as found with KO of Nagpa confirming the essential role of furin-mediated proprotein activation of this enzyme (FIG. 12t and FIG. 17, Panel 39).

In contrast, targeting the phosphokinase Fam20c and the phosphatidylinositol-4-phosphate (PI4P) effector Golph3 and Golgi protein Golph3l, did not substantially affect the N-glycosylation of GLA (FIG. 17, Panels 40-42).

Combinatorial Glycoengineering

The individual gene KO screen provides a matrix for design of combinatorial engineering to produce GLA with a wider range of desirable glycoforms known to affect cellular targeting receptors. We first explored designs of glycoforms without M6P-tagging. Stacking KO of Gnptab/g with KO of Mgat1 enabled production of GLA with high mannose N-glycans at all three glycosites (4-5 Man residues) (FIG. 13a and FIG. 17, Panel 44). Such high-Man glycoforms have been shown to bind MR expressed on macrophages and efficiently target the liver and spleen. Stacking KO of Man2a1/2 involved in the α-mannosidase trimming process of the α6-branch on top of Gnptab KO generated GLA with a mono-antennary hybrid structure with a complex sialylated α3-arm combined with three Man residues on the α6-arm (FIG. 13b and FIG. 17, Panel 45), which may alter binding to both MPRs and MR. Similarly, stacking with KO of Mgat2 enables production of GLA with mono-antennary hybrid N-glycan, but with a single Man residue at the α6-arm that may even further reduce MR binding (FIG. 13c and FIG. 17, Panel 46). This design was less homogeneous due to branching at the α3-arm, however, stacking KO of Gnptab g with KO of Mgat4b/5 enables production of GLA with homogeneous bi-antennary complex N-glycans with SA capping (FIG. 13d and FIG. 17, Panel 47), and this would also apply with the Mgat2 KO design. These glycoforms are all expected to have no interaction with the MPRs, and instead enable fine-tuning of interactions with the MR guided by the different exposure of terminal Man and content of SA capped glycans.

Next, we focused on improving M6P-tagging by first testing individual knock-in (KI) of GNPTG or GNPTAB, which enhanced M6P at N161 and N184, and with KI of GNPTAB induced bis-M6P at N184 (FIG. 13e,f and FIG. 17, Panels 48-51). We used targeted KI with Zinc-finger nucleases (ZFNs) (modified ObLiGaRe strategy, which is described in Maresca, M., Lin, V. G., Guo, N. & Yang, Y. Obligate ligation-gated recombination (ObLiGaRe): custom designed nuclease-mediated targeted integration through nonhomologous end joining. Genome Res 23, 539-546 (2013), incorporated herein by reference in its entirety) or CRISPR/Cas9 facilitated non-homologous end-joining into a CHO Safe-Harbor locus (as described in Geisinger, J. M., Turan, S., Hernandez, S., Spector, L. P. & Calos, M. P. In vivo blunt-end cloning through CRISPR/Cas9-facilitated non-homologous end-joining. Nucleic Acids Res 44, e76 (2016); Yang, Z. et al. Engineered CHO cells for production of diverse, homogeneous glycoproteins. Nat Biotechnol 33, 842-844 (2015); and Bahr, S., Cortner, L., Ladley, S. & Borgschulte, T. in BMC proceedings, Vol. 7 P3 (BioMed Central, 2013), each of which is incorporated herein by reference in its entirety). Moreover, combined KI of both genes induced a substantial increase in M6P-tagging at all three glycosites and with high content of the mono-antennary hybrid structure with SA and M6P (FIG. 13g and FIG. 17, Panels 52-53). KI of GNPTAB combined with KO of Alg3 enabled production of a unique high-Man N-glycan with efficient M6P-tagging at all N-glycosites exclusively on the α3-arm (FIG. 13h and FIG. 17, Panels 54, 55). The CI-MPR has multiple binding sites and the capacity to bind diverse M6P-tagged structures with different affinities[53], and increasing the M6P content and introducing bis-M6P are predicted to enhance uptake as demonstrated e.g. with the acid α-glucosidase (GAA) used for ERT of Pompe disease.

We also engineered cells to produce GLA with homogenous α2-6SA capping. CHO WT cells only have capacity for α2-3SA capping, and systematic studies of the influence of α2-3SA versus α2-6SA capping found on most human serum glycoproteins have not been performed in the past, although the interaction with many receptors are affected by the linkage of the SA, including e.g. Galectins that are blocked by α2-6SA and Siglecs that exhibit differential interactions with the different SAs. The AMR may have different interactions with glycans capped by α2-6SA. Stacked KO of Gnptab and St3gal4/6 with targeted KI of ST6GAL1 enabled production of GLA with homogeneous α2-6SA capping and higher content of bi-antenary structures (FIG. 13*i* and FIG. 17, Panel 58). KO of Mgat4b/5 with KI of ST3GAL4 enabled production of homogenous biantennary N-glycans capped with α2-3SA (FIG. 13*j* and FIG. 17, Panel 59). Combined with KO of Fut8, any glycoform may likely be produced without core fucose (FIG. 13*k,l* and FIG. 17, Panels 60, 61).

The Glycoengineering Matrix is Applicable to Other ERTs

Figure 14:
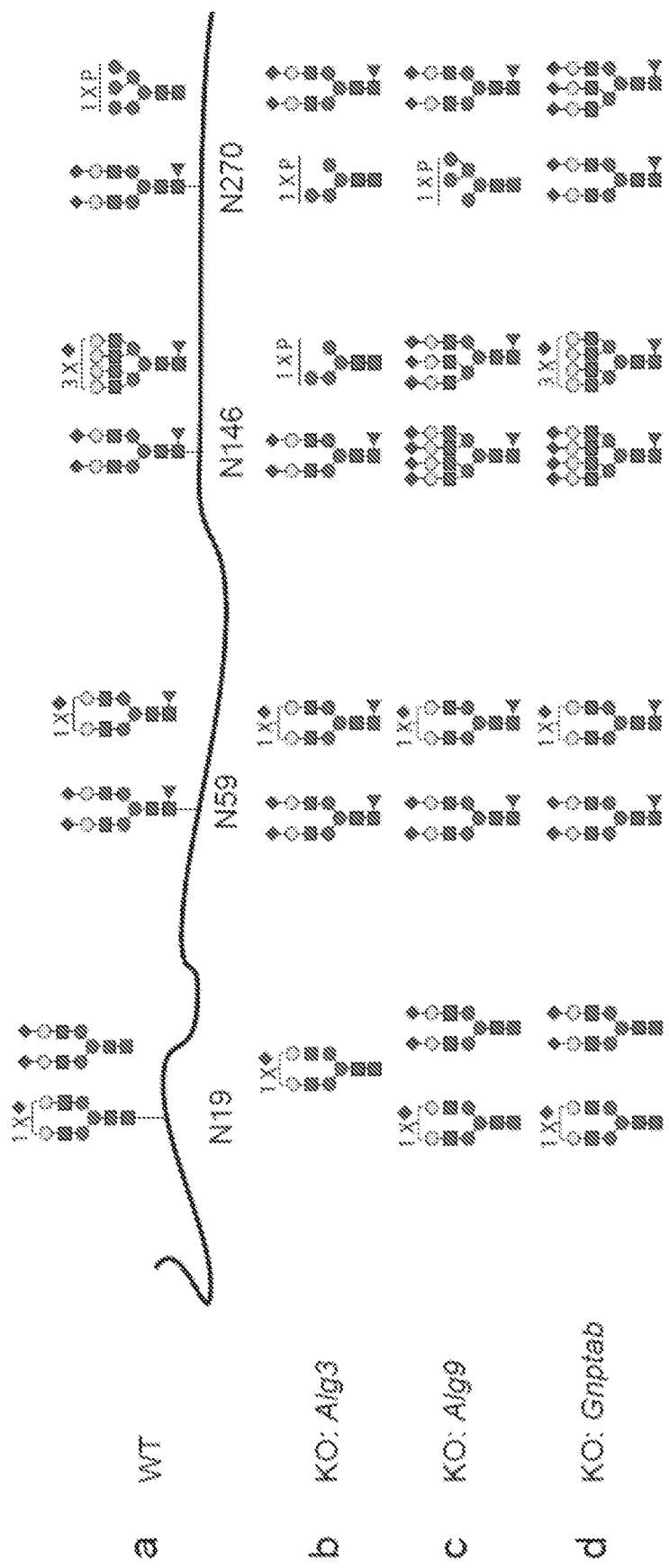
FIG. 14 shows tests demonstrating the universality of glycoengineering using recombinant GBA as reporter glycoprotein. The two most abundant glycan structures at N-glycosites N19, N59, N146 and N270 of GBA produced CHO WT (a) and CHO KO clones (b-h) are shown. Each glyco structure was confirmed by targeted MS/MS analysis. Details regarding the stacking ancestry, sequence analysis and N-glycans profiling are shown in Tables 8 and 9, and FIG. 19, respectively.
Figure 14:
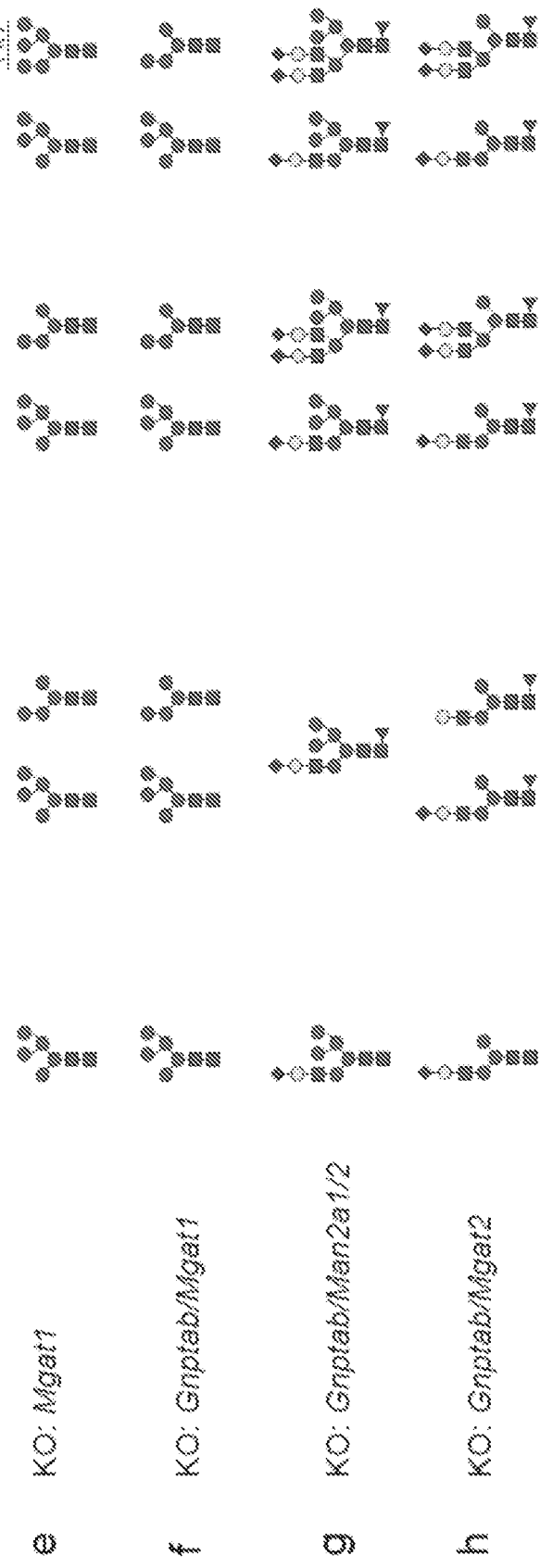
Figure 19:
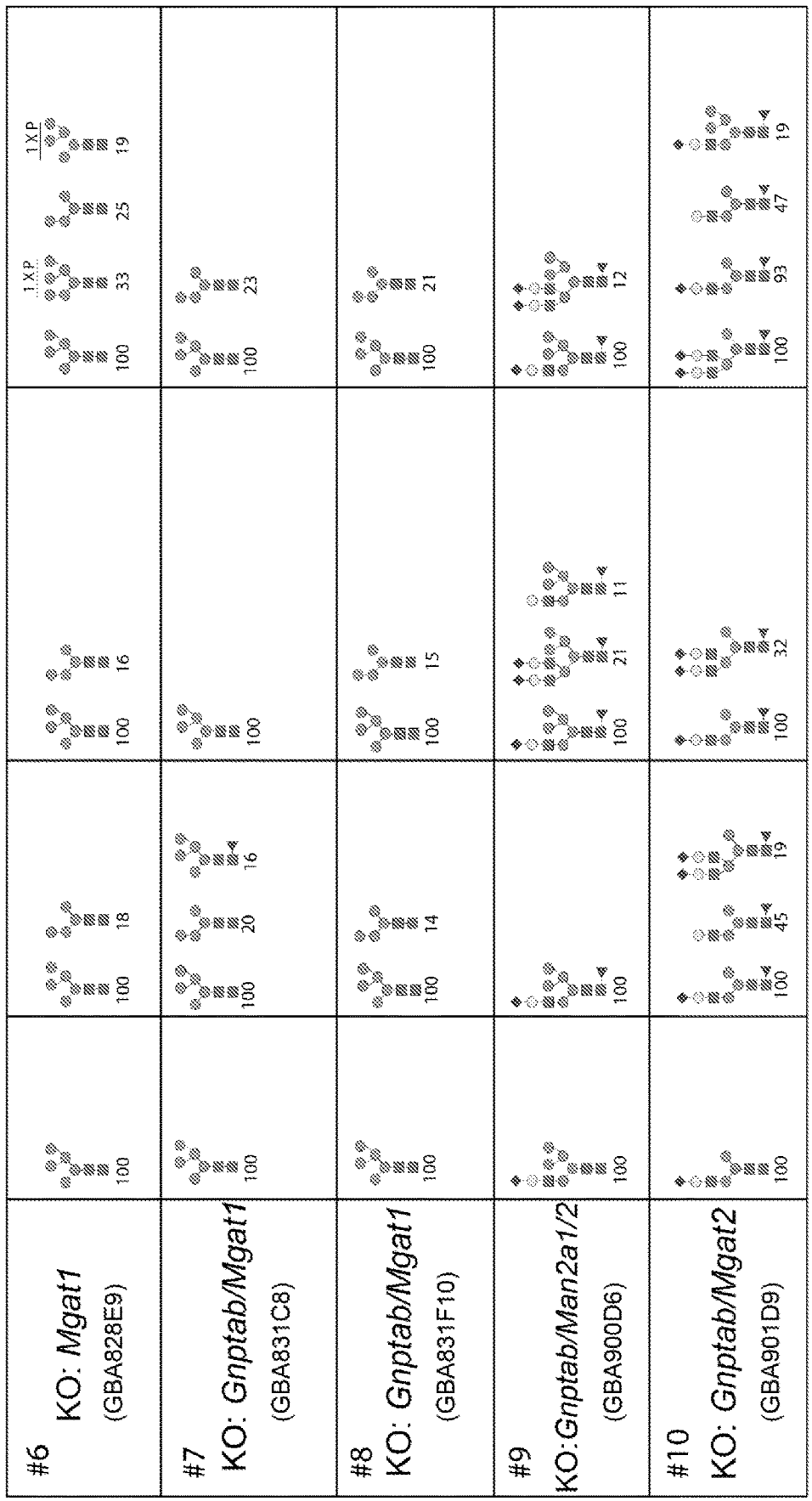
FIG. 19 shows detailed presentation of N-glycans identified by site-specific N-glycan profiling of GBA produced in CHO WT and engineered KO clones as indicated. N-glycan structures and their relative abundances at each of the four N-glycosites (N19, N59, N146, and N270) of GBA are illustrated with their relative abundance adjusted to the most abundant structure. Minor glycoforms identified with relative abundance less than 10% are not shown. Same N-glycan composition may represent isobaric structures.
Figure 20A:
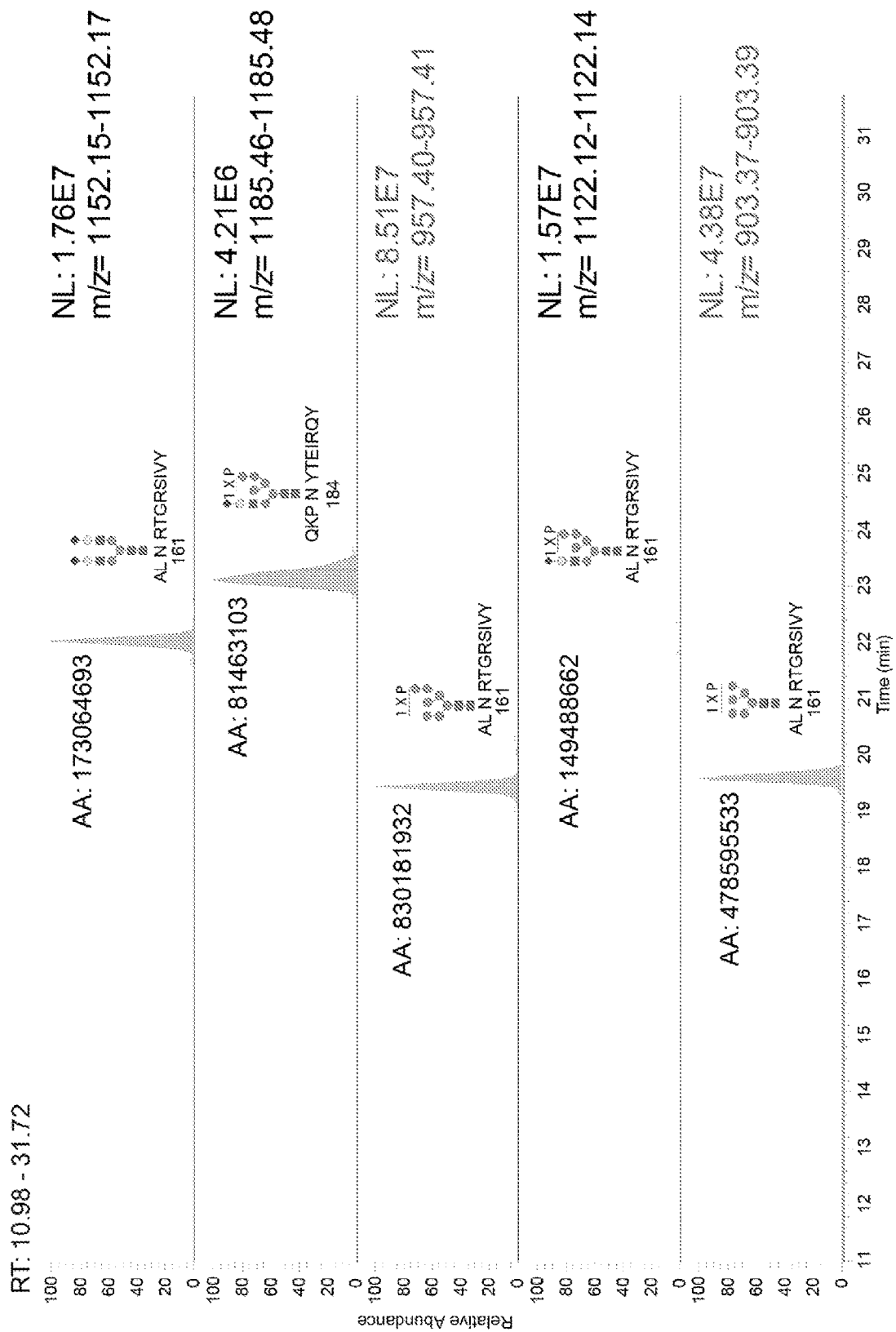
FIG. 20A shows extracted ion chromatograms of 5 representative glycopeptide precursors of GLA produced in CHO WT.
Figure 20:
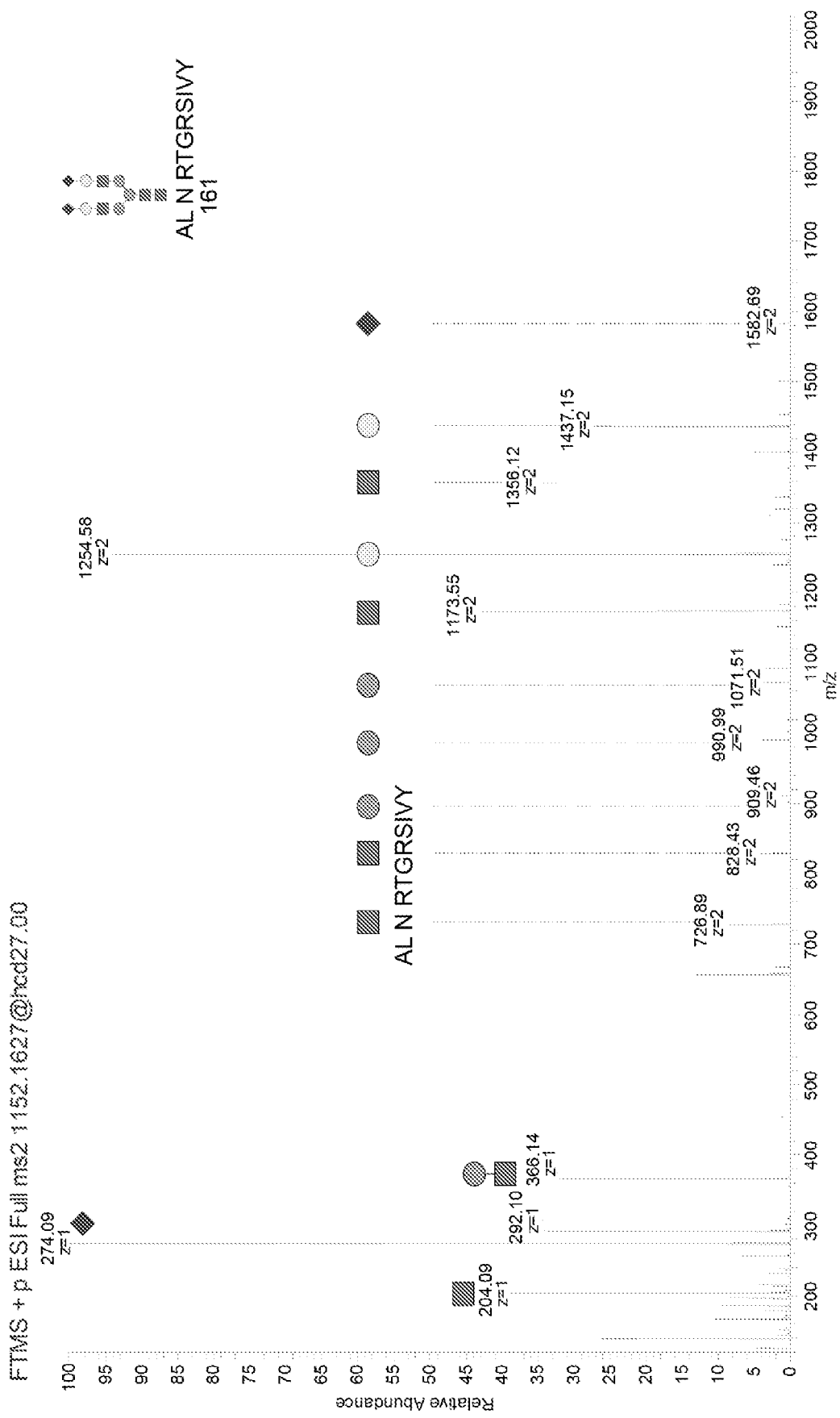
FIG. 20 shows targeted MS/MS manual annotation of the most representative glycopeptides.
Figure 20:
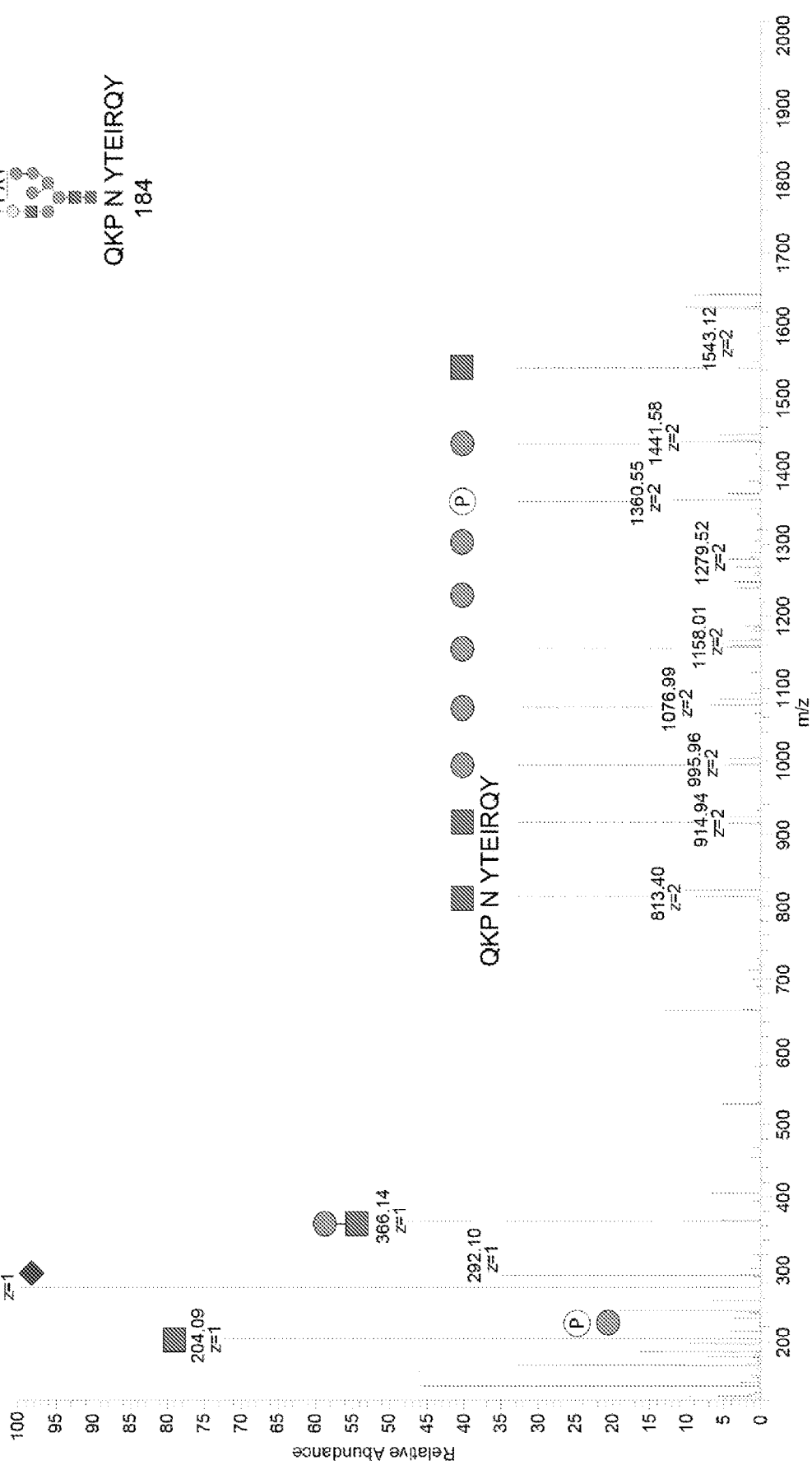
Figure 20:
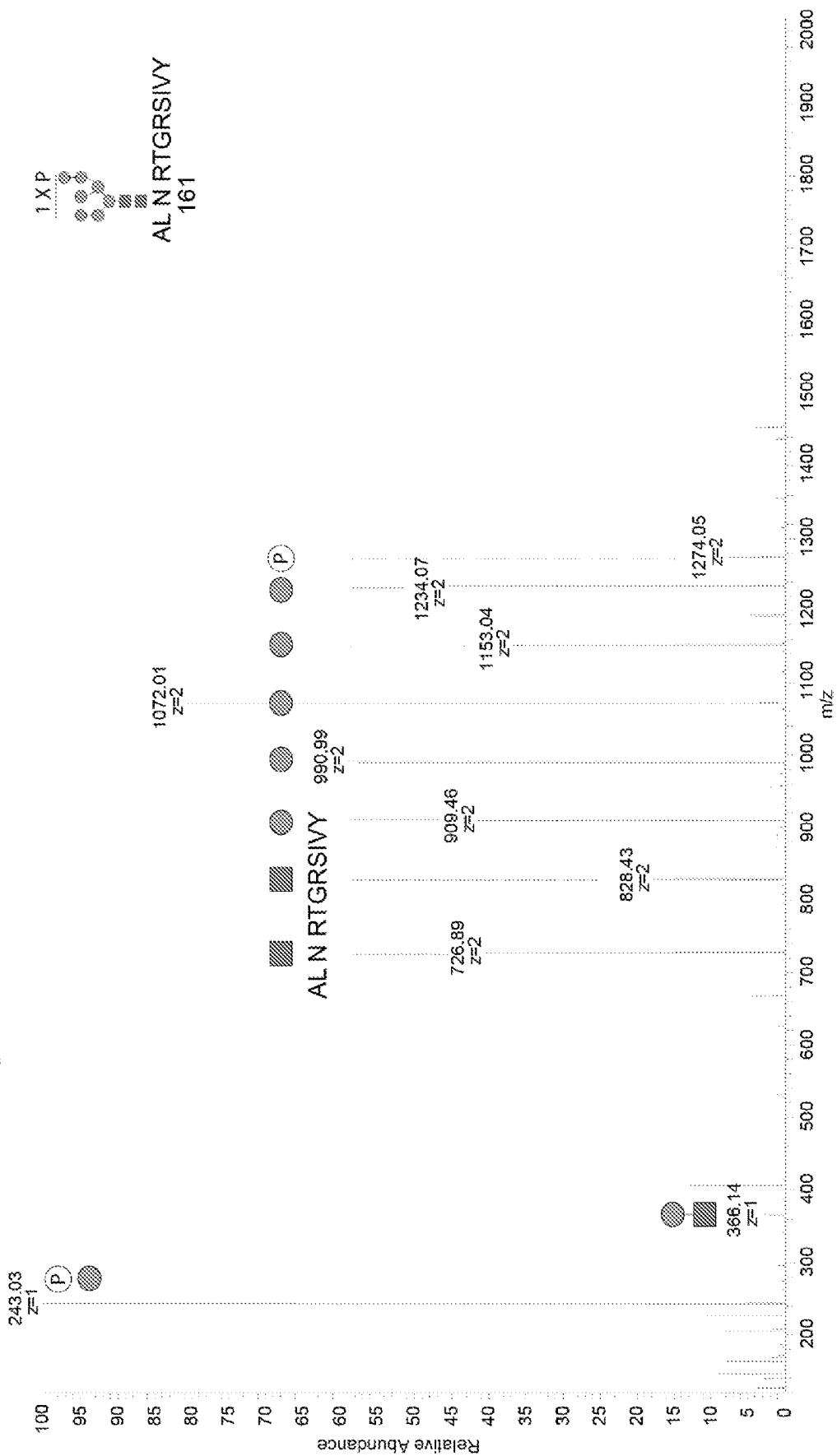
Figure 20:
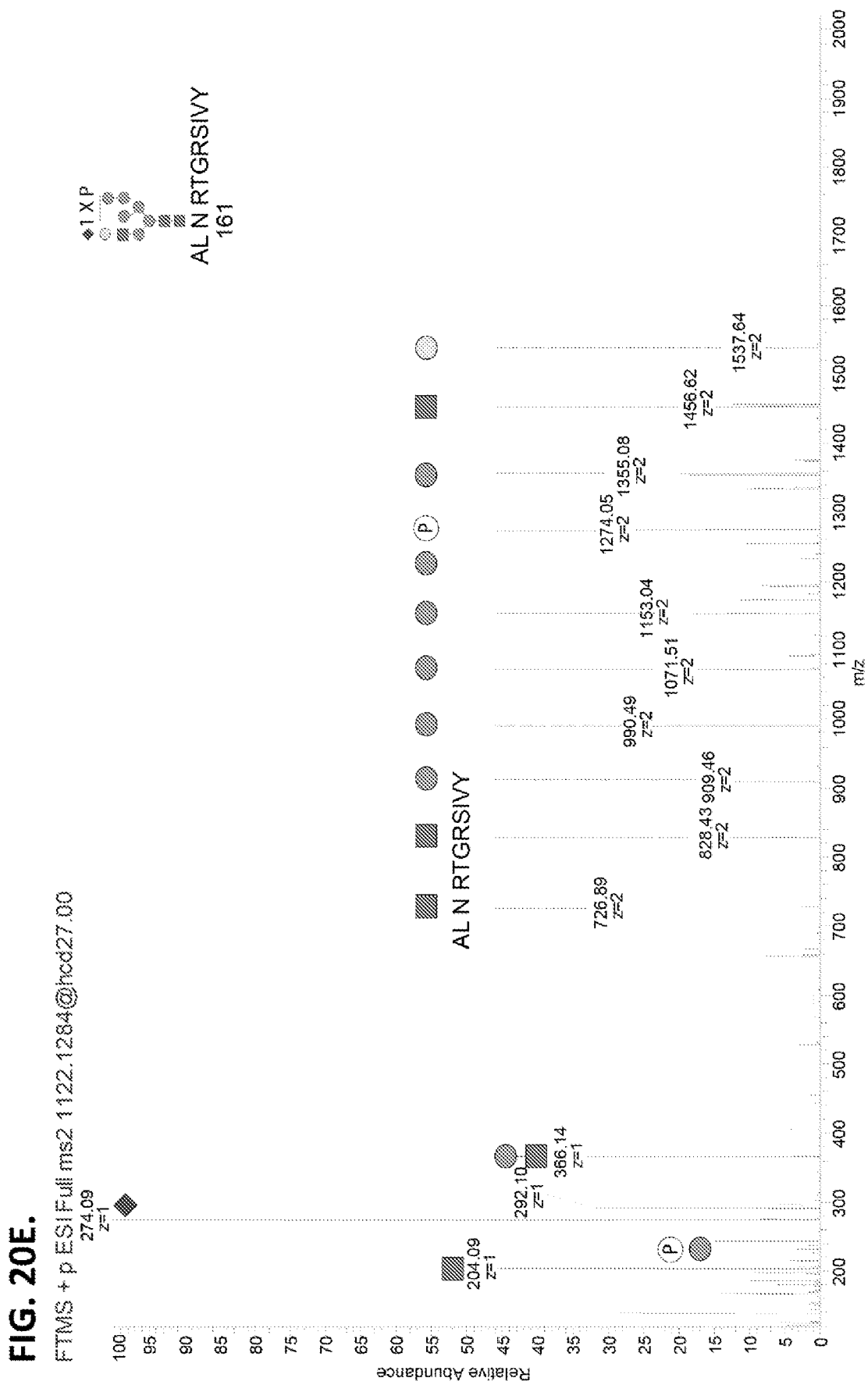
Figures 20, 20F:
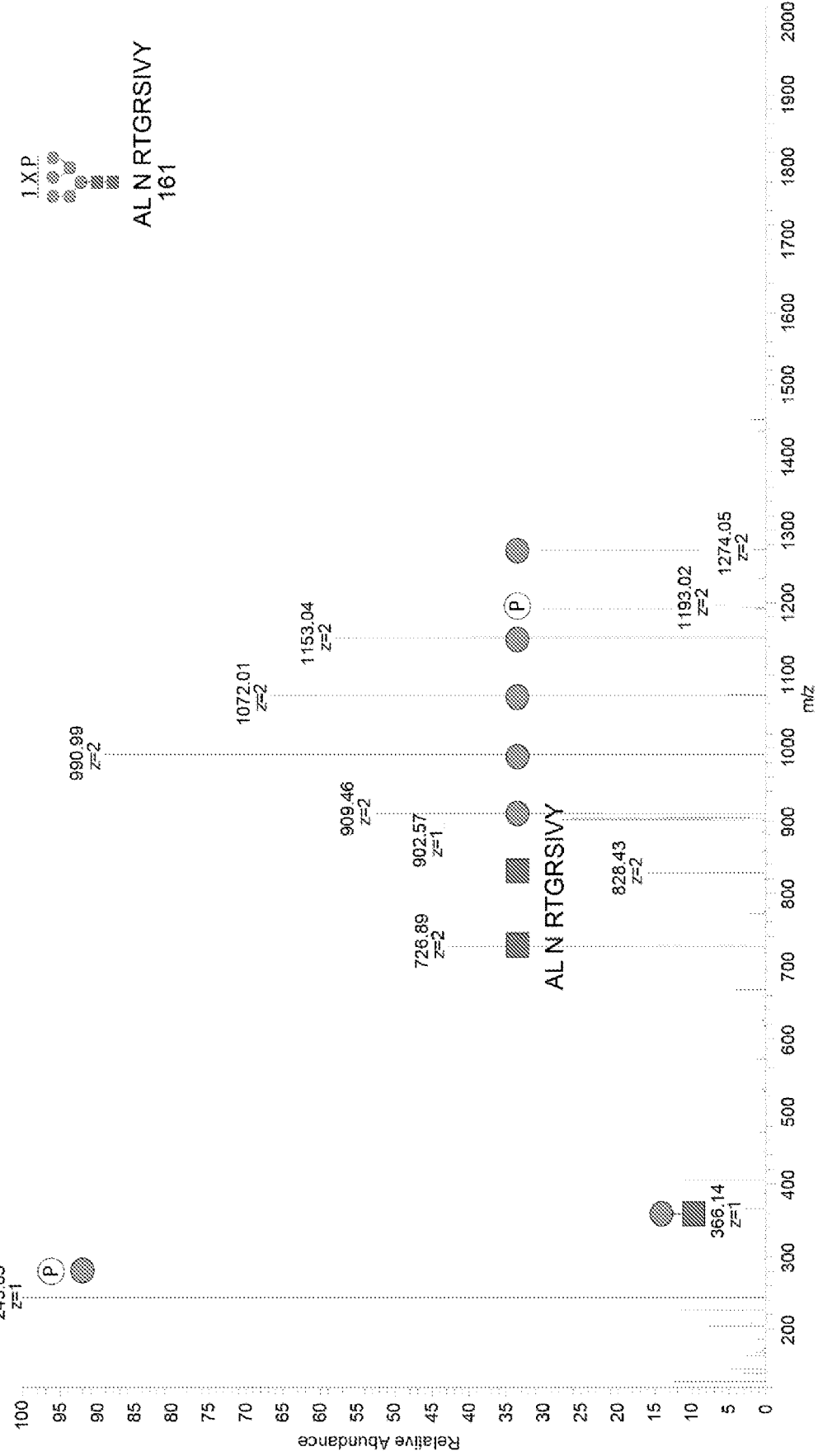

In order to explore the extent to which the glycoengineering designs are applicable to other lysosomal enzymes, we stably expressed human GBA in CHO WT and tested representative engineering designs (FIG. 14 and FIG. 19 and Supplementary Tables 4 and 5).

TABLE 8

Summary of CHO mutant clones stably expressing GBA and cell line ancestry.

| Project number | Targeted genes | Parental CHO line |
|---|---|---|
| GBA826 | KO Gnptab | GBA#A5 |
| GBA827 | KO Alg3 | GBA#A5 |
| GBA828 | KO Mgat1 | GBA#A5 |
| GBA829 | KO Alg9 | GBA#A5 |
| GBA831 | KO Gnptab/Mgat1 | GBA#A5 |
| GBA900 | KO Gnptab/Man2a1/2 | GBA826B1 |
| GBA901 | KO Gnptab/Mgat2 | GBA826B1 |

TABLE 9

Sequence analysis of CHO mutant clones stably expressing GBA.

| Clone | Targeted genes | | InDels | Alignment | SEQ ID NO: |
|---|---|---|---|---|---|
| GBA826B1 | KO Gnptab | | | | |
| | WT | | | GTCACATTCATCGCATCGAGGGG | 321 |
| | KO | | +1 bp | GTCACATTCATCGCATCCGAGGGG | 322 |
| GBA827C2 | KO Alg3 | | | | |
| | WT | | | GCTGCTGGGCTGCGGAAACGCGG | 323 |
| | KO | | −1 bp | GCTGCTGGGCTGCGGAAACGCGG | 324 |
| GBA827D2 | KO Alg3 | | | | |
| | WT | | | GCTGCTGGGCTGCGGAAACGCGG | 325 |
| | KO | | +1 bp | GCTGCTGGGCTGCGGAACACGCGG | 326 |
| GBA828D9 | KO Mgat1 | | | | |
| | WT | | | GAGGGGGTCGCAGGCACACGGGG | 327 |
| | KO | | +1 bp | GAGGGGGTCGCAGGCACCACGGGG | 328 |
| GBA828E9 | KO Mgat1 | | | | |
| | WT | | | GAGGGGGTCGCAGGCACACGGGG | 329 |
| | KO | | +1bp | GAGGGGGTCGCAGGCACcACGGGG | 330 |
| GBA829F2 | KO Alg9 | | | | |
| | WT | | | GAGCAGACATTTGAAAGCAGTGG | 331 |
| | KO-allel1 | | −7 bp | GAGCAGACATTGAAAGGCAGTGG | 332 |
| | KO-2alle2 | | −2 bp | GAGCAGACATTTGAtttGTGG | 333 |
| GBA831C8 | KO Mgat1 | | | | |
| | WT | | | GAGGGGGTCGCAGGCACACGGGG | 334 |
| | KO | | +1 bp | GAGGGGGTCGCAGGCACcACGGGG | 335 |
| | KO Gnptab | | | | |
| | WT | | | GTCACATTCATCGCATCGAGGGG | 336 |
| | KO | | +1 bp | GTCACATTCATCGCATCcGAGGGG | 337 |
| G3A831F10 | KO Mgat1 | | | | |
| | WT | | | GAGGGGGTCGCAGGCACACGGGG | 338 |
| | KO | | +1 bp | GAGGGGGTCGCAGGCACcACGGGG | 339 |
| | KO Gnptab | | | | |
| | WT | | | GTCACATTCATCGCATCGAGGGG | 340 |
| | KO | | +1 bp | GTCACATTCATCGCATCcGAGGGG | 341 |

TABLE 9-continued

Sequence analysis of CHO mutant clones stably expressing GBA.

| Clone | Targeted genes | InDels | Alignment | SEQ ID NO: |
|---|---|---|---|---|
| GBA900D6 | KO Man2a1 | | | |
| | WT | | GAGTGAAGCCTCGATCGGGTTGG | 342 |
| | KO | -4 bp | GAGTGAAGCCTCG*ATCG*GGTTGG | 343 |
| | KO Man2a2 | | | |
| | WT | | GCCCAGAGAAAGCGTCGTCGAGG | 344 |
| | KO | -1 bp | GCCCAGAGAAAGCGTCG*T*CGAGG | 345 |
| | KO Gnptab | | | |
| | WT | | GTCACATTCATCGCATCGAGGGG | 346 |
| | KO | +1 bp | GTCACATTCATCGCATCcGAGGGG | 347 |
| GBA901D9 | KO Mgat2 | | | |
| | WT | | GCGACCGGTACCGCAGCGTTAGG | 348 |
| | KO | +1 bp | GCGACCGGTACCGCAGCcGTTAGG | 349 |
| | KO Gnptab | | | |
| | WT | | GTCACATTCATCGCATCGAGGGG | 350 |
| | KO | -1 bp | GTCACATTCATCGCATCcGAGGGG | 351 |

NOTE:
Nucleic acids UNDERLINED are the gRNA targeting sequence,
Nucleic acids in BOLD and UNDERLINED are the PAM sequence,
Nucleic acids in lower case letters are insertions,
Nucleic acids in BOLD and *ITALICS* are deletions.

GBA has 4 N-glycan sites of which N19 and N59 are mainly occupied by complex biantennary N-glycans, while those at N146 and N270 contain a mixture of complex bi-, tri- and tetraantennary N-glycans and M6P-tagged N-glycans, with N270 being the major M6P-tagged glycosite (FIG. 14a and FIG. 19, Panel 1). This is in agreement with previous reports. KO of Alg3 increased the M6P content in general and in particular for the N146 and N270 glycans (FIG. 14b and FIG. 19, Panels 2). KO of Alg9 had little effect on the N-glycans at N19 and N59, but altered the oligomannose structures with M6P at N146 and N270 (FIG. 14c and FIG. 19, Panel 3). Targeting Gnptab resulted in rather homogeneous complex type N-glycans with SA capping at all four N-glycosites and no M6P content (FIG. 14d and FIG. 19, Panel 4). Targeting Mgat1 enabled production of GBA without complex type N-glycans, but with high mannose glycans and reduced M6P mainly at N270 (FIG. 14e and FIG. 19, Panels 5, 6). Stacked KO of Gnptab and Mgat1 enabled production of GBA with high mannose N-glycans without M6P at all glycosites and oligomannose structures consisting of 4-5 Man residues (FIG. 14f and FIG. 19, Panels 7, 8). Stacked KO of Man2a1/2 and Gnptab generated GBA with a rather homogeneous mono-antennary hybrid structure at all 4 glycosites with a complex sialylated α3-arm combined with three Man residues on the α6-arm (FIG. 14g and FIG. 19, Panel 9). Similarly, GBA with mono-antennary hybrid N-glycan carrying a single Man residue at the α6-arm was generated by stacking KO of Mgat2 and Gnptab (FIG. 14h and FIG. 19, Panel 10). These two designs may represent a glycodesign with lower MR binding and increased circulation. In general, the outcome of the engineering performed with GBA correlated well with the effects observed with GLA, when considering the inherent site-specificity of N-glycan processing found with the enzymes expressed in WT CHO cells. We predict that further studies with KI of GNPTAB and GNTPG may induce M6P-tagging at all N-glycosites similar to our findings for GLA and as reported previously.

Analyses of GLA Glycoforms in a Deficient Fabry Disease Mouse Model

Fabry disease is caused by deficiency in GLA and the leading ERT is Fabrazyme (GenZyme) produced in CHO cells. We first benchmarked GLA produced in our CHO WT cell (100 mgs/L) with a clinical lot of Fabrazyme (GenZyme) finding lower content of exposed Man residues on GLA produced by us (FIG. 15A and FIG. 17, Panels 1, 3). The two CHO WT produced GLA exhibited similar blood circulation half-time (FIG. 15B) with trends of higher liver targeting and lower spleen, kidney and heart targeting of our GLA, although only the lower kidney targeting was significant (FIG. 15D).

Figure 15E:
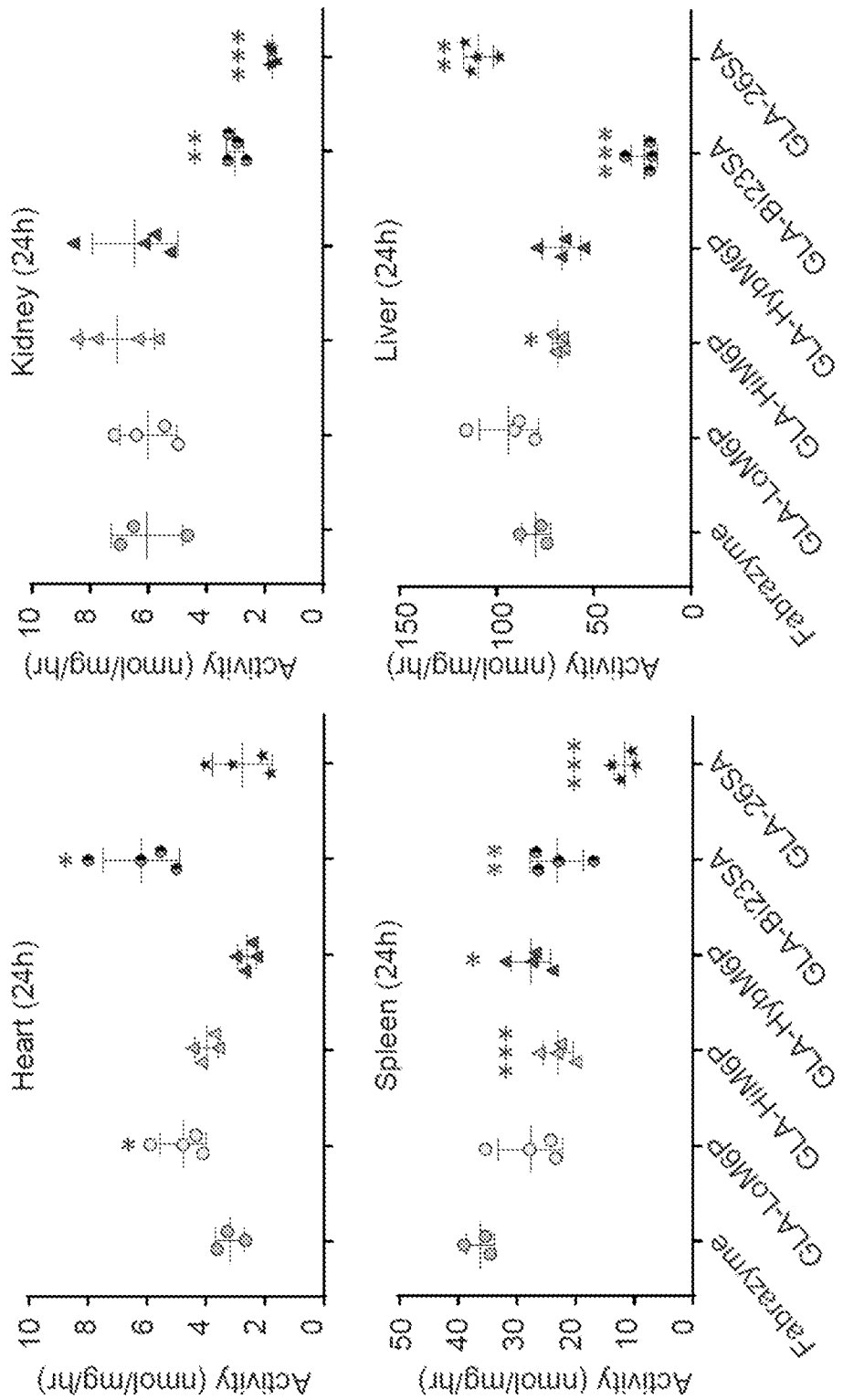

We then tested five engineered distinct glycoforms of GLA in direct comparison with Fabrazyme at 1 mg/kg dose (FIG. 15A). The engineering design and detailed structure analysis of the selected glycovariants are shown in FIG. 17, Panels 1, 6, 55, 52, 59 and 58). The specific activity and stability in plasma of these GLA glycovariants were essentially identical (FIG. 21). Three glycoforms designed with slightly lower M6P (LoM6P), higher M6P (HiM6P), or higher M6P content with mainly the hybrid-type (HybM6P) produced trends towards higher or lower circulation time with half-lifes of 15.4±1.1 min, 11.0±2.0 min, and 8.3±0.8 min, respectively, compared with 9.8±0.3 min for Fabrazyme (FIG. 15C). These three glycoforms showed minor differences in targeting to select organs compared to Fabrazyme with the LoM6P glycoform yielding significantly higher levels of enzyme activity in the heart and HiM6P and HybM6P exhibiting lower levels in spleen and liver (FIG. 15E). These trends are consistent with MPR-mediated uptake, and the relatively high level of M6P content of Fabrazyme likely influence the degree of differences.

In striking contrast, the two glycoforms designed with N-glycans capped by sialic acids and without M6P and exposed Man, produced significant changes in circulation and biodistribution (FIGS. 15C and 15E). GLA-Bi23 SA with homogeneous biantennary N-glycans capped with α2-3 SA (FIG. 15A), exhibited a markedly extended (3-fold) circulation time (half-life 27.5±0.8 min) (FIG. 15C), and lower enzyme activity in liver, spleen, and kidney, but the highest level of enzyme in the heart among all glycoforms tested (FIG. 15E). Importantly, the GLA-LoM6P showed the same trend as would be predicted. The most frequent cause of death in patients with Fabry disease is cardiomyopathy, and increased delivery to the cardiovascular system with glycoforms such as GLA-Bi23SA may present a promising solution. The impact of the 3-fold increase in circulation time of GLA-Bi23SA should be viewed in light of the finding that GLA has extremely poor stability in plasma at 37° C. with loss of more than 50% activity within 15 min (Kizhner, T. et al. Characterization of a chemically modified plant cell culture expressed human alpha-Galactosidase-A enzyme for treatment of Fabry disease. Mol Genet Metab 114, 259-267 (2015); Sakuraba, H. et al. Comparison of the effects of agalsidase alfa and agalsidase beta on cultured human Fabry fibroblasts and Fabry mice. J Hum Genet 51, 180-188 (2006), each of which is incorporated herein by reference in its entirety). A PEGylated version of GLA (PRX-102) only enhanced the stability in plasma approximately 2-fold (Kizhner 2015).

GLA-26SA was designed to have N-glycans capped with α2-6SA (FIG. 15A), and perhaps surprisingly (see Park, E. I., Mi, Y., Unverzagt, C., Gabius, H. J. & Baenziger, J. U. The asialoglycoprotein receptor clears glycoconjugates terminating with sialic acid alpha 2,6GalNAc. Proc Natl Acad Sci USA 102, 17125-17129 (2005), incorporated herein by reference in its entirety), this glycoform resulted in markedly increased liver uptake and corresponding decrease in spleen and kidney uptake (FIG. 15E), and the circulation time was only marginally elevated (FIG. 15C). The GLA-26SA glycoform produced the lowest level of enzyme activity in the kidney (FIG. 15E). The striking increase in liver uptake of the α2-6SA capped glycoform resembles previous studies obtained with an albumin neoglyconjugate suggesting interaction with the AMR, but several therapeutic glycoproteins produced in human cells including HEK293 have partial α2-6SA capping and appear to function similar to those produced in CHO cells with only α2-3SA.

Figure 15F:
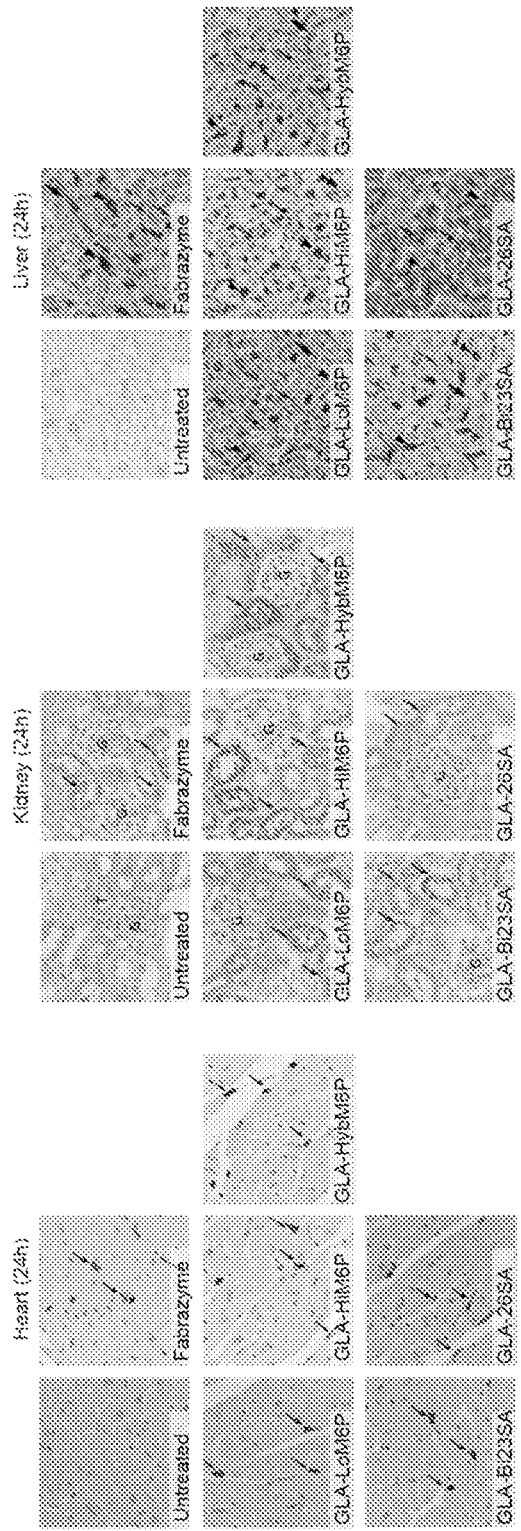
FIG. 15F shows IHC analysis with polyclonal anti-GLA antibody. Annotations used: liver—hepatocytes (small arrows), putative Kupffer cells (arrowheads), endothelial cells of sinusoidal capillaries (large arrows), and punctate lysosome-like distribution of positive signals (small arrows); kidney-cortical tubules (indicated as 'T'), glomeruli (indicated as 'G'), and tubular epithelial cells (arrows); heart—vascular and perivascular cells (arrows).

Cellular localization of Fabrazyme and the glycovariants in the heart, kidney and liver was assessed by immunohistochemistry (FIG. 15F). The localization pattern of Fabrazyme in these organs was consistent with that of agalsidase alfa reported in previous studies. In the heart, Fabrazyme and all five glycovariants were detected in vascular and/or perivascular cells, but not in cardiomyocytes (FIG. 15F). There were no clear differences between the tested variants. In the kidney, Fabrazyme and GLA-LoM6P, GLA-HiM6P, GLA-HybM6P, and GLA-Bi23SA were predominantly detected in tubular epithelial cells. However, GLA-26SA had significantly decreased number and intensity of positive signals in tubules compared to the other variants tested (FIG. 15F). In the liver, Fabrazyme, GLA-LoM6P, GLA-HiM6P, and GLA-HybM6P were detected in hepatocytes, putative Kupffer cells and endothelial cells of sinusoidal capillaries. GLA-Bi23SA was also detected in these cell types; however, the number of positive signals in hepatocytes was clearly decreased compared to Fabrazyme. Distribution of GLA-26SA in the liver was remarkably different from other variants; This variant was detected almost exclusively in hepatocytes, and the number of positive signals in hepatocytes was clearly increased compared to Fabrazyme (FIG. 15F).

Figure 15G:
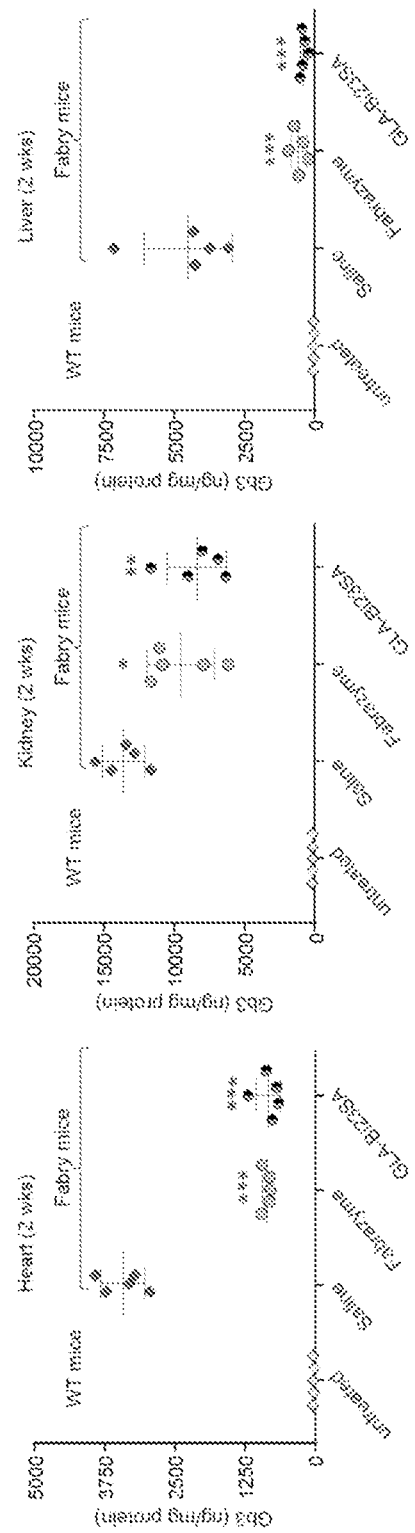
FIG. 15G shows Gb3 substrate levels quantified by mass spectrometry in organs 2 weeks after a single infusion of 1 mg/kg. (n=5). $*P<0.05$, $P<0.01$, $*P<0.001$.

Encouraged by the unique performance of GLA-Bi23SA we also tested the effect of this glycoform on reduction of accumulated globotriosylceramide (Gb3) substrate in organs 2 weeks after a single injection of 1 mg/kg. GLA-Bi23SA treatment resulted in a similar reduction of the Gb3 content in heart, kidney and liver as compared to Fabrazyme (FIG. 15G). This unequivocally demonstrate that glycoforms of GLA without the classical receptor ligands M6P and Man are efficiently taken up by cells, delivered to the lysosome, and functioning in reduction of the Gb3 substrate accumulation.

In summary, the glycoengineered GLA variants exhibited distinct pharmacodynamic profiles in Fabry mice. The α2-3SA sialylated design without M6P and terminal Man led to reduced uptake by hepatocytes, prolonged plasma half-life, and improved delivery to the heart. In contrast, the α2-6SA sialylated design led to preferential delivery to hepatocytes and decreased uptake by renal tubular cells. The longer circulation time of GLA-Bi23SA is likely to provide opportunity for wider organ distribution as evidenced by the markedly increase in uptake in the heart, which is critical for many LSDs. Longer circulation time may also provide opportunity for use of lower enzyme dose or application frequency of replacement enzymes, although further studies are needed to address this.

Discussion

The comprehensive engineering performed with GLA and GBA in CHO cells demonstrates that there are wide options for fine-tuning all key features of N-glycans on lysosomal enzymes known to be important for their cellular uptake, biodistribution and bioavailability. This includes a high degree of site-specific fine-tuning of M6P stoichiometry, exposure of Man, Gal, and GlcNAc residues, and capping by SA. We provide novel designs for recombinant lysosomal enzymes which lack recognition markers for classical MPRs and MRs but containing homogenous N-glycans capped by SA. Among these we discover GLA-Bi23SA that offer increased circulation time, efficient cellular uptake and improved organ distribution following its application in mice. This suggests that the α2-3 SA design can be used to overcome one of the arguably major obstacle for many ERTs, i.e. their rapid clearance from circulation by liver and spleen. Extended circulation is predicted to enable wider bioavailability and possibly transport across the blood-brain-barrier (Damme, M. et al. Chronic enzyme replacement therapy ameliorates neuropathology in alphamannosidosis mice. Ann Clin Transl Neurol 2, 987-1001 (2015), incorporated herein by reference in its entirety). The achieved control of N-glycosylation in CHO cells meets or surpass the glycoengineering opportunities previously presented with non-mammalian cells and postproduction modification strategies. The clinical features of LSDs and the organs affected differ greatly as do the biostructural properties of the respective deficient enzymes, and the design matrix and glycoengineered CHO cells developed here will be valuable tools for production and testing of optimal designs for individual ERTs, in order to improve a class of essential drugs with high costs and poor performance.

CHO cells are the preferred mammalian expression hosts for human therapeutics. Given the recent options for targeted and stable gene engineering of glycosylation capacities in mammalian cells, we undertook to explore the glycoengineering options for M6P-modified lysosomal replacement enzymes that represent one of the most complex challenges for the biopharmaceutical industry (Platt, F. M. Emptying the stores: lysosomal diseases and therapeutic strategies. Nat Rev Drug Discov 17, 133-150 (2018); Parenti, G., Pignata, C., Vajro, P. & Salerno, M. New strategies for the treatment of lysosomal storage diseases (review). Int J Mol Med 31, 11-20 (2013); Parenti, G., Andria, G. & Ballabio, A. Lysosomal storage diseases: from pathophysiology to therapy.

Figure 12:
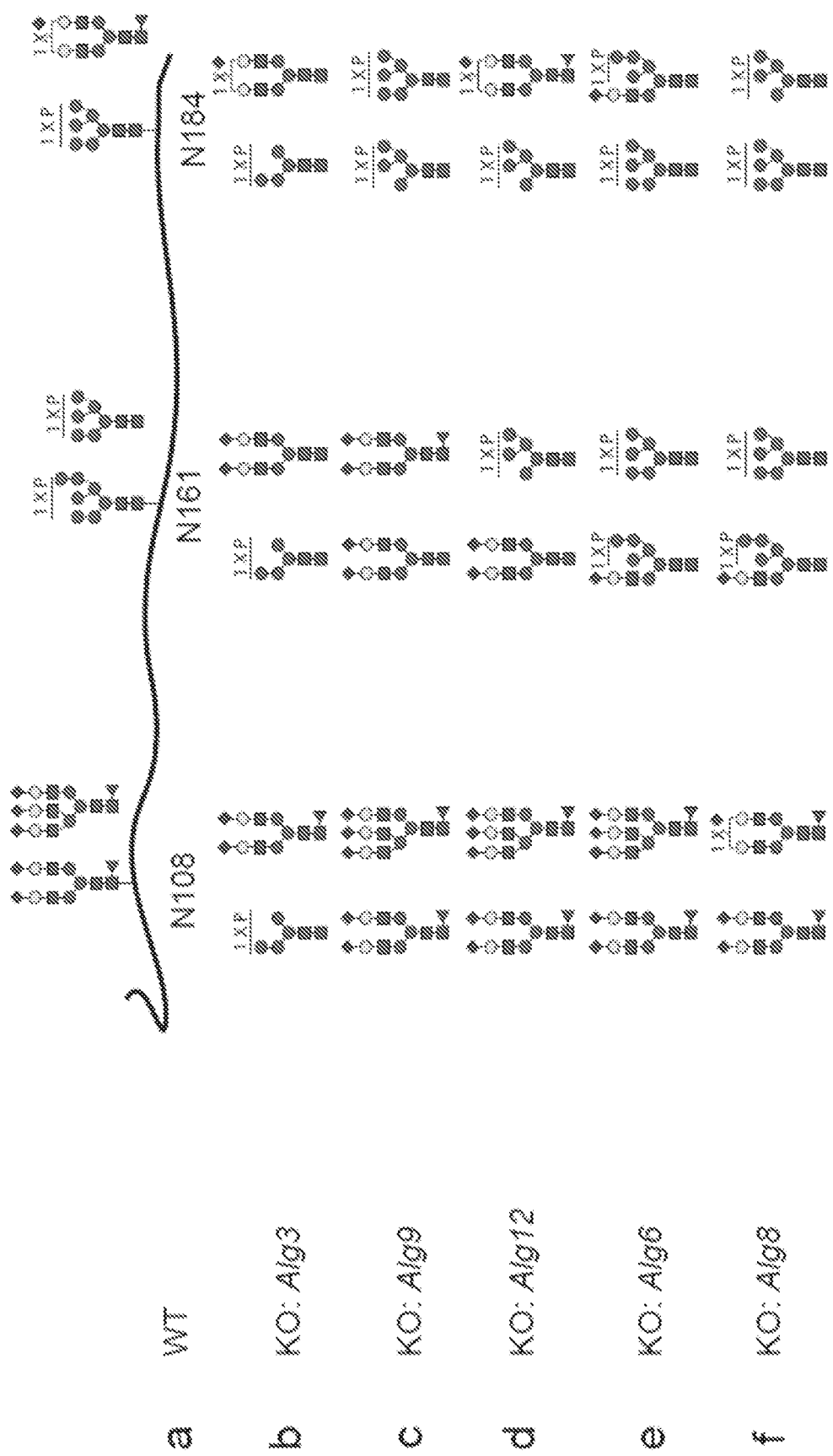
FIG. 12 shows site-specific glycan analyses of selected genes targeted in the initial KO screen. The two most abundant glycan structures at N-glycosites N108, N161 and N184 of GLA produced in CHO WT (a) and CHO KO clones (b-t) are shown. Additional KO targeting and a detailed N-glycan analyses are shown in FIG. 17. Each glycan structure was confirmed by targeted MS/MS analysis (FIG. 20). Details regarding the stacking ancestry, sequence analysis are shown in Supplementary Tables 2 and 3.
Figure 12:
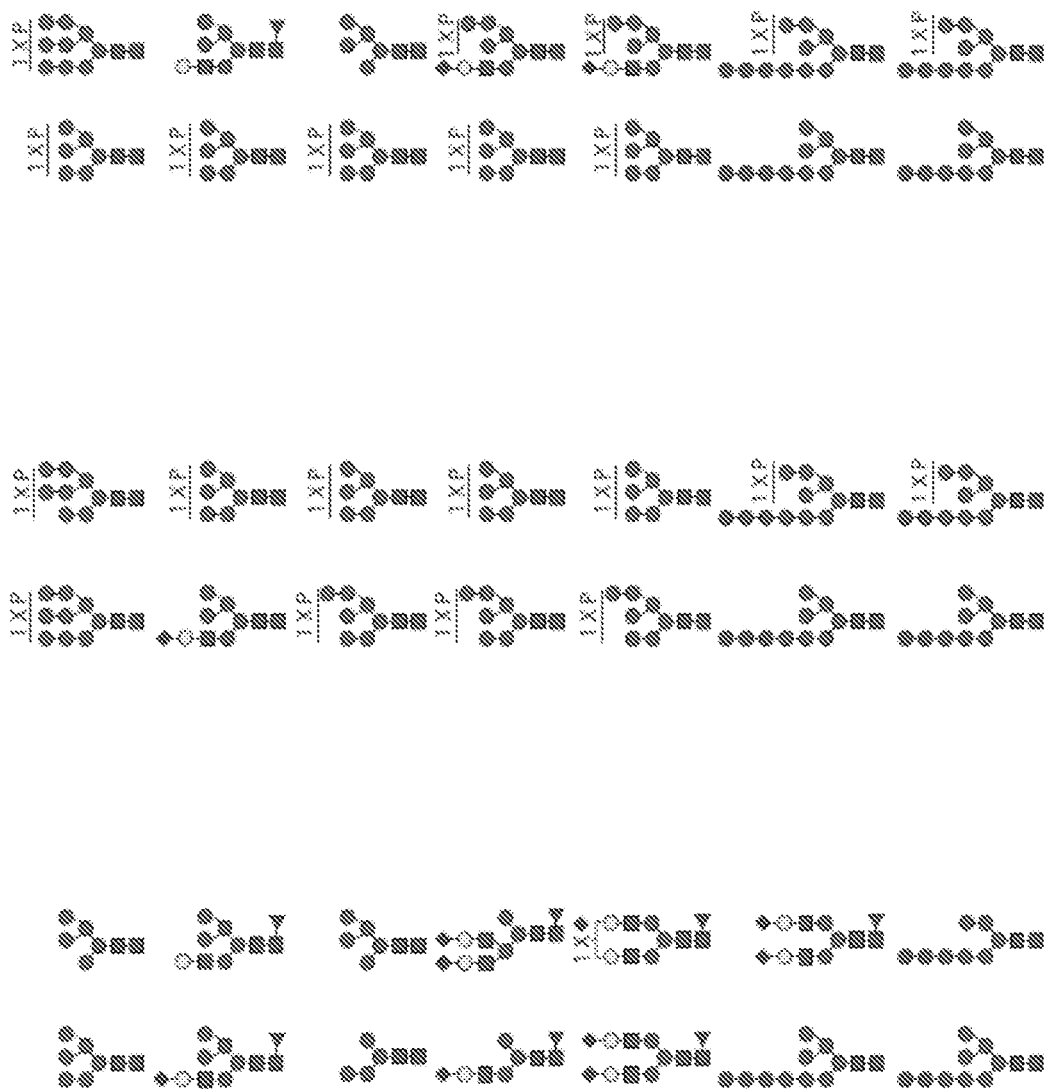
Figure 12:
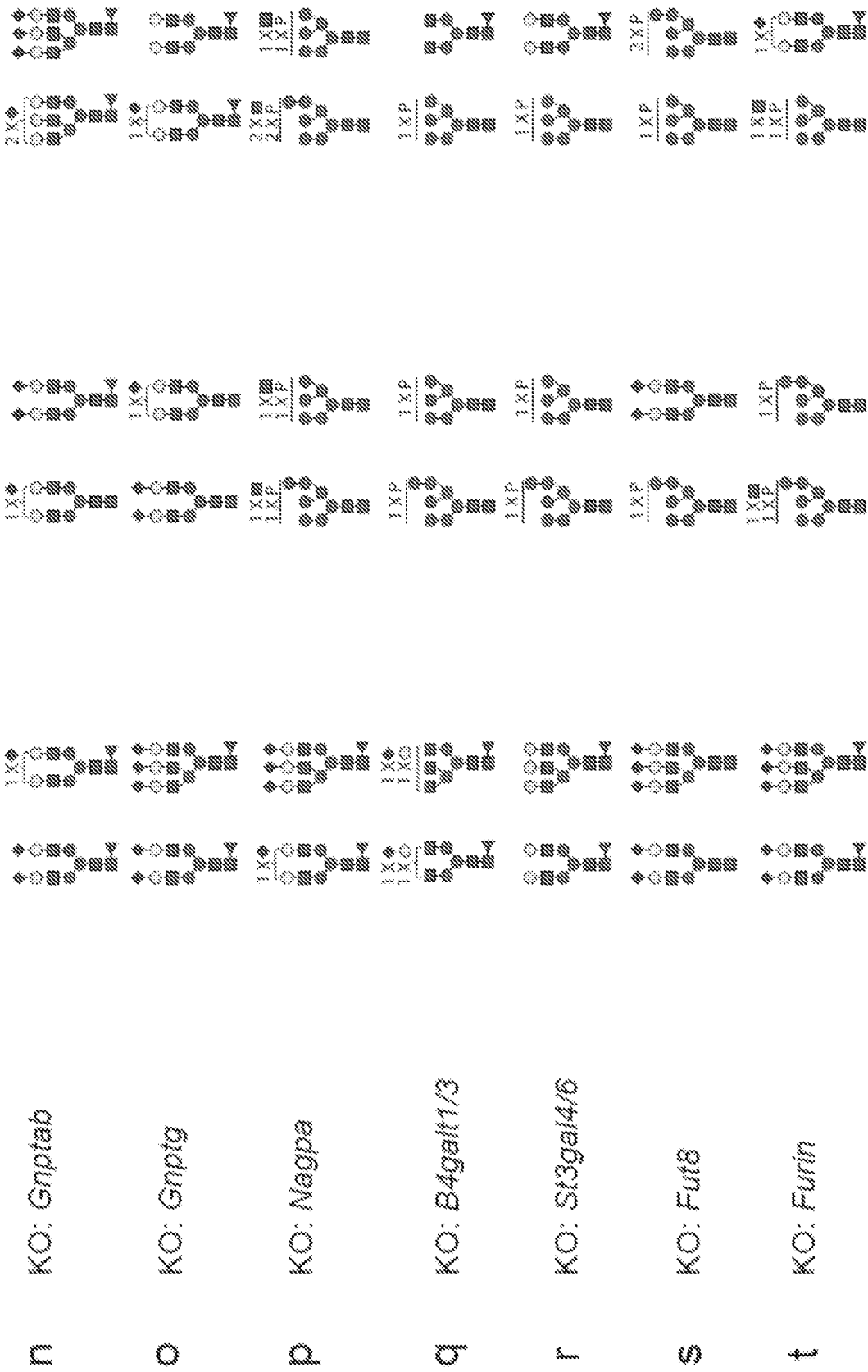
Figure 13:
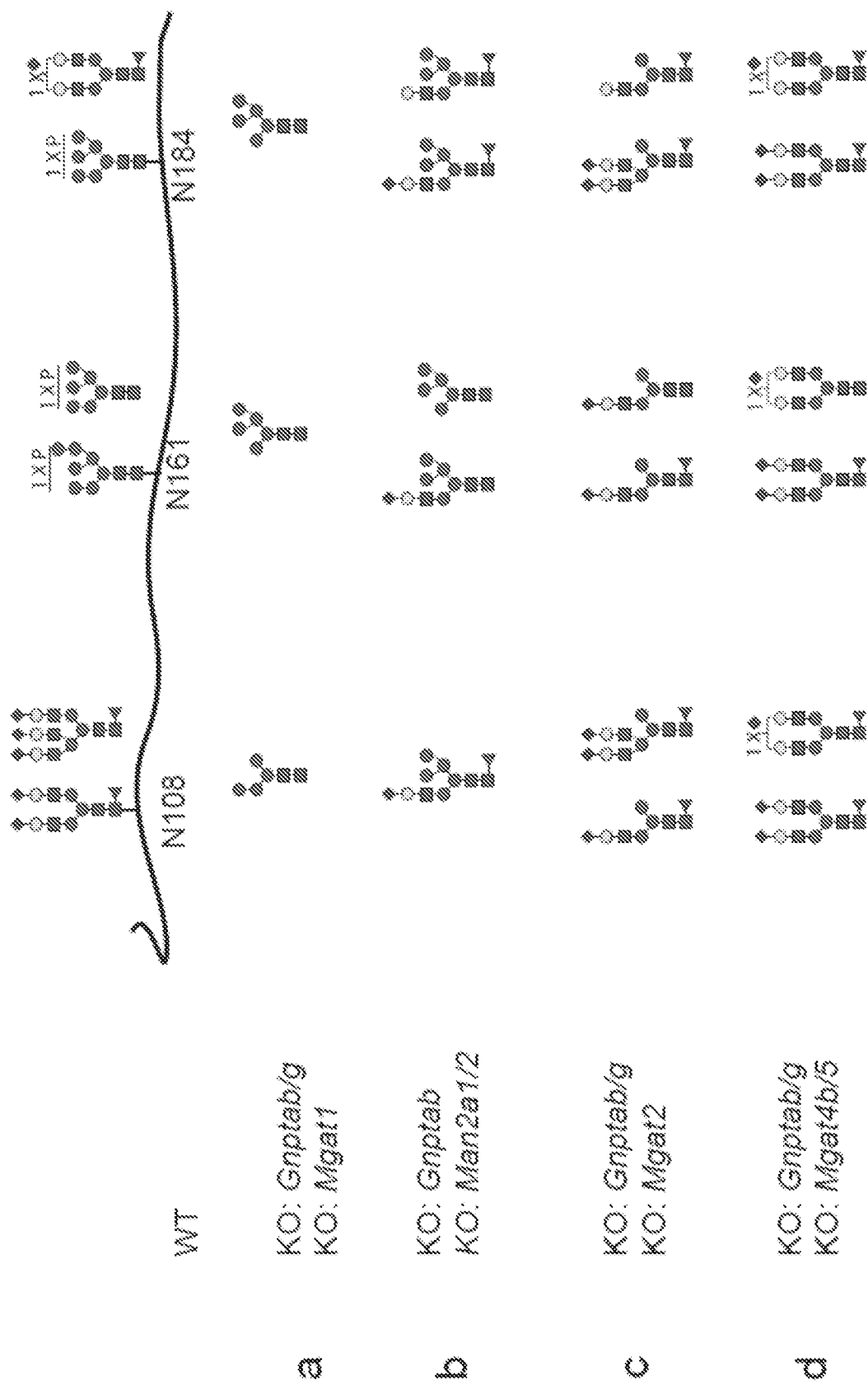
FIG. 13 shows site-specific glycan analyses of combinatorial gene engineering. The two most abundant glycan structures at N-glycosites N108, N161 and N184 of GLA produced in KO/KI engineered CHO clones are shown (a-l). Each glyco structure was confirmed by targeted MS/MS analysis. Additional KO targeting and a detailed N-glycan analyses are shown in FIG. 17. Each glyco structure was confirmed by targeted MS/MS analysis. Details regarding the stacking ancestry, sequence analysis are shown in Tables 6 and 7.
Figure 13:
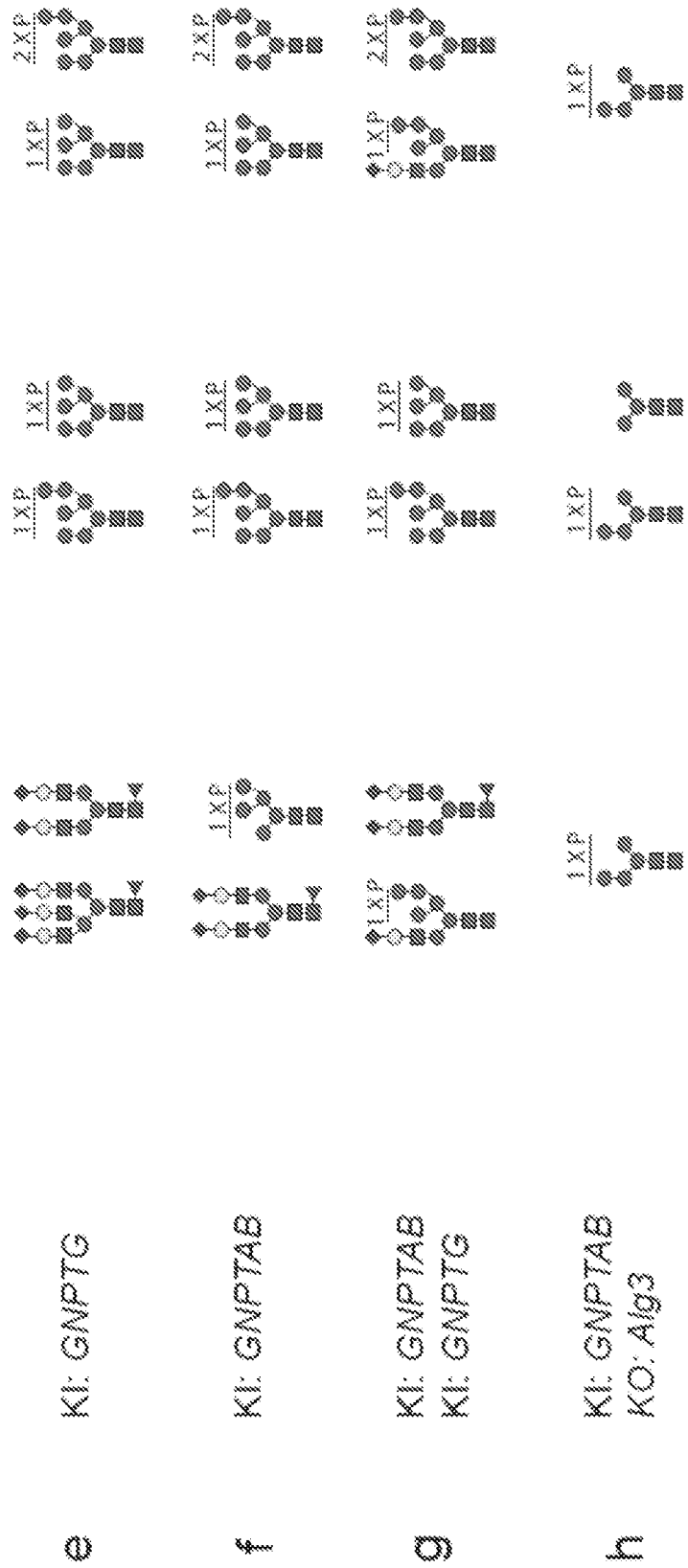
Figure 13:
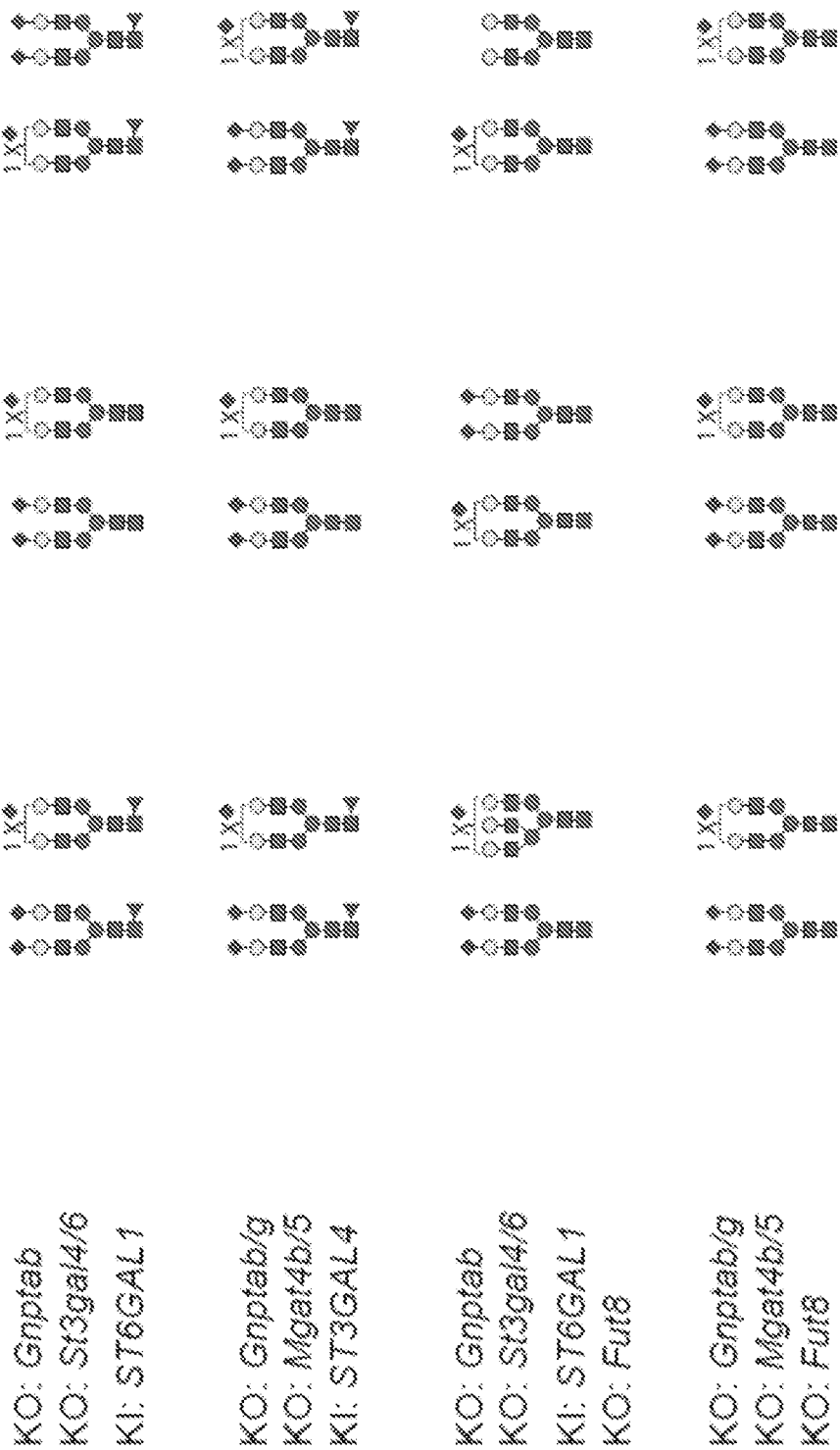

Annu Rev Med 66, 471-486 (2015), each of which is incorporated herein by reference in its entirety). Using GLA as an illustrative example we dissected virtually all steps in the genetic and biosynthetic control of N-glycosylation and M6P-tagging, and found surprising plasticity and control for fine-tuning complex N-glycan patterns even with a degree of glycosite specificity (FIGS. 12 and 13). Thus, M6P-tagging could be tuned up and down and directed to one (N184), two, or all three N-glycosites of GLA, and importantly combined with different degrees of high-Man or complex sialylated N-glycans. Moreover, it was possible to induce the hybrid N-glycan with a sialylated α3-arm and an M6P-tagged α6-arm. For the first time we also demonstrated production of glycoforms with homogenous SA capping but lacking M6P or exposed Man residues.

It has long been clear that the structure of N-glycans on replacement enzymes affects cellular uptake and circulation time by interacting with different cell surface receptors, and that altering the glycan composition can be used to direct organ-targeting. This was demonstrated first with targeting of GBA with high-Man structures for the MR on macrophages, and ERTs with glycans optimized for targeting specific receptors are already successfully used in the clinic. Different strategies have been applied to optimize N-glycans for specific cell and organ targeting requirements. To achieve N-glycans with high degree of Man exposure for MR-mediated liver targeting, e.g. for GBA treatment of Gaucher patients, the industry has used plant cells, human fibrosarcoma cells combined with N-glycan mannosidase inhibitors, and CHO cells combined with postproduction treatment with multiple exoglycosidases. We present engineered CHO cells capable of producing this high-Man glycoform of GBA (FIG. 14f), and importantly also related designs with different degrees of Man exposure and SA capping expected to influence kinetics of uptake and circulation half-life (FIG. 14g). To increase the M6P content in particular for targeting muscle cells, yeast has been used to produce the lysosomal α-glucosidase deficient in Pompe disease. Yeast modify human lysosomal enzymes with Man-Pi-6-Man, but the elegant introduction of an uncovering α-mannosidase enzyme results in production of α-glucosidase rich in M6P. Other strategies to increase M6P content include in vitro chemical conjugation, or co-expression of a truncated GlcNAc-1-phosphotransferase α/β precursor. These strategies do not enable fine control over the content (or site-specificity) of M6P and other glycan features including SA capping, and the presented engineering of high-M6P glycoforms in CHO cells fully match these strategies (FIGS. 13f-13h). Other postproduction modification strategies including oxidative reduction of glycans and PEGylation have been applied to reduce glycan-mediated receptor uptake and/or enhance circulation, and these may be met by the presented glycoform designs with homogeneous SA capping but lacking M6P or exposed Man residues (FIG. 13j). Thus, our study suggests that any of the more complex processes used for production of enzymes required for ERTs in the clinic today or in development, can be produced simpler and more effective in glycoengineered CHO cells. Moreover, there may be advantages in combining distinct glycoforms of lysosomal enzymes with emerging glycosylation-independent targeting strategies developed for blood-brain-barrier transport.

Figure 22:
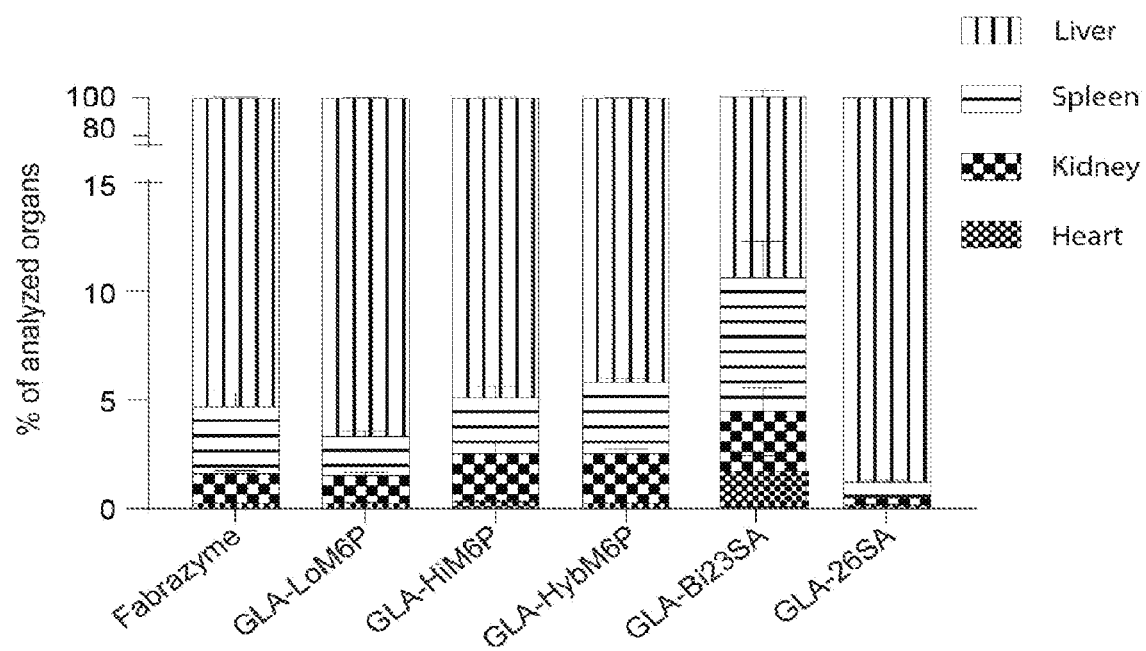
FIG. 22 shows relative distribution of GLA glycovariants among the four major visceral organs: liver, spleen, kidney, and heart.

The general factors determining glycan-mediated receptor uptake are the presence of exposed M6P, Man, Gal, and GlcNAc residues, but our understanding of and ability to predict the outcome of interactions between glycoproteins with heterogeneous N-glycans presenting these features and the multiple receptors involved is limited. Numerous studies have explored the binding and uptake of extreme glycoforms such as high-Man and high/low M6P-containing lysosomal enzymes, but systematic studies investigating the complex interplay between different glycan features have not been possible due to lack of methods to produce such glycoforms. Studies with e.g. the lysosomal alpha-mannosidase (LA-MAN) that contains multiple N-glycans with very low M6P-content and exposure of Man when produced in WT CHO cells, suggest that limited interaction with the MPRs and MR may be advantageous for wider biodistribution and crossing into the brain possibly due to extended circulation time. Similar findings were observed with postproduction modified enzymes with partially destroyed glycans. Here, we explored five distinct glycoforms of GLA including two lacking M6P or exposed Man residues in a Fabry disease mouse model, and found significant changes in circulation half-life and biodistribution (FIG. 15). Most significantly, the GLA glycoform with α2-3SA capped N-glycans not only showed enhanced circulation time but also demonstrated efficient uptake and function in all tested organs with improved distribution to the hard-to-reach heart compared to the leading Fabrazyme variant (FIG. 15E), as well as to a recent moss-produced high-Man variant. Evaluating the relative organ distributions of glycovariants among the four major visceral organs tested illustrate the substantial improved distribution of GLA-Bi23SA to the heart and other organs except the liver (FIG. 22). The mechanism for uptake of the α2-3SA capped GLA glycoform is not clear, but studies have shown that lysosomal targeting of GLA is at least partly independent on M6P-tagging, and other endocytic receptors such as sortilin (SORT1) and LRP2 (megalin) may be involved. The 3-fold increase in circulatory half-life for α2-3SA capped GLA is lower than the increase observed with e.g. oxidative degradation and reduction of the β-glucuronidase (GUS), but this likely reflects the extremely low stability of GLA in plasma. It may be interesting to explore combining this glycoform with the stabilizing molecular chaperone AT1001 (Benjamin, E. R. et al. Co-administration with the pharmacological chaperone AT1001 increases recombinant human alpha-galactosidase A tissue uptake and improves substrate reduction in Fabry mice. Mol Ther 20, 717-726 (2012); Xu, S. et al. Coformulation of a Novel Human alpha-Galactosidase A With the Pharmacological Chaperone AT1001 Leads to Improved Substrate Reduction in Fabry Mice. Mol Ther 23, 1169-1181 (2015), each of which is incorporated herein by reference in its entirety) or PEGylation (Kizhner, T., 2015), and also to consider therapeutic modalities comprised of multiple distinct glycoforms.

In summary, the comprehensive CHO glycoengineering performed and the design matrix generated for lysosomal enzymes, opens systematic studies on options for improving ERTs by designed glycan features. Past studies have demonstrated the value of changing the structures of glycans on enzymes needed for ERTs, but the full potential has clearly not been met by use of yeast and plant production platforms or postproduction modification strategies. The CHO production platform offer new design capabilities, and the remarkable performance of found for GLA capped with SA may represent a new design paradigm for many ERTs.

Methods

Establishment of Stable CHO Clones Expressing Recombinant Human GLA and GBA Enzymes.

An expression construct containing the entire coding sequence of human GLA was synthesized by Genewiz, USA. Full length cDNA of human GBA1 was purchased from Sino Biological Inc., China. Both constructs were subcloned into modified pCGS3 (Merck/formally known as Sigma-Aldrich) for glutamine selection in CHOZN GS-/- cells. CHO cells were maintained as suspension cultures in serum-free media (EX-CELL CHO CD Fusion, cat. no 14365C), supplemented with 4 mM L-glutamine in 50 mL TPP TubeSpin® Bioreactors with 180 rpm shaking speed at 37° C. and 5% C02. Cells were seeded at $0.5×10^6$ cells/mL in T25 flask (NUNC, Denmark) one day prior to transfection. Electroporation was conducted with $2×10^6$ cells and 8 µg endotoxin-free plasmids using Amaxa kit V and program U24 with Amaxa Nucleofector 2B (Lonza, Switzerland). Electroporated cells were subsequently plated in 6-wells with 3 mL growth media, and after 72 hrs cells were plated in 96-wells at 1,000 cells/well in 200 µl Minipool Plating Medium containing 80% EX CELL® CHO Cloning Medium (Cat. no C6366) and EX-CELL CHO CD Fusion serum-free media without glutamine. High expressing clones were selected by assaying the medium for enzyme activity (GLA) or with an ELISA using anti-HIS antibodies (for GBA), and selected clones were scaled-up in serum-free media without L-glutamine in 50 mL TPP TubeSpin® shaking Bioreactors (180 rpm, 37° C. and 5% $CO_2$) for enzyme production.

Purification of GLA and GBA

For GLA spent culture medium was centrifuged at 500×g for 20 min, filtered (0.45 m), diluted 3-fold with 25 mM MES (pH 6.0), and loaded onto a DEAE-Sepharose Fast Flow column (Sigma). The column was washed with 10 column volumes (CV) washing buffer (25 mM MES with 50 mM NaCl, pH 6.0) and eluted with 5 CV elution buffer (25 mM MES with 200 mM NaCl, pH 6.0). For mouse studies GLA was further purified by Mono-Q chromatography. For the HIS-tagged GBA culture medium was centrifuged, filtered, and mixed 3:1 (v/v) in 4× binding buffer (200 mM Tris, pH 8.0, 1.2 M NaCl) and applied to 0.3 ml packed NiNTA agarose (Invitrogen), pre-equilibrated in binding buffer (50 mM Tris, pH 8.0, 300 mM NaCl). The column was washed with binding buffer and eluted with binding buffer with 250 mM imidazole. Purity and quantification was evaluated by SDS-PAGE Coomassie staining.

CRISPR/Cas9 Targeted KO in CHO Cells

Gene targeting was performed in CHO clones stably expressing GLA or GBA. Cells were seeded at $0.5×10^6$ cells/mL in T25 flask (NUNC, Denmark) one day prior to transfection, and $2×10^6$ cells and 1 µg each of endotoxin free plasmid DNA of Cas9-GFP and gRNA in the plasmid U6GRNA (Addgene Plasmid #68370) were used for electroporation as described above. 48 hrs after nucleofection the 10-15% highest labeled (GFP) pool of cells were enriched by FACS, and after 1 week in culture cells were single cell sorted by FACS into 96-wells. KO clones were identified by Indel Detection by Amplicon Analysis (IDAA) as described (Lonowski, L. A. et al. Genome editing using FACS enrichment of nuclease-expressing cells and indel detection by amplicon analysis. Nature Protocols 12, 581-603 (2017), incorporated herein by reference in its entirety), as well as when possible by immunocytology with appropriate lectins or monoclonal antibodies. Selected clones were further verified by Sanger sequencing. The strategy enabled fast screening and selection of KO clones with frameshift mutations, and on average we selected 2-5 clones from each targeting event.

ZFNs/CRISPR-Mediated KI in CHO Cells

Site-specific CHO Safe-Harbor locus KI was based on ObLiGaRe strategy and performed with 2 µg of each ZFN (Merck/formerly known as Sigma-Aldrich) tagged with GFP/Crimson as previously described (Yang, Z, Nature Biotechnol 33, 2015), and 5 µg donor plasmid with full coding human genes (ST3GAL4, ST6GAL1, GNPTAB, or GNPTG). In brief, the EPB69 donor plasmid contained inverted CHO Safe-Harbor locus ZFN binding sites flanking the CMV promoter-ORF-BGH polyA terminator. Monoallelic targeted KI clones with one intact allele were selected by IDAA analysis (Yang, Z, Nucleic Acids Res 42, 2015). To stack a second gene into a Safe-Harbor locus, we first designed gRNA for the CHO Safe-Harbor locus flanking the ZFN binding site, followed by transfection with 1 µg of a donor PCR product of gene to be inserted with 1 µg Cas9-GFP and 1 µg gRNA. In brief, the donor PCR product was generated by using EPB69 donor plasmid as template which contained the CMV promoter-ORF-BGH polyA terminator. KI clones were screened by PCR with primers specific for the junction area between the donor plasmid and the Safe-Harbor locus. A primer set flanking the targeted KI locus was used to characterize the allelic insertion status, and when possible, KI clones were also screened by immunocytology with lectins and monoclonal antibodies.

GLA Enzyme Activity Assay

GLA enzyme activity was measured with 33 mM (unless otherwise specified) p-nitrophenyl-α-D-galactopyranoside (pNP-Gal) at 37° C. for 30 min at pH 4.6 in 20 mM citrate and 30 mM sodium phosphate, and the reaction was quenched with borate buffer (pH 9.8) and released p-nitrophenol was read at 405 nm. A standard curve was generated by using 1:2 serially diluted p-Nitrophenol in the same assay condition to calculate the amount of released product.

Site-Specific N-Glycopeptide Analysis

Approximately 10 µg of purified GLA or GBA in 50 mM Ammoniumbicarbonate buffer (pH 7.4) was reduced with dithiothreitol (10 mM) at 60° C. for 30 min and alkylated with iodoacetamide (20 mM) for 30 min in dark at room temperature. Chymotrypsin digestion was performed at a 1:25 enzyme: substrate ratio. The proteolytic digest was desalted by custom made modified StageTip columns containing 2 layers of C18 and 1 layer of C8 membrane (3M Empore disks, Sigma-Aldrich). Samples were eluted with 50% methanol in 0.1% formic acid, and then dried in SpeedVac and re-solubilized in 0.1% formic acid. LC MS/MS analysis was performed with an EASY-nLC 1000 LC system (ThermoFisher Scientific) interfaced via nanoSpray Flex ion source to an Orbitrap Fusion MS (ThermoFisher Scientific). Briefly, the nLC was operated in a single analytical column setup using PicoFrit Emitters (New Objectives, 75 m inner diameter) custom packed with Reprosil-Pure-AQ C18 phase (Dr. Maisch, 1.9-µm particle size, 19-21 cm column length). Each sample was injected onto the column and eluted in a gradient from 2 to 25% B in 45 min at 200 nL/min (Solvent A, 100% $H_2O$; Solvent B, 100% acetonitrile; both containing 0.1% (v/v) formic acid). A precursor MS1 scan (m/z 350-2,000) of intact peptides was acquired in the Orbitrap Fusion at the nominal resolution setting of 120,000, followed by Orbitrap HCD-MS2 and at the nominal resolution setting of 60,000 of the five most abundant multiply charged precursors in the MS1 spectrum; a minimum MS1 signal threshold of 50,000 was used for triggering data-dependent fragmentation events. Targeted MS/MS analysis was performed by setting up a targeted $MS^n$ ($tMS^n$) Scan Properties pane.

Data Analysis

Glycopeptide compositional analysis was performed from m/z features using in-house written SysBioWare software. For m/z feature recognition from full MS scans LFQ Profiler Node of the Proteome discoverer 2.1 (ThermoFisher Scientific) was used. A list of precursor ions (m/z, charge and retention time) was imported as ASCII data into SysBioWare and compositional assignment within 4 ppm mass tolerance was performed. The main building blocks used for the compositional analysis were: NeuAc, Hex, HexNAc, dHex and phosphate. The most prominent peptides corresponding to each potential glycosites were added as an additional building block for compositional assignment. The most prominent peptide sequence related to each N-glycosite was determined experimentally by comparing the yield of deamidated peptides before and after PNGase F treatment. A list of potential glycopeptides and glycoforms for each glycosite was generated and the top 10 of the most abundant candidates for each glycosite were selected for targeted MS/MS analysis to confirm the proposed structure. Each targeted MS/MS spectrum was subjected to manual interpretation. Same N-glycan composition may represent isobaric structures, so the listed glycan structure were assisted by and in agreement with literature data, predicted enzyme functions of the targeted genes together with useful information in MS/MS fragments.

Mouse Studies

Fabry mice (~3.5 months male) and WT controls were used as reported previously (Shen, J. S. et al. Mannose receptor-mediated delivery of moss-made alpha-galactosidase A efficiently corrects enzyme deficiency in Fabry mice. J Inherit Metab Dis 39, 293-303 (2016), incorporated herein by reference in its entirety). All animal procedures were reviewed and approved by the Institutional Animal Care and Use Committee of Baylor Research Institute. All injections were performed via the tail-vein with enzymes diluted in saline to a total volume of 200 µl per mouse.

Pharmacokinetics

Enzyme preparations were injected at a dose of 1 mg/kg body weight. At indicated time points, blood samples were collected from tail vein, plasma was separated by centrifugation, and used for enzyme assay.

Biodistribution and Tissue Kinetics.

Enzyme preparations were injected at a dose of 1 mg/kg body weight. At indicated time points, mice were perfused with saline (to remove blood), and heart, kidney, liver and spleen were dissected. The whole organs were homogenized in 0.2% Triton/saline for enzyme assay. Protein concentration was measured using BCA protein assay kit (Pierce).

Immunohistochemistry

Enzyme preparations were injected at a dose of 2 mg/kg body weight. Heart, kidney and Liver were harvested 24 h after enzyme infusion. Untreated Fabry mouse tissues were used as negative controls. Tissues were fixed in formalin, embedded in paraffin, and 5-micron sections were made. IHC was performed by the Histopathology and Tissue Shared Resource in Georgetown University (Washington, D.C.). In brief, after heat-induced epitope retrieval in citrate buffer, sections were treated with 3% hydrogen peroxide and 10% normal goat serum, and were incubated with rabbit polyclonal antibody to human GLA (Shire). After incubation with HRP-labeled secondary antibody, signals were detected by DAB chromogen, and the sections were counterstained with hematoxylin. Signal specificity was verified with control staining, in which the primary antibody incubation was omitted. We also developed a mouse monoclonal antibody to purified recombinant human GLA that was used to verify IHC.

Clearance of Tissue Gb3

Enzyme preparations or vehicle alone (saline) were injected into 6 months old female Fabry mice at doses of 1 mg/kg body weight. Heart, kidney, and liver were harvested 2 week after a single injection. Tissue Gb3 levels were analyzed by mass-spectrometry as described (Durant, B. et al. Sex differences of urinary and kidney globotriaosylceramide and lysoglobotriaosylceramide in Fabry mice. J Lipid Res 52, 1742-1746 (2011), incorporated herein by reference in its entirety).

Example 13—Role of Dose of GLA Enzyme for Biodistribution and Substrate Removal in Mouse Model of Fabry Disease To investigate the role dose plays in the biodistribution and therapeutic effect of our glycoengineered GLA enzymes, we used the Fabry mouse model. Fabrazyme and GLA-bi2,3SA was injected intravenously into Fabry mice in doses of 0.5 mg/kg and 0.2 mg/kg and enzyme biodistribution and activity was analyzed as described below.

Figure 23:
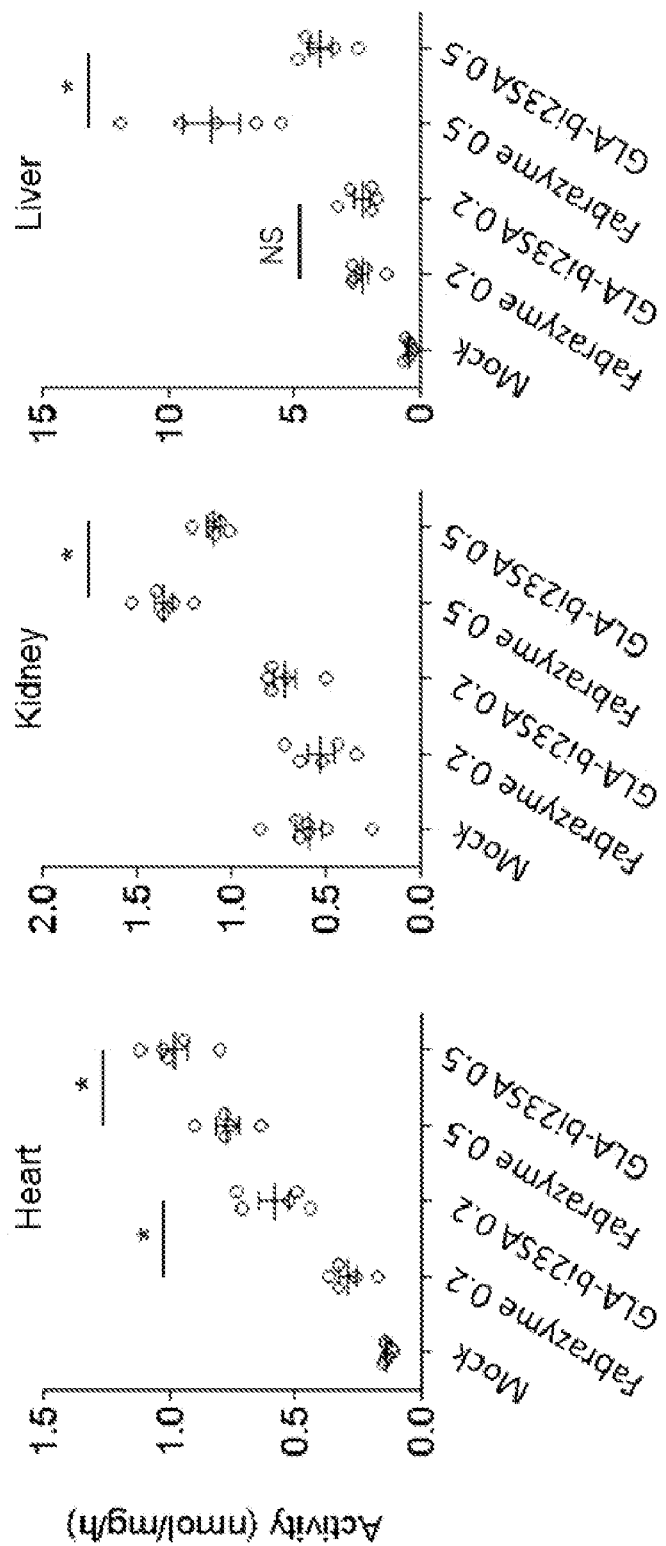
FIG. 23 shows similar biodistribution experiment as described in FIG. 22 Tissue distribution of the GLA-bi23SA enzyme sample was compared with Fabrazyme. Enzyme preparations were injected into Fabry mice at a dose of 0.2 or 0.5 mg/kg. Heart, kidney, and liver were dissected one week after injection and enzyme activity in the organ lysates was determined.

Experiment 1—Biodistribution of GLA-bi23SA and Fabrazyme given at 0.5 and 0.2 mg kg dose in Fabry mice: The methods used were as described in Example 3 except that organs were collected after 1 week. Enzyme preparations were injected into female Fabry mice (~5 months old) at a dose of 0.2 or 0.5 mg/kg. Heart, kidney, and liver were dissected at 1 week after a single injection. FIG. 23, reproduced from Tian et al. 2019, shows relative distribution of GLA variants into heart, kidney and liver. These data confirm the improved distribution of GLA-Bi23SA to heart and lower uptake in the liver compared to Fabrazyme, but also demonstrate dose dependency, suggesting that further studies of optimal dosing for GLA-Bi23SA may be beneficial.

Figure 24:
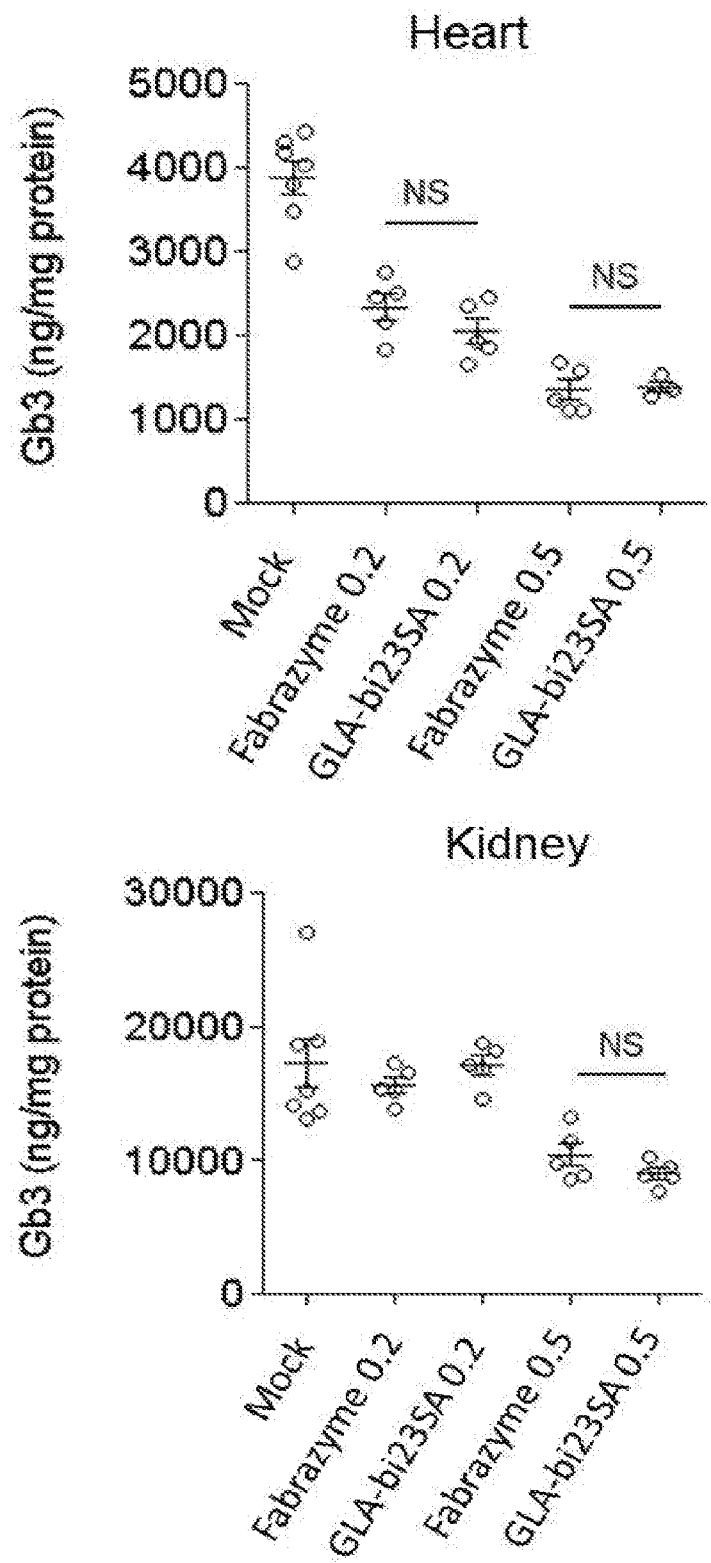
FIG. 24 shows the clearance of Gb3 substrate in tissues of Fabry mice. Residual Gb3 contents in kidney and heart was analyzed one weeks after a single injection of 0.5 or 0.2 mg/kg of GLA-bi23SA or Fabrazyme into 6 months old female Fabry mice via tail-vein. Data are presented as mean±S.D. (n=5). NS P>0.05.

Experiment 2—Substrate removal effect of GLA-bi23SA and Fabrazyme administered at 0.5 and 0.2 mg kg doses in Fabry mice: Heart and Kidney was analyzed for Gb3 substrate reduction as described in Example 4. GLA-Bi23SA or Fabrazyme enzyme preparations (0.5 or 0.2 mg/kg) or vehicle alone (saline) were injected into 6-month old female Fabry mice via tail-vein (n=5 per group). One week after injection, heart and kidney were dissected, and Gb3 levels were measured using mass-spectrometry. Results of the Gb3 analysis are shown in FIG. 24, reproduced from Tian et al. 2019, and confirm the efficient function of both GLA-Bi23SA and Fabrazyme after single dose administration. These data clearly demonstrate that glycoforms of GLA without Man6P are efficiently taken up by cells and delivered to the lysosome, where they efficaciously function to reduce Gb3.

Figure 25:
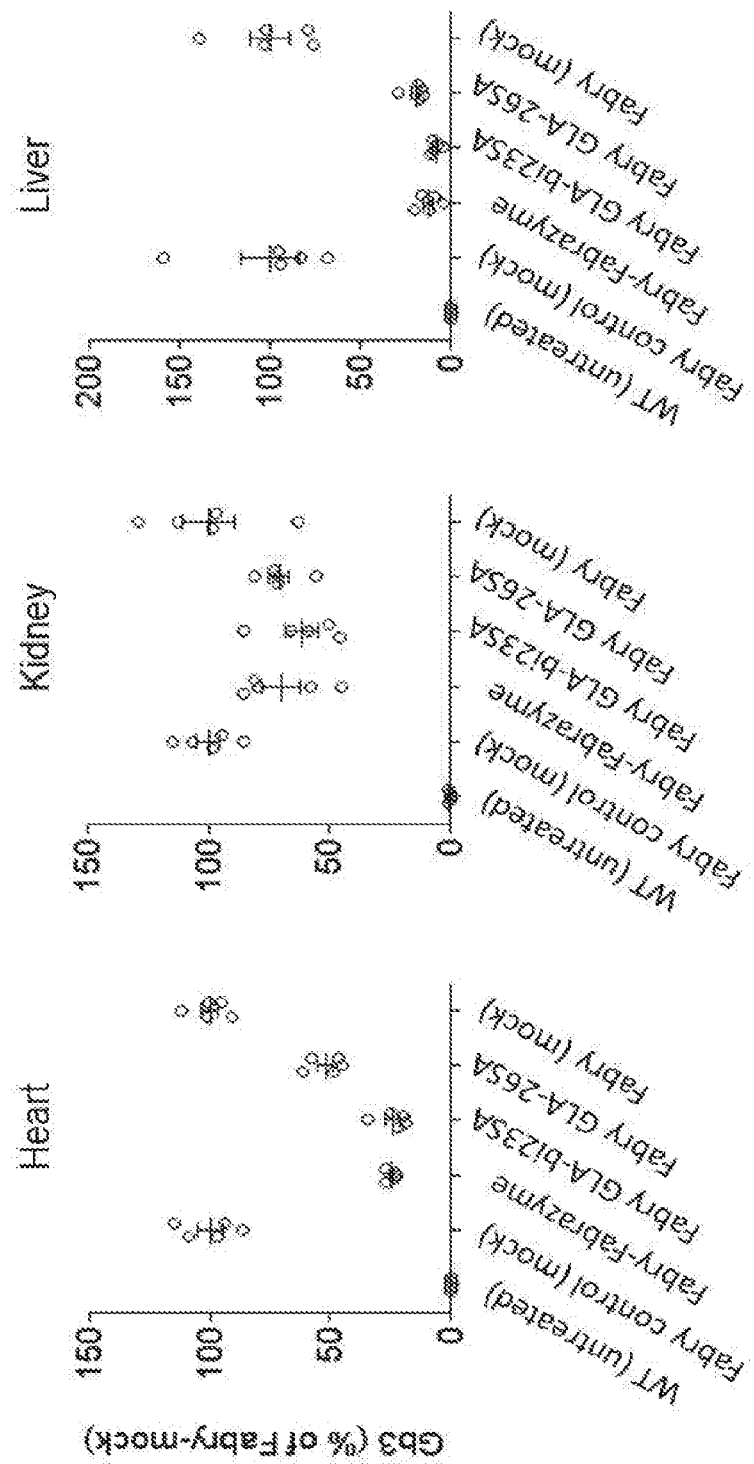
FIG. 25 shows the clearance of Gb3 substrate in tissues of Fabry mice. Residual Gb3 contents in kidney, liver, and heart was analyzed 2 weeks after a single injection of 1.0 mg/kg of GLA-26SA, GLA-Bi23SA or Fabrazyme into 6 months old female Fabry mice via tail-vein. Data are presented as mean±S.D. (n=5). NS P>0.05.

Example 14—Role of 2,6 Sialic Acid Linkage on Glycoengineered GLA Enzyme for Substrate Removal in Mouse Model of Fabry Disease To investigate the role of 2,6 sialic acid linkage in the efficacy of GLA enzyme, in vivo, GLA-26SA or vehicle alone (saline) was injected into 6-month old female Fabry mice via tail-vein (n=5 per group). At 2 weeks after injection, heart, kidney and liver were dissected. Gb3 levels were measured in GLA-26SA mouse tissues, and mock-treated Fabry mouse controls (samples from Example 4). For mock controls, the lysates from Example 4 were thawed, sonicated again and then were subjected to protein assay and glycolipid extraction together with new GLA-2,6SA samples. The Gb3 levels of the three organs are presented in FIG. 25, where data for Fabrazyme and GLA-bi23SA from Example 4 are included for comparison. GLA-26SA produced lower reduction of Gb3 levels in the heart and kidney compared to Fabrazyme and GLA-bi23SA, while the effect in liver was similar for all variants. This finding correlates with the lower level of GLA-26SA distributed to the heart and especially kidney (FIG. 6) and confirms that the specific type of sialic acid linkage is critically important for improving biodistribution and biological effects.

Example 15—Role of Glycans on GLA Enzyme for PK in Rat Model of Fabry Disease

To demonstrate the kinetics of glycoengineered GLA are not species-specific, but are applicable in a second animal, a rat model of Fabry disease was used for the following experiment. The model is based on a Dark Agouti strain lacking GLA activity as described in Miller 2018. The GLA-bi23SA variant was tested and GLA produced in wt cells was used as control. Enzyme preparations (1 mg/kg) was injected intravenously into 12- to 14-week old male Fabry rats via tail-vein (n=3 for GLA-bi23SA group and n=1 for control). At time points (5 min, 20 min, 60 min, 3 h, and 4 h post-injection), small amounts of blood samples were collected from the animals via their tail vein. Plasma was separated by centrifugation and was used for enzyme assays (see Example 1).

Figure 26:
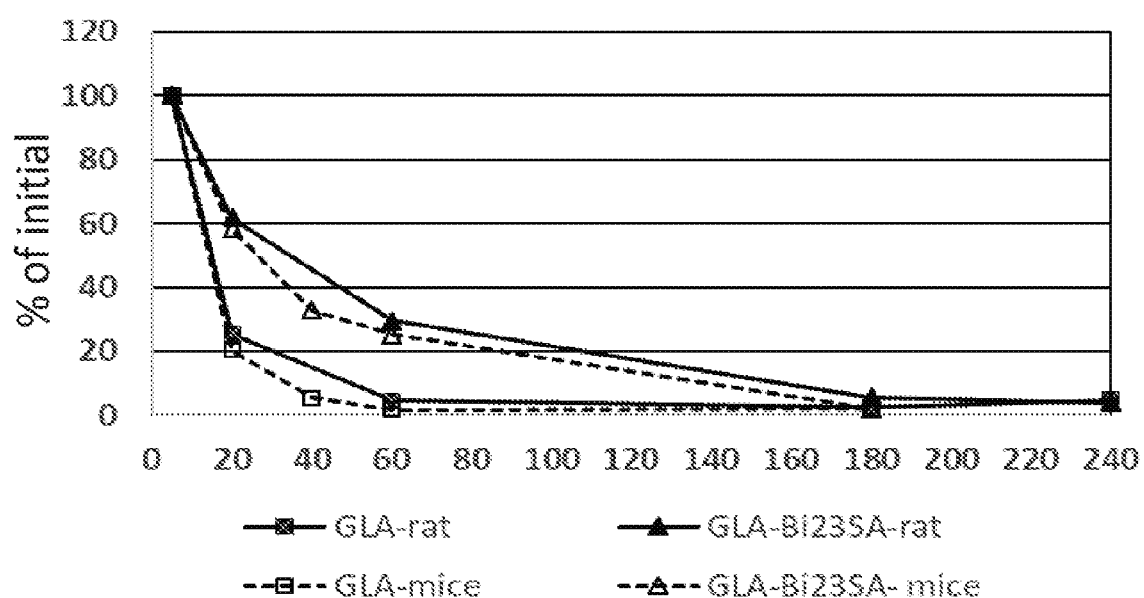
FIG. 26 shows enzyme activity in plasma at various time points after injection of GLA. Fabry rats were injected with 1 mg/kg dose of wt-CHO produced GLA (Control) or GLA-bi23SA via tail vein (n=3 for GLA-bi23SA and n=1 for control group, male mice, age 12-14 weeks). At indicated time points, small amount of blood samples was collected from tail vein and separated plasma was analyzed for GLA activity. Enzyme activities were shown as % of activity at 5 min after injection. For GLA-bi23SA the data are expressed as mean values (n=3). Solid lines are rat data and dashed lines are mouse data. The figure shows prolonged plasma clearance curves for GLA-bi23SA versus control GLA. For comparison the mouse data previously obtained for GLA-bi23SA and control enzyme (Example 3, FIG. 15) are reproduced from Tian et al. 2019 (average of n=5 per mouse group). For GLA-bi23SA and control GLA the plasma clearance curves in the rat are very similar to mouse curves, demonstrating same prolonged kinetics in rat and mouse.

The pharmacokinetics of the GLA-bi23SA showed a clearly prolonged blood clearance profile (FIG. 26) and an increased half-life by three fold (7.6 versus 22.1 min for GLA from wt cells) was observed. The pharmacokinetics of the GLA-bi23SA modified enzyme in the rat model are very similar to the kinetics seen in mouse model (Example 3, FIG. 5) demonstrating cross-species applicability of the glycoengineered variants species.

Example 16—Evaluating Pharmacokinetics/Stability of Other Lysosomal Enzymes

To characterize the effect of optimized glycans on pharmacokinetics we used balb/c mice were used. The plasma activity of endogenous mouse enzyme is negligible (<1%), compared to activities after intravenous injection, so enzyme kinetics at early time points may be evaluated in this model. Various optimized glycans were displayed on AGA, GUSB, Laman and GLA enzymes by performing gene modifications in COH cell lines stably expressing the enzymes. The enzymes produced in wild-type (wt) CHO cells are included for control. The enzymes and glycodesigns evaluated are shown in Table 10:

TABLE 10

Glycodesigns of modified lysosomal enzymes

| Enzyme variant | Design/Glycostructure | Cell engineering |
| --- | --- | --- |
| GLA-opt | No Man6P, High-antennary, high 2,3SA | KO: Gnptab, Mgat4b/5 KI: ST3GAL4/MGAT4A/5 |
| GLA | wt | No |
| AGA-opt | No Man6P, High 2,3SA | KO: Gnptab KI: ST3GAL4 |
| AGA | wt | No |
| GUSB-opt | No Man6P | KO: Gnptab |
| GUSB | wt | No |
| Laman-opt | No Man6P | KO: Gnptab |
| Laman | wt | No |

The enzyme variants were injected into 9-10 weeks old Balb/c mice via tail vein at a dose of 0.75 mg/kg body weight (n=2 for each enzyme variant). Blood samples were collected by cheek bleed at 30 and 120 min for AGA, GUSB and Laman enzymes (15 and 30 min for GLA). The enzyme activity in plasma was measured using the following substrates: Asp-AMC (L-Aspartic acid β-(7-amido-4methylcoumarin) for AGA activity, 4-Nitrophenyl β-D-glucuronide for GUSB activity, 4-Nitrophenyl α-D-mannopyranoside for Laman activity, and 4-Methylumbelliferyl alpha-D-Galactopyranoside for GLA activity. All enzyme activities were corrected for endogenous activity by subtracting enzyme activity of plasma from untreated mice. The initial plasma activity was based on total enzyme activity infused, which we assumed would initially be present in the plasma compartment. Plasma activity at the two time points as percentage of initial plasma activity is presented in FIG. 27. For all four enzymes, and all sampling times, the glyco-optimized variants from engineered cells showed higher activity in plasma compared to enzyme produced in unmodified wild-type CHO cells. FIGS. 27B, 27C, and 27D show that the glycoengineering involving removal of Man6P prolongs the circulation of the three enzymes AGA, GUSB and Laman, respectively. This demonstrates that the optimized glycodesigns are broadly applicable to lysosomal enzymes. In addition, the optimized GLA (GLA-opt in FIG. 27A) shows that a glycodesign without Man6P and with higher antennarity and high 2,3SialicAcid prolongs the circulatory half-life of GLA enzyme.

Example 17—Optimizing GLA Variants Stabilized by Protein Mutagenesis

The glyco-optimization introduced into GLA-bi23SA may be combined with enzyme stabilizing technologies involving amino acid mutations of the GLA sequence to obtain additive or synergistic effects. GLA mutants (mutGLA) with improved thermal or physical stability or improved cell uptake have been described in WO 2016/105889, incorporated herein by reference in its entirety.

The mutGLA is glycoengineered using the glycodesigns developed for GLA.

The following engineering is performed in CHO cells expressing mutGLA:
1) knock-out of Gnptab
2) knock-out of Gnptab/St6gal1
3) knock-out of Gnptab/St6gal1 and knock-in of ST3GAL4
4) knock-out of Gnptg/Gnptab/St6gal1 and knock-in of ST3GAL4
5) knock-out of Gnptg/Gnptab/St6 gal/Mgat4B/Mgat5 and knock-in of ST3GAL4

Cell pools or clonal cell lines are isolated, and glyco-optimized mutGLA variants are produced and characterized, as described in Examples 1 and 2.

Pharmacokinetics of mutGLA-bi23SA and other glycooptimized mutGLA variants are established by administrating 0.1/0.2/0.5 or 1.0 mg/kg to Fabry mice or rats. Pharmacokinetics are established as described in Example 3.

Tissue distribution of the mutGLA-bi23SA is established 24 h or 48 h after injection when animals are sacrificed and heart, kidney, liver and spleen are dissected. Biodistribution is determined a described in Example 3.

Substrate reduction effect of glycoengineered mutGLA variants is established by injecting GLA or glycooptimized mutGLA variants produced in glycoengineered cell lines (1-5 listed above) to Fabry mice and rats. At 1 or 2 weeks after injection the animals are sacrificed, and organs are collected and analyzed for Gb3 levels. The procedures are as described in Example 4.

All of the U.S. patents, U.S. patent application publications, U.S. patent applications, PCT patent application, PCT patent application publications, foreign patents, foreign patent applications and non-patent publications referred to in this specification or listed in any Application Data Sheet are incorporated herein by reference in their entirety. From the foregoing it will be appreciated that, although specific embodiments of the invention have been described herein for purposes of illustration, various modifications may be made without deviating from the spirit and scope of the invention.

LIST OF REFERENCES

Benjamin E R, Khanna R, Schilling A, Flanagan J J, Pellegrino L J, Brignol N, Lun Y, Guillen D, Ranes B E, Frascella M, Soska R, Feng J, Dungan L, Young B, Lockhart D J and Valenzano K J (2012) *Co-administration With the Pharmacological Chaperone ATJ001 Increases Recombinant Human α-Galactosidase A Tissue Uptake and Improves Substrate Reduction in Fabry Mice*. Mol Ther 20(4):717-726.

Damme, M. et al. (2015) *Chronic enzyme replacement therapy ameliorates neuropathology in alpha-mannosidosis mice*. Ann Clin Transl Neurol 2, 987-1001

Desnick R J, Schuchman E H. (2012) *Enzyme replacement therapy for lysosomal diseases: lessons from 20 years of experience and remaining challenges*. Annu. Rev. Genomics Hum. Genet. 13, 307-33510

Grubb J H, Vogler C, Levy B, Galvin N, Tan Y, Sly W S. (2008) *Chemically modified beta-glucuronidase crosses blood-brain barrier and clears neuronal storage in murine mucopolysaccharidosis VII*. Proc. Natl. Acad. Sci USA 105:2616-2621

Grubb, J. H., Vogler, C. & Sly, W. S. *New strategies for enzyme replacement therapy for lysosomal storage diseases*. Rejuvenation Res 13, 229-236 (2010)

Kishnani P. S. (2015) *Challenges of Enzyme Replacement Therapy: Poor Tissue Distribution in Lysosomal Diseases Using Pompe Disease as a Model*. In: Rosenberg A., Demeule B. (eds) Biobetters. AAPS Advances in the Pharmaceutical Sciences Series, vol 19. Springer, New York, N Y Kim J P, Olson L J, Dahms (2009) *Carbohydrate Recognition by the Mannose 6-phosphate Receptors*. Curr Opin Struct Biol 19(5):534-42 (2009)

Lee K, Jin X, Zhang K, Copertino L, Andrews L, Baker-Malcolm J, Geagan L, Qiu H, Seiger K, Barngrover D, McPherson J M, Edmunds T. (2003) *A biochemical and pharmacological comparison of enzyme replacement therapies for the glycolipid storage disorder Fabry disease*. Glycobiology 13(4): 305-313

Lonowski, L A, Narimatsu Y, Riaz A, Delay C E, Yang Z, Niola F, Duda K, Ober E A, Clausen H, Wandall H H, Hansen S H, Bennett E P, Frödin M. (2017) *Genome editing using FACS enrichment of nuclease-expressing cells and indel detection by amplicon analysis*. Nature Protocols 12, 581-603 (2017).

Miller J J, Aoki K, Moehring F, Murphy C A, O'Hara C L, Tiemeyer M, Stucky C L, Dahms N M (2018) *Neuropathic pain in a Fabry disease rat model*. JCI Insight; 3(6). pii: 99171

Narimatsu Y, Joshi H J, Zhang Y, Gomes C, Chen Y H, Lorenzetti F, Furukawa S, Schjoldager K, Hansen L, Clausen H, Bennett E P, Wandall H H (2018): *A validated gRNA library for CRISPR Cas9 targeting of the human glycosyltransferase genome*. Glycobiology 28(5):295-305.

Platt F M (2018) *Emptying the stores: lysosomal diseases and therapeutic strategies* Nat Rev Drug Disc 17: 133-150.

Rozaklis T, Beard H, Hassiotis S, Garcia A R, Tonini M, Luck A, Pan J, Lamsa J C, Hopwood J J, Hemsley K M (2011) *Impact of high-dose, chemically modified sulfamidase on pathology in a murine model of MPS IIIA*. Experimental Neurology 230:123-130.

Shen, J. S. et al. (2016) *Mannose receptor-mediated delivery of moss-made alpha-galactosidase A efficiently corrects enzyme deficiency in Fabry mice*. J Inherit Metab Dis 39, 293-303.

Tian W, Ye Z, Wang S, Schulz M A, Coillie J V, Sun L, Chen Y H, Narimatsu Y, Hansen L, Kristensen C, Mandel U, Bennett E P, Jabbarzadeh-Tabrizi S, Schiffmann R, Shen J S, Vakhrushev S, Clausen H, Yang Z (2019): *The glycosylation design space for recombinant lysosomal replacement enzymes produced in CHO cells*. Nature Communications 10 (1785). DOI: 10.1038/s41467-019-09809-3

Vakhrushev S Y, Dadimov D, Peter-Katalinic J. (2009) *Software platform for high-throughputglycomics*. Anal Chem 81, 3252-3260

Xu S et al (2015) *Coformulation of a Novel Human α-Galactosidase A With the Pharmacological Chaperone AT001 Leads to Improved Substrate Reduction in Fabry Mice*. Molecular Therapy vol. 23 no. 7, 1169-1181

Yang Z., Wang S, Halim A, Schulz M A, Frodin M, Rahman S H, Vester-Christensen M B, Behrens C, Kristensen C, Vakhrushev S Y, Bennett E P, Wandall H H, and Clausen H. (2015) *Engineered CHO cells for production of diverse, homogeneous glycoproteins*. Nature biotechnology 33, 842-844

Zhu Y, Li X, Kyazike J, Zhou Q, Thurberg B L, Raben N, Mattaliano R J and Cheng S H. (2004) *Conjugation of Mannose 6-Phosphate-containing Oligosaccharides to Acid—Glucosidase Improves the Clearance of Glycogen in Pompe Mice*. The Journal of Biological Chemistry 279: 50336-50341

Essentials of Glycobiology. 2017, 3$^{rd}$ edition. Varki A, Cummings R D, Esko J D, et al, editors. Cold Spring Harbor (N Y): Cold Spring Harbor Laboratory Press;

PATENT LITERATURE

U.S. Pat. No. 7,001,994 Methods for introducing Mannose 6 Phosphatre and other oligosaccharides onto Glycoproteins. Zhy Y (Genzyme)

WO2008/109677 Modified Enzyme and Treatment Method, Sly W S, Grubb J H, Vogler C A (St. Louis University)

WO 2015/150490 Modified Sulfamidase and Production Thereof, Berghard C, Nordling E, Svensson S G, Tjernberg A. (SOBI)

WO2017/194699 A cell-based array platform, Bennet E, Narimatsu Y, Steentoft C, Yang Z, Mandel U, Clausen H. (U Copenhagen)

WO2016091268 N-Glycosylation Rahman S H, Behrens C, Vester-Christensen M B, Clausen H, Zhang Y, Halim A F, Bennett E (U Copenhagen, Novo Nordisk A/S)

WO2017008982 Production of n-glycoproteins for enzyme assisted glycomodification Rahman S H, Behrens C, Vester-Christensen M B, Clausen H, Zhang Y, Halim A F, Bennett E (U Copenhagen, Novo Nordisk A/S)

WO 2016/105889 Human Alpha-Galactosidase variants Agard N J, Miller M G, Zhang X, Huisman, G W. (Codexis Inc)

The invention claimed is:

1. A modified recombinant lysosomal enzyme with increased circulation time in plasma as compared to an unmodified version of the same, wherein said enzyme comprises low mannose-6-phosphate (Man6P) and high sialic acid (SA) capping of alpha2,3 type (alpha2,3SA), wherein said enzyme comprises more than 4 mol alpha2,3SA per mol of enzyme.

2. The modified recombinant lysosomal enzyme according to claim 1, wherein the enzyme comprises less than 0.3 mol Man6P per mol of enzyme.

3. The modified recombinant lysosomal enzyme according to claim 1, wherein the enzyme comprises no detectable Man6P and high alpha2,3SA.

4. The modified recombinant lysosomal enzyme according to claim 1, wherein the enzyme comprises less than 0.05 mol Man6P per mol of enzyme.

5. The modified recombinant lysosomal enzyme according to claim 1, comprising more than 4.5 mol alpha2,3SA per mol of enzyme.

6. The modified recombinant lysosomal enzyme according to claim 1, comprising more than 4 mol alpha2,3SA per mol of enzyme and less than 1 mol alpha2,6SA.

7. The modified recombinant lysosomal enzyme according to claim 1, wherein said modified recombinant lysosomal enzyme comprises lowered Man6P tagging of N-glycans as compared to a similar unmodified recombinant lysosomal enzyme.

8. The modified recombinant lysosomal enzyme according to claim 1, wherein the modified recombinant lysosomal enzyme comprises a biantennary N glycan structure, a triantennary N glycan structure, a tetra antennary N glycan structure, or combinations thereof.

9. The modified recombinant lysosomal enzyme of claim 1, wherein the enzymes comprises low exposed Man6P.

10. The modified recombinant lysosomal enzyme of claim 1, wherein the enzymes comprises less than 0.3 mol of exposed Man6P per mol of enzyme.

11. The modified recombinant lysosomal enzyme according to claim 1, wherein the modified recombinant lysosomal enzyme is selected from Aspartylglucoaminidase (AGA), Alpha-Galactosidase A (GLA), Acid ceramidase, Acid alpha-L-fucosidase, Protective protein/Cathepsin A, Acid beta-glucosidase, or glucocerebrosidase (GBA), Acid beta-galactosidase, Iduronate-2-sulfatase (IDS), Alpha-LIduronidase (IDUA), Galactocerebrosidase/galactosylceramidase (GALC), Acid alphamannosidase, Acid beta-mannosidase, Arylsulfatase B, Arylsulfatase A, Acid betagalactosidase, N-Acetylglucosamine-1-phosphotransferase, and Lysosomal alpha-glucosidase (GAA).

12. The modified recombinant lysosomal enzyme according to claim 1, wherein the modified recombinant lysosomal enzyme is selected from GLA, GBA, GUS, and GAA.

13. A composition comprising a substantially pure preparation of the modified recombinant lysosomal enzyme according to claim 1.

* * * * *